US006391551B1

(12) United States Patent
Shultz et al.

(10) Patent No.: US 6,391,551 B1
(45) Date of Patent: *May 21, 2002

(54) DETECTION OF NUCLEIC ACID HYBRIDS

(75) Inventors: John William Shultz, Verona; Martin K. Lewis; Donna Leippe, both of Madison; Michelle Mandrekar, Oregon; Daniel Kephart, Cottage Grove; Richard Byron Rhodes, Madison; Christine Ann Andrews, Cottage Grove; James Robert Hartnett, Madison; Trent Gu, Madison; Ryan J. Olson, Madison; Keith V. Wood, Madison, all of WI (US); Roy Welch, Palo Alto, CA (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/383,316

(22) Filed: Aug. 25, 1999

Related U.S. Application Data

(63) Continuation-in-part of application No. 09/358,972, filed on Jul. 21, 1999, now Pat. No. 6,235,480, which is a continuation-in-part of application No. 09/252,436, filed on Feb. 18, 1999, now Pat. No. 6,159,693, which is a continuation-in-part of application No. 09/042,287, filed on Mar. 13, 1998, now Pat. No. 6,335,162.

(51) Int. Cl.$^7$ .......................... C12Q 1/68; C07H 21/04
(52) U.S. Cl. ...................... 435/6; 536/24.31; 536/24.32
(58) Field of Search .......................... 435/6; 536/24.31, 536/24.32

(56) References Cited

U.S. PATENT DOCUMENTS

| | | | |
|---|---|---|---|
| 4,303,752 A | 12/1981 | Kolehmainen et al. | 435/8 |
| 4,331,762 A | 5/1982 | Nakajima et al. | 435/190 |
| 4,338,395 A | 7/1982 | Leon et al. | 435/17 |
| 4,352,881 A | 10/1982 | Inagawa et al. | 435/17 |
| 4,357,420 A | 11/1982 | Bostick et al. | 435/8 |
| 4,368,261 A | 1/1983 | Klose et al. | 435/15 |
| 4,371,611 A | 2/1983 | Fusee | 435/14 |
| 4,394,445 A | 7/1983 | Nix et al. | 435/19 |
| 4,415,655 A | 11/1983 | De Castro et al. | 435/17 |
| 4,438,124 A | 3/1984 | Meister et al. | 424/270 |
| 4,443,594 A | 4/1984 | Buckmann | 536/27 |
| 4,446,231 A | 5/1984 | Self | 435/7 |
| 4,460,684 A | 7/1984 | Bauer | 435/14 |
| 4,485,177 A | 11/1984 | Siedel et al. | 436/547 |
| 4,595,655 A | 6/1986 | Self | 435/7 |
| 4,683,202 A | 7/1987 | Mullis et al. | 435/91 |
| 4,735,897 A | 4/1988 | Vary et al. | 435/17 |
| 4,743,561 A | 5/1988 | Shaffar | 436/501 |
| 4,755,458 A | 7/1988 | Rabbani et al. | 435/5 |
| 4,800,159 A | 1/1989 | Mullis et al. | 435/172.3 |
| 4,863,195 A | 9/1989 | Mullis et al. | 435/6 |
| 5,356,776 A | 10/1994 | Kambara et al. | 435/6 |

(List continued on next page.)

FOREIGN PATENT DOCUMENTS

| | | | |
|---|---|---|---|
| EP | 0 229 601 A | 11/1986 | |
| EP | 639 647 A | 7/1994 | |
| EP | 0 663 447 A | 12/1994 | |
| EP | 0 894 867 A | 11/1997 | |
| GB | 2055200 | 12/1981 | G01N/21/76 |
| WO | WO 90/05530 | 5/1990 | |
| WO | WO 91/17264 | 11/1991 | |
| WO | WO 92/13963 | 8/1992 | |
| WO | WO 94/25619 | 11/1994 | C12Q/1/00 |
| WO | WO 95/21938 | 8/1995 | |
| WO | WO 96/41014 | 12/1996 | |
| WO | WO 97/41256 | 11/1997 | |
| WO | WO 98/13523 | 4/1998 | C12Q/1/68 |
| WO | WO 98/54362 | 4/1998 | |
| WO | WO 98/28440 | 7/1998 | C12Q/1/68 |

(List continued on next page.)

OTHER PUBLICATIONS

A.E. Sippel, "Purification and Characterization of Adenosine Triphosphate: Ribonucleic Acid Adenyltransferase from *Escherichia coli*" *Eur. J. Biochem.* 37:31–40 (1973).

K. Chowdhury, N. Kaushik, V.N. Pandey and M.J. Modak, "Elucidiation of the Role of Arg 110 of Murine Leukemia Virus Reverse Transcriptase in the Catalytic Mechanism: Biochemical Characterization of Its Mutant Enzymes," *Biochemistry*, 35:16610–16620 (1996).

S. Karamohamed, M. Ronaghi and P. Nyren, "Biochemistry Method for Real–Time Detection of Reverse Transcriptase Activity", *Biotechniques*, 24:302–306 (Feb., 1998).

B. Hove–Jensen, K. W. Harlow, C.J. King, R.L. Switzer, "Phosphoribosylpyrosphosphate Synthetase of *Escherichia coli*", *J. Biol. Chem.*, 261(15):6765–6771 (1986).

P. Nyren, S. Karamohamed and M. Ronaghi, "Detection of Single–Base Changes Using a Bioluminometric Primer Extension Assay", *Anal. Biochem.*, 244:367–373 (Jan. 15, 1997).

M. Ronaghi, S. Karamohamed, B. Petterson, M. Uhlen and P. Nyren, "Real–Time DNA Sequencing Using Detection of Pyrophosphate Release," *Anal. Biochem.*, 242:84–89 (1996).

(List continued on next page.)

*Primary Examiner*—Jeffrey Fredman
*Assistant Examiner*—Suryaprabha Chunduru
(74) *Attorney, Agent, or Firm*—Welsh & Katz, Ltd.

(57) ABSTRACT

Processes are disclosed using the depolymerization of a nucleic acid hybrid to qualitatively and quantitatively analyze for the presence of a predetermined endogenous nucleic acid. Applications of those processes include the detection of single nucleotide polymorphisms, identification of single base changes, speciation, determination of viral load, genotyping, medical marker diagnostics, and the like.

122 Claims, 1 Drawing Sheet

U.S. PATENT DOCUMENTS

| | | | |
|---|---|---|---|
| 5,389,512 A | 2/1995 | Sninsky et al. | 435/5 |
| 5,391,480 A | 2/1995 | Davis et al. | 435/6 |
| 5,399,491 A | 3/1995 | Kacian et al. | 435/6 |
| 5,403,711 A | 4/1995 | Walder et al. | 435/6 |
| 5,445,933 A | 8/1995 | Eadie et al. | 435/6 |
| 5,494,810 A | 2/1996 | Barany et al. | 435/91.52 |
| 5,498,523 A | 3/1996 | Tabor et al. | 435/6 |
| 5,512,439 A | 4/1996 | Hornes et al. | 435/6 |
| 5,516,663 A | 5/1996 | Backman et al. | 435/91.2 |
| 5,530,192 A | 6/1996 | Murase et al. | 800/205 |
| 5,541,311 A | 7/1996 | Dahlberg et al. | 536/23.7 |
| 5,561,044 A | 10/1996 | Walker et al. | 435/6 |
| 5,573,906 A | 11/1996 | Bannwarth et al. | 435/6 |
| 5,622,824 A | 4/1997 | Koster et al. | 435/6 |
| 5,648,232 A | 7/1997 | Squirrell | 435/34 |
| 5,660,988 A | 8/1997 | Duck et al. | 435/6 |
| 5,667,964 A | 9/1997 | Ho | 435/5 |
| 5,683,877 A | 11/1997 | Lu-Chang et al. | 435/6 |
| 5,691,146 A | 11/1997 | Mayrand | 435/6 |
| 5,723,591 A | 3/1998 | Livak et al. | 536/22.1 |
| 5,731,146 A | 3/1998 | Duck et al. | 435/6 |
| 5,736,365 A | 4/1998 | Walker et al. | 435/91.2 |
| 5,741,635 A | 4/1998 | Boss et al. | 435/4 |
| 5,759,820 A | 6/1998 | Hornes et al. | 435/91.1 |
| 5,763,181 A | 6/1998 | Han et al. | 435/6 |
| 5,766,849 A | 6/1998 | McDonough et al. | 435/6 |
| 5,786,139 A | 7/1998 | Burke et al. | 435/6 |
| 5,786,183 A | 7/1998 | Ryder et al. | 435/91.2 |
| 5,814,491 A | 9/1998 | Vijg et al. | 435/91.2 |
| 5,824,517 A | 10/1998 | Cleuziat et al. | 435/91.2 |
| 5,834,202 A | 11/1998 | Auerbach | 435/6 |
| 5,840,873 A | 11/1998 | Nelson et al. | 536/24.3 |
| 5,843,660 A | 12/1998 | Schumm et al. | 435/6 |
| 5,849,547 A | 12/1998 | Cleuziat et al. | 435/91.21 |
| 5,853,981 A | 12/1998 | Kondo et al. | 435/6 |
| 5,854,033 A | 12/1998 | Lizardi | 435/91.2 |
| 5,861,242 A | 1/1999 | Chee et al. | 435/5 |
| 5,863,736 A | 1/1999 | Haaland | 435/6 |
| 5,866,337 A | 2/1999 | Schon | 435/6 |
| 5,869,252 A | 2/1999 | Bouma et al. | 435/6 |
| 5,871,902 A | 2/1999 | Weininger et al. | 435/5 |
| 5,876,924 A | 3/1999 | Zhang et al. | 435/5 |
| 5,876,930 A | 3/1999 | Livak et al. | 435/6 |
| 5,876,978 A | 3/1999 | Willey et al. | 435/91.2 |
| 5,880,473 A | 3/1999 | Ginestet | 250/458.1 |
| 5,882,856 A | 3/1999 | Shuber | 435/6 |
| 5,885,775 A | 3/1999 | Haff et al. | 435/6 |
| 5,888,819 A | 3/1999 | Goelet et al. | 435/5 |
| 5,902,722 A | 5/1999 | Di Cesare et al. | 435/4 |
| 6,007,987 A | 12/1999 | Cantor et al. | 435/6 |
| 6,066,483 A | 5/2000 | Riggs et al. | 435/194 |

OTHER PUBLICATIONS

T.A. Rozovskaya, V.O. Rechinsky, R.S. Bibilashvili, M.Y. Karpeisky, N.B. Tarusova, R.M. Khomutov, H.B.F. Dixon, "The Mechanism of Pyrophosphorolysis of RNA by RNA Polymerse", *Biochem. J.*, 224:645–650 (1989).

M.P. Deutscher and A. Kornberg, "Enzymatic Synthesis of Deoxyribonucleic Acid", *J. Biol. Chem.*, 244(11):3019–28 (1969).

J.D. Moyer and J.F. Henderson, "Nucleoside Triphosphate Specificity of Firefly Luciferase", *Anal. Biochem.*, 131:187–189 (1983).

C. Blondin, L. Serina, L. Weismuller, A. Gilles and O. Barzu, "Improved Spectrophotometric Assay of Nucleoside Monophosphate Kinase Activity Using the Pyruvate Kinase/Lactate Dehydrogenase Coupling System", *Anal. Biochem.*, 220:219–21 (1994).

S. Tabor and C.C. Richardson, "DNA Sequence Analysis With a Modified Bacteriophage T7 DNA Polymerase", *J. Biol. Chem.*, 265(14):8322–8328 (1990).

R.S. Chittock, J.–M. Hawronsky, J. Holah and C.W. Wharton, "Kinetic Aspects of ATP Amplification Reactions", *Anal. Biochem.*, 255:120–126 (Jan. 1, 1998).

Kung, et al., "Picogram Quantitation of Total DNA Using DNA–Binding Proteins in a Silicon Sensor–Based System", *Anal. Biochem.*, 187:220–227 (1990).

Srivastavan & Modak, *J. Biol. Chem.*, 255(5):2000–2004 (1980).

Sano & Feix, *Eur. J. Biochem.*, 71:577–583 (1976).

Sabina, et al., *Science*, 223:1193–1195 (1984).

Parks & Agarwal in *The Enzymes*, vol. 9:307–333, P. Boyer Ed. (1973).

Shimofuruya & Suzuki, *Biochem. Intl.*, 26(5):853–861 (1992).

Nyren, et al., "Detection of Single–Base Changes Using a Bioluminometric Primer Extension Assay", *Anal. Biochem.*, 244:367–373 (1997).

P. Bernard et al., *Am. J. Pathol.*, 153:1055–1061 (1998).

G. Garinis et al., *J. Clin. Lab. Anal.*, 13:122–125 (1999).

Holguin, et al., *Eur. J. Clin. Microbiol. Infect. Dis.*, 18:256–259 (1999).

Boriskin, et al., *Arch. Dis. Child.*, 80:132–136 (1999).

de Vega, et al., "Primer Terminus Stabilizing at the 3'–5' exonuclease active site of _29 DNA polymerase. Involvement of two amino acid residues highly conserved in proofreading DNA polymerases", *EMBO J.*, 15(5):1182–1192 (1996).

S. Patel et al., *Biochemistry*, 30:511–525 (1991).

I. Wong et al., *Biochemistry*, 30:526–537 (1991).

S. Zinnen et al., *J. Biological Chemistry*, 269(39):24195–24202 (1994).

J. Lindquist, Dept. of Bacteriology, University of Wisconsin–Madison, http://www.bact.wisc.edu/bact102/102dil3.html, undated.

J. Lindquist, Dept. of Bacteriology, University of Wisconsin–Madison, http://www.bact.wisc.edu/bact102/102dil3a.html, undated.

Most Probable No. (MPN), WQA Glossary of Terms, (1997) 3rd Ed., Water Quality Association.

P. Nyren, B. Pettersson, and M. Uhlen. "Solid Phase DNA Minisequencing by an Enzymatic Luminometric Inorganic Pyrophosphate Detection Assay," *Anal. Biochem.*, 208:171–175 (1993).

M. Ronaghi, S. Karamohamed, B. Pettersson, M. Uhlen, and P. Nyen, "Real–Time DNA Sequencing Using Detection of Pyrophosphate Release," *Anal. Biochem.*, 242:84–89 (1996).

J. Shultz, D. Leippe, K. Lewis, R. Lyke M. Nelson, and C. Reynolds., "Detection of Low Levels of Nucleic Acids by Enzymatic Conversion to Substrates for Luciferase", pp. 1–9 Poster presented Jul. 25–29, 1998 at a Protein Society meeting in San Diego, California.

Heid, et al., "Real Time Quantitative PCR", *Genome Research*, 6:986–994 (1996).

Nagano, et al., "Detection of Verotoxin–Producing *Escherichia coli* O157:H7 by Multiplex Polymerase Chain Reaction", *Microbiol. Immunol.*, 42(5), 372–376 (1998).

Sherlock, et al., "Assessment of diagnostic quantitative fluorescent multiplex polymerase chain reaction assays performed on single cells", *Ann. Hum. Genet.* 62:9–23 (1998).

Axton, et al., "A Single–Tube Multiplex System for the Simultaneous Detection of 10Common Cystic Fibrosis Mutations", *Human Mutation*, 5:260–262 (1995).

Poyser et al., "Multiplex genotyping for cystic fibrosis from filter paper blood spots", *Ann. Clin. Biochem.*, 35:611–615 (1998).

Caudai, et al., "Detection of HCV and GBV–C/HGV injection by multiplex PCR in plasma samples of transfused subjects", *J. Virol Meth.*, 70:79–83 (1998).

Songivilai, et al., "Improved Amplification System for Detection of Hepatitis C virus Genome that Simultaneously Differentiates Viral Genotype", *Southeast Asian J. Trop. Med. Public Health*, 27(2):237–243 (1996).

Oyofo, et al., "Detection of Enterotoxigenic *Escherichia coli*, Shigella and Campylobacter spp. by Multiplex PCR Assay", *J. Diarrhoeal Dis. Res.*, 14(3):207–210 (1996).

L. Ripoll, et al., "Multiplex PCR–mediated Site–directed Mutagenesis for One–step Determination of Factor V Leiden and G20210A Transition of the Prothrombin Gene", pp. 960–961 (1997).

L. Ripoll, et al., "Multiplex ASA PCR for a Simultaneous Determination of Factor V Leiden Gene, A—A20210 Prothrombin Gene and C—T 677 MTHFR Gene Mutations", *Thromb Haemost*, 79:1054–1055 (1998).

X. Xu et al., "Two Multiplex PCR–Based DNA Assays for the Thrombosis Risk Factors Prothrombin G20210A and Coagulation Factor V G1691A Polymorphisms", *Thrombosis Research* 93:265–269 (1999).

E. Gomez, et al., "Rapid Simultaneous Screening of Factor V Leiden and G20210A Prothrombin Variant by Multiplex Polymerase Chain Reaction of Whole Blood", *Blood* 91(6):2208–2211 (1998).

D. Linfert, et al., "Rapid Multiplex Analysis for the Factor V Leiden and Prothrombin G20210A Mutations Associated with Hereditary Thrombophilia", *Connecticut Medicine* 62(9):519–525 (1998).

P. Nyren, et al., *Anal. Biochem.*, 244:367–373 (1997).

S. Borman, "Developers of Novel DNA Sequencers Claim Major Performance Advances", *C&EN*, pp. 37–40 (Jul. 24, 1995).

P. Belgrader, et al., "PCR Detection of Bacteria in Seven Minutes", *Science Magazine* 284:449–450 (1999).

K. Hayashi *Genetic Analysis: Techniques and Applications* 9:73–79 (1992).

Newton et al., *Nucl. Acids Res.*, 17:2503–2516 (1989).

Wu et al., *Proc. Natl. Acad. Sci., USA*, 86:2757–2760 (1989).

T. Nikiforov, et al., *Nucl. Acids Res.*, 22:4167–4175 (1994).

C. Wittwer, et al., *Biotechniques*, 22:130–138 (1997).

P. Holland, et al., *Proc. Natl. Acad. Sci., USA*, 88:7276–7280 (1991).

R. Kramer, et al., *Nat. Biotechnol.*, 14:303–308 (1996).

J. Shultz, D. Leippe, K. Lewis and M. Nelson, "Non–radioactive Measurement of DNA Using Coupled Enzymatic Reactions", pp. 1–12 Presentation Mar. 16–20, 1998 at a Parenteral Drug Association meeting in San Francisco, California.

Seq. ID No. 1, "Blast Archaeal Gemone Sequences at Center of Marine Biotechnology" Online, May 21, 1999, Retrieved on 8/7/200 @ http://Combdna.umbi.umd.edu/bags.html. http://Comb5–156.umbi.umb.edu/cgi–bin/PfurGene-.PL?GeneID=894645&Dataset=Nayb&Geneidtxt–994645, Online! XP002144446, Retrieved from the internet on Aug. 7, 2000.

Giartosio, et al., "Thermal stability of hexameric and tetrameric nucleoside diphosphate kinases: Effect of subunit interaction", *J. Biol. Chem.*, 271(30):17845–17851 (1996).

Bi, W., et al., "Detection of known mutation by proof–reading PCR", *Nucleic Acid Research*, GB, 26(12):3073–3075 (1998).

Kawarabayashi, et al., "Complete Sequence and Gene Organization of the Genome of hyper–thermophilic Archaebacterium, *Pyrococcus horikoshii* OT3", *DNA Research*, 5:55–76 (1998).

SEQUENCE LISTING

<160> NUMBER OF SEQ ID NOS: 123

<210> SEQ ID NO 1
<211> LENGTH: 30
<212> TYPE: DNA
<213> ORGANISM: rabbit
<220> FEATURE:
<223> OTHER INFORMATION: probe to globin mRNA

<400> SEQUENCE: 1
agacttctcc tcactggaca gatgcaccat                30

<210> SEQ ID NO 2
<211> LENGTH: 26
<212> TYPE: DNA
<213> ORGANISM: rabbit
<220> FEATURE:
<223> OTHER INFORMATION: probe to globin mRNA

<400> SEQUENCE: 2
gggtccatgg gtagacaacc agcagc                26

<210> SEQ ID NO 3
<211> LENGTH: 65
<212> TYPE: DNA
<213> ORGANISM: Homo sapiens
<220> FEATURE:
<223> OTHER INFORMATION: target for human F actor V gene

<400> SEQUENCE: 3
ctaatctgta agagcagatc cctggacagg cgaggaatac agagggcagc a gacatcgaa      60 gagct                65

<210> SEQ ID NO 4
<211> LENGTH: 69
<212> TYPE: DNA
<213> ORGANISM: Homo sapiens
<220> FEATURE:
<223> OTHER INFORMATION: target for human F actor V gene

<400> SEQUENCE: 4
agctcttcga tgtctgctgc cctctgtatt cctcgcctgt ccaggatct g ctcttacag      60 attagagct                69

<210> SEQ ID NO 5
<211> LENGTH: 65
<212> TYPE: DNA
<213> ORGANISM: Homo sapiens
<220> FEATURE:
<223> OTHER INFORMATION: target for human Facto r V Leiden gene

<400> SEQUENCE: 5
ctaatctgta agagcagatc cctggacagg caaggaatac agagggcagc a gacatcgaa      60 gagct                65

<210> SEQ ID NO 6
<211> LENGTH: 69
<212> TYPE: DNA
<213> ORGANISM: Homo sapiens
<220> FEATURE:
<223> OTHER INFORMATION: target for human Facto r V Leiden gene

<400> SEQUENCE: 6

```
agctcttcga tgtctgctgc cctctgtatt ccttgcctgt ccagggatct g ctcttacag      60 attagagct                                                               69
```

<210> SEQ ID NO 7
<211> LENGTH: 22
<212> TYPE: DNA
<213> ORGANISM: Homo sapiens
<220> FEATURE:
<223> OTHER INFORMATION: probe for human Factor V gene

<400> SEQUENCE: 7

```
ctgctgccct ctgtattcct cg                                                22
```

<210> SEQ ID NO 8
<211> LENGTH: 22
<212> TYPE: DNA
<213> ORGANISM: Homo sapiens
<220> FEATURE:
<223> OTHER INFORMATION: probe for human Factor V gene

<400> SEQUENCE: 8

```
ctgctgccct ctgtattcct tg                                                22
```

<210> SEQ ID NO 9
<211> LENGTH: 22
<212> TYPE: DNA
<213> ORGANISM: Homo sapiens
<220> FEATURE:
<223> OTHER INFORMATION: probe for human Factor V gene

<400> SEQUENCE: 9

```
gacaaaatac ctgtattcct cg                                                22
```

<210> SEQ ID NO 10
<211> LENGTH: 22
<212> TYPE: DNA
<213> ORGANISM: Homo sapiens
<220> FEATURE:
<223> OTHER INFORMATION: probe for human Factor V gene

<400> SEQUENCE: 10

```
gacaaaatac ctgtattcct tg                                                22
```

<210> SEQ ID NO 11
<211> LENGTH: 20
<212> TYPE: DNA
<213> ORGANISM: Homo sapiens
<220> FEATURE:
<223> OTHER INFORMATION: probe for human cystic fibrosis gene

<400> SEQUENCE: 11

```
cattcacagt agcttaccca                                                   20
```

<210> SEQ ID NO 12
<211> LENGTH: 20
<212> TYPE: DNA
<213> ORGANISM: Homo sapiens
<220> FEATURE:
<223> OTHER INFORMATION: probe for human cystic fibrosis gene

<400> SEQUENCE: 12

```
gcagagtacc tgaaacagga                                                   20
```

<210> SEQ ID NO 13

```
<211> LENGTH: 19
<212> TYPE: DNA
<213> ORGANISM: Homo sapiens
<220> FEATURE:
<223> OTHER INFORMATION: probe for human cystic  fibrosis gene

<400> SEQUENCE: 13
catcatagga aacaccaag                                              19

<210> SEQ ID NO 14
<211> LENGTH: 19
<212> TYPE: DNA
<213> ORGANISM: Homo sapiens
<220> FEATURE:
<223> OTHER INFORMATION: probe for human cystic  fibrosis gene

<400> SEQUENCE: 14
catcatagga aacaccaat                                              19

<210> SEQ ID NO 15
<211> LENGTH: 24
<212> TYPE: DNA
<213> ORGANISM: Homo sapiens
<220> FEATURE:
<223> OTHER INFORMATION: probe for human cystic  fibrosis gene

<400> SEQUENCE: 15
ggcaccatta aagaaaatat catt                                        24

<210> SEQ ID NO 16
<211> LENGTH: 49
<212> TYPE: DNA
<213> ORGANISM: Homo sapiens
<220> FEATURE:
<223> OTHER INFORMATION: probe for human cystic  fibrosis gene

<400> SEQUENCE: 16
ctggcaccat taagaaaat atcattggtg tttcctatga tgaatatag              49

<210> SEQ ID NO 17
<211> LENGTH: 49
<212> TYPE: DNA
<213> ORGANISM: Homo sapiens
<220> FEATURE:
<223> OTHER INFORMATION: probe for human cystic  fibrosis gene

<400> SEQUENCE: 17
ctatattcat cataggaaac accaatgata ttttctttaa tggtgccag             49

<210> SEQ ID NO 18
<211> LENGTH: 52
<212> TYPE: DNA
<213> ORGANISM: Homo sapiens
<220> FEATURE:
<223> OTHER INFORMATION: target for wild-type c ystic fibrosis gene

<400> SEQUENCE: 18
ctggcaccat taagaaaat atcatctttg gtgtttccta tgatgaatat a g         52

<210> SEQ ID NO 19
<211> LENGTH: 52
<212> TYPE: DNA
<213> ORGANISM: Homo sapiens
<220> FEATURE:
<223> OTHER INFORMATION: target for mutant cyst ic fibrosis gene

<400> SEQUENCE: 19
```
ctatattcat cataggaaac accaaagatg atattttctt taatggtgcc a g    52

<210> SEQ ID NO 20
<211> LENGTH: 50
<212> TYPE: DNA
<213> ORGANISM: Homo sapiens
<220> FEATURE:
<223> OTHER INFORMATION: target for human proth rombin wild-type gene

<400> SEQUENCE: 20
tcccaataaa agtgactctc agcgagcctc aatgctccca gtgctattca    50

<210> SEQ ID NO 21
<211> LENGTH: 50
<212> TYPE: DNA
<213> ORGANISM: Homo sapiens
<220> FEATURE:
<223> OTHER INFORMATION: target for human proth rombin mutant gene

<400> SEQUENCE: 21
tcccaataaa agtgactctc agcaagcctc aatgctccca gtgctattca    50

<210> SEQ ID NO 22
<211> LENGTH: 16
<212> TYPE: DNA
<213> ORGANISM: Homo sapiens
<220> FEATURE:
<223> OTHER INFORMATION: probe for human prothr ombin gene

<400> SEQUENCE: 22
ggagcattga ggctcg    16

<210> SEQ ID NO 23
<211> LENGTH: 16
<212> TYPE: DNA
<213> ORGANISM: Homo sapiens
<220> FEATURE:
<223> OTHER INFORMATION: probe for human prothr ombin gene

<400> SEQUENCE: 23
ggagcattga ggcttg    16

<210> SEQ ID NO 24
<211> LENGTH: 23
<212> TYPE: DNA
<213> ORGANISM: Artificial Sequence
<220> FEATURE:
<223> OTHER INFORMATION: Description of Artificial  Sequence:probe for
      Rice genome (with phosphorothioate linkages)
<223> OTHER INFORMATION: phosphothioate linkages b etween first five
      bases

<400> SEQUENCE: 24
cccaacacct tacagaaatt agc    23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial  Sequence:probe for
      Rice genome

<400> SEQUENCE: 25
tctcaagaca caaataactg cag    23

```
<210> SEQ ID NO 26
<211> LENGTH: 15
<212> TYPE: DNA
<213> ORGANISM: Artificial Sequence
<220> FEATURE:
<223> OTHER INFORMATION: Description of Artificial  Sequence:probe for
      "G" allele of Rice

<400> SEQUENCE: 26
agaacatctg caagg                                                      15

<210> SEQ ID NO 27
<211> LENGTH: 15
<212> TYPE: DNA
<213> ORGANISM: Artificial Sequence
<220> FEATURE:
<223> OTHER INFORMATION: Description of Artificial  Sequence:probe for
      "T" allele of Rice

<400> SEQUENCE: 27
agaacatctg caagt                                                      15

<210> SEQ ID NO 28
<211> LENGTH: 58
<212> TYPE: DNA
<213> ORGANISM: Artificial Sequence
<220> FEATURE:
<223> OTHER INFORMATION: Description of Artificial  Sequence:THO locus with
      6x CATT repeat
<223> OTHER INFORMATION: THO locus with 6x C ATT repeat

<400> SEQUENCE: 28
ggtgaatgaa tgaatgaatg aatgaatgag ggaaataagg gaggaagagg c caatggg        58

<210> SEQ ID NO 29
<211> LENGTH: 62
<212> TYPE: DNA
<213> ORGANISM: Artificial Sequence
<220> FEATURE:
<223> OTHER INFORMATION: Description of Artificial  Sequence:THO locus
      with 7x CATT repeat
<223> OTHER INFORMATION: THO locus with 7x C ATT repeat

<400> SEQUENCE: 29
ggtgaatgaa tgaatgaatg aatgaatgaa tgagggaaat aagggaggaa g aggccaatg      60 gg                                                                    62

<210> SEQ ID NO 30
<211> LENGTH: 70
<212> TYPE: DNA
<213> ORGANISM: Artificial Sequence
<220> FEATURE:
<223> OTHER INFORMATION: Description of Artificial  Sequence:THO locus
      with 8x CATT repeat
<223> OTHER INFORMATION: THO locus with 8x C ATT repeat

<400> SEQUENCE: 30
ggtaggtgaa tgaatgaatg aatgaatgaa tgaatgaatg agggaaataa g ggaggaaga      60 ggccaatggg                                                            70

<210> SEQ ID NO 31
<211> LENGTH: 58
<212> TYPE: DNA
<213> ORGANISM: Artificial Sequence
<220> FEATURE:
<223> OTHER INFORMATION: Description of Artificial  Sequence:primer for
```

-continued

THO1 locus with 6x CATT repeats

<400> SEQUENCE: 31
cccattggcc tgttcctccc ttatttccct cattcattca ttcattcatt c attcacc        58

<210> SEQ ID NO 32
<211> LENGTH: 62
<212> TYPE: DNA
<213> ORGANISM: Artificial Sequence
<220> FEATURE:
<223> OTHER INFORMATION: Description of Artificial  Sequence:probe for
      THO1 locus with 7x CATT repeats

<400> SEQUENCE: 32
cccattggcc tgttcctccc ttatttccct cattcattca ttcattcatt c attcattca      60 cc                                                                      62

<210> SEQ ID NO 33
<211> LENGTH: 66
<212> TYPE: DNA
<213> ORGANISM: Artificial Sequence
<220> FEATURE:
<223> OTHER INFORMATION: Description of Artificial  Sequence:probe for
      THO1 locus with 8x CATT repeats

<400> SEQUENCE: 33
cccattggcc tgttcctccc ttatttccct cattcattca ttcattcatt c attcattca      60 ttcacc                                                                  66

<210> SEQ ID NO 34
<211> LENGTH: 54
<212> TYPE: DNA
<213> ORGANISM: Artificial Sequence
<220> FEATURE:
<223> OTHER INFORMATION: Description of Artificial  Sequence:probe for
      THO1 locus with 5x CATT repeats

<400> SEQUENCE: 34
cccattggcc tgttcctccc ttatttccct cattcattca ttcattcatt c acc            54

<210> SEQ ID NO 35
<211> LENGTH: 58
<212> TYPE: DNA
<213> ORGANISM: Artificial Sequence
<220> FEATURE:
<223> OTHER INFORMATION: Description of Artificial  Sequence:probe for
      THO1 locus with 6x CATT repeats

<400> SEQUENCE: 35
cccattggcc tgttcctccc ttatttccct cattcattca ttcattcatt c attcacc        58

<210> SEQ ID NO 36
<211> LENGTH: 62
<212> TYPE: DNA
<213> ORGANISM: Artificial Sequence
<220> FEATURE:
<223> OTHER INFORMATION: Description of Artificial  Sequence:probe for
      THO1 locus with 7x CATT repeats

<400> SEQUENCE: 36
cccattggcc tgttcctccc ttatttccct cattcattca ttcattcatt c attcattca      60 cc                                                                      62

<210> SEQ ID NO 37

```
<211> LENGTH: 66
<212> TYPE: DNA
<213> ORGANISM: Artificial Sequence
<220> FEATURE:
<223> OTHER INFORMATION: Description of Artificial  Sequence:probe for
      THO1 locus with 8x CATT repeats

<400> SEQUENCE: 37
cccattggcc tgttcctccc ttatttccct cattcattca ttcattcatt c attcattca    60 ttcacc                                                                66

<210> SEQ ID NO 38
<211> LENGTH: 70
<212> TYPE: DNA
<213> ORGANISM: Artificial Sequence
<220> FEATURE:
<223> OTHER INFORMATION: Description of Artificial  Sequence:probe for
      THO1 locus with 9x CATT repeats

<400> SEQUENCE: 38
cccattggcc tgttcctccc ttatttccct cattcattca ttcattcatt c attcattca    60 ttcattcacc                                                            70

<210> SEQ ID NO 39
<211> LENGTH: 58
<212> TYPE: DNA
<213> ORGANISM: Artificial Sequence
<220> FEATURE:
<223> OTHER INFORMATION: Description of Artificial  Sequence:probe for
      THO locus with 2 base pair mi smatch

<400> SEQUENCE: 39
cccattggcc tgttcctccc ttatttccct cattcattca ttcattcatt c attcagc      58

<210> SEQ ID NO 40
<211> LENGTH: 58
<212> TYPE: DNA
<213> ORGANISM: Artificial Sequence
<220> FEATURE:
<223> OTHER INFORMATION: Description of Artificial  Sequence:probe to
      THO locus with A to C mutatio n 3 from 3' terminus

<400> SEQUENCE: 40
cccattggcc tgttcctccc ttatttccct cattcattca ttcattcatt c attcccc      58

<210> SEQ ID NO 41
<211> LENGTH: 58
<212> TYPE: DNA
<213> ORGANISM: Artificial Sequence
<220> FEATURE:
<223> OTHER INFORMATION: Description of Artificial  Sequence:probe to
      THO locus with A to G mutatio n 3 from 3' terminus

<400> SEQUENCE: 41
cccattggcc tgttcctccc ttatttccct cattcattca ttcattcatt c attcgcc      58

<210> SEQ ID NO 42
<211> LENGTH: 58
<212> TYPE: DNA
<213> ORGANISM: Artificial Sequence
<220> FEATURE:
<223> OTHER INFORMATION: Description of Artificial  Sequence:probe to
      THO locus with additional base p air mismatches 4 from 3' terminus

<400> SEQUENCE: 42
cccattggcc tgttcctccc ttatttccct cattcattca ttcattcatt c attgacc      58
```

<210> SEQ ID NO 43
<211> LENGTH: 58
<212> TYPE: DNA
<213> ORGANISM: Artificial Sequence
<220> FEATURE:
<223> OTHER INFORMATION: Description of Artificial Sequence:probe for
      THO locus with additional base p air mismatches 4 from 3' terminus

<400> SEQUENCE: 43
cccattggcc tgttcctccc ttatttccct cattcattca ttcattcatt c attaacc        58

<210> SEQ ID NO 44
<211> LENGTH: 48
<212> TYPE: DNA
<213> ORGANISM: Artificial Sequence
<220> FEATURE:
<223> OTHER INFORMATION: Description of Artificial  Sequence:TPOX allele

<400> SEQUENCE: 44
ggcacttagg gaaccctcac tgaatgaatg aatgaatgaa tgaatatt                    48

<210> SEQ ID NO 45
<211> LENGTH: 52
<212> TYPE: DNA
<213> ORGANISM: Artificial Sequence
<220> FEATURE:
<223> OTHER INFORMATION: Description of Artificial  Sequence:TPOX allele

<400> SEQUENCE: 45
ggcacttagg gaaccctcac tgaatgaatg aatgaatgaa tgaatgaata t t               52

<210> SEQ ID NO 46
<211> LENGTH: 56
<212> TYPE: DNA
<213> ORGANISM: Artificial Sequence
<220> FEATURE:
<223> OTHER INFORMATION: Description of Artificial  Sequence:TPOX allele

<400> SEQUENCE: 46
ggcacttagg gaaccctcac tgaatgaatg aatgaatgaa tgaatgaatg a atatt          56

<210> SEQ ID NO 47
<211> LENGTH: 60
<212> TYPE: DNA
<213> ORGANISM: Artificial Sequence
<220> FEATURE:
<223> OTHER INFORMATION: Description of Artificial  Sequence:TPOX allele

<400> SEQUENCE: 47
ggcacttagg gaaccctcac tgaatgaatg aatgaatgaa tgaatgaatg a atgaatatt      60

<210> SEQ ID NO 48
<211> LENGTH: 63
<212> TYPE: DNA
<213> ORGANISM: Unknown
<220> FEATURE:
<223> OTHER INFORMATION: :

<400> SEQUENCE: 48
gcacttaggg aaccctcact gaatgaatga atgaatgaat gaatgaatga a tgaatgaat      60 att                                                                     63

<210> SEQ ID NO 49
<211> LENGTH: 68

```
<212> TYPE: DNA
<213> ORGANISM: Artificial Sequence
<220> FEATURE:
<223> OTHER INFORMATION: Description of Artificial  Sequence:TPOX allele

<400> SEQUENCE: 49
ggcacttagg gaaccctcac tgaatgaatg aatgaatgaa tgaatgaatg a atgaatgaa    60 tgaatatt                                                              68

<210> SEQ ID NO 50
<211> LENGTH: 72
<212> TYPE: DNA
<213> ORGANISM: Artificial Sequence
<220> FEATURE:
<223> OTHER INFORMATION: Description of Artificial  Sequence:TPOX allele

<400> SEQUENCE: 50
ggcacttagg gaaccctcac tgaatgaatg aatgaatgaa tgaatgaatg a atgaatgaa    60 tgaatgaata tt                                                         72

<210> SEQ ID NO 51
<211> LENGTH: 76
<212> TYPE: DNA
<213> ORGANISM: Artificial Sequence
<220> FEATURE:
<223> OTHER INFORMATION: Description of Artificial  Sequence:TPOX allele

<400> SEQUENCE: 51
ggcacttagg gaaccctcac tgaatgaatg aatgaatgaa tgaatgaatg a atgaatgaa    60 tgaatgaatg aatatt                                                     76

<210> SEQ ID NO 52
<211> LENGTH: 241
<212> TYPE: DNA
<213> ORGANISM: Homo sapiens
<220> FEATURE:
<223> OTHER INFORMATION: target allele 6 with 6 TGAA repeats

<400> SEQUENCE: 52
ggcacttagg gaaccctcac tgaatgaatg aatgaatgaa tgaatgtttg g gcaaataaa    60 cgctgacaag gacagaaggg cctagcggga agggaacagg agtaagacca g cgcacagcc   120 cgacttgtgt tcagaagacc tgggattgga cctgaggatt caattttgga t gaatctctt   180 aattaacctg tgtggttccc agttcctccc ctgagcgccc aggacagtag a gtcaacctc   240 a                                                                    241

<210> SEQ ID NO 53
<211> LENGTH: 245
<212> TYPE: DNA
<213> ORGANISM: Homo sapiens
<220> FEATURE:
<223> OTHER INFORMATION: target allele 7 with 7 TGAA repeats

<400> SEQUENCE: 53
ggcacttagg gaaccctcac tgaatgaatg aatgaatgaa tgaatgaatg t ttgggcaaa    60 taaacgctga caaggacaga agggcctagc gggaagggaa caggagtaag a ccagcgcac   120 agcccgactt gtgttcagaa gacctgggat tggacctgag gattcaattt t ggatgaatc   180 tcttaattaa cctgtgtggt tcccagttcc tccctgagc gccaggaca g tagagtcaa    240 cctca                                                                245
```

<210> SEQ ID NO 54
<211> LENGTH: 249
<212> TYPE: DNA
<213> ORGANISM: Homo sapiens
<220> FEATURE:
<223> OTHER INFORMATION: target allele 8 with 8 TGAA repeats

<400> SEQUENCE: 54

```
ggcacttagg gaaccctcac tgaatgaatg aatgaatgaa tgaatgaatg a atgtttggg      60
caaataaacg ctgacaagga cagaagggcc tagcgggaag ggaacaggag t aagaccagc     120
gcacagcccg acttgtgttc agaagacctg ggattggacc tgaggattca a ttttggatg    180
aatctcttaa ttaacctgtg tggttcccag ttcctcccct gagcgccag g acagtagag     240
tcaacctca                                                              249
```

<210> SEQ ID NO 55
<211> LENGTH: 253
<212> TYPE: DNA
<213> ORGANISM: Homo sapiens
<220> FEATURE:
<223> OTHER INFORMATION: target allele 9 with 9 TGAA repeats

<400> SEQUENCE: 55

```
ggcacttagg gaaccctcac tgaatgaatg aatgaatgaa tgaatgaatg a atgaatgtt     60
tgggcaaata aacgctgaca aggacagaag ggcctagcgg gaagggaaca g gagtaagac   120
cagcgcacag cccgacttgt gttcagaaga cctgggattg gacctgagga t tcaattttg   180
gatgaatctc ttaattaacc tgtgtggttc ccagttcctc ccctgagcgc c aggacagt    240
agagtcaacc tca                                                         253
```

<210> SEQ ID NO 56
<211> LENGTH: 257
<212> TYPE: DNA
<213> ORGANISM: Homo sapiens
<220> FEATURE:
<223> OTHER INFORMATION: target allele 10 with 10 TGAA repeats

<400> SEQUENCE: 56

```
ggcacttagg gaaccctcac tgaatgaatg aatgaatgaa tgaatgaatg a atgaatgaa     60
tgtttgggca aataaacgct gacaaggaca gaagggccta gcgggaaggg a acaggagta  120
agaccagcgc acagcccgac ttgtgttcag aagacctggg attggacctg a ggattcaat  180
tttggatgaa tctcttaatt aacctgtgtg gttcccagtt cctcccctga g cgcccagga  240
cagtagagtc aacctca                                                    257
```

<210> SEQ ID NO 57
<211> LENGTH: 261
<212> TYPE: DNA
<213> ORGANISM: Homo sapiens
<220> FEATURE:
<223> OTHER INFORMATION: target allele 11 with 11 TGAA repeats

<400> SEQUENCE: 57

```
ggcacttagg gaaccctcac tgaatgaatg aatgaatgaa tgaatgaatg a atgaatgaa     60
tgaatgtttg gcaaataaa cgctgacaag gacagaaggg cctagcggga a gggaacagg   120
agtaagacca gcgcacagcc cgacttgtgt tcagaagacc tgggattgga c ctgaggatt  180
caattttgga tgaatctctt aattaacctg tgtggttccc agttcctccc c tgagcgccc  240
aggacagtag agtcaacctc a                                              261
```

<210> SEQ ID NO 58
<211> LENGTH: 265
<212> TYPE: DNA
<213> ORGANISM: Homo sapiens
<220> FEATURE:
<223> OTHER INFORMATION: target allele 12 with 12 TGAA repeats

<400> SEQUENCE: 58

```
ggcacttagg gaaccctcac tgaatgaatg aatgaatgaa tgaatgaatg a atgaatgaa    60
tgaatgaatg tttgggcaaa taaacgctga caaggacaga agggcctagc g ggaagggaa   120
caggagtaag accagcgcac agcccgactt gtgttcagaa gacctgggat t ggacctgag   180
gattcaattt tggatgaatc tcttaattaa cctgtgtggt tcccagttcc t ccctgagc   240
gcccaggaca gtagagtcaa cctca                                         265
```

<210> SEQ ID NO 59
<211> LENGTH: 269
<212> TYPE: DNA
<213> ORGANISM: Homo sapiens
<220> FEATURE:
<223> OTHER INFORMATION: target allele 13 with 13 TGAA repeats

<400> SEQUENCE: 59

```
ggcacttagg gaaccctcac tgaatgaatg aatgaatgaa tgaatgaatg a atgaatgaa    60
tgaatgaatg aatgtttggg caaataaacg ctgacaagga cagaagggcc t agcgggaag  120
ggaacaggag taagaccagc gcacagcccg acttgtgttc agaagacctg g gattggacc  180
tgaggattca attttggatg aatctcttaa ttaacctgtg tggttcccag t tcctcccct  240
gagcgcccag gacagtagag tcaacctca                                     269
```

<210> SEQ ID NO 60
<211> LENGTH: 24
<212> TYPE: DNA
<213> ORGANISM: Homo sapiens
<220> FEATURE:
<223> OTHER INFORMATION: probe to E. coli

<400> SEQUENCE: 60

```
cactttatgc ttccggctcg tatg                                           24
```

<210> SEQ ID NO 61
<211> LENGTH: 26
<212> TYPE: DNA
<213> ORGANISM: Homo sapiens
<220> FEATURE:
<223> OTHER INFORMATION: probe to E. coli

<400> SEQUENCE: 61

```
gggataggtt acgttggtgt agatgg                                         26
```

<210> SEQ ID NO 62
<211> LENGTH: 20
<212> TYPE: DNA
<213> ORGANISM: Escherichia coli
<220> FEATURE:
<223> OTHER INFORMATION: common probe for E. coli lac

<400> SEQUENCE: 62

```
gttgggaagg gcgatcggtg                                                20
```

<210> SEQ ID NO 63

```
<211> LENGTH: 21
<212> TYPE: DNA
<213> ORGANISM: Artificial Sequence
<220> FEATURE:
<223> OTHER INFORMATION: Description of Artificial  Sequence:probe to E.
      coli lac

<400> SEQUENCE: 63
gggatgtgct gcaaggcgat t                                              21

<210> SEQ ID NO 64
<211> LENGTH: 20
<212> TYPE: DNA
<213> ORGANISM: Artificial Sequence
<220> FEATURE:
<223> OTHER INFORMATION: Description of Artificial  Sequence:probe for
      lac deletion in E. coli

<400> SEQUENCE: 64
ggattcactg gccgtcgtgg                                                20

<210> SEQ ID NO 65
<211> LENGTH: 65
<212> TYPE: DNA
<213> ORGANISM: Cytomegalovirus
<220> FEATURE:
<223> OTHER INFORMATION: target for cytomegaloviru s

<400> SEQUENCE: 65
cgtgtatgcc actttgatat tacacccatg aacgtgctca tcgacgtgaa c ccgcacaac   60 gagct                                                                65

<210> SEQ ID NO 66
<211> LENGTH: 65
<212> TYPE: DNA
<213> ORGANISM: Cytomegalovirus
<220> FEATURE:
<223> OTHER INFORMATION: target for cytomegaloviru s

<400> SEQUENCE: 66
cgttgtgcgg gttcacgtcg atgagcacgt tcatgggtgt aatatcaaag t ggcatacac   60 gagct                                                                65

<210> SEQ ID NO 67
<211> LENGTH: 65
<212> TYPE: DNA
<213> ORGANISM: Cytomegalovirus
<220> FEATURE:
<223> OTHER INFORMATION: target for cytomegaloviru s

<400> SEQUENCE: 67
cgtgtatgcc actttgatat tacacccgtg aacgtgctca tcgacgtgaa c ccgcacaac   60 gagct                                                                65

<210> SEQ ID NO 68
<211> LENGTH: 65
<212> TYPE: DNA
<213> ORGANISM: Cytomegalovirus
<220> FEATURE:
<223> OTHER INFORMATION: target for mutant cyto megalovirus

<400> SEQUENCE: 68
cgttgtgcgg gttcacgtcg atgagcacgt tcacgggtgt aatatcaaag t ggcatacac   60
```

```
gagct                                                              65

<210> SEQ ID NO 69
<211> LENGTH: 26
<212> TYPE: DNA
<213> ORGANISM: Cytomegalovirus
<220> FEATURE:
<223> OTHER INFORMATION: probe for cytomegalovirus

<400> SEQUENCE: 69
tcacacagga aacagctatg accatg                                       26

<210> SEQ ID NO 70
<211> LENGTH: 24
<212> TYPE: DNA
<213> ORGANISM: Artificial Sequence
<220> FEATURE:
<223> OTHER INFORMATION: Description of Artificial  Sequence:M13 forward
      probe
<223> OTHER INFORMATION: M13 forward probe

<400> SEQUENCE: 70
gcaaggcgat taagttgggt aacg                                         24

<210> SEQ ID NO 71
<211> LENGTH: 21
<212> TYPE: DNA
<213> ORGANISM: Cytomegalovirus
<220> FEATURE:
<223> OTHER INFORMATION: cytomegalovirus probe

<400> SEQUENCE: 71
cactttgata ttacacccat g                                            21

<210> SEQ ID NO 72
<211> LENGTH: 21
<212> TYPE: DNA
<213> ORGANISM: Cytomegalovirus
<220> FEATURE:
<223> OTHER INFORMATION: probe for cytomegalovirus

<400> SEQUENCE: 72
cactttgata ttacacccgt g                                            21

<210> SEQ ID NO 73
<211> LENGTH: 18
<212> TYPE: DNA
<213> ORGANISM: Homo sapiens
<220> FEATURE:
<223> OTHER INFORMATION: CAH oligo 6 for mut ation site 1

<400> SEQUENCE: 73
cggagcctcc acctcccg                                                18

<210> SEQ ID NO 74
<211> LENGTH: 18
<212> TYPE: DNA
<213> ORGANISM: Homo sapiens
<220> FEATURE:
<223> OTHER INFORMATION: CAH oligo 2 for mut ation site 2

<400> SEQUENCE: 74
caccctccag cccccagc                                                18

<210> SEQ ID NO 75
<211> LENGTH: 18
```

```
<212> TYPE: DNA
<213> ORGANISM: Homo sapiens
<220> FEATURE:
<223> OTHER INFORMATION: CAH oligo 1 for mut ation site 1

<400> SEQUENCE: 75
cggagcctcc acctcctg                                                 18

<210> SEQ ID NO 76
<211> LENGTH: 19
<212> TYPE: DNA
<213> ORGANISM: Homo sapiens
<220> FEATURE:
<223> OTHER INFORMATION: CAH oligo 3 for mut ation site 3

<400> SEQUENCE: 76
cctcacctgc agcatcaac                                                19

<210> SEQ ID NO 77
<211> LENGTH: 18
<212> TYPE: DNA
<213> ORGANISM: Homo sapiens
<220> FEATURE:
<223> OTHER INFORMATION: CAH oligo 7 for mut ation site 2

<400> SEQUENCE: 77
caccctccag cccccaac                                                 18

<210> SEQ ID NO 78
<211> LENGTH: 19
<212> TYPE: DNA
<213> ORGANISM: Homo sapiens
<220> FEATURE:
<223> OTHER INFORMATION: CAH oligo 8 for mut ation site 3

<400> SEQUENCE: 78
cctcacctgc agcatcatc                                                19

<210> SEQ ID NO 79
<211> LENGTH: 15
<212> TYPE: DNA
<213> ORGANISM: Homo sapiens
<220> FEATURE:
<223> OTHER INFORMATION: CAH oligo 4 for mut ation site 4

<400> SEQUENCE: 79
cctggaaggg cactt                                                    15

<210> SEQ ID NO 80
<211> LENGTH: 15
<212> TYPE: DNA
<213> ORGANISM: Homo sapiens
<220> FEATURE:
<223> OTHER INFORMATION: CAH oligo site 9 fo r mutation site 4

<400> SEQUENCE: 80
cctggaaggg cacgt                                                    15

<210> SEQ ID NO 81
<211> LENGTH: 18
<212> TYPE: DNA
<213> ORGANISM: Homo sapiens
<220> FEATURE:
<223> OTHER INFORMATION: CAH oligo 5 for mut ation site 5

<400> SEQUENCE: 81
```

```
gattcagcag cgactgta                                               18

<210> SEQ ID NO 82
<211> LENGTH: 18
<212> TYPE: DNA
<213> ORGANISM: Homo sapiens
<220> FEATURE:
<223> OTHER INFORMATION: CAH oligo 10 for mu tation site 5

<400> SEQUENCE: 82
gattcagcag cgactgca                                               18

<210> SEQ ID NO 83
<211> LENGTH: 18
<212> TYPE: DNA
<213> ORGANISM: Homo sapiens
<220> FEATURE:
<223> OTHER INFORMATION: CAH oligo 11 for mu tation site 6

<400> SEQUENCE: 83
cgaggtgctg cgcctgcg                                               18

<210> SEQ ID NO 84
<211> LENGTH: 18
<212> TYPE: DNA
<213> ORGANISM: Homo sapiens
<220> FEATURE:
<223> OTHER INFORMATION: CAH oligo 12 for mu tation site 6

<400> SEQUENCE: 84
cgaggtgctg cgcctgtg                                               18

<210> SEQ ID NO 85
<211> LENGTH: 20
<212> TYPE: DNA
<213> ORGANISM: Homo sapiens
<220> FEATURE:
<223> OTHER INFORMATION: CAH oligo 23 for mu tation site 7

<400> SEQUENCE: 85
gggatcacat cgtggagatg                                             20

<210> SEQ ID NO 86
<211> LENGTH: 20
<212> TYPE: DNA
<213> ORGANISM: Homo sapiens
<220> FEATURE:
<223> OTHER INFORMATION: CAH oligo 24 for mu tation site 7

<400> SEQUENCE: 86
gggatcacaa cgaggagaag                                             20

<210> SEQ ID NO 87
<211> LENGTH: 15
<212> TYPE: DNA
<213> ORGANISM: Artificial Sequence
<220> FEATURE:
<223> OTHER INFORMATION: Description of Artificial  Sequence:probe to
     Alu1 human gene

<400> SEQUENCE: 87 agacccatc tctaa                                                   15

<210> SEQ ID NO 88
<211> LENGTH: 17
<212> TYPE: DNA
```

```
<213> ORGANISM: Artificial Sequence
<220> FEATURE:
<223> OTHER INFORMATION: Description of Artificial  Sequence:probe to
      Alu2 human gene

<400> SEQUENCE: 88
gcctgggtga cagagca                                                    17

<210> SEQ ID NO 89
<211> LENGTH: 29
<212> TYPE: DNA
<213> ORGANISM: Artificial Sequence
<220> FEATURE:
<223> OTHER INFORMATION: Description of Artificial  Sequence:probe which
      forms hairpin when allowed to se lf-anneal

<400> SEQUENCE: 89
atgaacgtac gtcggatgag cacgttcat                                       29

<210> SEQ ID NO 90
<211> LENGTH: 29
<212> TYPE: DNA
<213> ORGANISM: Artificial Sequence
<220> FEATURE:
<223> OTHER INFORMATION: Description of Artificial  Sequence:probe which
      forms hairpin when allowed to se lf-anneal

<400> SEQUENCE: 90
gtgaacgtac gtcggatgag cacgttcat                                       29

<210> SEQ ID NO 91
<211> LENGTH: 29
<212> TYPE: DNA
<213> ORGANISM: Artificial Sequence
<220> FEATURE:
<223> OTHER INFORMATION: Description of Artificial  Sequence:probe which
      forms hairpin when allowed to se lf-anneal

<400> SEQUENCE: 91
ataaacgtac gtcggatgag cacgttcat                                       29

<210> SEQ ID NO 92
<211> LENGTH: 24
<212> TYPE: DNA
<213> ORGANISM: Artificial Sequence
<220> FEATURE:
<223> OTHER INFORMATION: Description of Artificial  Sequence:probe which
      forms hairpin when allowed to se lf-anneal

<400> SEQUENCE: 92
ataaacgtac gtcggatgag cacg                                            24

<210> SEQ ID NO 93
<211> LENGTH: 68
<212> TYPE: DNA
<213> ORGANISM: Artificial Sequence
<220> FEATURE:
<223> OTHER INFORMATION: Description of Artificial  Sequence:probe to
      Alu which forms a hairpin

<400> SEQUENCE: 93
ctccagcctc ggtgacagag caagaccctg tctcaaaaaa aaagcctcgg t gcagggtct    60 tgctctgt                                                              68

<210> SEQ ID NO 94
<211> LENGTH: 69
```

```
<212> TYPE: DNA
<213> ORGANISM: Artificial Sequence
<220> FEATURE:
<223> OTHER INFORMATION: Description of Artificial  Sequence:probe to
      Alu which forms a hairpin

<400> SEQUENCE: 94
ctccagcctg agcaacacag caagaccctg tctcaaaaca aaacgcctga g ccagggtct    60 tgctgtgtt                                                             69

<210> SEQ ID NO 95
<211> LENGTH: 34
<212> TYPE: DNA
<213> ORGANISM: Artificial Sequence
<220> FEATURE:
<223> OTHER INFORMATION: Description of Artificial  Sequence:probe
      for cytochrome B

<400> SEQUENCE: 95
aaactgcagc ccctcagaat gatatttgtc ctca                                 34

<210> SEQ ID NO 96
<211> LENGTH: 35
<212> TYPE: DNA
<213> ORGANISM: Artificial Sequence
<220> FEATURE:
<223> OTHER INFORMATION: Description of Artificial  Sequence:probe for
      cytochrome B

<400> SEQUENCE: 96
aaaaagcttc catccaacat ctcagcatga tgaaa                                35

<210> SEQ ID NO 97
<211> LENGTH: 12
<212> TYPE: DNA
<213> ORGANISM: Homo sapiens
<220> FEATURE:
<223> OTHER INFORMATION: Description of Artificial  Sequence:human
      cytochrome B
<223> OTHER INFORMATION: human cytochrome B

<400> SEQUENCE: 97
ccagacgcct ca                                                         12

<210> SEQ ID NO 98
<211> LENGTH: 12
<212> TYPE: DNA
<213> ORGANISM: Homo sapiens
<220> FEATURE:
<223> OTHER INFORMATION: human cytochrome B

<400> SEQUENCE: 98
accttcacgc ca                                                         12

<210> SEQ ID NO 99
<211> LENGTH: 11
<212> TYPE: DNA
<213> ORGANISM: Unknown
<220> FEATURE:
<223> OTHER INFORMATION: Description of Unknown Organism:common probe
      to cytochrome B

<400> SEQUENCE: 99
tgccgagacg t                                                          11

<210> SEQ ID NO 100
```

<211> LENGTH: 12
<212> TYPE: DNA
<213> ORGANISM: chicken
<220> FEATURE:
<223> OTHER INFORMATION: Description of Artificial  Sequence:chicken
      cytochrome B
<223> OTHER INFORMATION: chicken cytochrome B

<400> SEQUENCE: 100
gcagacacat cc                                                            12

<210> SEQ ID NO 101
<211> LENGTH: 12
<212> TYPE: DNA
<213> ORGANISM: chicken
<220> FEATURE:
<223> OTHER INFORMATION: chicken cytochrome B

<400> SEQUENCE: 101
ggaatctcca cg                                                            12

<210> SEQ ID NO 102
<211> LENGTH: 12
<212> TYPE: DNA
<213> ORGANISM: cow
<220> FEATURE:
<223> OTHER INFORMATION: bovine cytochrome B

<400> SEQUENCE: 102
acatacacgc aa                                                            12

<210> SEQ ID NO 103
<211> LENGTH: 12
<212> TYPE: DNA
<213> ORGANISM: dog
<220> FEATURE:
<223> OTHER INFORMATION: canine cytochrome B

<400> SEQUENCE: 103
atatgcacgc aa                                                            12

<210> SEQ ID NO 104
<211> LENGTH: 22
<212> TYPE: DNA
<213> ORGANISM: Artificial Sequence
<220> FEATURE:
<223> OTHER INFORMATION: Description of Artificial  Sequence:probe to
      prothrombin pcr productm, with phos phorothioate linkages between
      the first five bases on the 5 ' end

<400> SEQUENCE: 104
atagcactgg gagcattgag gc                                                 22

<210> SEQ ID NO 105
<211> LENGTH: 20
<212> TYPE: DNA
<213> ORGANISM: Homo sapiens
<220> FEATURE:
<223> OTHER INFORMATION: probe for human prothr ombin gene

<400> SEQUENCE: 105
gcacagacgg ctgttctctt                                                    20

<210> SEQ ID NO 106
<211> LENGTH: 13
<212> TYPE: DNA
<213> ORGANISM: Homo sapiens

```
<220> FEATURE:
<223> OTHER INFORMATION: probe for Prothrombin mutant

<400> SEQUENCE: 106
gtgattctca gca                                                          13

<210> SEQ ID NO 107
<211> LENGTH: 13
<212> TYPE: DNA
<213> ORGANISM: Homo sapiens
<220> FEATURE:
<223> OTHER INFORMATION: probe for wild-type Pr othrombin

<400> SEQUENCE: 107
gtgattctca gcg                                                          13

<210> SEQ ID NO 108
<211> LENGTH: 22
<212> TYPE: DNA
<213> ORGANISM: Artificial Sequence
<220> FEATURE:
<223> OTHER INFORMATION: Description of Artificial  Sequence:
      amplification primer

<400> SEQUENCE: 108
ggagctgcag atgctgacca ac                                                22

<210> SEQ ID NO 109
<211> LENGTH: 20
<212> TYPE: DNA
<213> ORGANISM: Artificial Sequence
<220> FEATURE:
<223> OTHER INFORMATION: Description of Artificial  Sequence:
      amplification primer

<400> SEQUENCE: 109
gctactggcc gctgaagggc                                                   20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial  Sequence:
      interrogation primer

<400> SEQUENCE: 110
gctgaccatc aataaggaag                                                   20

<210> SEQ ID NO 111
<211> LENGTH: 62
<212> TYPE: DNA
<213> ORGANISM: Artificial Sequence
<220> FEATURE:
<223> OTHER INFORMATION: Description of Artificial  Sequence:
      hypothetical example

<400> SEQUENCE: 111
cccggagaga cctccttaag gggccatatt atttcgtcga ttccagtgtt g gccaaacgg       60 at                                                                      62

<210> SEQ ID NO 112
<211> LENGTH: 41
<212> TYPE: DNA
<213> ORGANISM: Artificial Sequence
<220> FEATURE:
```

```
<223> OTHER INFORMATION: Description of Artificial  Sequence:
      hypothetical example

<400> SEQUENCE: 112
ggggccatat tatttcgccg tttggccaac actggaatcg a                              41

<210> SEQ ID NO 113
<211> LENGTH: 77
<212> TYPE: DNA
<213> ORGANISM: Artificial Sequence
<220> FEATURE:
<223> OTHER INFORMATION: Description of Artificial  Sequence:
      hypothetical example

<400> SEQUENCE: 113
gggcctctct ggaggaattc cccggtataa taaagcagct aaggtcacaa c cggtttgcc         60 gctttattat accgggg                                                         77

<210> SEQ ID NO 114
<211> LENGTH: 16
<212> TYPE: DNA
<213> ORGANISM: Artificial Sequence
<220> FEATURE:
<223> OTHER INFORMATION: Description of Artificial  Sequence:
      hypothetical example

<400> SEQUENCE: 114
cccggagaga cctcct                                                          16

<210> SEQ ID NO 115
<211> LENGTH: 77
<212> TYPE: DNA
<213> ORGANISM: Artificial Sequence
<220> FEATURE:
<223> OTHER INFORMATION: Description of Artificial  Sequence:
      hypothetical example

<400> SEQUENCE: 115
cccggagaga cctccttaag gggccatatt atttcgtcga ttccagtgtt g gccaaacgg         60 cgaaataata tggcccc                                                         77

<210> SEQ ID NO 116
<211> LENGTH: 35
<212> TYPE: DNA
<213> ORGANISM: Escherichia coli

<400> SEQUENCE: 116
ttacccaact taatcagggg gatgtgctgc aaggc                                     35

<210> SEQ ID NO 117
<211> LENGTH: 38
<212> TYPE: DNA
<213> ORGANISM: Escherichia coli

<400> SEQUENCE: 117
cgttacccaa cttaatcgcc ttgcagcaca tcccccctt                                 38

<210> SEQ ID NO 118
<211> LENGTH: 50
<212> TYPE: DNA
<213> ORGANISM: Escherichia coli

<400> SEQUENCE: 118
ttacccaact taatcagggg gatgtgctgc aaggcgatta agttgggtaa                     50
```

<210> SEQ ID NO 119
<211> LENGTH: 75
<212> TYPE: DNA
<213> ORGANISM: Campylobacter jejuni
<220> FEATURE:
<223> OTHER INFORMATION: probe to Campylobacter jejuni

<400> SEQUENCE: 119
cttgaagcat agttcttgtt tttaaactttt gtccatcttg agccgcttga g ttgagttgc    60 cttagtttta atagt                                                       75

<210> SEQ ID NO 120
<211> LENGTH: 70
<212> TYPE: DNA
<213> ORGANISM: Campylobacter jejuni
<220> FEATURE:
<223> OTHER INFORMATION: probe to Campylobacter jejuni

<400> SEQUENCE: 120
actattaaaa ctaaggcaac tcaagcggct caagatggac aaagtttaaa a acaagaact    60 atgcttcaag                                                             70

<210> SEQ ID NO 121
<211> LENGTH: 30
<212> TYPE: DNA
<213> ORGANISM: Campylobacter jejuni
<220> FEATURE:
<223> OTHER INFORMATION: probe to Campylobacter jejuni

<400> SEQUENCE: 121
agttcttgtt tttaaactttt gtccatcttg                                      30

<210> SEQ ID NO 122
<211> LENGTH: 30
<212> TYPE: DNA
<213> ORGANISM: Campylobacter jejuni
<220> FEATURE:
<223> OTHER INFORMATION: probe to Campylobacter jejuni

<400> SEQUENCE: 122
caagatggac aaagtttaaa aacaagaact                                       30

<210> SEQ ID NO 123
<211> LENGTH: 11
<212> TYPE: DNA
<213> ORGANISM: Human immunodeficiency virus
<220> FEATURE:
<223> OTHER INFORMATION: probe for 'colirep' sequence from E. coli

<400> SEQUENCE: 123
agtgactggg g                                                           11

DETECTION OF NUCLEIC ACID HYBRIDS

CROSS-REFERENCE TO RELATED APPLICATIONS

This application is a continuation-in-part of U.S. Ser. No. 09/358,972, filed on Jul. 21, 1999, (now U.S. Pat. No. 6,235,480) which is a continuation-in-part of U.S. Ser. No. 09/252,436, (now U.S. Pat. No. 6,159,693) filed on Feb. 18, 1999, which is a continuation-in-part of U.S. Ser. No. 09/042,287, filed Mar. 13, 1998, now U.S. Pat. No. 6,335, 162 all of which are incorporated herein by reference.

FIELD OF THE INVENTION

The invention relates to nucleic acid detection. More specifically, the invention relates to the detection of targeted, predetermined endogenous nucleic acid sequences in nucleic acid target hybrids, and the various applications of their detection.

BACKGROUND OF THE INVENTION

Methods to detect nucleic acids and to detect specific nucleic acids of interest provide a foundation upon which the large and rapidly growing field of molecular biology is built. There is constant need for alternative methods and products. The reasons for selecting one method over another are varied, and include a desire to avoid radioactive materials, the lack of a license to use a technique, the cost or availability of reagents or equipment, the desire to minimize the time spent or the number of steps, the accuracy or sensitivity for a certain application, the ease of analysis, or the ability to automate the process.

The detection of nucleic acids or specific nucleic acids is often a portion of a process rather than an end in itself. There are many applications of the detection of nucleic acids in the art, and new applications are always being developed. The ability to detect and quantify nucleic acids is useful in detecting microorganisms, viruses and biological molecules, and thus affects many fields, including human and veterinary medicine, food processing and environmental testing. Additionally, the detection and/or quantification of specific biomolecules from biological samples (e.g. tissue, sputum, urine, blood, semen, saliva) has applications in forensic science, such as the identification and exclusion of criminal suspects and paternity testing as well as medical diagnostics.

Some general methods to detect nucleic acids are not dependent upon a priori knowledge of the nucleic acid sequence. A nucleic acid detection method that is not sequence specific, but is RNA specific is described in U.S. Pat. No. 4,735,897, where RNA is depolymerized using a polynucleotide phosphorylase (PNP) in the presence of phosphate or using a ribonuclease. PNP stops depolymerizing when a double-stranded RNA segment is encountered, sometimes as the form of secondary structure of single-stranded RNA, as is common in ribosomal RNA, transfer RNA, viral RNA, and the message portion of mRNA. PNP depolymerization of the polyadenylated tail of mRNA in the presence of inorganic phosphate forms ADP. Alternatively, depolymerization using a ribonuclease forms AMP. The formed AMP is converted to ADP with myokinase, and ADP is converted into ATP by pyruvate kinase or creatine phosphokinase. Either the ATP or the byproduct from the organophosphate co-reactant (pyruvate or creatine) is detected as an indirect method of detecting mRNA.

In U.S. Pat. No. 4,735,897, ATP is detected by a luciferase detection system. In the presence of ATP and oxygen, luciferase catalyzes the oxidation of luciferin, producing light that can then be quantified using a luminometer. Additional products of the reaction are AMP, pyrophosphate and oxyluciferin.

Duplex DNA can be detected using intercalating dyes such as ethidium bromide. Such dyes are also used to detect hybrid formation.

Hybridization methods to detect nucleic acids are dependent upon knowledge of the nucleic acid sequence. Many known nucleic acid detection techniques depend upon specific nucleic acid hybridization in which an oligonucleotide probe is hybridized or annealed to nucleic acid in the sample or on a blot, and the hybridized probes are detected.

A traditional type of process for the detection of hybridized nucleic acid uses labeled nucleic acid probes to hybridize to a nucleic acid sample. For example, in a Southern blot technique, a nucleic acid sample is separated in an agarose gel based on size and affixed to a membrane, denatured, and exposed to the labeled nucleic acid probe under hybridizing conditions. If the labeled nucleic acid probe forms a hybrid with the nucleic acid on the blot, the label is bound to the membrane. Probes used in Southern blots have been labeled with radioactivity, fluorescent dyes, digoxygenin, horseradish peroxidase, alkaline phosphatase and acridinium esters.

Another type of process for the detection of hybridized nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe. PCR-based methods are of limited use for the detection of nucleic acid of unknown sequence.

In a PCR method, the amplified nucleic acid product may be detected in a number of ways, e.g. incorporation of a labeled nucleotide into the amplified strand by using labeled primers. Primers used in PCR have been labeled with radioactivity, fluorescent dyes, digoxygenin, horseradish peroxidase, alkaline phosphatase, acridinium esters, biotin and jack bean urease. PCR products made with unlabeled primers may be detected in other ways, such as electrophoretic gel separation followed by dye-based visualization.

Fluorescence techniques are also known for the detection of nucleic acid hybrids. U.S. Pat. No. 5,691,146 describes the use of fluorescent hybridization probes that are fluorescence-quenched unless they are hybridized to the target nucleic acid sequence. U.S. Pat. No. 5,723,591 describes fluorescent hybridization probes that are fluorescence-quenched until hybridized to the target nucleic acid sequence, or until the probe is digested. Such techniques provide information about hybridization, and are of varying degrees of usefulness for the determination of single base variances in sequences. Some fluorescence techniques involve digestion of a nucleic acid hybrid in a 5'→3' direction to release a fluorescent signal from proximity to a fluorescence quencher, for example, TaqMan® (Perkin Elmer; U.S. Pat. Nos. 5,691,146 and 5,876,930).

Enzymes having template-specific polymerase activity for which some 3'→5' depolymerization activity has been reported include E. coli DNA Polymerase (Deutscher and Kornberg, J. Biol. Chem., 244(11):3019–28 (1969)), T7

DNA Polymerase (Wong et al., *Biochemistry* 30:526–37 (1991); Tabor and Richardson, *J. Biol. Chem.* 265:8322–28 (1990)), *E. coli* RNA polymerase (Rozovskaya et al., *Biochem. J.* 224:645–50 (1994)), AMV and RLV reverse transcriptases (Srivastava and Modak, *J. Biol. Chem.* 255:2000–4 (1980)), and HIV reverse transcriptase (Zinnen et al., *J. Biol. Chem.* 269:24195–202 (1994)). A template-dependent polymerase for which 3' to 5' exonuclease activity has been reported on a mismatched end of a DNA hybrid is phage 29 DNA polymerase (de Vega, M. et al. *EMBO J.*, 15:1182–1192, 1996).

A variety of methodologies currently exist for detection of single nucleotide polymorphisms (SNPs) that are present in genomic DNA. SNPs are DNA point mutations or insertions/deletions that are present at measurable frequencies in the population. SNPs are the most common variations in the genome. SNPs occur at defined positions within genomes and can be used for gene mapping, defining population structure, and performing functional studies. SNPs are useful as markers because many known genetic diseases are caused by point mutations and insertions/deletions.

In rare cases where an SNP alters a fortuitous restriction enzyme recognition sequence, differential sensitivity of the amplified DNA to cleavage can be used for SNP detection. This technique requires that an appropriate restriction enzyme site be present or introduced in the appropriate sequence context for differential recognition by the restriction endonuclease. After amplification, the products are cleaved by the appropriate restriction endonuclease and products are analyzed by gel electrophoresis and subsequent staining. The throughput of analysis by this technique is limited because samples require processing, gel analysis, and significant interpretation of data before SNPs can be accurately determined.

Single strand conformational polymorphism (SSCP) is a second technique that can detect SNPs present in an amplified DNA segment (Hayashi, K. *Genetic Analysis: Techniques and Applications* 9:73–79, 1992). In this method, the double stranded amplified product is denatured and then both strands are allowed to reanneal during electrophoresis in non-denaturing polyacrylamide gels. The separated strands assume a specific folded conformation based on intramolecular base pairing. The electrophoretic properties of each strand are dependent on the folded conformation. The presence of single nucleotide changes in the sequence can cause a detectable change in the conformation and electrophoretic migration of an amplified sample relative to wild type samples, allowing SNPs to be identified. In addition to the limited throughput possible by gel-based techniques, the design and interpretation of SSCP based experiments can be difficult. Multiplex analysis of several samples in the same SSCP reaction is extremely challenging. The sensitivity required in mutation detection and analysis has led most investigators to use radioactively labeled PCR products for this technique.

In the amplification refractory mutation system (ARMS, also known as allele specific PCR or ASPCR), two amplification reactions are used to determine if a SNP is present in a DNA sample (Newton et al. *Nucl Acids Res* 17:2503, 1989; Wu et al. *PNAS* 86:2757, 1989). Both amplification reactions contain a common primer for the target of interest. The first reaction contains a second primer specific for the wild type product which will give rise to a PCR product if the wild type gene is present in the sample. The second PCR reaction contains a primer that has a single nucleotide change at or near the 3' end that represents the base change that is present in the mutated form of the DNA. The second primer, in conjunction with the common primer, will only function in PCR if genomic DNA that contains the mutated form of genomic DNA is present. This technique requires duplicate amplification reactions to be performed and analyzed by gel electrophoresis to ascertain if a mutated form of a gene is present. In addition, the data must be manually interpreted.

Single base extension is a technique that allows the detection of SNPs by hybridizing a single strand DNA probe to a captured DNA target (Nikiforov, T. et al. *Nucl Acids Res* 22:4167–4175). Once hybridized, the single strand probe is extended by a single base with labeled dideoxynucleotides. The labeled, extended products are then detected using calorimetric or fluorescent methodologies.

A variety of technologies related to real-time (or kinetic) PCR have been adapted to perform SNP detection. Many of these systems are platform based, and require specialized equipment, complicated primer design, and expensive supporting materials for SNP detection. In contrast, the process of this invention has been designed as a modular technology that can use a variety of instruments that are suited to the throughput needs of the end-user. In addition, the coupling of luciferase detection sensitivity with standard oligonucleotide chemistry and well-established enzymology provides a flexible and open system architecture. Alternative analytical detection methods, such as mass spectroscopy, HPLC, and fluorescence detection methods can also be used in the process of this invention, providing additional assay flexibility.

SNP detection using real-time amplification relies on the ability to detect amplified segments of nucleic acid as they are during the amplification reaction. Three basic real-time SNP detection methodologies exist: (i) increased fluorescence of double strand DNA specific dye binding, (ii) decreased quenching of fluorescence during amplification, and (iii) increased fluorescence energy transfer during amplification (Wittwer, C. et al. *Biotechniques* 22:130–138, 1997). All of these techniques are non-gel based and each strategy will be briefly discussed.

A variety of dyes are known to exhibit increased fluorescence in response to binding double stranded DNA. This property is utilized in conjunction with the amplification refractory mutation system described above to detect the presence of SNP. Production of wild type or mutation containing PCR products are continuously monitored by the increased fluorescence of dyes such as ethidium bromide or SYBER Green as they bind to the accumulating PCR product. Note that dye binding is not selective for the sequence of the PCR product, and high non-specific background can give rise to false signals with this technique.

A second SNP detection technology for real time PCR, known generally as exonuclease primers (TaqMan® probes), utilizes the 5' exonuclease activity of thermostable polymerases such as Taq to cleave dual-labeled probes present in the amplification reaction (Wittwer, C. et al. *Biotechniques* 22:130–138, 1997; Holland, P et al *PNAS* 88:7276–7280, 1991). While complementary to the PCR product, the probes used in this assay are distinct from the PCR primer and are dually-labeled with both a molecule capable of fluorescence and a molecule capable of quenching fluorescence. When the probes are intact, intramolecular quenching of the fluorescent signal within the DNA probe leads to little signal. When the fluorescent molecule is liberated by the exonuclease activity of Taq during amplification, the quenching is greatly reduced leading to increased fluorescent signal.

An additional form of real-time PCR also capitalizes on the intramolecular quenching of a fluorescent molecule by use of a tethered quenching moiety. The molecular beacon technology utilizes hairpin-shaped molecules with an internally-quenched fluorophore whose fluorescence is restored by binding to a DNA target of interest (Kramer, R. et al. *Nat. Biotechnol.* 14:303–308, 1996). Increased binding of the molecular beacon probe to the accumulating PCR product can be used to specifically detect SNPs present in genomic DNA.

A final general fluorescent detection strategy used for detection of SNPs in real time utilizes synthetic DNA segments known as hybridization probes in conjunction with a process known as fluorescence resonance energy transfer (FRET) (Wittwer, C. et al. *Biotechniques* 22:130–138, 1997; Bernard, P. et al. *Am. J. Pathol.* 153:1055–1061, 1998). This technique relies on the independent binding of labeled DNA probes on the target sequence. The close approximation of the two probes on the target sequence increases resonance energy transfer from one probe to the other, leading to a unique fluorescence signal. Mismatches caused by SNPs that disrupt the binding of either of the probes can be used to detect mutant sequences present in a DNA sample.

A number of gene-level defects have been implicated in the etiology of human disease. Researchers have used several techniques to detect these genetic mutations for prevention or diagnosis of these disease states. Van Essen et al. [*J. Med. Genet.* 34:805–12 (1997)] report that 65–70% of Duchenne and Becker muscular dystrophy patients exhibit rearrangements in the dystrophin gene, as detected by Southern blotting or multiplex PCR. Microlesions in these two forms of muscular dystrophy are typically detected using single strand conformational analysis, heteroduplex analysis, and the protein truncation test.

Calvano et al. [*Clin. Genet.* 52:17–22 (1997)] report the use of PCR fragments used as fluorescent probes for the detection of female carriers of Duchenne and Becker muscular dystrophy. Jongpiputvanich et al. [*J. Med. Assoc. Thai.* 79(Supp. 1):S15–21 (1996)] report the use of multiplex PCR and microsatellite or STR analysis for diagnosis and carrier detection in a Duchenne muscular dystrophy family. Pastore et al. [*Mol. Cell. Probes* 10:129–37 (1996)] developed a quantitative PCR analysis method using radiolabeled PCR products for the detection of macrodeletion carriers of Duchenne and Becker muscular dystrophy. Katayama et al. [*Fetal Diagn. Ther.* 9:379–84 (1994)] studied the efficacy of PCR for prenatal diagnosis of Duchenne muscular dystrophy. These workers used PCR-restriction fragment length polymorphism analysis, multiplex PCR, and dinucleotide repeat polymorphism analysis to diagnose affected male fetuses and detect carrier female fetuses in the first trimester.

A polymorphism in the human gap junctional protein connexin 37 was studied as a prognostic marker for atherosclerosis. Boerma et al. *Intern. Med.* 246:211–218 (1999). A restriction fragment length polymorphism in the proline variant of the connexin 37 gene was used to show that this allele was over-represented in patients with atherosclerotic plaques. Shohet et al. [*Arterioscler. Thromb. Vasc. Biol.* 19:1975–78 (1999)] report the frequency of the −514T allele of hepatic lipase in white men with coronary artery disease. In this population, postheparin plasma hepatic lipase activity was 15 to 20% lower in heterozygotes and 30% lower in homozygotes compared to controls. A novel missense mutation in the presenilin-1 gene was detected in a family with presenile familial Alzheimer's disease (FAD). Sugiyama et al. *Mutat.* 14:90 (1999). These workers report that over 50 such missense mutations in the presenilin-1 gene have been reported in families with FAD. Sensitive, reliable assays for these and other gene-level defects have several potential diagnostic and preventative applications in human and animal health care.

In summary, there is a need for alternative methods for the detection of nucleic acid hybrids. There is a great demand for such methods to determine the presence or absence of nucleic acid sequences that differ slightly from sequences that might otherwise be present. There is a great demand for methods to determine the presence or absence of sequences unique to a particular species in a sample. There is also a great demand for methods that are more highly sensitive than the known methods, highly reproducible and automatable.

It would be beneficial if another method were available for detecting the presence of a sought-after, predetermined target nucleotide sequence or allelic variant. It would also be beneficial if such a method were operable using a sample size of the microgram to picogram scale. It would further be beneficial if such a detection method were capable of providing multiple analyses in a single assay (multiplex assays). The disclosure that follows provides such methods.

BRIEF SUMMARY OF THE INVENTION

A method of this invention is used to determine the presence or absence of a predetermined (known) endogenous nucleic acid target sequence in a nucleic acid sample. Such a method utilizes an enzyme that can depolymerize the 3'-terminus of an oligonucleotide probe hybridized to a nucleic acid target sequence to release one or more identifier nucleotides whose presence can then be determined.

One embodiment of the invention contemplates a method for determining the presence or absence of a predetermined endogenous nucleic acid target sequence in a nucleic acid sample. Thus, the presence or absence of at least one predetermined endogenous nucleic acid target sequence is sought to be determined. More than one such predetermined endogenous target sequence can also be present in the sample being assayed, and the presence or absence of more than one predetermined endogenous nucleic acid target sequence can be determined. The embodiment comprises the following steps.

A treated sample is provided that may contain a predetermined endogenous nucleic acid target sequence hybridized with a nucleic acid probe that includes an identifier nucleotide in the 3'-terminal region. The treated sample is admixed with a depolymerizing amount of an enzyme whose activity is to release one or more nucleotides from the 3'-terminus of a hybridized nucleic acid probe to form a treated reaction mixture. The treated reaction mixture is maintained under depolymerizing conditions for a time period sufficient to permit the enzyme to depolymerize hybridized nucleic acid and release identifier nucleotides therefrom.

An analytical output is obtained by analyzing for the presence or absence of released identifier nucleotides. The analytical output indicates the presence or absence of the nucleotide at the predetermined region, and, thereby, the presence or absence of a first nucleic acid target. The analytical output is obtained by various techniques as discussed herein.

It is contemplated that an analytical output of the methods of the invention can be obtained in a variety of ways. The analytical output can be ascertained by luminescence spectroscopy. In some preferred embodiments, analysis for released 3'-terminal region indicator nucleotides comprises the detection of ATP, either by a luciferase detection system (luminescence spectroscopy) or an NADH detection system (absorbance spectroscopy). In particularly preferred embodiments where greater sensitivity is desired, ATP molecules are formed by a phosphate transferring step, for example using an enzyme such as NDPK in the presence of ADP, from the nucleoside triphosphates produced by the depolymerizing step. In some embodiments the ATP is amplified to form a plurality of ATP molecules. In the ATP detection embodiments, typically the enzyme (NDPK) for converting nucleotides and added ADP into ATP is present in the depolymerization reaction with the depolymerizing enzyme, and when they are present together, they are denoted as a "one pot" method.

In an alternative embodiment, the analytical output is obtained by fluorescence spectroscopy. Use of a wide variety of fluorescence detection methods is contemplated. In one exemplary contemplated method, an identifier nucleotide includes a fluorescent label. An identifier nucleotide can be fluorescently labeled prior to, or after, release of the identifier nucleotide. It is also contemplated that other than a released identifier nucleotide contains a fluorescent tag. In such an embodiment, the release of nucleotides in a process of the invention is ascertained by a determination of a difference in the length of the polynucleotide probe, for example by capillary electrophoresis imaged by a fluorescent tag at the 5' terminus of the probe or in a region other than the 3' terminal region.

In an alternative embodiment the analytical output is obtained by mass spectrometry. It is preferred here that an identifier nucleotide be a nucleotide analog or a labeled nucleotide and have a molecular mass that is different from the mass of a usual form of that nucleotide, although a difference in mass is not required. It is also noted that with a fluorescently labeled identifier nucleotide, the analytical output can also be obtained by mass spectrometry. It is also contemplated that the analysis of released nucleotide be conducted by ascertaining the difference in mass of the probe after a depolymerization step of a process of the invention.

In another alternative embodiment, the analytical output is obtained by absorbance spectroscopy. Such analysis monitors the absorbance of light in the ultraviolet and visible regions of the spectrum to determine the presence of absorbing species. In one aspect of such a process, released nucleotides are separated from hybridized nucleic acid and other polynucleotides by chromatography (e.g. HPLC or GC) or electrophoresis (e.g. PAGE or capillary electrophoresis). Either the released identifier nucleotide or the remainder of the probe can be analyzed for to ascertain the release of the identifier nucleotide in a process of the invention. In another aspect of such a process a label may be incorporated in the analyzed nucleic acid.

In a contemplated embodiment, a sample to be assayed is admixed with one or more nucleic acid probes under hybridizing conditions to form a hybridization composition. The 3'-terminal region of the nucleic acid probe hybridizes with partial or total complementarity to the nucleic acid target sequence when that sequence is present in the sample. The 3'-terminal region of the nucleic acid probe includes an identifier nucleotide. The hybridization composition is maintained under hybridizing conditions for a time period sufficient to form a treated sample that may contain said predetermined nucleic acid target sequence hybridized with a nucleic acid probe. The treated sample is admixed with a depolymerizing amount of an enzyme whose activity is to release one or more nucleotides from the 3'-terminus of a hybridized nucleic acid probe to form a treated reaction mixture. The treated reaction mixture is maintained under depolymerizing conditions for a time period sufficient to permit the enzyme to depolymerize hybridized nucleic acid and release identifier nucleotides therefrom. The presence of released identifier nucleotides is analyzed to obtain an analytical output, the analytical output indicating the presence or absence of the nucleic acid target sequence. The analytical output may be obtained by various techniques as discussed above.

One method of the invention contemplates interrogating the presence or absence of a specific base in a nucleic acid target sequence in a sample to be assayed, and comprises the following steps.

A hybridization composition is formed by admixing a sample to be assayed with one or more nucleic acid probes under hybridizing conditions. The sample to be assayed may contain a nucleic acid target sequence to be interrogated. The nucleic acid target comprises at least one base whose presence or absence is to be identified. The hybridization composition includes at least one nucleic acid probe that is substantially complementary to the nucleic acid target sequence and comprises at least one predetermined nucleotide at an interrogation position, and an identifier nucleotide in the 3'-terminal region.

A treated sample is formed by maintaining the hybridization composition under hybridizing conditions for a time period sufficient for base pairing to occur when a probe nucleotide at an interrogation position is aligned with a base to be identified in the target sequence. A treated reaction mixture is formed by admixing the treated sample with an enzyme whose activity is to release one or more identifier nucleotides from the 3'-terminus of a hybridized nucleic acid probe to depolymerize the hybrid. The treated reaction mixture is maintained under depolymerizing conditions for a time period sufficient to permit the enzyme to depolymerize the hybridized nucleic acid and release an identifier nucleotide.

An analytical output is obtained by analyzing for the presence or absence of released identifier nucleotides. The analytical output indicates the presence or absence of the specific base or bases to be identified. The analytical output is obtained by various techniques, as discussed herein. Preferably, an identifier nucleotide is at the interrogation position.

In one aspect of a method of the invention, the nucleic acid target sequence is selected from the group consisting of deoxyribonucleic acid and ribonucleic acid.

A method that identifies the particular base present at an interrogation position, optionally comprises a first probe, a second probe, a third probe, and a fourth probe. An interrogation position of the first probe comprises a nucleic acid residue that is a deoxyadenosine or adenosine residue. An interrogation position of the second probe comprises a nucleic acid residue that is a deoxythymidine or uridine residue. An interrogation position of the third probe comprises a nucleic acid residue that is a deoxyguanosine or guanosine residue. An interrogation position of the fourth nucleic acid probe comprises a nucleic acid residue that is a deoxycytosine or cytosine residue.

In another aspect of the invention, the sample containing a plurality of target nucleic acid sequences is admixed with a plurality of the nucleic acid probes. Several analytical outputs can be obtained from such multiplexed assays. In a first embodiment, the analytical output obtained when at least one nucleic acid probes hybridizes with partial complementarity to one target nucleic acid sequence is greater than the analytical output when all of the nucleic acid probes hybridize with total complementarity to their respective nucleic acid target sequences. In a second embodiment, the analytical output obtained when at least one nucleic acid probe hybridizes with partial complementarity to one target nucleic acid sequence is less than the analytical output when all of the nucleic acid probes hybridize with total complementarity to their respective nucleic acid target sequences. In a third embodiment, the analytical output obtained when at least one nucleic acid probe hybridizes with total complementarity to one nucleic acid target sequence is greater than the analytical output when all of the nucleic acid probes hybridize with partial complementarity to their respective nucleic acid target sequences. In a fourth embodiment, the analytical output obtained when at least one nucleic acid probe hybridizes with total complementarity to one target nucleic acid sequence is less than the analytical output when all of the nucleic acid probes hybridize with partial complementarity to their respective nucleic acid target sequences. The depolymerizing enzymes are as described herein.

Yet another embodiment of the invention contemplates a method for determining the presence or absence of a first endogenous nucleic acid target in a nucleic acid sample that may contain that target or may contain a substantially identical second target. For example, the second target may have a base substitution, deletion or addition relative to the first nucleic acid target. This embodiment comprises the following steps.

A sample to be assayed is admixed with one or more nucleic acid probes under hybridizing conditions to form a hybridization composition. The first and second nucleic acid targets each comprise a region of sequence identity except for at least a single nucleotide at a predetermined position that differs between the targets. The nucleic acid probe is substantially complementary to the nucleic acid target region of sequence identity and comprises at least one nucleotide at an interrogation position. An interrogation position of the probe is aligned with the predetermined position of a target when a target and probe are hybridized. The probe also includes an identifier nucleotide in the 3'-terminal region.

The hybridization composition is maintained under hybridizing conditions for a time period sufficient to form a treated sample wherein the nucleotide at the interrogation position of the probe is aligned with the nucleotide at the predetermined position in the region of identity of the target.

A treated reaction mixture is formed by admixing the treated sample with a depolymerizing amount of an enzyme whose activity is to release one or more nucleotides from the 3'-terminus of a hybridized nucleic acid probe. The reaction mixture is maintained under depolymerization conditions for a time period sufficient to permit the enzyme to depolymerize the hybridized nucleic acid and release the identifier nucleotide.

An analytical output is obtained by analyzing for the presence or absence of released identifier nucleotides. The analytical output indicates the presence or absence of the nucleotide at the predetermined region, and; thereby, the presence or absence of a first nucleic acid target.

One aspect of the above method is comprised of a first probe and a second probe. The first probe comprises a nucleotide at an interrogation position that is complementary to a first nucleic acid target at a predetermined position. The second probe comprises a nucleotide at an interrogation position that is complementary to a second nucleic acid target at a predetermined position.

In one aspect of a process of the invention, the depolymerizing enzyme, whose activity is to release nucleotides, is a template-dependent polymerase, whose activity is to depolymerize hybridized nucleic acid whose 3'-terminal nucleotide is matched, in the 3'→5' direction in the presence of pyrophosphate ions to release one or more nucleotides. Thus, the enzyme's activity is to depolymerize hybridized nucleic acid to release nucleotides under depolymerizing conditions. Preferably, this enzyme depolymerizes hybridized nucleic acids whose bases in the 3'-terminal region of the probe are matched with total complementarity to the corresponding bases of the nucleic acid target. The enzyme will continue to release properly paired bases from the 3'-terminus and will stop when the enzyme arrives at a base that is mismatched.

In an alternative aspect of the process (method), the depolymerizing enzyme, whose activity is to release nucleotides, exhibits a 3'→5' exonuclease activity in which hybridized nucleic acids having one or more mismatched bases at the 3'-terminus of the hybridized probe are depolymerized. Thus, the enzyme's activity is to depolymerize hybridized nucleic acid to release nucleotides under depolymerizing conditions. In this embodiment, the hybrid may be separated from the free probe prior to enzyme treatment. In some embodiments, an excess of target may be used so that the concentration of free probe in the enzyme reaction is extremely low.

In still another alternative aspect of a process of the invention, the depolymerizing enzyme exhibits a 3' to 5' exonuclease activity on a double-stranded DNA substrate having one or more matched bases at the 3' terminus of the hybrid. The enzyme's activity is to depolymerize hybridized nucleic acid to release nucleotides containing a 5' phosphate under depolymerizing conditions.

A further embodiment of the invention, such as is used for Single Tandem Repeat (STR) detection, contemplates a method for determining the number of known sequence repeats that are present in an endogenous nucleic acid target sequence in a nucleic acid sample. A method for determining the number of known sequence repeats comprises the following steps. A plurality of separate treated samples is provided. Each treated sample contains a nucleic acid target sequence hybridized with a nucleic acid probe. The nucleic acid target sequence contains a plurality of known sequence repeats and a downstream non-repeated region. Each nucleic acid probe contains a different number of complementary repeats of the known sequence, an identifier nucleotide in the 3'-terminal region and a 5'-terminal locker sequence. The 5'-terminal locker sequence is complementary to the downstream non-repeated region of the target and comprises 1 to about 20 nucleotides, preferably 5 to 20 nucleotides, most preferably 10 to 20 nucleotides. The various probes represent complements to possible alleles of the target nucleic acid. A treated depolymerization reaction mixture is formed by admixing each treated sample with a depolymerizing amount of an enzyme whose activity is to release one or more nucleotides from the 3'-terminus of a hybridized nucleic acid probe. The treated depolymerization reaction mixture is maintained under depolymerizing conditions for a time period sufficient to permit the enzyme to depolymerize the hybridized nucleic acid probe and release an identifier nucleotide. The samples are analyzed for the presence or absence of released identifier nucleotide to obtain an analytical output. The analytical output from the sample whose probe contained the same number of sequence repeats as present in the target nucleic acid is indicative of and determines the number of sequence repeats present in the nucleic acid target.

In one aspect of the method, the nucleic acid sample contains two nucleic acid targets representing alleles at a locus, and is homozygous with respect to the number of known sequence repeats of the two alleles. In an alternative method of the invention, the nucleic acid sample is heterozygous with respect to the two alleles at the locus. In another method of the invention, an identifier nucleotide is a nucleotide that is part of the region containing a repeated sequence. In an alternative method of the invention, an identifier nucleotide of the probe sequence is part of the region containing a non-repeating sequence that is complementary to that located in the target nucleic acid 5' to the repeated known sequence. In this latter aspect of the method, the identifier nucleotide is present in a sequence containing 1 to about 20 nucleic acids that is complementary to a non-repeating sequence of the target nucleic acid located in the probe 3' to the known sequence repeats. The repeated known sequence present in a nucleic acid target sequence typically has a length of 2 to about 24 bases per repeat.

A further embodiment of the invention contemplates a method using thermostable DNA polymerase as a depolymerizing enzyme for determining the presence or absence of at least one predetermined endogenous nucleic acid target sequence in a nucleic acid sample, and comprises the following steps.

A treated sample is provided that may contain a predetermined endogenous nucleic acid target sequence hybridized to a nucleic acid probe whose 3'-terminal region is complementary to the predetermined nucleic acid target sequence and includes an identifier nucleotide in the 3'-terminal region. A treated depolymerization reaction mixture is formed by admixing a treated sample with a depolymerizing amount of a enzyme whose activity is to release an identifier nucleotide from the 3'-terminus of a hybridized nucleic acid probe. In a preferred one-pot embodiment, the depolymerizing enzyme is thermostable and more preferably, the treated reaction mixture also contains (i) adenosine 5' diphosphate, (ii) pyrophosphate, and (iii) a thermostable nucleoside diphosphate kinase (NDPK).

The treated sample is maintained under depolymerizing conditions at a temperature of about 4° C. to about 90° C., more preferably at a temperature of about 20° C. to about 90° C., and most preferably at a temperature of about 25° C. to about 80° C., for a time period sufficient to permit the depolymerizing enzyme to depolymerize the hybridized nucleic acid probe and release an identifier nucleotide as a nucleoside triphosphate. In preferred one-pot reactions, the time period is also sufficient to permit NDPK enzyme to transfer a phosphate from the released nucleoside triphosphate to added ADP, thereby forming ATP. The presence or absence of a nucleic acid target sequence is determined from the analytical output obtained using ATP. In a preferred method of the invention, analytical output is obtained by luminescence spectrometry.

In another aspect of the thermostable enzyme one-pot method for determining the presence or absence of a predetermined endogenous nucleic acid target sequence in a nucleic acid sample, the treated sample is formed by the following further steps. A hybridization composition is formed by admixing the sample to be assayed with one or more nucleic acid probes under hybridizing conditions. The 3'-terminal region of the nucleic acid probe (i) hybridizes with partial or total complementarity to a nucleic acid target sequence when that sequence is present in the sample, and (ii) includes an identifier nucleotide. A treated sample is formed by maintaining the hybridization composition under hybridizing conditions for a time period sufficient for the predetermined endogenous nucleic acid target sequence to hybridize with the nucleic acid probe.

Preferably, the depolymerizing enzyme is from a group of thermophilic DNA polymerases comprising Tne triple mutant DNA polymerase, Tne DNA polymerase, Taq DNA polymerase, Ath DNA polymerase, Tvu DNA polymerase, Bst DNA polymerase, and Tth DNA polymerase. The Tne triple mutant DNA polymerase is a preferred thermophilic enzyme and is discussed in greater detail hereinafter. In another aspect of the method, the NDPK is that encoded for by the thermophilic bacteria *Pyrococcus furiosis* (Pfu).

A still further method of the invention contemplates determining whether the presence or absence of a nucleic acid target sequence in a nucleic acid sample results from a locus that is homozygous or heterozygous for the two alleles at the locus. This method is comprised of the following steps. A plurality of separate treated samples is provided. Each sample may contain a nucleic acid target sequence hybridized with a nucleic acid probe. The nucleic acid target sequence consists of either a first allele, a second allele, or a mixture of first and second alleles of the nucleic acid target. The alleles differ in sequence at an interrogation position. The nucleic acid probe contains an identifier nucleotide in the 3'-terminal region that is aligned at an interrogation nucleotide position of the target sequence when the probe and target are hybridized.

A treated reaction mixture is formed by admixing each treated sample with a depolymerizing amount of an enzyme whose activity is to release one or more nucleotides from the 3'-terminus of a hybridized nucleic acid probe. The treated reaction mixture is maintained under depolymerizing conditions for a time period sufficient to permit the enzyme to depolymerize the hybridized nucleic acid probe and release an identifier nucleotide. The samples are analyzed for the presence or absence of released identifier nucleotides to obtain an analytical output. The analytical output is quantifiable and thus determines whether the sample is homozygous or heterozygous when compared to the analytical output of appropriate controls.

A multiplexed version of this embodiment is also contemplated, wherein probes for two or more alleles are provided in one reaction—each probe is distinguishable, but preferably each probe has the same length. Then, after hybridization, depolymerization, and analysis according to the invention, the relative analytical output for the various distinguishable identifier nucleotides or remaining probes will show whether the sample is homozygous or heterozygous and for which alleles. Another multiplexed version of this embodiment is contemplated, wherein probes for alleles at a plurality of loci are provided. Preferably, the different loci have substantially different target sequences. Probes for the various alleles at each locus are preferably of the same length. Each of the probes should be distinguishable either by analysis of the released identifier nucleotide or by analysis of the remaining probe after depolymerization.

Another embodiment of the invention contemplates a method for determining the loss of heterozygosity (LOH) of a locus of an allele that comprises the following steps.

A plurality of separate treated samples is provided, each sample containing a nucleic acid target sequence hybridized with a nucleic acid probe. The nucleic acid target sequence is that of a first allele or a mixture of the first allele and a second allele of the nucleic acid target, wherein the alleles differ in sequence. The nucleic acid probe contains a 3'-terminal region that hybridizes to a target sequence when the probe and target are hybridized.

Each treated sample is admixed with a depolymerizing amount of an enzyme whose activity is to release one or more nucleotides from the 3'-terminus of a hybridized nucleic acid probe to form a treated reaction mixture. The treated reaction mixture is maintained under depolymerizing conditions for a time period sufficient to depolymerize hybridized nucleic acid probe and release identifier nucleotides. The samples are then analyzed for the quantity of released identifier nucleotides to obtain an analytical output, the analytical output indicating whether the nucleic acid target sequence in a nucleic acid sample has lost heterozygosity at the locus of the allele.

In preferred LOH embodiments, the analytical output is obtained by luminescence spectroscopy, absorbance spectrometry, mass spectrometry or fluorescence spectroscopy. In another preferred embodiment, the released identifier nucleotide includes a fluorescent label. The identifier nucleotide is optionally fluorescently labeled after release from the hybrid.

It is contemplated that in the above analytical methods, either the released identifier nucleotide or the remainder of the probe can be evaluated to determine whether identifier nucleotide had been released, as described herein.

In another preferred LOH embodiment, the enzyme whose activity is to release nucleotides is a template-dependent polymerase that, in the presence of pyrophosphate ions, depolymerizes hybridized nucleic acids whose bases in the 3'-terminal region are completely complementary to bases of the nucleic acid target. The depolymerization proceeds from the 3' terminal nucleotide of the probe and stops when it reaches a base that is not complementary to the corresponding target base.

In one aspect of the LOH embodiment, the quantity of the released identifier nucleotides for the first allele is substantially less than the quantity of the released identifier nucleotide for the first allele of a known heterozygous control sample, and the quantity of the released identifier nucleotides for the second allele is substantially similar to that of the released identifier nucleotide for the second allele of a known heterozygous control sample, indicating a loss of heterozygosity at the locus of the first allele.

In another aspect of the LOH embodiment, the quantity of the released identifier nucleotides for the second allele is substantially less than the quantity of the released identifier nucleotides for the second allele of a known heterozygous control sample, and the quantity of the released identifier nucleotides for the first allele is substantially similar to that of the released identifier nucleotide for the first allele of a known heterozygous control sample, indicating a loss of heterozygosity at the locus of the second allele. The known heterozygous control has analytical output for its treated sample indicating alleles one and two are present in the sample at about a 1:1 ratio. A sample with loss of heterozygosity has an analytical output for the treated samples indicating alleles one and two are present in the sample at a 1:0 or 0:1 ratio respectively when compared to the analytical output of a known heterozygous control sample.

A still further preferred embodiment of the invention contemplates a method for determining the presence of trisomy of an allele that comprises the following steps.

A plurality of separate treated samples is provided, wherein each sample contains a nucleic acid target sequence hybridized with a nucleic acid probe. The nucleic acid target sequence is that of a first allele, a second allele or a mixture of the first and second alleles of the nucleic acid target. The alleles differ in sequence at an interrogation position. The nucleic acid probe contains a 3'-terminal region that hybridizes to a region of the nucleic acid target sequence containing the interrogation nucleotide position when the probe and target are hybridized. The nucleic acid probe also contains an identifier nucleotide.

Each treated sample is admixed with a depolymerizing amount of an enzyme whose activity, under depolymerizing conditions, is to release one or more nucleotides from the 3'-terminus of a hybridized nucleic acid probe to form a treated reaction mixture. The treated reaction mixture is maintained for a time period sufficient to depolymerize hybridized nucleic acid probe and release identifier nucleotides. The samples are analyzed for released identifier nucleotides to obtain an analytical output, the magnitude of the analytical output relative to an analytical output of an appropriate control sample indicating whether a trisomy is present in the nucleic acid target sequence.

For trisomy analysis, preferably the analytical output is obtained by luminescence spectroscopy, absorbance spectrometry, fluorescence spectroscopy, or mass spectrometry. In one preferred embodiment, the released identifier nucleotide includes a fluorescent label. The identifier nucleotide is optionally fluorescently labeled after release from the hybrid.

In a preferred embodiment for trisomy analysis, the enzyme whose activity is to release nucleotides is a template-dependent polymerase, that, in the presence of pyrophosphate ions, depolymerizes hybridized nucleic acids whose bases in the 3' terminal region are completely complementary to bases of said nucleic acid target.

In one embodiment, the quantity of released identifier nucleotides for the first allele is substantially greater than the quantity of the released identifier nucleotides of a control sample homozygous for the first allele, indicating that the nucleic acid target sequence has a trisomy. Preferably, the quantity of released identifier nucleotides is expressed as a ratio. For example, a normal heterozygote has about a 1:1 ratio of the analytical output for the two alleles. If the trisomy is homozygous for either allele, the ratio is about three times the value for that allele in a normal heterozygote that has none of the other allele. If the trisomy is heterozygous, then the ratio is about 2:1 of one allele to the other when compared to the analytical output of a control heterozygote.

A still further embodiment of the invention contemplates determining the presence or absence of a nucleic acid target sequence in a nucleic acid sample with a probe that is hybridized to the target and then modified to be able to form a hairpin structure. This embodiment comprises the following steps.

A treated sample is provided that contains a nucleic acid sample that may include a nucleic acid target sequence having an interrogation position hybridized with a nucleic acid probe. The probe is comprised of at least two sections. The first section contains the probe 3'-terminal about 10 to about 30 nucleotides. These nucleotides are complementary to the target strand sequence at positions beginning about 1 to about 30 nucleotides downstream of the interrogation position. The second section of the probe is located at the 5'-terminal region of the probe and contains about 10 to about 20 nucleotides of the target sequence. This sequence spans the region in the target from the nucleotide at or just upstream (5') of the interrogation position, to the nucleotide just upstream to where the 3'-terminal nucleotide of the probe anneals to the target. An optional third section of the probe, from zero to about 50, and preferably about zero to about 20 nucleotides in length and comprising a sequence that does not hybridize with either the first or second section, is located between the first and second sections of the probe.

The probe of the treated sample is extended in a template-dependent manner, as by admixture with dNTPs and a template-dependent polymerase, at least through the interrogation position, thereby forming an extended probe/target hybrid. In a preferred embodiment, the length of the probe extension is limited by omission from the extension reaction of a dNTP complementary to a nucleotide of the target sequence that is present upstream of the interrogation position and absent between the nucleotide complementary to the 3'-end of the interrogation position.

The extended probe/target hybrid is separated from any unreacted dNTPs. The extended probe/target hybrid is denatured to separate the strands. The extended probe strand is permitted to form a hairpin structure.

A treated reaction mixture is formed by admixing the hairpin structure-containing composition with a depolymerizing amount of an enzyme whose activity is to release one or more nucleotides from the 3'-terminus of an extended probe hairpin structure. The reaction mixture is maintained under depolymerizing conditions for a time period sufficient for the depolymerizing enzyme to release 3'-terminus nucleotides, and then analyzed for the presence of released identifier nucleotides. The analytical output indicates the presence or absence of the nucleic acid target sequence.

A still further embodiment of the invention, termed REAPER™, also utilizes hairpin structures. This method contemplates determining the presence or absence of a nucleic acid target sequence, or a specific base within the target sequence, in a nucleic acid sample, and comprises the following steps. A treated sample is provided that contains a nucleic acid sample that may include a nucleic acid target sequence hybridized with a first nucleic acid probe strand.

The hybrid is termed the first hybrid. The first probe is comprised of at least two sections. The first section contains the probe 3'-terminal about 10 to about 30 nucleotides that are complementary to the target nucleic acid sequence at a position beginning about 5 to about 30 nucleotides downstream of the target interrogation position. The second section of the first probe contains about 5 to about 30 nucleotides that are a repeat of the target sequence from the interrogation position to about 10 to about 30 nucleotides downstream of the interrogation position, and does not hybridize to the first section of the probe. An optional third section of the probe, located between the first and second sections of the probe, is zero to about 50, preferably up to about 20, nucleotides in length and comprises a sequence that does not hybridize to either the first or second section.

The first hybrid in the treated sample is extended at the 3'-end of the first probe, thereby extending the first probe past the interrogation position and forming an extended first hybrid whose sequence includes an interrogation position. The extended first hybrid is comprised of the original target nucleic acid and extended first probe. The extended first hybrid is then denatured in an aqueous composition to separate the two nucleic acid strands of the hybridized duplex and form an aqueous solution containing a separated target nucleic acid and a separated extended first probe.

A second probe, that is about 10 to about 2000, preferably about 10 to about 200, most preferably about 10 to about 30 nucleotides in length and is complementary to the extended first probe at a position beginning about 5 to about 2000, preferably about 5 to about 200, nucleotides downstream of the interrogation position in extended first probe, is annealed to the extended first probe, thereby forming the second hybrid. The second hybrid is extended at the 3'-end of the second probe until that extension reaches the 5'-end of the extended first probe, thereby forming a second extended hybrid whose 3'-region includes an identifier nucleotide. In preferred embodiments the extending polymerase for both extensions does not add a nucleotide to the 3' end that does not have a corresponding complementary nucleotide in the template.

An aqueous composition of the extended second hybrid is denatured to separate the two nucleic acid strands. The aqueous composition so formed is cooled to form a "hairpin structure" from the separated extended second probe when the target sequence is present in the original nucleic acid sample.

A treated reaction mixture is formed by admixing the hairpin structure-containing composition with a depolymerizing amount of an enzyme whose activity is to release one or more nucleotides from the 3'-terminus of a nucleic acid hybrid. The reaction mixture is maintained under depolymerizing conditions for a time period sufficient to release 3'-terminal region identifier nucleotides, and then analyzed for the presence of released identifier nucleotides. The analytical output indicates the presence or absence of the nucleic acid target sequence.

The present invention has many benefits and advantages, several of which are listed below.

One benefit of the invention is that, in some embodiments, nucleic acid hybrids can be detected with very high levels of sensitivity without the need for radiochemicals or electrophoresis.

An advantage of the invention is that the presence or absence of one or more target nucleic acid(s) can be detected reliably, reproducibly, and with great sensitivity.

A further benefit of the invention is that quantitative information can be obtained about the amount of a target nucleic acid sequence in a sample.

A further advantage of the invention is that very slight differences in nucleic acid sequence are detectable, including single nucleotide polymorphisms (SNPs).

Yet another benefit of the invention is that the presence or absence of a number of target nucleic acid sequences can be determined in the same assay.

Yet another advantage of the invention is that the presence or absence of a target nucleic acid can be determined with a small number of reagents and manipulations.

Another benefit of the invention is that the processes lend themselves to automation.

Still another benefit of the invention is its flexibility of use in many different types of applications and assays including, but not limited to, detection of mutations, translocations, and SNPs in nucleic acid (including those associated with genetic disease), determination of viral load, species identification, sample contamination, and analysis of forensic samples.

Still further benefits and advantages of the invention will become apparent from the specification and claims that follow.

BRIEF DESCRIPTION OF THE DRAWING

In the drawings forming a portion of this disclosure,

FIG. 1A illustrates the first hybrid formed by the annealing of nucleic acid target SEQ ID NO:111 (111) to first probe SEQ ID NO:112 (112). An arrow points to an interrogation position in 111.

FIG. 1B illustrates the first extended hybrid formed by the annealing of 111 to the extended 112. Extended 112 is first extended probe SEQ ID NO:113 (113).

FIG. 1C illustrates the second hybrid formed by annealing of 113 from the denatured nucleic acid molecule shown in FIG. 1B to the second probe denoted SEQ ID NO:114 (114). An arrow points to the interrogation position in 113.

FIG. 1D illustrates the extended second hybrid formed by the annealing of 113 and the extended 114 strand denoted SEQ ID NO:115 (115).

FIG. 1E illustrates the 115 strand denatured from FIG. 1D and forming a hairpin structure. An arrow points to the interrogation position at the 3'-terminus of the hybrid.

DEFINITIONS

Figure 1:
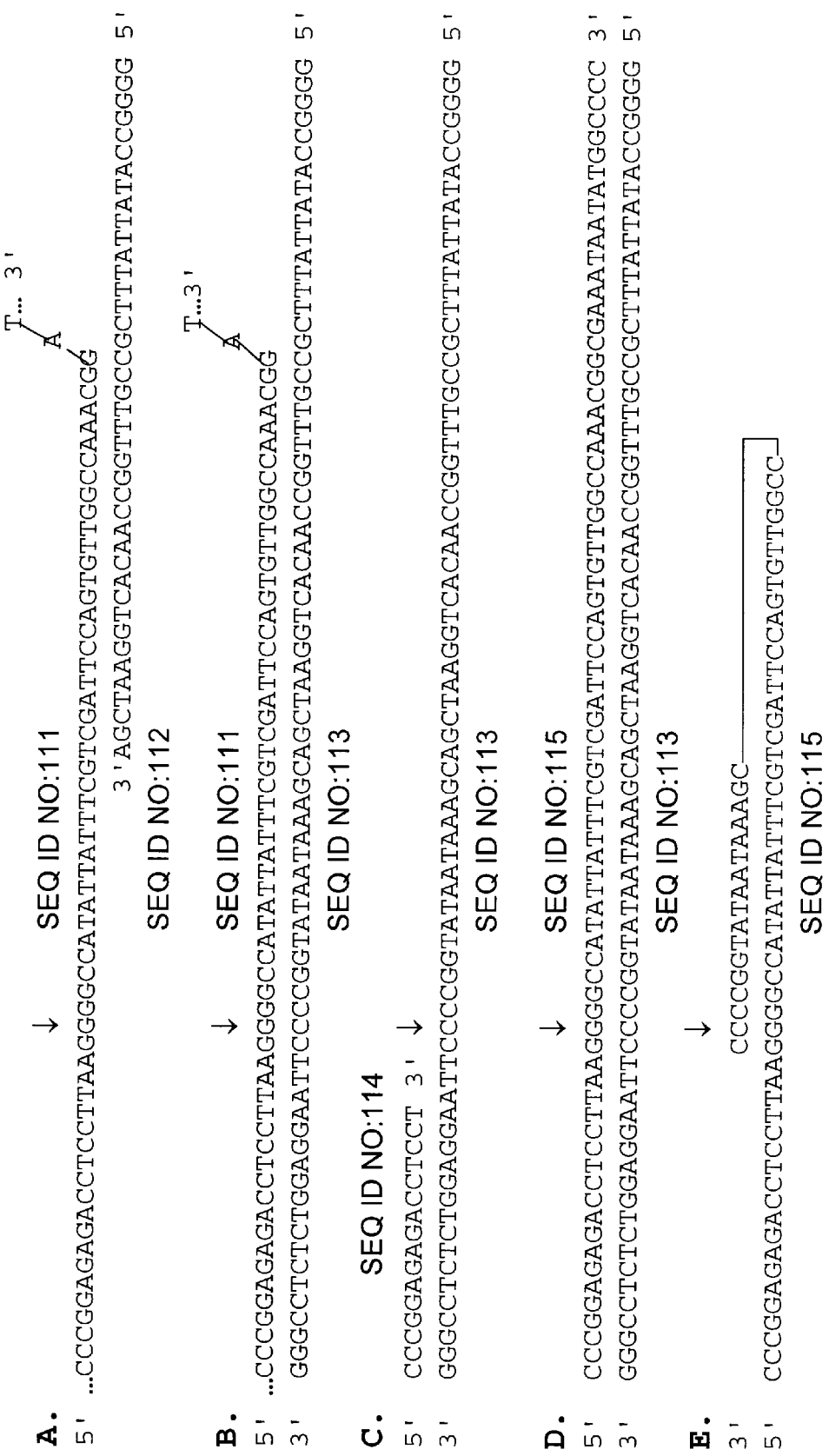
FIG. 1. illustrates the Reaper™ assay as illustrated in Example 89.

To facilitate understanding of the invention, a number of terms are defined below.

"Nucleoside", as used herein, refers to a compound consisting of a purine [guanine (G) or adenine (A)] or pyrimidine [thymine (T), uridine (U) or cytidine (C)] base covalently linked to a pentose, whereas "nucleotide" refers to a nucleoside phosphorylated at one of its pentose hydroxyl groups. "XTP", "XDP" and "XMP" are generic designations for ribonucleotides and deoxyribonucleotides, wherein the "TP" stands for triphosphate, "DP" stands for diphosphate, and "MP" stands for monophosphate, in conformity with standard usage in the art. Subgeneric designations for ribonucleotides are "NMP", "NDP" or "NTP", and subgeneric designations for deoxyribonucleotides are "dNMP", "dNDP" or "dNTP". Also included as "nucleoside", as used herein, are materials that are commonly used as substitutes for the nucleosides above such as modified forms of these bases (e.g. methyl guanine) or synthetic materials well known in such uses in the art, such as inosine.

A "nucleic acid," as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides. A "polynucleotide," as used herein, is a nucleic acid containing a sequence that is greater than about 100 nucleotides in length. An "oligonucleotide," as used herein, is a short polynucleotide or a portion of a polynucleotide. An oligonucleotide typically contains a sequence of about two to about one hundred bases. The word "oligo" is sometimes used in place of the word "oligonucleotide".

A base "position" as used herein refers to the location of a given base or nucleotide residue within a nucleic acid.

A "nucleic acid of interest," as used herein, is any particular nucleic acid one desires to study in a sample.

The term "isolated" when used in relation to a nucleic acid or protein, refers to a nucleic acid sequence or protein that is identified and separated from at least one contaminant (nucleic acid or protein, respectively) with which it is ordinarily associated in its natural source. Isolated nucleic acid or protein is present in a form or setting that is different from that in which it is found in nature. In contrast, nonisolated nucleic acids or proteins are found in the state they exist in nature.

As used herein, the term "purified" or "to purify" means the result of any process which removes some contaminants from the component of interest, such as a protein or nucleic acid. The percent of a purified component is thereby increased in the sample.

The term "wild-type," as used herein, refers to a gene or gene product that has the characteristics of that gene or gene product that is most frequently observed in a population and is thus arbitrarily designated the "normal" or "wild-type" form of the gene. In contrast, the term "modified" or "mutant" as used herein, refers to a gene or gene product that displays modifications in sequence and/or functional properties (i.e., altered characteristics) when compared to the wild-type gene or gene product.

Nucleic acids are known to contain different types of mutations. As used herein, a "point" mutation refers to an alteration in the sequence of a nucleotide at a single base position. A "lesion", as used herein, refers to site within a nucleic acid where one or more bases are mutated by deletion or insertion, so that the nucleic acid sequence differs from the wild-type sequence.

A "single nucleotide polymorphism" or SNP, as used herein, is a variation from the most frequently occurring base at a particular nucleic acid position.

Homologous genes or alleles from different species are also known to vary in sequence. Regions of homologous genes or alleles from different species can be essentially identical in sequence. Such regions are referred to herein as "regions of identity." It is contemplated herein that a "region of substantial identity" can contain some "mismatches," where bases at the same position in the region of identity are different. This base position is referred to herein as "mismatch position."

DNA molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. As used herein, a nucleic acid sequence, even if internal to a larger oligonucleotide or polynucleotide, also can be said to have 5'- and 3'- ends. For example, a gene sequence located within a larger chromosome sequence can still be said to have a 5'- and 3'-end.

As used herein, the 3'-terminal region of the nucleic acid probe refers to the region of the probe including nucleotides within about 10 residues from the 3'-terminal position.

In either a linear or circular DNA molecule, discrete elements are referred to as being "upstream" or "5'" relative to an element if they are bonded or would be bonded to the 5'-end of that element. Similarly, discrete elements are "downstream" or "3'" relative to an element if they are or would be bonded to the 3'-end of that element. Transcription proceeds in a 5' to 3' manner along the DNA strand. This means that RNA is made by the sequential addition of ribonucleotide-5'-triphosphates to the 3'-terminus of the growing chain (with the elimination of pyrophosphate).

As used herein, the term "target nucleic acid" or "nucleic acid target" refers to a particular nucleic acid sequence of interest. Thus, the "target" can exist in the presence of other nucleic acid molecules or within a larger nucleic acid molecule.

As used herein, the term "nucleic acid probe" refers to an oligonucleotide or polynucleotide hat is capable of hybridizing to another nucleic acid of interest. A nucleic acid probe may occur naturally as in a purified restriction digest or be produced synthetically, recombinantly or by PCR amplification. As used herein, the term "nucleic acid probe" refers to the oligonucleotide or polynucleotide used in a method of the present invention. That same oligonucleotide could also be used, for example, in a PCR method as a primer for polymerization, but as used herein, that oligonucleotide would then be referred to as a "primer". Herein, oligonucleotides or polynucleotides may contain a phosphorothioate bond.

As used herein, the terms "complementary" or "complementarity" are used in reference to nucleic acids (i.e., a sequence of nucleotides) related by the well-known base-pairing rules that A pairs with T and C pairs with G. For example, the sequence 5'-A-G-T-3', is complementary to the sequence 3'-T-C-A-5'. Complementarity can be "partial," in which only some of the nucleic acid bases are matched according to the base pairing rules. On the other hand, there may be "complete" or "total" complementarity between the nucleic acid strands when all of the bases are matched according to base pairing rules. The degree of complementarity between nucleic acid strands has significant effects on the efficiency and strength of hybridization between nucleic acid strands as known well in the art. This is of particular importance in detection methods that depend upon binding between nucleic acids, such as those of the invention. The term "substantially complementary" refers to any probe that can hybridize to either or both strands of the target nucleic acid sequence under conditions of low stringency as described below or, preferably, in polymerase reaction buffer (Promega, M195A) heated to 95° C. and then cooled to room temperature. As used herein, when the nucleic acid probe is referred to as partially or totally complementary to the target nucleic acid, that refers to the 3'-terminal region of the probe (i.e. within about 10 nucleotides of the 3'-terminal nucleotide position).

As used herein, the term "hybridization" is used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the $T_m$ (melting temperature) of the formed hybrid, the presence of other components (e.g., the presence or absence of polyethylene glycol), the molarity of the hybridizing strands and the G:C content of the nucleic acid strands.

As used herein, the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together. The art knows well that numerous equivalent conditions can be employed to comprise low stringency conditions.

As used herein, the term "$T_m$" is used in reference to the "melting temperature". The melting temperature is the temperature at which 50% of a population of double-stranded nucleic acid molecules becomes dissociated into single strands. The equation for calculating the $T_m$ of nucleic acids is well-known in the art. The $T_m$ of a hybrid nucleic acid is often estimated using a formula adopted from hybridization assays in 1 M salt, and commonly used for calculating $T_m$ for PCR primers: [(number of A+T)×2° C. +(number of G+C)× 4° C.]. C. R. Newton et al. *PCR*, $_2$nd Ed., Springer-Verlag (New York: 1997), p. 24. This formula was found to be inaccurate for primers longer that 20 nucleotides. Id. Other more sophisticated computations exist in the art which take structural as well as sequence characteristics into account for the calculation of $T_m$. A calculated $T_m$ is merely an estimate; the optimum temperature is commonly determined empirically.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous."

When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency.

When used in reference to a single-stranded nucleic acid sequence, the term "substantially homologous," as used herein, refers to a probe that can hybridize to (i.e., is the complement of) the single-stranded nucleic acid template sequence under conditions of low stringency.

The term "interrogation position," as used herein, refers to the location of a given base of interest within a nucleic acid probe. For example, in the analysis of SNPs, the "interrogation position" in the probe is in the position that would be complementary to the single nucleotide of the target that may be altered from wild type. The analytical output from a method of the invention provides information about a nucleic acid residue of the target nucleic acid that is complementary to an interrogation position of the probe. An interrogation position is within about ten bases of the actual 3'-terminal nucleotide of the nucleic acid probe, although not necessarily at the 3'-terminal nucleotide position. The interrogation position of the target nucleic acid sequence is opposite the interrogation position of the probe, when the target and probe nucleic acids are hybridized.

The term "identifier nucleotide," as used herein, refers to a nucleotide whose presence is to be detected in a process of the invention to identify that a depolymerization reaction has occurred. The particular application of a method of the invention affects which residues are considered an identifier nucleotide. For a method using ATP detection (e.g. luciferase/luciferin or NADH) wherein, during analysis, all nucleotides released in the depolymerization are "converted" to ATP with an enzyme such as NDPK, all nucleotides released are identifier nucleotides. Similarly, for a method using absorbance detection that does not distinguish between nucleotides, all released nucleotides are identifier nucleotides. For a mass spectrometric detection wherein all the released nucleotides are analyzed, all released nucleotides can be identifier nucleotides; alternatively a particular nucleotide (e.g. a nucleotide analog having a distinctive mass) can be detected. For fluorescence detection, a fluorescently-labeled nucleotide is an identifier nucleotide. The nucleotide may be labeled prior to or after release from the nucleic acid. For radiographic detection, a radioactively-labeled nucleotide is an identifier nucleotide. In some cases, the release of identifier nucleotide is deduced by analyzing the remainder of the probe after a depolymerization step of the invention. Such analysis is generally by a determination of the size or mass of the remaining probe and can be by any of the described analytical methods (e.g. a fluorescent tag on the 5'-terminus of the probe to monitor its molecular weight following capillary electrophoresis).

As used herein, the terms "restriction endonucleases" and "restriction enzymes" refer to a class of enzymes, each of which cut double-stranded DNA. Some restriction endonucleases cut double strand DNA at or near a specific nucleotide sequence, such as the enzyme commonly referred to as BamH I that recognizes the double strand sequence 5'GGATCC 3'. However, other representatives of such enzymes cut DNA in a non-specific manner such as the DNA endonuclease DNase I.

The term "sample," as used herein, is used in its broadest sense. A sample suspected of containing a nucleic acid can comprise a cell, chromosomes isolated from a cell (e.g., a spread of metaphase chromosomes), genomic DNA, RNA, cDNA and the like.

The term "detection," as used herein, refers to quantitatively or qualitatively identifying a nucleotide or nucleic acid within a sample.

The term "depolymerization," as used herein, refers to the removal of a nucleotide from the 3' end of a nucleic acid.

The term "allele," as used herein, refers to an alternative form of a gene and the term "locus," as used herein, refers to a particular place on a nucleic acid molecule.

DETAILED DESCRIPTION OF THE INVENTION

A method of this invention is used to determine the presence or absence of at least one predetermined (known) endogenous nucleic acid target sequence in a nucleic acid sample. A nucleic acid target is "predetermined" in that its sequence must be known to design a probe that hybridizes with that target. However, it should be noted that a nucleic acid target sequence, as used with respect to a process of this invention, may merely act as a reporter to signal the presence of a different nucleic acid whose presence is desired to be determined. That other nucleic acid of interest does not have to have a predetermined sequence. Furthermore, in many embodiments, a process of the invention is useful in determining the identity of a base within a target where only enough of the sequence is known to design a probe that hybridizes to that target with partial complementarity at the 3'-terminal region of the probe.

Such a method utilizes an enzyme that can depolymerize the 3'-terminus of an oligonucleotide probe hybridized to the nucleic acid target sequence to release one or more identifier nucleotides whose presence or absence can then be determined as an analytical output that indicates the presence or absence of the target sequence.

A nucleic acid target sequence is predetermined (or known) in that a nucleic acid probe is provided to be partially or totally complementary to that nucleic acid target sequence. A nucleic acid target sequence is a portion of nucleic acid sample with which the probe hybridizes if that target sequence is present in the sample.

A nucleic acid target is "endogenous" when it is a natural part of the sample being assayed. For example, analysis of a human body sample to ascertain its genetic makeup (e.g. trisomy or Duchennes muscular dystrophy analysis) will have an endogenous nucleic acid target. On the other hand, analysis of a human body sample to search for the presence of a viral pathogen has an exogenous target. However, analysis of a microbiological sample to determine its genetic makeup (e.g. speciation) has an endogenous target.

A first step of the method is admixing a sample to be assayed with one or more nucleic acid probes. The admixing of the first step is typically carried out under low stringency hybridizing conditions to form a hybridization composition. In such a hybridization composition, the 3'-terminal region of the nucleic acid probe(s) (i) hybridizes with partial or total complementarity to a nucleic acid target sequence that may be present in the sample; and (ii) includes an identifier nucleotide in the 3'-terminal region.

Preferably, the nucleic acid probe is designed to not hybridize with itself to form a hairpin structure in such a way as to interfere with hybridization of the 3'-terminal region of the probe to the target nucleic acid. Parameters guiding probe design are well known in the art.

The hybridization composition is maintained under hybridizing conditions for a time period sufficient to form a treated sample that may contain at least one predetermined nucleic acid target sequence hybridized with a nucleic acid probe.

In the event that the sample to be assayed does not contain a target sequence to which the probe hybridizes, no hybridization takes place. When a method of the present invention is used to determine whether a particular target sequence is present or absent in a sample to be assayed, the resulting treated sample may not contain a substrate for the enzymes of the present invention. As a result, a 3' terminal region identifier nucleotide is not released and the analytical output is at or near background levels.

The treated sample is admixed with a depolymerizing amount of an enzyme whose activity is to release one or more identifier nucleotides from the 3'-terminal region of the probe that is hybridized to the nucleic acid target to form a depolymerization reaction mixture. The choice of enzyme used in the process determines if a match or mismatch at the 3'-terminal nucleotide results in release of that 3'-terminal nucleotide. Further information regarding specific enzyme reaction conditions is discussed in detail hereinafter.

The depolymerization reaction mixture is maintained under depolymerizing conditions for a time period sufficient to permit the enzyme to depolymerize hybridized nucleic acid and release identifier nucleotides therefrom to form a treated reaction mixture.

The presence or absence of released identifier nucleotides is then determined to obtain an analytical output. The analytical output indicates the presence or absence of at least the one nucleic acid target sequence.

Processes of the invention can also be concerned with the degree of hybridization of the target to the 3'-terminal region of the probe. Examples hereinafter show that the distinction between a matched and mismatched base becomes less notable as a single mismatch is at a position further upstream from the 3'-terminal region position. There is very little discrimination between a match and mismatch when a single mismatch is ten to twelve residues from the 3'-terminal nucleotide position, whereas great discrimination is observed when a single mismatch is at the 3'-terminus. Therefore, when the degree of complementarity (partial or total complementarity) of a nucleic acid probe hybridized to a target nucleic acid sequence is referred to herein in regard to an identifier nucleotide, this is to be understood to be referring to within the 3'-terminal region, up to about ten residues of the 3'-terminal position.

The sufficiency of the time period for hybridization can be empirically ascertained for a control sample for various hybridizing conditions and nucleic acid probe/target combinations. Exemplary maintenance times and conditions are provided in the specific examples hereinafter and typically reflect low stringency hybridization conditions. In practice, once a suitable set of hybridization conditions and maintenance time periods are known for a given set of probes, an assay using those conditions provides the correct result if the nucleic acid target sequence is present. Typical maintenance times are about 5 to about 60 minutes.

The conditions and considerations with respect to hybridization of PCR primers to template nucleic acid in PCR are applicable to the hybridization of nucleic acid probes to target sequences in a process of the invention. Such hybridization conditions are well known in the art, and are a matter of routine experimentation depending on factors including the sequence of the nucleic acid probe and the target nucleic acid [sequence identity (homology), length and G+C content] molar amounts of nucleic acid present, buffer, salt content and duplex $T_m$ among other variables.

Processes of the invention are sensitive and hybridization conditions of low stringency (e.g. temperature of 0–4° C.) are sufficient, but moderate stringency conditions (i.e. temperatures of 40–60° C.) also permit hybridization and provide acceptable results. This is true for all processes of the invention.

In one contemplated embodiment of the invention, the enzyme whose activity is to depolymerize hybridized nucleic acid to release nucleotides from the probe 3'-terminal end is a template-dependent polymerase. In such an embodiment, the reverse of a polymerase reaction is used to depolymerize a nucleic acid probe, and the identifier nucleotide is released when the 3'-terminal nucleotide of the nucleic acid probe hybridizes with total complementarity to its nucleic acid target sequence. A signal confirms the presence of a nucleic acid target sequence that has the sequence sufficiently complementary to the nucleic acid probe to be detected by the process of the invention.

In an embodiment that uses a 3'→5' exonuclease activity of a polymerase, such as Klenow or T4 DNA polymerase (but not limited to those two enzymes), to depolymerize a nucleic acid probe, an identifier nucleotide is released when the 3'-terminal residue of the nucleic acid probe is mismatched and therefore there is only partial complementarity of the 3'-terminus of the nucleic acid probe to its nucleic acid target sequence. In this embodiment, to minimize background, the hybrid is typically purified from the un-annealed nucleic acid prior to the enzyme reaction, which releases identifier nucleotides. A signal confirms the presence of a nucleic acid target sequence that is not totally complementary to the nucleic acid probe.

In an embodiment that uses a 3'→5' exonuclease activity of Exonuclease III to depolymerize a nucleic acid probe, an identifier nucleotide is released when the 3'-terminal residue of the nucleic acid probe is matched to the target nucleic acid in the hybrid. A signal confirms the presence of a nucleic acid target that is complementary to the probe at the released identifier nucleotide.

It is thus seen that hybridization and depolymerization can lead to the release of an indicator nucleotide or to little or no release of such a nucleotide, depending upon whether the probe: target hybrid is matched or mismatched at the 3'-terminal region. This is also dependent on the type of enzyme used and the type of end, matched or mismatched, that the enzyme requires for depolymerization activity.

The magnitude of a contemplated analytical output under defined conditions is dependent upon the amount of released nucleotides. Where an identifier nucleotide is released, an analytical output can be provided that has a value greater than background. Where an identifier nucleotide is not released either because the target sequence was not present in the original sample or because the probe and depolymerizing enzyme chosen do not provide release of a 3'-terminal nucleotide when the target is present, or if the match/mismatch state of the 3'-terminal nucleotide did not match that required for the enzyme used to release a 3'-terminal nucleotide, the analytical output is substantially at a background level.

In an example dealing with background levels, the net relative light values for analytical output are typically calculated as follows. First the results from matching samples are averaged, then the net light production from the matching and mismatching samples is determined and the net light production from the matching reaction is divided by that seen in the mismatch reaction. The net light production was determined by subtracting the estimated light contribution from the probes and template present in the reactions from the total light produced. The light production from the template reaction was considered to be the total of that contributed from the template specifically and that contributed by contaminating ATP from various reaction components. The net increase from the probes alone was calculated by subtracting the average "No Target DNA" values from the probe values since this subtracts the contributions from contaminating ATP from the probe values. Thus, the formula used to determine the net light production from the reactions was:

Net Light=Total light−[(target alone) +(probe alone−No DNA)]

For example, in the case of an assay to determine which of two alleles are present, the net light values are used to determine the signal ratio by dividing the signal from the first allele probe by the signal from the second allele probe.

It has been observed that very different detection ratios can be calculated from two sets of probes but that the signal ratios from the different target genotypes are easily distinguishable from each other. In addition, a mismatching allele probe gave a relatively low light signal in the absence of nucleic acid target using low concentrations of Klenow exo-. If such manipulations were not used, the light signal from the probe alone would be a large contribution to the total signal of the samples containing the probe, making sensitive allele discrimination more difficult.

Depolymerization reactions and enzymes useful in such reactions are discussed below.

Depolymerization

Nucleic acid polymerases generally catalyze the elongation of nucleic acid chains. The reaction is driven by the cleavage of a pyrophosphate released as each nucleotide is added. Each nucleoside-5'-triphosphate has three phosphate groups linked to carbon five of the ribose or deoxyribose sugar. The addition of a nucleotide to a growing nucleic acid results in formation of an internucleoside phosphodiester bond. This bond is characterized in having a 3' linkage to carbon 3 of ribose or deoxyribose and a 5' linkage to carbon 5 of ribose or deoxyribose. Each nucleotide is added through formation of a new 3'→5' linkage, so the nucleic acid strand grows in a 5' to 3' direction.

Depolymerization in its strictest sense means the reverse of polymerization so that in the present context, an internucleotide phosphodiester bond is broken between the two 3'-terminal bases in the presence of pyrophosphate and a polymerase enzyme to form a nucleic acid that is one nucleotide shorter and a nucleoside triphosphate. A somewhat more encompassing definition is contemplated here. In accordance with that definition, the 3'-terminal nucleotide is removed from a nucleic acid in a reaction catalyzed by an enzyme, but the nucleotide formed can be a monophosphate and pyrophosphate is not always required.

The former reactions are referred to herein as pyrophosphorolysis reactions whereas the latter reactions are referred to as exonuclease reactions. These two types of depolymerization are discussed below.

It is to be understood that the depolymerization reaction of interest in the invention is that depolymerization occurring in the 3'-terminal region of the nucleic acid probe. This depolymerization reaction releases identifier nucleotide, as discussed herein.

A. Pyrophosphorolysis

In some embodiments of the present invention, a method comprises depolymerizing the nucleic acid (NA) at a 3'-terminal nucleotide by enzymatically cleaving the terminal internucleoside phosphodiester bond in the presence of pyrophosphate, or an analogue thereof, to form an XTP as illustrated by the following reaction on double-stranded DNA having a 5' overhang:

5'... TpApCpGpGpCpT-3'OH
3'... ApTpGpCpCpGpApCpTp-5'

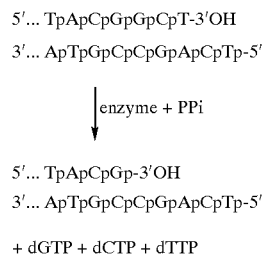

5'... TpApCpGp-3'OH
3'... ApTpGpCpCpGpApCpTp-5'

+ dGTP + dCTP + dTTP

Several polymerases are known to catalyze the reverse of the polymerization process. This reverse reaction is called "pyrophosphorolysis." The pyrophosphorolysis activity of DNA polymerase was demonstrated by Deutscher and Kornberg, *J. Biol. Chem.*, 244:3019–28 (1969). Other template-dependent nucleic acid polymerases capable of pyrophosphorolysis include, but are not limited to, DNA polymerase α, DNA polymerase β, T4 DNA polymerase, Taq polymerase, Tne polymerase, Tne triple mutant polymerase, Tth polymerase, Tvu polymerase, Ath polymerase, Bst polymerase, *E. coli* DNA polymerase I, Klenow fragment, Klenow exo minus (exo-), AMV reverse transcriptase, RNA polymerase and MMLV reverse transcriptase. However, not all polymerases are known to possess pyrophosphorolysis activity. For example, poly(A) polymerase has been reported to not catalyze pyrophosphorylation. (See Sippel, *Eur. J. Biochem.* 37:31–40 (1973)).

A mechanism of pyrophosphorolysis has been suggested for RNA polymerase. Although understanding of the mechanism is not necessary to use the present invention, it is believed that the partial transfer of a $Mg^{2+}$ ion from the attacking pyrophosphate to the phosphate of the internucleoside phosphodiester bond of the RNA can increase the nucleophilic reactivity of the pyrophosphate and the electrophilicity of the diester as described in Rozovskaya et al., *Biochem. J.*, 224:645–50 (1984). The internucleoside phosphodiester bond is enzymatically cleaved by the addition of pyrophosphate to the nucleoside 5' phosphate and a new phosphodiester bond is formed between the pyrophosphate and the nucleoside monophosphate.

The pyrophosphorolysis reaction can be summarized as follows:

Reaction 1: $NA_n + PP_i \rightarrow NA_{n-1} + XTP$ wherein NA is a nucleic acid, n is the number of nucleotide bases, $PP_i$ is pyrophosphate and XTP is either a dNTP molecule or NTP molecule. The reaction can then be repeated so as to produce at least two XTP molecules. It should be noted that the reaction can be repeated on the same nucleic acid molecule or on a plurality of different nucleic acid molecules.

In a preferred embodiment in the case of the reverse of polymerase activity (pyrophosphorolysis), a preferred substrate is a DNA probe hybridized to a nucleic acid target sequence with total complementarity at its 3'-terminus, including an identifier residue at the 3'-terminal region. In an example of this preferred embodiment, when the nucleic acid probe is hybridized to a nucleic acid target sequence such that there is one base mismatch at the 3'-terminal nucleotide of the nucleic acid probe, the nucleic acid probe is inefficiently depolymerized through the reverse polymerization reaction. Thus, such a substrate is not an ideal substrate for depolymerization.

The non-ideality of the substrate for depolymerization via a reverse of the polymerization reaction is recognized with a single base mismatch as far in as about 10 residues from the 3'-terminus of the nucleic acid probe. With a single base mismatch 12 residues from the 3'-terminus of the probe, the depolymerization reaction can occur to approximately the same extent as when there is no mismatch and the nucleic acid probe is totally complementary to the nucleic acid target sequence.

It is thus contemplated that the reactivity of the depolymerization reaction is a continuum that is related to the efficiency of the substrate. A partially complementary hybrid is a less efficient depolymerization substrate than a totally complementary hybrid for the reverse of a polymerization reaction. It is contemplated that this differential reactivity be used to enhance the discrimination between matches and mismatches at certain positions (e.g. an interrogation position). When a substrate hybrid is totally complementary, it will give a fairly high analytical output. A mismatch can be intentionally introduced to destabilize the substrate hybrid. Such a destabilization can increase the difference in analytical output between bases substituted at an interrogation position that is different from the destabilizing base position.

Several chemical compounds are known in the art to be substitutable for pyrophosphate in pyrophosphorolysis reactions. Rozovskaya, et al., *Biochem. J.*, 224:645–650 (1984). Exemplary compounds and their released nucleotide product are shown in the table below, along with the nucleotide product (where the ribonucleoside or deoxyribonucleoside is denoted "Nuc") of pyrophosphorolysis.

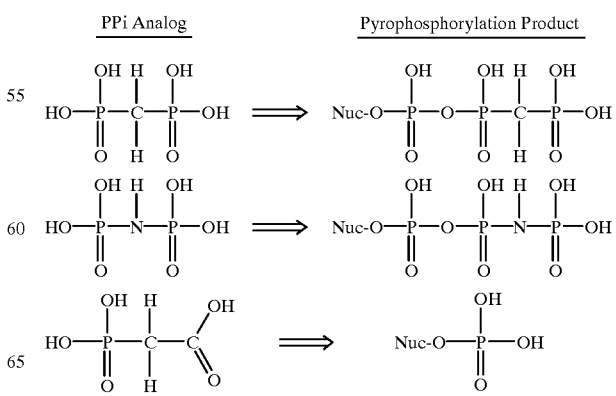

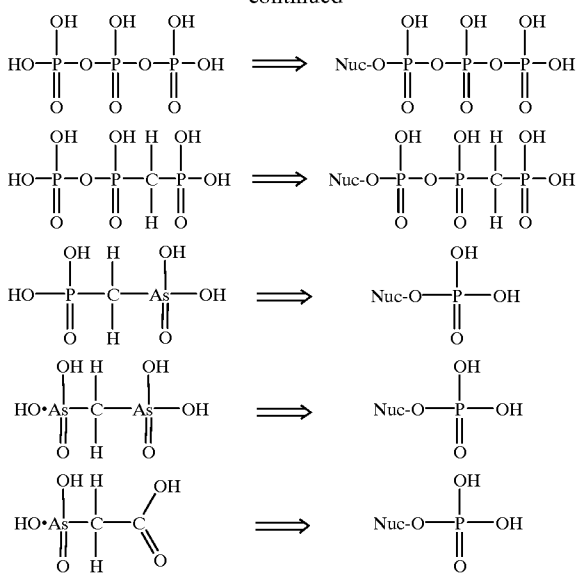

Preferred reaction mixtures for depolymerization by pyrophosphorolysis, including suitable buffers for each nucleic acid polymerase analyzed, are described in greater detail in the Examples. Typically, under these conditions, sufficient NTP or dNTP is released to accurately detect or assay extremely low amounts of nucleic acids (e.g., about 5–1000 picograms). ATP can be produced by conversion from XTP by an enzyme such as NDPK (in the presence of ADP) prior to analysis or the ATP can be further amplified prior to analysis.

Even though the preferred reaction conditions for polymerization and depolymerization by pyrophosphorolysis are similar, the rates of these reactions can vary greatly. For example, AMV and RLV reverse transcriptases catalyze pyrophosphorolysis under optimal conditions at a rate of about fifty- to one hundred-fold less than polymerization as demonstrated in Srivastavan and Modak, *J. Biol. Chem.*, 255(5):2000–04 (1980). Thus, the high efficiency of the pyrophosphorolysis reaction was unexpected, and appears to be associated with extremely low levels of DNA substrate, in contrast to previous DNA pyrophosphorolysis studies conducted using much greater amounts of DNA.

Although not wishing to be bound by theory, a possible explanation for this effect might also be that the molar concentrations of free deoxyribonucleoside triphosphates produced at very low DNA levels would be predicted to be very low. Indeed, these levels are expected to be far below the Michaelis constant ($K_m$) of the enzyme. Thus, reincorporation of released dNTPs would be expected to be vanishingly small.

The pyrophosphorolysis activity of different nucleic acid polymerases also varies. For example, T4 polymerase and Tne DNA polymerase possess very high pyrophosphorolysis activity as measured by a luciferase assay for ATP produced by pyrophosphorolysis. Pyrophosphorolysis using T4 polymerase resulted in about a 10 fold increase in light production as compared to MMLV-RT and a 4 fold increase in light production as compared to Taq polymerase.

During the development of the invention disclosed in the parent application, it was discovered that the detection of some types of nucleic acids at low picogram levels is generally enhanced by fragmenting or partially digesting the nucleic acid. Preferably, fragmentation is accomplished by sonication or restriction enzyme digestion of the nucleic acid in order to provide a plurality of smaller nucleic acid fragments. Although an understanding of the mechanism is not necessary in order to practice the present invention, this step probably enhances detection because the pyrophosphorolysis reaction only proceeds from the nucleic acid ends. By providing a greater number of nucleic acid ends, more reactions are allowed to occur at any one time.

It should be noted that DNA ends can be present within a molecule as well as at the end of a linear DNA fragment. For example, polymerases can catalyze pyrophosphorolysis from a gap or a nick in a DNA segment. The type of enzyme and substrate used for pyrophosphorolysis reactions determine whether fragmentation is necessary.

The type of DNA end resulting from restriction enzyme digestion also affects the pyrophoshorolysis activity of different nucleic acid polymerases. For example, Klenow exo-, MMLV-RT and Taq polymerase catalyze pyrophosphorolysis of DNA fragments with 5'-overhangs and with blunt-ends, but have little or no pyrophosphorolysis activity with 3'-overhangs. In contrast, T4 DNA polymerase catalyzes both 3'- and 5'-end overhang and blunt-end mediated pyrophosphorolysis. Thus, T4 DNA polymerase is a preferred enzyme for pyrophosphorolysis of a hybrid with a 3'-overhang. When other nucleic acid polymerases are utilized for pyrophosphorolysis of restriction enzyme treated DNA, it is contemplated that care is taken to match the end specificity of the polymerase with the type of end created by the restriction endonuclease. Such care is well within the skill of those in the art.

Tabor and Richardson, *J. Biol. Chem.* 265 (14):8322–28 (1990) reported unwanted pyrophosphorolysis mediated by T7 DNA polymerase-catalyzed DNA sequencing by the chain termination method. Those authors note that, even at the most sensitive sites, the rate of unwanted pyrophosphorolysis is at least 100,000 times slower than the rate of polymerization.

By definition, DNA sequencing is directed to ascertaining an unknown DNA sequence, rather than the detection of a known DNA sequence. In DNA sequencing by the chain termination method, oligonucleotide primers are extended by T7 DNA polymerase supplied with exogenous dNTPs and dideoxy NTPs. When a dideoxy NTP is incorporated into an elongating primer, no further polymerization can take place. These dideoxy-terminated fragments are then resolved on a DNA sequencing gel. However, in certain instances unwanted pyrophosphorolysis removes a 3'-terminal dideoxynucleotide from the elongated primer, which allows T7 DNA polymerase to catalyze additional polymerization. This additional polymerization leads to the degradation (loss) of specific dideoxynucleotide-terminated fragments on DNA sequencing gels. In other words, the resulting DNA sequencing gel will exhibit "holes" or gaps where the DNA sequence cannot be determined.

Tabor and Richardson, above, noted that when dNTPs are present in high concentrations, these pyrophosphorolysis sites occur once in several thousand nucleotides. Those authors have identified a canonical sequence, 5' dIdAdN$_1$ddN$_2$ 3', which is especially sensitive to pyrophosphorolysis when dITP is substituted for dGTP. This unwanted T7 DNA polymerase-mediated pyrophosphorolysis reaction can be avoided by the addition of pyrophosphatase, which eliminates $PP_i$ from the DNA sequencing reaction mixture. Pyrophosphatase, it is reported, eliminates the gaps in a DNA sequencing gel, permitting the accurate determination of a DNA sequence using T7 DNA polymerase-mediated dideoxy sequencing.

The present invention, in contrast, seeks to exploit DNA polymerase-mediated pyrophosphorolysis, by optimizing conditions for this reverse reaction to take place. The present invention is directed to the detection of a known sequence in a target nucleic acid, rather than ascertaining an unknown nucleic acid sequence using the polymerization activity of T7 DNA polymerase.

The pyrophosphorolysis reported by Tabor and Richardson cannot detect the presence of a specific nucleic acid sequence. In fact, DNA sequencing by the dideoxy method relies upon the incorporation of dideoxy nucleotides into an elongating primer. The T7 DNA polymerase-mediated pyrophosphorolysis reported by those authors is equally random, although there is reported a preference for the above-mentioned canonical sequence. According to Tabor and Richardson, in the absence of pyrophosphatase, one would only note gaps in a DNA sequencing gel, and those gaps would not provide any information as to the DNA sequence at those gaps. There is accordingly no method disclosed for identifying the release of 3'dideoxy nucleotides by the reported T7 DNA polymerase-mediated pyrophosphorolysis.

Further, it is contemplated that the type of polymerase used in the pyrophosphorolysis reaction is matched to the correct nucleic acid substrate in order to produce the best results. In general, DNA polymerases and reverse transcriptases are preferred for depolymerizing DNA, whereas RNA polymerases are preferred for depolymerizing RNA. Reverse transcriptases or DNA polymerases with reverse transcriptase activity are preferred for depolymerizing RNA-DNA hybrids.

In the parent application, it was surprisingly determined that poly(A) polymerase can catalyze pyrophosphorolysis, even though no such reaction had been previously reported. Indeed, poly(A) polymerase has been widely reported to not catalyze pyrophosphorolysis. (See e.g., Sippel, *Eur. J. Biochem.*, 37:31–40 (1973) and Sano and Feix, *Eur. J. Biochem.*, 71:577–83 (1976)). In these preferred embodiments of the invention disclosed in the parent application, the manganese chloride present in the previously reported buffers is omitted, the concentration of sodium chloride is decreased, and the pH value is lowered from about 8.0 to about 7.5. Furthermore, the poly(A) polymerase pyrophosphorolysis reaction buffer contains about 50 mM Tris-Cl pH 7.5, 10 mM $MgCl_2$, 50 mM NaCl, and 2 mM $NaPP_i$ (sodium pyrophosphate).

It is important to note that the depolymerization reaction is the reverse of the polymerization reaction. Therefore, as increasing amounts of free nucleoside triphosphates are produced by depolymerization, a state of equilibrium can theoretically be attained in which polymerization and depolymerization reactions are balanced. Alternatively, where small amounts of nucleic acid are detected, the reaction can go essentially to completion without reaching equilibrium, (i.e., the nucleic acid target is depolymerized into its constituent subunit nucleotides by greater than 50%). This factor is important in quantitative assays because the total amount of nucleotides released is proportional to the amount of signal generated in the detection assay.

When used for qualitative detection of nucleic acid, as long as a threshold level of nucleotides is produced, it is not necessary that the reaction reach equilibrium or go essentially to completion. In preferred embodiments, the mixture of nucleoside triphosphate molecules produced by depolymerization is preferably converted to ATP as described below. For either quantitative or qualitative detection, a detectable threshold ATP concentration of approximately $1 \times 10^{-12}$ molar in 100 $\mu$l of sample is preferably provided for detection of light in a typical luciferase assay.

In some preferred embodiments, oligonucleotide probes are typically utilized at about 100 ng to about 1 $\mu$g per 20 $\mu$L depolymerization reaction. That amount provides a probe to target weight ratio of about 200:1 to about 1,000:1.

In a preferred embodiment of the present invention, nucleic acid polymerase and pyrophosphate ($PP_i$) or an analogue thereof, are added to a hybridized sample containing from less than about 100 $\mu$g of target nucleic acid, to less than about 10 pg of nucleic acid. Typical target nucleic acids are present at about 1 to about 5 ng in the sample to be assayed, with a target nucleic acid length of about 30 to about 1000 bp being preferred.

Next, the hybridized nucleic acid is degraded (depolymerized) by pyrophosphorolysis, releasing free NTPs or dNTPs. Enzymes useful in the pyrophosphorolysis reaction include, but are not limited to, those noted previously such as the following polymerases: AMV reverse transcriptase, MMLV reverse transcriptase, DNA polymerase alpha and beta, Taq polymerase, Tne polymerase, Ath polymerase, Tvu polymerase, Tne triple mutant polymerase, T4 DNA polymerase, *E. coli* DNA polymerase I, Klenow fragment, Klenow exo minus, Tth polymerase, and poly(A) polymerase.

Most preferably, Klenow exo minus (Klenow exo-) or Tne triple mutant polymerase is utilized for DNA pyrophosphorolysis reactions because of their efficient utilization of 5' overhanging DNA ends.

When using enzymes that utilize 5' overhang substrates, it is preferred that the 3' end of the target nucleic acid extends beyond the 5' end of the nucleic acid probe. In this way, the only 5' overhang substrate is that where the 5' end of the target nucleic acid overhangs the 3' terminal region of the nucleic acid probe. An alternative method of limiting depolymerization to the nucleic acid probe is chemical modification of the ends of other nucleic acids in the sample, such as, for example, making a phosphorothioate linkage at the 3'-terminus of the target nucleic acid.

A depolymerizing enzyme is preferably present in an amount sufficient to depolymerize a hybridized target:probe. That amount can vary with the enzyme used, the depolymerization temperature, the buffer, and the like, as are well-known in the art. For a typical reaction carried out in a 20 $\mu$L volume, about 0.25 to about 1 unit (U) of an enzyme such as Klenow exo- is used. About 1 to about 5 U of the thermostable enzymes are used for depolymerization at elevated temperatures.

Luciferase, which is part of the preferred ATP detection system, is inhibited by $PP_i$. In preferred embodiments, care is taken to avoid transferring a highly inhibiting amount of $PP_i$ to the ATP detection reaction. Preferably, the amount of $PP_i$ carried over to the ATP detection reaction results in a concentration of $PP_i$ in the luciferase detection reaction of less than about 100 $\mu$M, although less than about 10 $\mu$M is desirable. Therefore, the amount of $PP_i$ utilized in the pyrophosphorolysis reaction is determined by the size of the aliquot that is taken for use in the luciferase detection system. It is contemplated that the aliquot size can vary depending upon the test system used, but the amount of $PP_i$ transferred or carried over to the luciferase detection reaction corresponds to the $PP_i$ concentration parameters described above, so that the concentration of $PP_i$ is at least below about 100 $\mu$M, and preferably below about 10 $\mu$M.

In one preferred embodiment of the invention, the enzyme whose activity is to depolymerize is a template-dependent polymerase. The depolymerization reaction is a reverse of the polymerization reaction. In a contemplated embodiment, the polymerization reaction is reversed in the presence of pyrophosphate in a reaction referred to as pyrophosphorolysis.

In some preferred embodiments, the reaction conditions are preferably adjusted to further favor depolymerization of a nucleic acid probe that is hybridized with its target nucleic acid sequence by providing a higher concentration of nucleic acid probe than its target nucleic acid sequence.

One strategy to favor the depolymerization of a probe: target hybrid is that the probe be in excess over the nucleic acid target in the hybridization step after denaturing of duplex target nucleic acid.

Another strategy to favor the depolymerization of a probe:target hybrid is to isolate only the strand of nucleic acid target to which the probe is complementary. There are several techniques that can be used to achieve this end.

In one technique, phosphorothioate linkages are utilized at the 5'-terminus of a target nucleic acid amplifying primer sequence, e.g., at the 1 to about 10 5'-most residues. Upon PCR amplification of the target, the phosphorothioate linkages of the primer become incorporated into the amplified target nucleic acid as part of one of a pair of complementary strands. Treatment of the double-stranded resulting molecule with T7 polymerase exonuclease 6 removes the non-phosphorothioate-containing strand. This technique is illustrated in detail in the Examples hereinafter.

In another technique, strand isolation can be accomplished by amplifying the target nucleic acid using PCR primers incorporated into the extended nucleic acid strand (with which a nucleic acid probe useful herein is designed to hybridize) that are not labeled, whereas primers for the complementary strand are labeled, such as with biotin. Then, the amplified nucleic acid is denatured and added to streptavidin linked to a solid support. A useful material is Streptavidin MagneSphere® paramagnetic particles (Promega, Z548A), where a magnet can be used to separate the desired target nucleic acid strand from its biotinylated complementary strand.

B. Exonuclease Digestion

In other embodiments of the present invention, a method comprises depolymerizing the nucleic acid at a 3'-terminal nucleotide by enzymatically cleaving the terminal internucleoside phosphodiester bond to form an XMP as illustrated by the following reaction on double-stranded DNA having a 5'-overhang:

5'... GpCpTpApApGpT-3'OH
3'... CpGpApTpTpCpApCpTp-5'

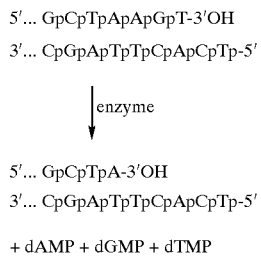

5'... GpCpTpA-3'OH
3'... CpGpApTpTpCpApCpTp-5'

+ dAMP + dGMP + dTMP

For example, such a hydrolysis reaction can be catalyzed by Klenow or Exonuclease III in the presence or absence of NTPs.

In some embodiments (e.g., quantitative assays for nucleic acids), the depolymerizing step is repeated essentially to completion or equilibrium to obtain at least two nucleotide molecules from a strand of minimally three nucleotides in order to increase detection sensitivity. In alternative embodiments, (e.g., qualitative detection of DNA), the depolymerizing step need not be repeated if there are sufficient nucleic acid molecules present to generate a signal.

In another embodiment of the present invention, terminally mismatched hybridized nucleic acid probes are first depolymerized into NMP or dNMP by exonuclease digestion according to the following reaction:

Reaction 2: $NA_n + H_2O \rightarrow NA_{n-1} + XMP$ wherein $NA_n$ is a nucleic acid, XMP is either a dNMP or NMP, and n is the number of nucleotides in the nucleic acid.

This depolymerization reaction is shown more specifically below in the following reaction on double-stranded DNA having a 5'-overhang and mismatched bases at the 3'-terminus:

5'... CpTpApApGpC-3'OH
3'... GpApTpTpCpApCpTp-5'

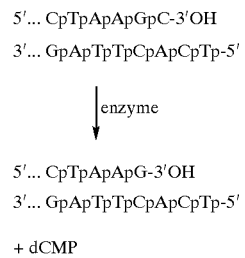

5'... CpTpApApG-3'OH
3'... GpApTpTpCpApCpTp-5'

+ dCMP

For example, such a depolymerization reaction can be catalyzed by bacteriophage T4 polymerase in the absence of NTPS. In preferred embodiments, the released nucleotides, XMPs, are produced by nuclease digestion.

Nuclease digestion can be accomplished by a variety of nucleases that release a nucleotide with a 5' phosphate, including S1 nuclease, nuclease BAL 31, mung bean nuclease, exonuclease III and ribonuclease H. Nuclease digestion conditions and buffers are known in the art. Nucleases and buffers for their use are available from commercial sources.

In the biosynthesis of purine and pyrimidine mononucleotides, phosphoribosyl-1-pyrophosphate (PRPP) is the obligatory ribose-5'-phosphate donor. PRPP itself is formed in a reaction catalyzed by PRPP synthetase through the transfer of pyrophosphate from ATP to ribose-5'-phosphate. This reaction is known to be reversible as described in Sabina et al., *Science*, 223:1193–95 (1984).

In some embodiments of the present invention, the NMP or dNMP produced by nuclease digestion is preferably converted directly to NTP or dNTP by the enzyme PRPP synthetase in the following reaction:

Reaction 3: $XMP + PRPP \rightarrow XTP + ribose\text{-}5'\text{-}PO_4$ wherein XMP is either AMP or dAMP, and XTP is either ATP or dATP. Preferably, this reaction produces a threshold ATP concentration of approximately $1 \times 10^{-12}$ M in 100 µL of sample.

In this reaction, the pyrophosphate group of PRPP is enzymatically transferred to XMP molecules, forming XTP molecules. Examples of suitable reaction conditions and buffers are set forth elsewhere herein.

Utilization of the PRPP reaction in the nucleic acid detection system of the present invention has advantages over previously reported methods. For example, only one step is necessary to convert an AMP or dAMP to ATP or dATP, thereby simplifying the detection system. In addition, contamination of the detection reaction with exogenous ATP, ADP, or AMP is less likely using methods of the present invention, as compared to previously reported methods.

In an embodiment wherein the depolymerizing enzyme exhibits 3'→5' exonuclease activity, the substrate is a double-stranded or single-stranded nucleic acid having a 3'-hydroxyl terminus. Enzymes having 3'→5' exonuclease activity that are useful in a process of the invention include E. coli DNA polymerase I, Klenow fragment and bacteriophage T4 DNA polymerase. E. coli DNA polymerase I holoenzyme is not preferred in a process of the invention because it is preferable to avoid the 5'→3' exonuclease activity that degrades probe:target hybrids regardless of the degree of hybridization at the 3'-terminus. Bacteriophage λ exonuclease has only 5'→3' exonuclease activity, so it is not a contemplated enzyme. Similarly, Taq DNA polymerase has a very low level of 3'→5' exonuclease activity. Exonuclease III (Exo III) has 3' exonuclease activity on blunt-ended substrates or those having 5'-overhangs or nicks with 3'-hydroxyl groups, and is thus useful in a process of the invention for depolymerizing hybrids with matched 3' terminal nucleotides. However, Exo III is not limited to hybrids having only partially complementary 3'-termini, it requires a double stranded end, i.e. a matched terminal nucleotide.

In an embodiment of the invention where the enzyme's activity is a 3'→5' exonuclease activity, the hybridized nucleic acid probe is depolymerized from its 3'-terminal nucleotide. In a preferred embodiment in the case of a 3'→5' exonuclease activity of a polymerase, the preferred substrate is a nucleic acid probe hybridized to a nucleic acid target sequence with partial complementarity at its 3'-terminal region, most preferably with a mismatch at its 3'-terminal residue that is an identifier nucleotide.

A contemplated method is particularly useful in a multiplex assay environment in which a plurality of probes is utilized to determine whether one or more of a plurality of predetermined endogenous nucleic acid sequences is present or absent in a sample. A particularly useful area for such multiplex assays is in screening assays where the usual analytical output indicates that the sought-after gene target is absent.

In one illustrative embodiment, a nucleic acid sample is screened for the presence of a plurality of predetermined mutant genes. In this embodiment, the mutants usually are not present and the analytical output is, for example, at about background levels except where a mutation is present. In another embodiment, a plurality of samples is examined for the presence or absence of microbe-specific genes. Here, again, where a population of healthy individuals, animals, or presumably sterile food is sampled, the absence of the sought-after genes provides an analytical output that is about background levels, and only in the rare instance does a greater than the background output appear.

In a multiplexed embodiment of the above process, the sample is admixed with a plurality of different nucleic acid probes, preferably after amplification of the multiple nucleic acid targets as needed. In this embodiment of the invention, the analytical output for a certain result with one of the probes is distinguishable from the analytical output from the opposite result with all of the probes.

In preferred embodiments, the ATP produced via NDPK conversion of released nucleotides in the presence of ADP is detected by a luciferase detection system or an NADH detection system. In still another embodiment of the present invention, the pyrophosphate transferring step and the phosphate transferring step are performed in a single pot reaction. In other preferred embodiments, if increased sensitivity is required, the ATP molecules can be amplified.

In a contemplated multiplex embodiment, information about the presence or absence of a plurality of endogenous nucleic acid target sequences is determined using a process of the invention on a single nucleic acid sample, by admixing the sample with a plurality of nucleic acid probes for the various endogenous nucleic acid targets.

In a first multiplex embodiment of the invention, the analytical output obtained when at least one of the nucleic acid probes hybridizes with partial complementarity to its target nucleic acid sequence is greater than the analytical output when all of the nucleic acid probes hybridize with total complementarity to their respective nucleic acid target sequences. Preferably, in such an embodiment, the enzyme whose activity is to depolymerize hybridized nucleic acid to release nucleotides exhibits a 3'→5'-exonuclease activity, depolymerizing hybridized nucleic acids having one or more mismatched bases at the 3'-terminus of the hybridized probe.

In a second multiplex embodiment of the invention, the analytical output obtained when at least one of said nucleic acid probes hybridizes with partial complementarity to its target nucleic acid sequence is less than the analytical output when all of the nucleic acid probes hybridize with total complementarity to their respective nucleic acid target sequences. Preferably, in such an embodiment, the enzyme whose activity is to depolymerize hybridized nucleic acid to release nucleotides is a template-dependent polymerase.

In a third multiplex embodiment of the invention, the analytical output obtained when at least one of said nucleic acid probes hybridizes with total complementarity to its nucleic acid target sequence is greater than the analytical output when all of the nucleic acid probes hybridize with partial complementarity to their respective nucleic acid target sequences. Preferably, in such an embodiment, the enzyme whose activity is to depolymerize hybridized nucleic acid to release nucleotides is a template-dependent polymerase.

In a fourth multiplex embodiment of the invention, the analytical output obtained when at least one of said nucleic acid probes hybridizes with total complementarity to its target nucleic acid sequence is less than the analytical output when all of the nucleic acid probes hybridize with partial complementarity to their respective nucleic acid target sequences. Preferably, in such an embodiment, the enzyme whose activity is to depolymerize hybridized nucleic acid to release nucleotides exhibits a 3'→5'-exonuclease activity, depolymerizing hybridized nucleic acids having one or more mismatched bases at the 3'-terminus of the hybridized probe.

Analytical Output

The analytical output is obtained by detection of the released identifier products, either the released nucleotides or the remainder of the probe. Exemplary detection systems include the light emitting luciferase detection system, the NADH light adsorption detection system (NADH detection system), fluorescence emissions and mass spectrometry. These detection systems are discussed hereinbelow.

The fact that nucleotides were released (a qualitative determination), or even the number of nucleotides released (a quantitative determination) can be deduced through examination of the probe after depolymerization. The determination of the size of an oligonucleotide is well known in the art. For example gel separation and chromatographic separations are well known. Gel imaging techniques that take advantage of fluorescence and absorbance spectroscopy as well as radiographic methods. Mass spectrometry of oligonucleotides is also becoming more common.

A. Detection Of ATP

Luciferase detection systems are particularly useful for detecting ATP. In the presence of ATP and oxygen, luciferase catalyzes the oxidation of luciferin, producing light that can then be quantified using a luminometer. Additional products of the reaction are AMP, pyrophosphate and oxyluciferin.

In particularly preferred embodiments, ATP detection buffer referred to as L/L reagent (Promega, FF2021) is utilized. In some embodiments, Luciferase Assay Reagent (LAR) buffer (Promega, E152A) is used instead of L/L reagent. Preferably, about 5 to 10 ng of luciferase are used in the reaction. Although it is not intended that the present invention be limited to a specific concentration of luciferase, greater amounts of luciferase have a tendency to increase non-specific background.

It is contemplated that in some embodiments, the dNTPs or NTPs produced by pyrophosphorolysis or nuclease digestion are converted to XTP, which can then be used directly as substrate for luciferase, permitting detection of the nucleic acid. However, the preferred substrate for luciferase is ATP, as demonstrated by Moyer and *Henderson, Anal. Biochem.,* 131:187–89 (1983). When DNA is the initial substrate, NDPK is conveniently utilized to catalyze the conversion of dNTPs to ATP by the following general reaction:

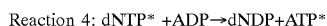

Reaction 4: dNTP* +ADP→dNDP+ATP* wherein dNTP is a mixture of deoxyribonucleoside triphosphates and dNDP is the corresponding deoxyribonucleoside diphosphate. In Reaction 4, the terminal 5'-triphosphate (P*) of the dNTP is transferred to ADP to form ATP.

Enzymes catalyzing this reaction are generally known as nucleoside diphosphate kinases (NDPKs). NDPKs are ubiquitous, relatively nonspecific enzymes. For a review of NDPK, see Parks and Agarwal, in *The Enzymes,* Volume 8, P. Boyer Ed. (1973).

The conversion of NTPs or dNTPs to ATP by NDPK is preferably accomplished by adding NDPK and a molar excess of ADP over the amounts of NTPs or dNTPs expected to be produced by pyrophosphorolysis or nuclease digestion, followed by pyrophosphorylation by PRPP synthetase. The utilization of ADP requires optimization of the amount of ADP added. Too much ADP results in high background levels.

NDPK (EC 2.7.4.6) preparations from several biological sources are commercially available from several suppliers. For example yeast NDPK is available from Sigma Chemical Co., St. Louis, Mo., whereas bovine NDPK is available from ICN Biochemicals, Inc., Costa Mesa, Calif. The particular NDPK selected for most uses described herein is typically a matter of choice.

A further embodiment of the invention, such as is used for Single Tandem Repeat (STR) detection, contemplates a method for determining the number of known repeated sequences that are present in a nucleic acid target sequence in a nucleic acid sample. A method for determining the number of repeated known sequences comprises the following steps. A plurality of separately treated samples is provided. Each sample contains a nucleic acid target sequence, containing a plurality of known repeated sequences and a non-repeated region, hybridized with a nucleic acid probe. Each nucleic acid probe contains a different number of complementary known repeated sequences of alleles of the target nucleic acid, an identifier nucleotide in the 3'-terminal region and a 5'-terminal locker sequence that is complementary to the non-repeated region of the target. A treated reaction mixture is formed by admixing each treated sample with a depolymerizing amount of an enzyme whose activity is to release one or more nucleotides from the 3'-terminus of a hybridized nucleic acid probe. The treated reaction mixture is maintained for a time period sufficient to permit the enzyme to depolymerize the hybridized nucleic acid probe and release an identifier nucleotide. The samples are analyzed for the presence or absence of released identifier nucleotide to obtain an analytical output. The analytical output from the sample whose probe contained the same number of sequence repeats as present in the target nucleic acid is indicative of and determines the number of sequence repeats present in the nucleic acid target.

In one aspect of the method, the target nucleic acid is homozygous with respect to the number of the repeated sequences at the two alleles. In an alternative method of the invention, the target nucleic acid is heterozygous for the repeated sequences. In another method of the invention, an identifier nucleotide is a nucleotide that is part of the region containing a repeated sequence. In an alternative method of the invention, an identifier nucleotide of the probe sequence is part of the region containing a non-repeating sequence that is complementary to that located in the target nucleic acid 5' to the repeated sequences. In this latter aspect of the method, the identifier nucleotide is present in a sequence containing 1 to about 20 nucleic acids that is complementary to a non-repeating sequence of the target nucleic acid located in the probe 3' to the repeated sequences. The repeated known sequence present in a nucleic acid target sequence typically has a length of 2 to about 24 bases per repeat. Di- and tri-nucleotide repeats are well known in the art.

A contemplated thermostable NDPK, such as Pfu NDPK, is advantageously utilized in a so-called one-step or one-pot method of this invention. Here, a treated sample that may contain the predetermined nucleic acid target sequence hybridized with a nucleic acid probe that includes an identifier nucleotide in the 3'-terminal region is admixed with a depolymerizing amount of an enzyme whose activity in the presence of pyrophosphate is to release identifier nucleotides as nucleoside triphosphates from the hybridized nucleic acid probe, adenosine 5' diphosphate (ADP), pyrophosphate and NDPK to form a treated reaction mixture. The treated reaction mixture so formed is maintained for a time period sufficient to permit the enzyme to depolymerize the probe and to permit NDPK to convert the XTP present into ATP (as shown in reaction 4). The amount of ATP formed is determined by the production of an analytical output, with that output providing the indication of the presence or absence of the presence of the target nucleic acid sequence.

Although yeast, bovine or another NDPK can be used in these reactions, it is preferred to utilize a thermostable NDPK such as the Pfu NDPK along with a thermostable depolymerizing enzyme such as the Tne triple mutant DNA polymerase (discussed below), Bst DNA polymerase, Ath DNA polymerase, Taq DNA polymerase and Tvu DNA polymerase along with a reaction temperature of about 50° C. to about 90° C. The use of these thermostable enzymes at an above temperature can enhance the sensitivity of the method.

The Tne triple mutant DNA polymerase is described in detail in WO 96/41014, whose disclosures are incorporated by reference, and its 610 residue amino acid sequence is provided as SEQ ID NO:35 of that document. That enzyme is referred to in WO 96/41014 as Tne M284 (D323A, D389A).

Briefly, that enzyme is a triple mutant of the polymerase encoded by the thermophilic eubacterium *Thermotoga neapolitana* (ATCC 49049). The amino-terminal 283 residues of the native sequence are deleted and the aspartic acid residues at positions 323 and 389 of the native sequence are replaced by alanine residues in this recombinant enzyme. This recombinant enzyme is thus a deletion and replacement mutant of the native enzyme.

Deletion of the amino-terminal sequence removes the 5' exonuclease activity of the native enzyme, whereas replacement of the two aspartic acid residues removes a magnesium binding site whose presence facilitates exonuclease activity, and this triple mutant also exhibited no 3' exonuclease activity relative to the recombinant native enzyme. This triple mutant enzyme exhibited a half-life at 97.5° C. of 66 minutes as compared to the full length recombinant enzyme that exhibited a half-life of only 5 minutes at that temperature.

A reaction containing NDPK contains about 0.01 to 0.50 $\mu$M ADP, preferably about 0.05 $\mu$M ADP. Various useful buffers and other reaction components are set forth elsewhere. NDPK is itself present in an amount sufficient to catalyze the desired conversion of ADP to ATP. In a typical assay starting from a 20 $\mu$L depolymerization reaction, about 0.1 U of NDPK are used.

Where larger volumes of reactants are used, with the target and probe concentrations being approximately proportionally larger, the amount of NDPK or the other enzymes discussed herein can be used in a similar larger proportion relative to the amount discussed for the 20 $\mu$L reaction. Indeed, a 20 $\mu$L reaction has been successfully scaled down about two fold and scaled upwardly by a factor of about 20.

B. NADH Detection

In the NADH detection system, a combination of two enzymes, phosphoglycerate kinase and glyceraldehyde phosphate dehydrogenase, is used to catalyze the formation of NAD from NADH in the presence of ATP. Because NADH is fluorescent whereas NAD is not, ATP is measured as a loss in fluorescence intensity. Examples of NADH based ATP assays are disclosed in U.S. Pat. Nos. 4,735,897, 4,595,655, 4,446,231 and 4,743,561, and UK Patent Application GB, 2,055,200, all of which are herein incorporated by reference.

C. Mass Spectrometric Analysis

In one method of the invention, the presence of released nucleotides is analyzed via mass spectrometry. In an embodiment of a method using mass spectrometry, the treated reaction mixture is ionized in a manner such that all components of the treated reaction mixture in the molecular weight range of the released identifier nucleotides are measured. Very small differences in molecular weight can be detected using mass spectrographic methods (different isotopes of the same atom are detectable), so any variation from a natural nucleic acid, including a single atom substitution (e.g. a fluorine in place of a hydrogen atom or a replacement of a hydrogen by a deuterium atom) in the identifier nucleotide gives rise to a detectable difference. Nucleic acid analogs used in methods of the invention should not interfere with either the hybridization of the nucleic acid probe or depolymerization of the hybridized probe.

Additionally, mass spectrometry can discriminate between individual nucleotides or nucleosides. For example, if the 3'-identifier nucleotide used in the instant invention was a G nucleotide, mass spectrometry can be used to detect the release of that G nucleotide in a method of the present invention. Similarly, mass spectrometry can detect the release of an A, T or C nucleotide, based on the differences in atomic weight of these compounds. Thus, in a multiplexing embodiment of the present invention, mass spectrometry can be used to resolve the presence of one or more of these 3'-identifier nucleotides.

In a particularly useful aspect of this embodiment, a mass spectral technique referred to as DIOS (desorption/ionization on silicon) was recently reported by Wei et al., *Nature*, 399:243(1999) that can accurately perform one or multiple assays on picogram or attagram amounts using commercially available mass spectrographs adapted with a specialized porous silicon sample well. The older, well known, MALDI mass spectrographic assay techniques can also be utilized.

In an embodiment of a multiplex method using mass spectrometry, multiple different identifier nucleotides can be used in the various nucleic acid probes. Using such a technique the presence of the different identifier nucleotides is direct evidence of the presence of the nucleic acid target sequences.

D. Fluorescence Spectroscopic Analysis

A wide variety of fluorescence detection methods can be used herein. In one exemplary contemplated method, an identifier nucleotide includes a fluorescent label. An identifier nucleotide can be fluorescently labeled prior to, or after, release of the identifier nucleotide. In one embodiment when the nucleotide is a fluorescent label, the analytical output is obtained by fluorescence spectroscopy. In an alternative embodiment when the nucleotide is a fluorescent label, the analytical output is obtained by mass spectrometry.

In a preferred embodiment of the invention, the fluorescent label is part of a fluorescent analog of a nucleotide. Fluorescent nucleotide analogs are widely known and commercially available from several sources. An exemplary source is NEN™ Life Science Products (Boston, Mass.), who offer dideoxy-, deoxy-, and ribonucleotide analogs a labeled with fluorescein, coumarin, tetramethylrhodamine, naphthofluorescein, pyrene, Texas Red®, and Lissamine™. Other suppliers include Amersham Pharmacia Biotech (Uppsala, Sweden; Piscataway, N.J.) and MBI Fermentas, Inc. (Amherst, N.Y.).

An advantage to using fluorescent labels and fluorescence spectroscopy analysis is that there are multiple different labels. Such different labels would be particularly useful in a multiplex embodiment of the invention. Different fluorescent labels would be used in different probes, so that the detection of a particular fluorescently-labeled nucleotide analog as a released identifier nucleotide could be used to deduce which nucleic acid targets are present.

For example, fluorescein has a 488 nm excitation and 520 nm emission wavelength, whereas rhodamine (in the form of tetramethyl rhodamine) has 550 nm excitation and 575 nm emission wavelength. A fluorescence detector provides an excitation source and an emission detector. The emission wavelengths of 520 nm and 575 nm are easily distinguishable using fluorescence spectroscopy.

On a per molecule basis, fluorescence spectroscopy is about 10-fold more sensitive than absorbance spectroscopy. A very wide variety of fluorescence spectroscopy-based detectors are commercially available for reading fluorescence values of single tubes, flow cells and multi-well plates, among others. For example, Labsystems Multiskan models of microplate readers are widely available with a spectral range of 400 to 750 nm, and filters for 340, 405, 414, 450, 492, 540, 620, and 690 nm (e.g. Fisher Scientific, Pittsburgh, Pa.).

It is contemplated that a released identifier nucleotide could be labeled before or after depolymerization using cross-linking chemistry well known in the art with commercially available reagents. For example, fluorescein isothiocyanate and rhodamine B isothiocyanate are both available from Aldrich Chemical Company (Milwaukee, Wis.). References to fluorescein isothiocyanate's use in labeling biological molecules include *Nature*, 193:167 (1962), *Methods Enzymol.* 26:28 (1972), *Anal. Biochem.*, 57:227 (1974), *Proc. Natl. Acad. Sci., U.S.*, 72:459 (1975).

It is contemplated that for many embodiments of the invention, it is useful to separate released fluorescent identifier nucleotides from those bound to an oligonucleotide, such as a probe. Thus, the separation techniques well known in the art and discussed above are useful with such an embodiment, including HPLC fitted with a fluorescence detector. The enhanced sensitivity of fluorescence relative to other spectroscopic techniques can be used to increase the sensitivity of a detection or quantification process of the invention.

E. Absorbance Spectroscopic Analysis

An absorbance spectrographic analysis step is contemplated to provide an analytical output, thereby provide for the determination of the presence or absence released identifier nucleotide, and indicate the presence or absence of said nucleic acid target sequence. This embodiment contemplates the chromatographic separation of a reaction mixture that has been treated with a depolymerizing amount of an enzyme whose activity is to release one or more nucleotides from the 3'-terminus of a hybridized nucleic acid.

In an illustrative embodiment, a multiplexed assay for the presence of several different nucleic acid target sequences in a sample is analyzed by absorbance spectroscopy. Several labeled probes to various nucleic acid target sequences are added to a nucleic acid sample. The labels on the probes may be various nucleotide analogs, a different one for each probe. A depolymerizing enzyme is added, such as Klenow exo-, releasing the labeled nucleotides and other nucleotides from the 3'-termini of probes hybridized to target sequences when the 3' terminal nucleotide is matched.

The reaction solution is loaded onto a pre-equilibrated High Pressure Liquid Chromatography (HPLC) column and eluted under conditions that separate the nucleotide analogs from the natural nucleotides. Useful media for chromatographic separation of nucleotides, bases, and nucleosides include reverse phase media, such as a reverse phase C18 column or ODS-80TM or ODS-120T TSK-GEL by Toso-Haas (Montgomeryville, Pa.), anion exchange media, such as DEAE-25SW or SP-25W TSK-GEL by TosoHaas (Montgomeryville, Pa.), or affinity media, such as Boronate-5PW TSK-GEL by TosoHaas (Montgomeryville, Pa.). Example 20 illustrates an embodiment of the present invention using HPLC.

The HPLC column is fitted with an absorbance detector to monitor the column effluent. Hence, "absorbance spectroscopy" for this type of analysis. Typical wavelengths for monitoring HPLC detection of nucleotides are 250 nm, 260 nm and 280 nm. Such separations of nucleotides and nucleotide analogs are well known in the art. Revich et al., J. Chromatography, 317:283–300 (1984), and Perrone & Brown, J. Chromatography, 317:301–310 (1984) provide examples of the HPLC separation of dNTPs.

Identification of the separated nucleotide analogs can be accomplished by comparison of the retention times (as monitored by absorbance of effluent at various times) of standards of the nucleotide analogs separated on the same HPLC column under the same conditions. Alternatively, the identity of the nucleotide analogs collected in separate fractions (as determined by continually monitoring the absorbance of the column effluent) can be determined by other standard analytical methods, such as nuclear magnetic resonance or atomic analysis (H,C,N).

In this illustrative example using depolymerization with Klenow exo-, the presence of a released identifier nucleotide from a particular probe indicates the presence of the target sequence that hybridize with that probe.

In an alternative embodiment, the released nucleotides from a depolymerization reaction mixture are separated on a gas chromatograph fitted with an absorbance detector to monitor column effluent.

Coupled Reactions

In some embodiments, certain of the above reactions can be performed as single pot reactions. A "single pot reaction" is a reaction wherein at least two enzymes (i.e., E1 and E2) with catalytic activity are present in the same reaction mix and act on one or more substrate(s) (i.e., S1 and S2). In some embodiments, the reactions catalyzed by the enzymes occur simultaneously where E1 acts on S1 and E2 acts on S2. Alternatively, the reactions catalyzed by E1 and E2 can occur in a step-wise or coupled manner (e.g., where E1 acts on S1 to produce an intermediate $S2_i$ and E2 then acts on $S2_i$). Of course, in yet other embodiments, such a coupled reaction can also be essentially simultaneous.

The ability to utilize combinations or mixtures of the enzymes of the present invention in single pot reactions is surprising, in light of the extremely low levels of nucleic acid detection that are achieved using the present invention. This low level detection is possible even though some enzymes are used under suboptimal conditions. As previously described, it was found to be necessary to optimize the concentration of $PP_i$ utilized in the pyrophosphorolysis reactions to minimize inhibition of luciferase. Therefore, aliquots from the NMP-, dNMP-, NTP-, dNTP- and ATP-producing reactions can be directly added to L/L Reagent for luciferase detection without any purification of the reaction products. The luciferase reaction is not poisoned or otherwise quenched by the components of the reactions. This desirable feature permits automation and high throughput analysis with a minimal amount of time and effort, and it also permits great flexibility in the design of the overall detection schemes. However, it is not intended that the present invention be limited to any particular reaction condition, reagents, or embodiments.

In some preferred embodiments, the pyrophosphorolysis reaction producing dNTP and the NDPK catalyzed reaction in which the NTPs or dNTPs are converted to ATP are performed in a single pot reaction in the nucleic acid polymerase buffer in these embodiments. NDPK activity is sufficient to convert dNTP to ATP, even though the polymerase buffer conditions are suboptimal for NDPK activity.

The polymerase enzyme and NDPK can both be present initially in the reaction, or the NDPK can be added directly to the reaction after an incubation period sufficient for the production of NTP or dNTP. Alternatively, a nucleic acid polymerase and NDPK can be provided in the same vessel or mixture for use in the reactions described above. The mixture preferably contains the nucleic acid polymerase and NDPK in a concentration sufficient to catalyze the production of ATP when in the presence of a nucleic acid, pyrophosphate and ADP.

Preferably, the polymerase is provided in a concentration of about 0.1 to 100 U/reaction (i.e., where "U" is units) most preferably at about 0.5 U/reaction. Preferably, the NDPK is provided in a concentration of 0.1 to 100 U/reaction, most preferably at about 0.1 U/reaction. In further preferred embodiments, the mixture is substantially free of contaminating ATP.

Similarly, the PRPP synthetase and NDPK reactions can be carried out in a single pot reaction in the PRPP synthetase buffer. Again, in these embodiments, NDPK activity is sufficient even though conditions for NDPK activity are suboptimal.

The nuclease-digested sample containing free NMPs and dNMPs can be added to a reaction mix initially containing PRPP synthetase and NDPK, or added to a PRPP synthetase reaction followed by addition to a reaction mix containing NDPK. By way of example, certain preferred buffers and reaction components can be found in the Examples. However, it is not intended that the present invention be limited to specific buffers or reaction components.

PRPP synthetase and NDPK can be provided in the same vessel or mixture for use in the reactions described above. The mixture preferably contains the PRPP synthetase and NDPK in a concentration sufficient to catalyze the production of ATP when in the presence of PRPP and ADP. Preferably, the NDPK is provided in a concentration of 0.1 to 100 U/reaction, most preferably at about 0.1U/reaction. Preferably, the PRPP synthetase is provided in a concentration of 0.001 to 10 U/reaction, most preferably at about 0.01 U/reaction. If amplification is desired, the PRPP synthetase reaction is preferably heat inactivated, otherwise the PRPP synthetase converts the added AMP to ATP.

The pyrophosphorolysis reaction and amplification reaction can also be performed in a single pot reaction. In this single pot reaction, poly(A) polymerase or any suitable template-dependent polymerase can be used, including, but not limited to, AMV reverse transcriptase, MMLV reverse transcriptase, DNA polymerase alpha or beta, Taq polymerase, Tth polymerase, Tne polymerase, Tne triple mutant polymerase, Tvu polymerase, Ath polymerase, *E. coli* DNA polymerase I, T4 DNA polymerase, Klenow fragment, Klenow exo minus, or poly(A) polymerase.

In some embodiments, a first enzyme for converting AMP to ADP can be myokinase (e.g., adenylate kinase) or NMPK, and in other embodiments, a second enzyme for converting ADP to ATP can be pyruvate kinase or NDPK. In addition, in preferred embodiments, the reaction is fed AMP. In particularly preferred embodiments, apyrase-treated AMP is utilized to reduce background due to contaminating ADP and ATP. Preferably 1 µL of 1 U/µL apyrase is added to 19 µL of 10 mM AMP, followed by incubation at room temperature for 30 minutes and heat inactivation of the apyrase by incubation at 70° C. for 10 minutes.

High energy phosphate donors are also added to the reaction. In preferred embodiments, when pyruvate kinase is utilized, PEP is added. In other preferred embodiments, when NDPK is utilized, dCTP is added. Preferably, the high energy phosphate donor is added about 15 minutes after a pre-incubation with the polymerase, although this is not necessary. These reactions can be characterized as follows:

Reaction 5: $NA_n+PP_i \rightarrow NA_{n-1}+XTP$ $XTP+AMP \rightarrow ADP+XDP$
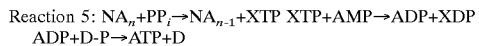

wherein NA is a nucleic acid, XTP is a nucleoside triphosphate (either a deoxynucleoside or ribonucleoside triphosphate), XDP is a nucleoside diphosphate (either a deoxynucleoside or ribonucleoside diphosphate), and D-P is a high energy phosphate donor. It should be appreciated that this reaction produces ATP, the preferred substrate for luciferase, from dNTPs.

The amplification reaction proceeds as described in reaction 5 to produce a threshold ATP concentration of approximately $1 \times 10^{-12}$ Molar in 100 µL of sample. Preferably, the polymerase is provided in a concentration of about 0.1 to 100 U/reaction, most preferably at about 0.5 U/reaction. Preferably, the NDPK is provided in a concentration of 0.1 to 100 U/reaction, most preferably at about 0.1 U/reaction. Preferably, the mixture is substantially free of contaminating ATP.

Probe-Mediated Specific Nucleic Acid Detection

Depolymerization reactions can be used to interrogate the identity of a specific base in a nucleic acid. For example, the identity of single base point mutations, deletions, or insertions in a nucleic acid can be determined as follows.

In one embodiment, a nucleic acid probe is synthesized that is substantially complementary to a target nucleic acid containing or suspected of containing a point mutation. It will be recognized that various hybridization conditions can be used, so as to vary the stringency at which hybridization occurs. Thus, depending upon the system utilized, the complementarity of the probe can be varied. Depending on the length of the probe, the GC content, and the stringency of the hybridization conditions, the probe can have as many as 10 base mismatches with the target nucleic acid, and preferably less than 5 mismatches. Most preferably, the probe has only one base mismatch with the target nucleic acid or is completely complementary to the target nucleic acid.

The nucleic acid probe comprises single-stranded nucleic acid (e.g., DNA or RNA). The probe can be of varying lengths, preferably from about 10 to 100 bases, most preferably about 10 to 30 bases. In particularly preferred embodiments, the probe is complementary to the target at all bases between an interrogation position and 3' end of the nucleic acid probe.

In preferred embodiments, the probe is designed to have a predetermined nucleotide at an interrogation position. When the complementary probe base pairs or hybridizes to the target nucleic acid, the base at an interrogation position aligns with the base in the nucleic acid target whose identity is to be determined under conditions such that base pairing can occur. It is contemplated that an interrogation position can be varied within the probe. For example, in some preferred embodiments, an interrogation position is preferably within 10 bases of the 3' end of the nucleic acid probe. In still other preferred embodiments, an interrogation position is within 6 bases of the 3' end of the nucleic acid probe. In particularly preferred embodiments, an interrogation position is at the next to last or last base at the 3' end of the nucleic acid probe.

In some preferred embodiments, four different probes of equal length are synthesized, each having a different nucleotide at an interrogation position. Accordingly, it is contemplated that in some embodiments, a set of DNA probes includes a first probe with a deoxyadenosine residue at an interrogation position, a second probe with a deoxythymidine residue at an interrogation position, a third probe with a deoxyguanosine residue at an interrogation position, and a fourth probe with a deoxycytosine residue at an interrogation position. Likewise, it is also contemplated that a set of RNA probes includes a first probe with an adenosine residue at an interrogation position, a second probe with a uridine residue at an interrogation position, a third probe with a guanosine residue at an interrogation position, and a fourth probe with a cytosine residue at an interrogation position.

In the next step of some embodiments, the probe or probes are hybridized to the target nucleic acid in separate reactions so that a probe nucleic acid-target nucleic acid complex is formed. It is contemplated that hybridization conditions can vary depending on the length and base composition of the probe. In the probe-target nucleic acid complex, the nucleotide at an interrogation position is aligned with the specific base to be identified in the nucleic acid. In embodiments in which a set of probes is utilized, a different reaction is performed with each probe. In a multiplex embodiment, the set of probes can be used simultaneously. Because the probes differ at an interrogation position, only one of the probes is complementary to the specific base in the target nucleic acid that is aligned with an interrogation position.

In the next step of some embodiments, the nucleic acid probe-target nucleic acid complexes are individually reacted under conditions permitting depolymerization of the probe. The preferred reaction conditions for depolymerization are described above and in the following Examples. The nucleotides are then detected. In preferred embodiments, the reaction mix also contains reagents necessary to catalyze the conversion of XTP to ATP equivalents as described in reaction 4 and in the following Examples. In some preferred embodiments, the nucleotides and/or ATP produced by the depolymerization reaction are then detected by either a luciferase or NADH detection system. Complementarity of the base at an interrogation position of the nucleic acid probe to the corresponding base in the nucleic acid target is characterized by detection of a signal generated from ATP following depolymerization.

In particularly preferred embodiments, the identity of the specific base is determined by comparing the amount of ATP produced in each reaction. Depolymerization of the probe proceeds from its 3' end. When the base at an interrogation position is not complementary to the specific base in he nucleic acid, very little or no ATP is produced, and thus no signal results. In alternative embodiments, this method can be practiced with from one to four probes. It is contemplated that utilizing multiple probes, (e.g., each with a different base at an interrogation position), may prove unnecessary if a positive signal is produced (e.g., with the first probe tested).

In yet another preferred embodiment, the probe-mediated specific nucleic acid detection method of the present invention can be used to simply identify or detect a nucleic acid of interest. For this method, a nucleic acid probe (e.g., DNA or RNA) is utilized which is substantially complementary to the target nucleic acid;, which can be RNA or DNA. In a particularly preferred embodiment, the nucleic acid probe is entirely complementary to the target nucleic acid. The nucleic acid probe comprises single-stranded nucleic acid (e.g., DNA or RNA). The probe can be of varying lengths, preferably from about 10 to about 1000 bases, most preferably about 10 to 100 bases. Detection is carried out as described above. The nucleic acid probe-nucleic acid target complex is exposed to conditions permitting depolymerization of the probe, which results in the production of XTPs. Detection of the nucleic acid of interest is characterized by a difference in the signal generated by the XTPs produced. Preferably, the XTPs are converted to ATP as described above and the ATP detected by a luciferase or NADH detection system.

In another embodiment, the presence or absence of a lesion in the target nucleic acid can be detected. A lesion may either be an insertion mutation or a deletion mutation in the wild-type target nucleic acid. The wild-type target nucleic acid contains a region of complementarity, to which the nucleic acid probe can hybridize. Thus, the region of complementarity in the wild-type target nucleic acid is defined by the 5' and 3' ends of the nucleic acid probe. When the region of complementarity contains a lesion, the nucleic acid probe may still hybridize to the target nucleic acid, but the hybridization is only partial. Depending on the size and nature of the lesion, either the 5' or 3' end of the probe may hybridize to the target nucleic acid, or a hybridization structure characterized by the presence of a loop may be formed. In each of these cases, depolymerization will be prevented. Preferably, the nucleic acid probe is designed so that the lesion to be detected begins about less than ten bases from 3' end of the probe, preferably less than about 6 bases. The nucleic acid probe comprises single-stranded nucleic acid (e.g., DNA or RNA). The probe can be of varying lengths, preferably from about 10 to about 1000 bases, most preferably about 10 to 100 bases.

Detection of a nucleic acid containing a lesion is characterized by the difference of a signal generated from the XTP produced. Preferably, the XTPs are converted to ATP as described above and the ATP detected by a luciferase or NADH detection system.

It is contemplated that an increase in the signal (analytical output) produced by the probe-mediated specific nucleic acid detection methods of the invention can be realized by a novel cycling method. In this embodiment of the invention, two probes are designed that are complementary to each other and have a 3' overhang at each end when they hybridize to one another. In preferred embodiments, the probes are designed so that the 3' overhang is a single base overhang. In alternative embodiments, the probes also can hybridize to a target nucleic acid. In particularly preferred embodiments, a polymerase that acts from the 3' end of nucleic acids and does not recognize 3' overhangs is utilized for the depolymerization reaction, such as Klenow exo-.

In preferred embodiments, the first step of the reaction involves hybridization of an excess of one of the probes to the target nucleic acid in the presence of the polymerase and under conditions permitting depolymerization as described above. In some embodiments, no 3' overhang exists, and the depolymerase reaction proceeds from the 3' end of the probe. In some embodiments, the reaction is terminated by separating the probe from the target nucleic acid by heating the probe-target nucleic acid complexes. On average, as few as one base is removed from probes that were bound to the target nucleic acid, and fractions of shortened probes are created.

In the second step, an excess of the second probe is added to the reaction. Due to the law of mass action, the shortened probes produced in the first step have a tendency to bind to the newly added complementary probes, whereas the non-shortened probes bind to the target nucleic acid. The shortened probes that bind to the complementary probes produce a complex with no 3' overhang on one end, and are depolymerized. This effectively doubles the amount of substrate available for the depolymerization reaction. Steps one and two can be repeated additional times until the desired level of detection is achieved. In an alternative preferred embodiment, the reactions can be coupled with NDPK as described above, to produce ATP equivalents that are detectable by a luciferase-based or NADH-based assay system.

The ability to interrogate the identity of a specific base in a nucleic acid also permits discrimination between nucleic acids from different species, or even from different alleles. The ability to detect and discriminate between nucleic acids of related or unrelated species also permits the identification of species contained within a given nucleic acid-containing sample. For example, the method can be used to determine which species of several related bacteria are contained within a sample (e.g., clinical samples, environmental samples, or samples from non-human animals).

In preferred embodiments of this method, nucleic acids with substantially identical sequences from at least two species or alleles are detected. The region of identity (target nucleic acid sequence) contains at least a single nucleotide mismatch between the species or alleles in at least one predetermined position and also contains a 3' end and a 5' end or the identification of a nucleic acid sequence unique to each species to be identified.

Next, in some embodiments, an RNA or DNA probe that is substantially complementary to the region of identity is synthesized. The probe can be of varying lengths, preferably from about 10 to 1000 bases, most preferably about 10 to 100 bases. As above, this complementary probe includes an interrogation position.

An interrogation position can be varied within the probe. For example, an interrogation position is preferably within 10 bases of the 3' end of the nucleic acid probe. More preferably, an interrogation position is within 6 bases of the 3' end of the nucleic acid probe. Most preferably, an interrogation position is at the next to last or last base of the 3' end of the nucleic acid probe.

The nucleic acid probes are designed so that the base at an interrogation position is complementary to the nucleotide at the predetermined position of one species or allele, but not another due to the mismatch. Likewise, a second probe can be synthesized that is complementary at an interrogation position to the nucleotide at the predetermined position of a second species or allele.

This same procedure can be employed to identify the presence or absence of multiple species within a given sample. In these embodiments, all that is required is the identification of substantially identical sequences between species that contain base mismatches or the identification of a nucleic acid sequence unique to each species to be identified. Similarly, this procedure can be used for quantitative analysis of the number of alleles at a loci in a sample. By comparing the quantity of analytical output relative to an appropriate internal or external control, the number of alleles at a locus can be determined. These comparative quantities can be expressed in terms of the ratio of one allele to the other in one sample versus that same ratio measurement in a control sample. In this process, events such as loss of heterozygosity or trisomy can be detected.

For example, a normal heterozygous control has a ratio of about 1:1 with respect to the two alleles that make up the heterozygote. That is, each allele of the heterozygote can be detected when a nucleic acid probe is used to detect the presence of that allele. If the quantity of analytical output obtained by the release of identifier nucleotide when the first and second alleles are detected is expressed as a ratio, the relative amounts of the first and second allele would be about the same for a sample which is heterozygous at that locus. When a sample has lost heterozygosity, one of the two alleles is not detectable. If the first allele is lost, then the first allele will not be detected in the sample if the sample is assayed using a nucleic acid probe for the first allele. The second allele will, however, be present at a similar amount as would be present in a known heterozygous control sample, so assaying the sample with a nucleic acid probe for the second allele will provide an analytical output. If the quantity of the analytical output for the first and second alleles for a sample having a loss of heterozygosity of the first allele is expressed as a ratio, the ratio will be about 0:1, indicating the absence of the first allele. Conversely, where the second allele is lost, the ratio of the quantity of analytical output for the first and second allele would be about 1:0, indicating the absence of the second allele.

The presence of trisomy of an allele is detected in a similar fashion. In a trisomy event, four outcomes are possible with respect to a first and second allele. The trisomy can be homozygous for the first allele, in which case three copies of the first allele will be present and no copies of the second allele will be present. Thus, the ratio of the quantity of analytical output for the first and second allele will be 3:0. If the trisomy is homozygous for the second allele, three copies of the second allele will be present. The ratio of the quantity of analytical output for the first and second allele will be 0:3. Two cases of heterozygous trisomy are possible: two copies of allele one and one copy of allele two, or one copy of allele one and two copies of allele two. These two heterozygous trisomy outcomes can be detected by determining the ratios of the quantity of analytical output for the first and second alleles, preferably in comparison to a known heterozygous control sample. If the ratio is 2:1, then the heterozygous trisomy has two copies of the first allele and one copy of the second allele. If the ratio is 1:2, then the heterozygous trisomy has one copy of the first allele and two copies of the second allele.

The use of an appropriate control, for example a heterozygous control, allows the appropriate interpretation of the ratios obtained from the analysis of a sample suspected of having a loss of heterozygosity or of trisomy.

In the next step of some embodiments, separate reactions are performed utilizing each probe. The probes are hybridized to the target nucleic acid to form a probe nucleic acid-target nucleic acid complex. In the probe nucleic acid-target nucleic acid complex, the nucleotide at an interrogation position of the probe is aligned with the nucleotide at the predetermined position in the nucleic acid, so that base pairing occurs. The probe-target nucleic acid complex is then reacted under conditions permitting depolymerization of the probe from its 3' end.

Preferred conditions for depolymerization (depolymerization conditions) are described herein. The nucleotides are then detected. In some preferred embodiments, the nucleotides are converted to ATP equivalents as described in reaction 4 and in the Examples. In preferred embodiments, the ATP is detected by luciferase or NADH detection systems.

These embodiments of the present invention permit discrimination between nucleic acids from different species or alleles, as NTPs are produced by depolymerization only when the nucleotide at an interrogation position of the probe is complementary to the nucleotide at the predetermined position of the nucleic acid from the species. As described above, significant depolymerization proceeds only if the base at an interrogation position is complementary to the base at the predetermined position in the target nucleic acid. The NTP concentration, including the ATP concentration, differs when a mismatch is present as compared to when a mismatch is not present. These differences can be detected (e.g., by either an ATP or NADH detection system).

A method contemplated by the present invention has wide applicability in assaying nucleic acids. In some aspects, an endogenous nucleic acid is assayed to determine whether a particular native or mutant sequence is present or absent. This type of analysis is sometimes referred to as genotyping because the genetic makeup of the subject from which the nucleic acid sample is obtained is determined. Speciation, the identity of an organism, such as the identification of a human, dog, chicken, bovine or the like can be determined by use of species-specific nucleic acid probes such as probes to selected regions of the gene encoding cytochrome B.

Using a contemplated method, one can illustratively determine whether a human patient, for example, has the Leiden V mutation, a mutant β-globin gene, the cystic fibrosis-related gene in the region of the delta 508 allele, a mutation in a prothrombin gene, congenital adrenal hyperplasia, a translocation that takes place in the region of the bcr gene along with involvement of a segment of the abl gene, the number of repeated sequences in a gene such as are present in THO 1 alleles or the TPOX alleles, as well as the loss of heterozygosity of the locus of certain alleles as is found in certain cancers and also allelic trisomy. Genomic typing can also be used to assay plant genomes such as that of rice, soy or maize, and the genomes of microbes such as *Campylobacter jejuni,* cytomegalovirus (CMV) or human immunodeficiency virus (HIV) to determine whether a drug-resistant strain is present in a sample.

In one illustrative application of a method of the invention, detection of economically significant plant SNPs is performed. In rice, amylose content is generally considered to be the most important factor that determines rice processing and cooking quality. A G T transition in the 5'-leader sequence of the rice starch synthase pre-mRNA alters normal splicing of the message. Reliable and cost-effective detection of economically important SNPs such as the rice starch synthase SNP using a method of the invention provides an important tool to the agricultural industry.

The determination of an appropriate nucleic acid target sequence useful for designing nucleic acid probes for use in a method of the invention is within the skill of the art. Databases of genetic sequences, such as Genbank, can be used to ascertain the uniqueness of the selected nucleic acid target. Commercially available software for designing PCR primers can be used to assist in the design of probes for use in the invention.

Determination of Repeated Sequences

A process of the invention is useful for determining the presence of repeated sequences in a nucleic acid sample. The repeated known sequence present in a nucleic acid target sequence typically has a length of 2 to about 24 bases per repeat. Di- and tri-nucleotide repeats are well known in the art. An application of this process is Single Tandem Repeat (STR) detection. Typically, different alleles of the target nucleic acid have different numbers of the repeated sequences, so the determination of the number of repeats is useful in genotyping. Such methods have important applications in the forensic sciences in identity testing. A method for determining the number of repeated known sequences is as follows.

Special nucleic acid probes are designed and obtained that contain multiples of a known repeating sequence. Each probe contains a different number of a repeated sequence that is complementary to that of the nucleic acid target sequence. Each probe has a 5'-terminal locker sequence that is complementary to the non-repeated region of the target that is downstream of the repeated region in the target. The probes typically have an identifier nucleotide in the 3'-terminal region, but as described herein, the release of nucleotides from the 3' terminus during a depolymerization step of the invention can alternatively be ascertained by the size of the remaining probe.

The use of a 5'-terminal locker sequence fixes the 5'-terminus of the probe relative to the repeated region. Thus, for example when the probe has fewer repeats than the target, it is not free to hybridize anywhere throughout the repeated region, but only along the first matching group of repeats. in this embodiment, the probe will be completely complementary to the target sequence, even though it is shorter than the target. However, when the probe has more repeats than the target, the probe extends into the adjacent non-repeated region and is mismatched at its 3'-terminal region.

In some cases, it is desirable to determine the number of repeats by comparison with standard nucleic acid samples having known numbers of repeats (and how they respond to the various probes). In other cases, the number of repeats can be deduced by the shape of the curve of a graph having its ordinate (x-) axis be the number of repeats in the probe and its abscissa (y-) axis be the analytical output indicating the number of nucleotides released, such as light output in luminescence spectroscopic analysis of all of the released nucleotide converted to ATP.

In such a graph, for example when the depolymerizing enzyme is a template-dependent polymerase or exoIII, the output is greater when the probe has the same or fewer repeats than the target, relative to the output when the probe has more repeats than the target. The S-shaped curve changes most rapidly after the number of repeats in the probe surpasses the number of repeats in the target. Thus, the derivative of the curve is greatest at that point. Similar results when the depolymerizing enzyme preferentially releases nucleotides from mismatched substrates, except that the output is less when the probe has the same or fewer repeats than the target.

Thus, in a preferred embodiment of a process to determine the number of repeats of a known sequence, a plurality of separately treated samples is provided. Each sample contains a nucleic acid target sequence, containing a plurality of known repeated sequences and a downstream non-repeated region on the target relative to the repeated sequences. The sample is hybridized with an above-described nucleic acid probe.

A treated reaction mixture is formed by admixing each treated sample with a depolymerizing amount of an enzyme whose activity is to release one or more nucleotides from the 3'-terminus of a hybridized nucleic acid probe. The treated reaction mixture is maintained for a time period sufficient to permit the enzyme to depolymerize the hybridized nucleic acid probe and release an identifier nucleotide.

The samples are analyzed for the presence or absence of released identifier nucleotide to obtain an analytical output. The analytical output from the sample whose probe contained the same number of sequence repeats as present in the target nucleic acid is indicative of and determines the number of sequence repeats present in the nucleic acid target. The analytical output is obtained by luminescence spectroscopy, mass spectroscopy, fluorescence spectroscopy or absorption spectroscopy, including visualization of the remaining probe, as described herein with regard to the general method of the invention.

In one aspect of the method, the target nucleic acid is homozygous with respect to the number of the repeated sequences at the two alleles. In an alternative method of the invention, the target nucleic acid is heterozygous for the repeated sequences.

In one method of the invention, an identifier nucleotide is a nucleotide that is part of the region containing a repeated sequence. In an alternative method of the invention, the nucleic acid probe further comprises a second non-repeating sequence that is located downstream of the repeated sequences in the probe (3' of them). This second non-repeating sequence is complementary to a non-repeating sequence located in the target nucleic acid 5' to its repeated sequences. In this embodiment, it is contemplated that an identifier nucleotide of the probe sequence is part of the region containing the second non-repeating sequence. Thus, the identifier nucleotide is present in a sequence containing 1 to about 20 nucleic acids that is complementary to a non-repeating sequence of the target nucleic acid located in the probe 3' to the repeated sequences.

Assays Using Hairpin Structures

Although it is preferred that the probes be constructed to be free of hairpin structures, assays in which hairpin structures are constructed are also useful. An embodiment of the invention, such as demonstrated in Example 23, contemplates use of a hairpin structure for determining the presence or absence of a nucleic acid target sequence in a nucleic acid sample with a probe that is hybridized to the target and then modified to be able to form a hairpin structure. This embodiment comprises the following steps.

A treated sample is provided that contains a nucleic acid sample that may include a nucleic acid target sequence having an interrogation position. The target sequence, if present in the nucleic acid sample is hybridized with a nucleic acid probe. The probe is comprised of at least two sections. The first section contains the probe 3'-terminal about 10 to about 30 nucleotides. These nucleotides are complementary to the target strand sequence at positions beginning about 1 to about 30 nucleotides downstream of the interrogation position. The second section of the probe is located at the 5'-terminal region of the probe and contains about 10 to about 20 nucleotides of the target sequence. This same sequence, therefore, exists in both the target and the probe in the same 5' to 3' orientation. This sequence spans the region in the target from the nucleotide at or just upstream (5') of the interrogation position, to the nucleotide just upstream to where the 3'-terminal nucleotide of the probe anneals to the target. An optional third section of the probe, from zero to about 50, preferably from zero to about 20, nucleotides in length and comprising a sequence that does not hybridize with either the first or second section, is located between the first and second sections of the probe.

The probe of the treated sample is extended in a template-dependent manner, by admixture with dNTPs and a template-dependent polymerase, at least through the interrogation position, thereby forming an extended probe/target hybrid. In a preferred embodiment, the length of the probe extension is limited by omission from the extension reaction of a dNTP complementary to a nucleotide of the target sequence that is present upstream of the interrogation position and absent between the nucleotide complementary to the 3'-end of the interrogation position.

The extended probe/target hybrid is separated from any unreacted dNTPs; i.e., purified at least to the degree needed to use the extended probe strand to determine the presence or absence of the interrogation region in the sample or the identity of the base at the interrogation position. The extended probe/target hybrid is denatured to separate the strands. The extended probe strand is permitted to form a hairpin structure.

It is preferred that the polymerase enzyme utilized for an extension reaction be a template-dependent polymerase that is free of activity that adds a 3'-terminal deoxyadenosine in a template-nonspecific manner. Thus, it is preferred to use other than a polymerase such as Taq for a contemplated extension.

A treated reaction mixture is formed by admixing the hairpin structure-containing composition with a depolymerizing amount of an enzyme whose activity is to release one or more nucleotides from the 3'-terminus of an extended probe hairpin structure. The reaction mixture is maintained under depolymerizing conditions for a time period sufficient for the depolymerizing enzyme to release 3'-terminus nucleotides, and then analyzed for the presence of released identifier nucleotides. The analytical output indicates the presence or absence of the nucleic acid target sequence. That analytical output can be determined as discussed elsewhere herein.

A still further embodiment of the invention, such as that termed REAPER™ and demonstrated in Example 24 and FIG. 1, also contemplates use of hairpin structures in determining the presence or absence of a nucleic acid target sequence, or a specific base within the target sequence, in a nucleic acid sample, and comprises the following steps. A treated sample is provided that contains a nucleic acid sample that may include a nucleic acid target sequence hybridized with a first nucleic acid probe strand (FIG. 1A).

The hybrid is termed the first hybrid. The first probe is comprised of at least two sections. The first section contains the probe 3'-terminal about 10 to about 30 nucleotides that are complementary to the target nucleic acid sequence at a position beginning about 5 to about 30 nucleotides downstream of the target interrogation position. The second section of the first probe contains about 5 to about 30 nucleotides that are a repeat of the target sequence from the interrogation position to about 10 to about 30 nucleotides downstream of the interrogation position, and does not hybridize to the first section of the probe. That is, the second sequence is a repeat of the region in the target sequence from the interrogation position downstream to the position where the 3'-terminal nucleotide of the first probe aligns with the target. An optional third section of the probe, located between the first and second sections of the probe, is zero to about 50, preferably to about 20, nucleotides in length and comprises a sequence that does not hybridize to either the first or second section.

The first hybrid in the treated sample is extended at the $3^1$-end of the first probe, thereby extending the first probe past the interrogation position and forming an extended first hybrid (FIG. 1B) whose sequence includes an interrogation position. The extended first hybrid is comprised of the original target nucleic acid and extended first probe. The extended first hybrid is then denatured in an aqueous composition to separate the two nucleic acid strands of the hybridized duplex and form an aqueous solution containing a separated target nucleic acid and a separated extended first probe.

A second probe, that is about 10 to about 2000, more preferably about 10 to about 200, most preferably about 10 to about 30 nucleotides in length and is complementary to the extended first probe at a position beginning about 5 to about 2000, preferably about 5 to about 200, nucleotides downstream of the interrogation position in extended first probe, is annealed to the extended first probe, thereby forming the second hybrid (FIG. 1C). The second hybrid is extended at the 3'-end of the second probe until that extension reaches the 5'-end of the extended first probe, thereby forming a second extended hybrid (FIG. 1D) whose 3'-region includes an identifier nucleotide.

It is preferred that the polymerase enzyme utilized for an extension reaction be a template-dependent polymerase that is free of activity that adds a 3'-terminal deoxyadenosine in a template-nonspecific manner. Thus, it is preferred to use other than a polymerase such as Taq for a contemplated extension.

An aqueous composition of the extended second hybrid is denatured to separate the two nucleic acid strands; i.e., the extended second probe and the extended first probe. The aqueous composition so formed is cooled to form a "hairpin structure" from the separated extended second probe (FIG. 1E) when the target sequence is present in the original nucleic acid sample. Thus, when the target sequence is present in the original nucleic acid sample, the 3'-terminal sequence of the second extended probe in the second extended hybrid hybridizes with the sequence of the second extended probe from a region comprising the interrogation position and nucleotides downstream from the interrogation position of second extended probe to the nucleotide position where the 3'-terminal nucleotide of the original (first-named) probe annealed to the original target.

A treated reaction mixture is formed by admixing the hairpin structure-containing composition with a depolymerizing amount of an enzyme whose activity is to release one or more nucleotides from the 3'-terminus of a nucleic acid hybrid. The reaction mixture is maintained under depolymerizing conditions for a time period sufficient to release 3'-terminal region identifier nucleotides, and then analyzed for the presence of released identifier nucleotides. The analytical output indicates the presence or absence of the nucleic acid target sequence. Again, the analytical output can be determined by one of the several methods discussed elsewhere herein.

As was the case in the previous embodiment, dNTPs are utilized in the extension reactions. It is preferred that the hairpin structures be separated from the dNTPs prior to depolymerization to enhance the analysis for the identifier nucleotide.

Kits

Other embodiments of the invention contemplate a kit for determining the presence or absence of a predetermined endogenous nucleic acid target sequence in a nucleic acid sample. Such a kit comprises an enzyme whose activity is to release one or more nucleotides from the 3' terminus of a hybridized nucleic acid probe and at least one nucleic acid probe, said nucleic acid probe being complementary to nucleic acid target sequence. The kit optionally further comprises a nucleoside diphosphate kinase. Preferably, the nucleoside diphosphate kinase is that encoded by *Pyrococcus furiosis*. The kit optionally further comprises instructions for detecting said nucleic acid by depolymerization. Preferably the enzyme whose activity is to release nucleotides in the kit is a template dependent polymerase that, in the presence of pyrophosphate ions, depolymerizes hybridized nucleic acids whose bases in the 3'-terminal region are matched with total complementarity. Alternatively, the enzyme whose activity is to release nucleotides in the kit exhibits a 3' to 5' exonuclease activity, depolymerizing hybridized nucleic acids having one or more mismatched bases at the 3' terminus of the hybridized probe.

It is to be understood that such a kit is useful for any of the methods of the present invention. The choice of particular components is dependent upon the particular method the kit is designed to carry out. Additional components can be provided for detection of the analytical output, as measured by the release of identifier nucleotide, or by detection of the remaining probe after depolymerization. For example, ethidium bromide can be provided in the kits of the invention for detection of a probe that has had identifier nucleotide released from the 3'-terminal region.

The instructions present in such a kit instruct the user on how to use the components of the kit to perform the various methods of the present invention. These instructions can include a description of the detection methods of the invention, including detection by luminescence spectroscopy, mass spectrometry, fluorescence spectroscopy, and absorbance spectroscopy.

In another embodiment, the invention contemplates a kit for determining the presence or absence of at least one predetermined nucleic acid target sequence in a nucleic acid sample comprising the following components: an enzyme whose activity in the presence of pyrophosphate is to release identifier nucleotide as a nucleoside triphosphate from hybridized nucleic acid probe; adenosine 5' diphosphate; pyrophosphate; a nucleoside diphosphate kinase; and at least one nucleic acid probe, wherein the nucleic acid probe is complementary to the predetermined nucleic acid target sequence.

Preferably, the enzyme whose activity in the presence of pyrophosphate is to release identifier nucleotides is selected from the group consisting of the Tne triple mutant DNA polymerase, Klenow exo-, Klenow, T4 DNA polymerase, Ath DNA polymerase, Taq DNA polymerase and Tvu DNA polymerase. Preferably, the nucleoside diphosphate kinase is that encoded by *Pyrococcus furiosis*.

The kit optionally comprises instructions for use.

In another embodiment, the invention, contemplates a kit for determining the presence or absence of a predetermined nucleic acid target sequence in a nucleic acid sample comprising an enzyme whose activity is to release one or more nucleotides from the 3' terminus of a hybridized nucleic acid probe and instructions for use. Such a kit optionally comprises a nucleoside diphosphate kinase. Preferably, the nucleoside diphosphate kinase is that encoded by *Pyrococcus furiosis*. The kit further optionally comprises a nucleic acid probe complementary to the predetermined nucleic acid target sequence.

In other embodiments of the present invention, nucleic acid detection test kits are provided for performing a depolymerization method contemplated by this invention, and particularly a depolymerization detection method.

In one embodiment, the kit includes a vessel containing an enzyme capable of catalyzing pyrophosphorolysis, including, but not limited to Taq polymerase, Tne polymerase, Tne triple mutant polymerase, Tth polymerase, Tvu polymerase, Ath polymerase, T4 DNA polymerase, Klenow fragment, Klenow exo minus, *E. coli* DNA polymerase I, AMV reverse transcriptase, MMLV reverse transcriptase, or poly(A) polymerase. In another embodiment, the kit contains a vessel that contains an exonuclease such as S1 nuclease, nuclease BAL 31, mung bean nuclease, exonuclease III and ribonuclease H.

Either of the above enzyme types is utilized in a contemplated method in a depolymerizing effective amount. That is, the enzyme is used in an amount that depolymerizes the hybridized probe to release an identifier nucleotide. This amount can vary with the enzyme used and also with the temperature at which depolymerization is carried out. An enzyme of a kit is typically present in an amount of about 0.1 to 100 U/reaction; in particularly preferred embodiments, the concentration is about 0.5 U/reaction. An amount of enzyme sufficient to carry out at least one assay, with its controls is provided.

As noted elsewhere, the preferred analytical output for determining the presence or absence of identifier nucleotide is luminescence caused by the reaction of ATP with luciferin in the presence of luciferase. A kit containing a pyrophosphorylation enzyme for use in DNA detection using luminescence also preferably includes a vessel containing NDPK and a vessel containing ADP. Similarly, a kit containing an exonuclease enzyme for use in DNA detection using luminescence also preferably includes a vessel containing PRPP synthetase and a vessel containing ADP. The NDPK or PRPP synthetase is provided in concentration of about 0.01 to 100 U/reaction, preferably about 0.1 to about 1.0 U/reaction.

Preferably, these reagents, and all of the reagents utilized in the kits discussed herein, are free of contaminating ATP and adenylate kinase. Some of the contaminants can be removed from the enzymes by dialysis treatment.

Optionally, the kit contains vessels with reagents for amplification of dNTPs or NTP to ATP. Amplification reagents include, but are not limited to pyruvate kinase, adenylate kinase, NMPK, NDPK, AMP (e.g., as the amplification enzymes and substrate), and dCTP or AMP-CPP (e.g., as high-energy phosphate donors). In particularly preferred embodiments, the kit can be packaged in a single enclosure including instructions for performing the assay methods. In some embodiments, the reagents are provided in containers and are of a strength suitable for direct use or use after dilution. In alternative preferred embodiments, a standard set can also be provided in order to permit quantification of results. In yet other preferred embodiments, test buffers for optimal enzyme activity are included.

In yet other embodiments, a contemplated kit comprises a nuclease, PRPP synthetase, PRPP, NDPK, and ADP together with luciferase and luciferin. In preferred embodiments, the nuclease is provided in a concentration of about 1 to 500 U/reaction; in particularly preferred embodiments at a concentration of about 20 U/reaction. In a particularly preferred embodiment, the PRPP synthetase is provided in concentration of about 0.01 U/reaction to 10 U/reaction, preferably about 0.1 U/reaction. In some preferred embodiments, the kit includes all these reagents with luciferase and luciferin being provided as a single reagent solution.

In other preferred embodiments, these reagents include, but are not limited to, a high energy phosphate donor which cannot be utilized by luciferase, preferably dCTP, and AMP together with luciferase and luciferin. In alternative preferred embodiments, the kit includes all these reagents with luciferase and luciferin being provided in the same solution.

In still further embodiments of the present invention, the kits described above can contain a probe or probes for probe-mediated specific nucleic acid detection. In some embodiments, the kit contains at least one nucleic acid probe for a nucleic acid target of interest. In other embodiments, the kits contain multiple probes, each of which contain a different base at an interrogation position or which are designed to interrogate different target DNA sequences.

In each of the embodiments, the kits contain instructions for use in interrogating the identity of a specific base within a nucleic acid target, for discriminating between two homologous nucleic acid targets that differ by one or more base pairs, or for determining whether a nucleic acid target contains a deletion or insertion mutation. The types of nucleic acid probes that can be included in the kits and their uses are described in greater detail below.

EXAMPLE 1

Specific Detection of RNA: Comparison of Signals from RNA Species that Match Probe Sequences in Reactions With and Without Added Extraneous Target RNA For the pyrophosphorylation reaction to be used to detect specific target sequences, another requirement of the system is that the probes should give a very similar signal in the presence and absence of extraneous RNA. In this Example, the strength of the signal of probes designed to detect target globin mRNA in the presence of a large amount of yeast RNA is compared to the signal seen in the absence of added yeast RNA.

Hybridization solutions containing various levels of yeast RNA, Probe 6 (SEQ ID NO:1) or Probe 8 (SEQ ID NO:2) and target globin mRNA (Gibco BRL, 18103-028) were assembled by adding 5 $\mu$L 500 ng/$\mu$L either probe 6 or probe 8 to 5$\mu$L 40 ng/$\mu$L of target globin mRNA and 10 $\mu$L yeast RNA (Sigma Chemical Co. R3629) in 1X TE buffer (10 mM Tris, 1 mM EDTA) to produce solutions containing total amounts of yeast RNA of 0, 2, 20, 200, 400, and 800 ng. The solutions were heated at 50° C. for 15 minutes and then permitted to cool to room temperature for 15.

The following master reaction mixture was assembled:

| | |
|---|---|
| Nanopure water | 346.5 $\mu$L |
| MMLV-RT 5X Reaction Buffer (Promega M195A) | 132 $\mu$L |
| Sodium pyrophosphate (Promega M531) | 16.5 $\mu$L |
| NDPK (1 U/$\mu$L) | 33 $\mu$L |
| ADP (2 $\mu$M) | 33 $\mu$L |
| MMLV-RT (adjusted to 100 U/$\mu$L) (Promega, M1701) | 33 $\mu$L |

Aliquots of the above master mix (18 $\mu$L) was placed in each of 18 tubes. After cooling 15 minutes, 2 $\mu$L of the various hybridization solutions containing probe 6 were added to the tubes and the tubes were placed in a 37° C. heating block.

After 15 minutes of incubation of the hybridization mixture with the reaction master mix, 20 $\mu$L of the solution were added to 100 $\mu$L of L/L reagent (Promega, F202A) and the light output of the resulting reaction was measured using a Turner® TD-20/20 luminometer.

After the probe 6 data were collected, an identical set of reactions was performed using the hybridization solutions containing probe 8.

The following data were obtained:

| Yeast RNA | relative light units | | | Average |
|---|---|---|---|---|
| | Probe 6 Reactions | | | |
| None | 96 | 109 | 111 | 105.3 |
| 2 ng | 98.4 | 85.0 | 118.5 | 100.7 |
| 20 ng | 117.9 | 110.9 | 82.7 | 103.65 |
| 200 ng | 56.4 | 110.1 | 93.2 | 86.6 |
| 400 ng | 115.7 | 110.7 | 124.6 | 117 |
| 800 ng | 127.6 | 128.7 | 143.1 | 133.1 |
| | Probe 8 Reactions | | | |
| None | 105.8 | 97.0 | 82.3 | 95.0 |
| 2 ng | 84.5 | 84.6 | 93.7 | 87.6 |
| 20 ng | 99.6 | 111.7 | 104.9 | 105.4 |
| 200 ng | 83.6 | 75.9 | 95.6 | 85.1 |
| 400 ng | 94.7 | 97.2 | 81.9 | 91.2 |
| 800 ng | 50.7 | 89.0 | 82.1 | 73.9 |

These data indicate that addition of very large amounts of yeast RNA to the hybridization reaction does not greatly lower the signal from hybridized probes for specific target RNA species.

Probe 6   SEQ ID   5'AGACTTCTCCTCACTGGACAGATGCACC
          NO:1     AT3'

Probe 8   SEQ ID   5'GGGTCCATGGGTAGACAACCAGCAGC3'
          NO: 2

EXAMPLE 2

Determination of the Presence of the Leiden Mutation of Factor V

A synthetic first nucleic acid target of the Factor V gene was designed to have the wild type sequence that contains a G at position 32 of FV1 (SEQ ID NO:3). The complementary strand, FV2, (SEQ ID NO:4) had 4 additional bases at its 3'-terminus. A second synthetic nucleic acid target of Factor V was designed to have the Leiden mutation, an A residue at position 32 of FV3 (SEQ ID NO:5). The mutant complementary strand, FV4 (SEQ ID NO:6) also had 4 additional bases at its 3'-terminus. The nucleic acid target oligonucleotides, FV1 to FV4, were separately dissolved at a concentration of one mg/mL in water.

Nucleic acid probe FV5 (SEQ ID NO:7) was synthesized to be totally complementary to one strand of the first target, FV1. The probe was synthesized to place the complementary C residue at an interrogation position penultimate to the 3'-terminal nucleotide of the probe FV5, corresponding to the G at position 32 of FV1. Similarly, a synthetic nucleic acid probe was prepared having sequence FV6 (SEQ ID NO:8) that is totally complementary to one strand of the second target, Factor V with the Leiden mutation, FV3. The probe was synthesized to place the complementary T residue at an interrogation position penultimate to the 3'-terminal nucleotide of the probe FV6, corresponding to the A at position 32 of FV3. Nucleic acid probe stock solutions had a concentration of one mg/mL in water.

The FV1 oligonucleotide was mixed with an equal amount of its complementary strand, FV2, heated to 95° C. for about 15 minutes and then cooled to room temperature to produce a first sample containing a double stranded DNA segment including the first nucleic acid target, corresponding to the wild type sequence of the Factor V gene.

The FV3 oligonucleotide was mixed with an equal amount of its complementary strand having FV4, heated to 95° C. for about 15 minutes, and then cooled to room temperature to produce a second sample that included a double stranded DNA (dsDNA) segment containing the second target, the sequence of the Factor V gene in the region of the Leiden mutation.

One microliter of the dsDNA sample to be assayed for the presence of the first or second target was admixed with 1 µL of a nucleic acid probe and 18 µL of water to form separate hybridization compositions. Controls had 1 µL of the dsDNA sample and 19 µL of water.

They were denatured by heating to 95° C. for three minutes, then maintained for 10 minutes under hybridizing conditions (in a 37° C. incubator) to form separate treated samples.

A master mix was assembled containing 10X DNA Polymerase Buffer (20 µL; Promega, M195), sodium pyrophosphate (5 µL of 40 mM Na$_4$P$_2$O$_7$ solution; Promega, C113), Klenow Exo Minus (5 µL; 5U; Promega, M218), NDPK (1 µL of a 10U/µL solution of NDPK [Sigma, N0379], dissolved in water), ADP (2 µL of a 10 µM solution of ADP [Sigma, A5285] dissolved in water), and water (67 µL).

The hybridized, treated samples (20 µL) were each mixed with the master mix and maintained for 15 minutes at 37° C. to form a depolymerized sample.

The depolymerized sample was added to 100 µL L/L reagent (Promega, F202A), and the amount of light produced was read on a Turner® TD20/20 luminometer. A total of 8 samples and two controls were analyzed. The averaged results are shown below.

| Assay No. | Nucleic Acid Target in Sample | Nucleic Acid Probe | Average Relative Light Units |
|---|---|---|---|
| 1,2 | Factor V | Factor V | 1063 |
| 3,4 | Factor V | Factor V Leiden | 88.8 |
| 5 | Factor V | none | 8.652 |
| 6,7 | Factor V Leiden | Factor V | 139.8 |

-continued

| Assay No. | Nucleic Acid Target in Sample | Nucleic Acid Probe | Average Relative Light Units |
|---|---|---|---|
| 8,9 | Factor V Leiden | Factor V Leiden | 1016 |
| 10 | Factor V Leiden | none | 7.587 |

The data show that the light signal is about 10 fold greater when the nucleic acid probe is exactly complementary to the nucleic acid target (Assay Nos. 1, 2, 8 and 9) than when the nucleic acid probe is partially complementary to the nucleic acid target with the mismatch at the position penultimate to the 3'-terminal nucleotide (Assay Nos. 3, 4, 6, and 7). The latter signal is in turn about 10-fold greater than the light generated when there is no probe to hybridize to the nucleic acid target (Assay Nos. 5 and 10).

FV1 5' CTAATCTGTAAGAGCAGATCCCTGGA-CAGGCGAGGAATACAGAGGGCAGCA GACATC-GAAGAGCT 3' SEQ ID NO:3

FV2 5' AGCTCTTCGATGTCTGCTGCCCTCTG-TATTCCTCGCCTGTCCAGGGATCTG CTCTTACA-GATTAGAGCT 3' SEQ ID NO:4

FV3 5' CTAATCTGTAAGAGCAGATCCCTGGA-CAGGCAAGGAATACAGAGGGCAGCA GACATC-GAAGAGCT 3' SEQ ID NO:5

FV4 5'AGCTCTTCGATGTCTGCTGCCCTCTG-TATTCCTTGCCTGTCCAGGGATCTG CTCTTACA-GATTAGAGCT 3' SEQ ID NO:6

FV5 5' CTGCTGCCCTCTGTATTCCTCG 3' SEQ ID NO:7

FV6 5' CTGCTGCCCTCTGTATTCCTTG 3' SEQ ID NO:8

EXAMPLE 3

Determination of the Presence or Absence of a Nucleotide Sequence in a Sample Known to be Associated with the Factor V Leiden Phenotype in Humans with Additional Interrogation Probes In this Example, another pair of probes, complementary to the opposite template strand as those used in Example 2, were used to detect the gene sequences of the wild type Factor V gene and the Leiden allele of this gene. Oligonucleotides FV7 (SEQ ID NO:9) and FV8 (SEQ ID NO:10) were dissolved at 1 mg/mL in water. Oligonucleotides FV1 (SEQ ID NO:3), FV2 (SEQ ID NO:4), FV3 (SEQ ID NO:5) and FV4 (SEQ ID NO:6) were used as targets, and the following solutions were assembled.

| Solution | Target (µL) | Probe (µL) | Water (µL) |
|---|---|---|---|
| 1 and 2 | 1 FV1 + FV2 | 1 FV7 | 18 |
| 3 and 4 | 1 FV1 + FV2 | 1 FV8 | 18 |
| 5 | 1 FV1 + FV2 | none | 19 |
| 6 and 7 | 1 FV3 + FV4 | 1 FV7 | 18 |
| 8 and 9 | 1 FV3 + FV4 | 1 FV8 | 18 |
| 10 | 1 FV3 + FV4 | none | 19 |

The above solutions were heated to 95° C. for three minutes, then placed in a 37° C. incubator for 10 minutes. The following master mix was assembled:

| | |
|---|---|
| 10X DNA Polymerase Buffer (Promega M195) | 20 µL |
| 40 mM Sodium Pyrophosphate (Promega C113) | 5 µL |
| 10 U/µl Klenow Exo Minus (Promega M218) | 5 µL |
| NDPK (Sigma, N0379 at 10 U/µL in water) | 1 µL |
| ADP (Sigma A5285, 10 µM in water) | 2 µL |
| Water | 67 µL |
| | 100 µL |

Twenty microliters of master mix were added to each of the heated nucleotide mixes after incubation at 37° C. for 10 minutes. The resulting reactions were incubated for 15 minutes at 37° C. and then added to 100 µL L/L reagent (Promega, F202A) and the light produced was immediately read using a Turner® TD20/20 luminometer.
The following results were obtained.

| Reaction | Relative Light Units |
|---|---|
| 1 | 217.9 |
| 2 | 237.9 |
| 3 | 47.76 |
| 4 | 48.33 |
| 5 | 5.903 |
| 6 | 18.79 |
| 7 | 19.19 |
| 8 | 186.8 |
| 9 | 181.5 |
| 10 | 5.837 |

These data show that probe FV7 gave a much stronger signal than FV8 on DNA containing a sequence corresponding the native Factor V gene, and thus can be used to detect this DNA sequence in a sample. Probe FV8 gave a much stronger signal than FV7 on DNA containing a sequence encoding the Factor V gene in the region of the Leiden mutation.

EXAMPLE 4

Detection of a Sequence in the Cystic Fibrosis Gene in the Region of the Delta 508 Mutation In this Example, an assay was performed to detect a sequence that encodes a segment of the cystic fibrosis gene spanning the mutation known as the delta F508 allele.

Oligonucleotides CF1 (SEQ ID NO:11) and CF2 (SEQ ID NO:12) were synthesized and redissolved in water at a concentration of 50 pmol/µL. These primers were used to produce an amplified segment of the human chromosomal DNA by PCR amplification. PCR reactions contained 20 ng human genomic DNA, 50 pmol each primer, 1X Promega Taq Reaction Buffer with 1.5 mM MgCl2 (Promega, M188A), 200 µM dNTPs, and 1.25 U Taq DNA Polymerase (Promega M186A). Cycling conditions were 1×2 minutes at 94° C., 35×[0.5 minutes at 94° C., 1 minute at 60° C., 1 minute at 72° C.], 1×7 minutes at 72° C., 4° C. soak. The amplified DNA was purified using Wizard PCR Preps (Promega A7170) by mixing 25 µL PCR product with 1 mL resin and washing with 3×1 mL 80% isopropanol. This DNA was used to represent wild type human DNA encoding the cystic fibrosis gene spanning the delta F508 mutation.

Oligonucleotides CF6 (SEQ ID NO:16) and CF7 (SEQ ID NO:17) were dissolved in water at a concentration of 1 mg/mL, mixed and annealed to form a double strand DNA segment as described for oligonucleotide FV1 and FV2 above. This DNA was used to represent human DNA encoding the delta F508 mutation at this locus.

Oligonucleotide probes CF3 (SEQ ID NO:13), CF4 (SEQ ID NO:14) and CF5 (SEQ ID NO:15) were prepared. The sequence of probe CF3 is completely complementary to wild type cystic fibrosis gene. The sequence of probe CF4 was identical to that of probe CF3 except for the 3'-terminal nucleotide that is complementary to the nucleotide present in the delta F508 mutation, and thus was completely complementary to one strand of that mutant sequence. The sequence of probe CF5 was completely complementary to the second strand of that F508 mutant sequence, and also therefore differed from a total complement of probe CF3 at the 3'-terminal nucleotide. The probes were separately dissolved in water to a concentration of 1 mg/mL. The following solutions were assembled.

```
FV1
5'CTAATCTGTAAGAGCAGATCCCTGGACAGGCGAGGAATACAGAGGGCAGCA   SEQ ID NO:3

GACATCGAAGAGCT 3'

FV2
5'AGCTCTTCGATGTCTGCTGCCCTCTGTATTCCTCGCCTGTCCAGGGATCTG   SEQ ID NO:4

CTCTTACAGATTAGAGCT 3'

FV3
5'CTAATCTGTAAGAGCAGATCCCTGGACAGGCAAGGAATACAGAGGGCAGCA   SEQ ID NO:5

GACATCGAAGAGCT 3'

FV4
5'AGCTCTTCGATGTCTGCTGCCCTCTGTATTCCTTGCCTGTCCAGGGATCTG   SEQ ID NO:6

CTCTTACAGATTAGAGCT 3'

FV7
5' GACAAAATACCTGTATTCCTCG 3'                             SEQ ID NO:9

FV8
5' GACAAAATACCTGTATTCCTTG 3'                             SEQ ID NO:10
```

| Solution | Probe (μL) | Target (μL) | Water (μL) |
|---|---|---|---|
| 1 and 2 | 1, CF3 | 4, purified, Amplified DNA | 15 |
| 3 and 4 | 1, CF4 | 4, purified, Amplified DNA | 15 |
| 5 and 6 | 1, CF5 | 4, purified, Amplified DNA | 15 |
| 7 | none | 4, purified, Amplified DNA | 16 |
| 8 and 9 | 1, CF3 | 1, Annealed (CF6 + CF7) | 18 |
| 10 and 11 | 1, CF4 | 1, Annealed (CF6 + CF7) | 18 |
| 12 and 13 | 1, CF5, | 1, Annealed (CF6 + CF7) | 18 |
| 14 | none | 1, Annealed (CF6 + CF7) | 19 |

These solutions were heated at 95° C. for 3 minutes and then placed in a 37° C. incubator for 10 minutes.

A master mix was assembled as described in Example 3 and 20 μL of this solution were added to each of solutions 1–14 above. They were incubated for another 15 minutes at 37° C.

The solutions were added to 100 μL of L/L reagent (Promega F202A)) and the light produced by the reactions was immediately measured using a Turner® TD 20/20 luminometer. The following results were obtained.

| Solution | Relative Light Units | Net Average RLU* |
|---|---|---|
| 1 | 1527 | 762 |
| 2 | 1683 | |
| 3 | 766.7 | (−48.5) |
| 4 | 823.5 | |
| 5 | 893.2 | 44.1 |
| 6 | 881.0 | |
| 7 | 843.4 | |
| 8 | 72.73 | 11.0 |

| Solution | Relative Light Units | Net Average RLU* |
|---|---|---|
| 9 | 80.05 | |
| 10 | 310.9 | 306.5 |
| 11 | 302.1 | |
| 12 | 439.0 | 434.4 |
| 13 | 429.8 | |
| 14 | 65.90 | |

*The net value is calculated by averaging the duplicate samples and subtracting the target alone value measured for the different sets.

These data show that probe CF3 provided much higher signals with wild type DNA than were provided by either of probes CF4 or CF5 that had a mismatched nucleotide at the site of the mutation. In addition, both probes CF4 and CF5 that were completely complementary to the mutant sequence provided much higher signals with DNA encoding the delta F508 mutant than with wild type DNA.

```
CF1
5' CATTCACAGTAGCTTACCCA 3'                                            SEQ ID NO:11

CF2
5' GCAGAGTACCTGAAACAGGA 3'                                            SEQ ID NO:12

CF3
5' CATCATAGGAAACACCAAG 3'                                             SEQ ID NO:13

CF4
5' CATCATAGGAAACACCAAT 3'                                             SEQ ID NO:14

CF5
5' GGCACCATTAAAGAAAATATCATT 3'                                        SEQ ID NO:15

CF6
5' CTGGCACCATTAAAGAAAATATCATTGGTGTTTCCTATGATGAATATAG                  SEQ ID NO:16

CF7
5' CTATATTCATCATAGGAAACACCAATGATATTTTCTTTAATGGTGCC                    SEQ ID NO:17
AG 3'
```

EXAMPLE 5

Detection of a Sequence in the Cystic Fibrosis Gene in the Region of the Delta 508 Mutation including a Sample Containing Both the Normal and Delta F508 Alleles This Example demonstrates an assay that detects a sequence encoding a segment of the cystic fibrosis gene spanning the mutation known as the delta F508 allele. The assay is illustrated using the wild type human sequence of this gene in this region and using a sample that has both alleles. The results here demonstrate that the assay can discriminate between homozygotes for these alleles, and can be used to detect heterozygote samples in which both alleles are present together, as would be the case with a carrier for a wide variety of genetic diseases.

Oligonucleotides CF8 (SEQ ID NO:18) and CF9 (SEQ ID NO:19), a synthetic wild type target, were dissolved in water and annealed as described for Example 2. CF6 (SEQ ID NO:16) and CF7 (SEQ ID NO:17) were also used as targets. CF3 (SEQ ID NO:13) and CF4 (SEQ ID NO:14) were used as probes. The following solutions were assembled.

| Solution | Probe (µL) | Target (s) (µL) | Water (µL) |
|---|---|---|---|
| 1 and 2 | 1, CF3 | 1, Annealed (CF8 + CF9) | 18 |
| 3 and 4 | 1, CF4 | 1, Annealed (CF8 + CF9) | 18 |
| 5 | none | 1, Annealed (CF8.+ CF9) | 19 |
| 6 and 7 | 1, CF3 | 1, Annealed (CF6 + CF7) and 1, Annealed (CF8 + CF9) | 17 |
| 8 and 9 | 1, CF4 | 1, Annealed (CF6 + CF7) and 1, Annealed (CF8 + CF9) | 17 |
| 10 | none | 1, Annealed (CF6 + CF7) and 1, Annealed (CF8 + CF9) | 18 |
| 11 and 12 | 1, CF3 | 1, Annealed (CF6 + CF7) | 18 |
| 13 and 14 | 1, CF4 | 1, Annealed (CF6 + CF7) | 18 |
| 15 | none | 1, Annealed (CF6 + CF7) | 19 |

The above solutions were heated at 95° C. for 3 minutes, then placed in a 37° C. incubator for 10 minutes. A master mix was made as in Example 3 and 20 µL of this solution were then added to each of tubes 1–15. The tubes were incubated at 37° C. for an additional 15 minutes, then the solutions were added to 100 µL of L/L reagent (Promega F202A) and the light produced by the reactions was read immediately using a Turner® TD20/20 luminometer. The following data were obtained.

| Solution | Relative Light Units | Adjusted Net Light Value* |
|---|---|---|
| 1 | 310.1 | 307.9 |
| 2 | 342.3 | |
| 3 | 22.45 | 4.41 |
| 4 | 23.02 | |
| 5 | 18.29 | |
| 6 | 400.2 | 346.98 |
| 7 | 393.7 | |
| 8 | 332.3 | 269.38 |
| 9 | 306.4 | |
| 10 | 49.97 | |
| 11 | 96.67 | 37.68 |
| 12 | 109.1 | |
| 13 | 371.3 | 305.4 |
| 14 | 369.8 | |
| 15 | 65.22 | |

*This value was calculated by averaging the duplicate reactions and subtracting the value measured for the appropriate target alone control reaction.

These data again show that probe CF3 provided a much stronger signal with normal (wild type; homozygous) DNA than did probe CF4, and probe CF4 provided a much stronger signal with the homozygous delta F508 mutation target than did probe CF3. In addition, when both targets were present in the sample, as in a heterozygote, signals were provided from both probes to indicate the presence of a heterozygote. Thus, the analytical output from this method illustrated whether the nucleic acid target sequence in a nucleic acid sample was homozygous or heterozygous, and when homozygous, which of the alleles was present.

```
CF3
5' CATCATAGGAAACACCAAG 3'                                    SEQ ID NO:13

CF4
5' CATCATAGGAAACACCAAT 3'                                    SEQ ID NO:14

CF6
5' CTGGCACCATTAAAGAAAATATCATTGGTGTTTCCTATGATGAATA            SEQ ID NO:16
TAG 3'

CF7
5'CTATATTCATCATAGGAAACACCAATGATATTTTCTTTAATGGTGCC            SEQ ID NO:17
AG 3'

CF8
5'CTGGCACCATTAAAGAAAATATCATCTTTGGTGTTTCCTATGATGAA            SEQ ID NO:18
TATAG 3'

CF9
5'CTATATTCATCATAGGAAACACCAAAGATGATATTTTCTTTAATGGT            SEQ ID NO:19
GCCAG 3'
```

EXAMPLE 6

Detection of DNA Sequences Corresponding to the Prothrombin Gene in the Region of a Single Nucleotide Polymorphism An assay for the presence or absence of a mutation in the human prothrombin gene is illustrated in this Example. This SNP is characterized by a G to A substitution in the prothrombin gene.

Oligonucleotides PT1 (SEQ ID NO:20), PT2 (SEQ ID NO:21), PT3 (SEQ ID NO:22), and PT4 (SEQ ID NO:23)

were synthesized and dissolved in water to a concentration of 1 mg/mL. A sample of PT1 and PT2 were then diluted to 0.3 ng in water for use in the solutions below, and the following solutions were made.

| Solution | Probe (µL) | Target (µL) | Water (µL) |
|---|---|---|---|
| 1 and 2 | 1, PT3 | 1, PT1 | 18 |
| 3 and 4 | 1, PT4 | 1, PT1 | 18 |
| 5 | none | 1, PT1 | 19 |
| 6 and 7 | 1, PT3 | 1, PT2 | 18 |
| 8 and 9 | 1, PT4 | 1, PT2 | 18 |
| 10 | none | 1, PT2 | 19 |

These solutions were heated at 95° C. for three minutes then placed in a 37° C. incubator for 10 minutes.

A master mix was assembled as in Example 3 and 20 µL of this solution were added to each of solutions 1–10, above, and all solutions were incubated for 15 minutes at 37° C. After this incubation, these solutions were added to 100 µL of L/L reagent (Promega F202A) and the light produced by the solutions immediately read using a Turner® TD 20/20 luminometer. The following results were obtained.

| Sample | Relative Light Units |
|---|---|
| 1 | 240.9 |
| 2 | 253.3 |
| 3 | 56.10 |
| 4 | 55.88 |
| 5 | 5.88 |
| 6 | 29.61 |
| 7 | 31.49 |
| 8 | 738.0 |
| 9 | 646.8 |
| 10 | 6.21 |

These data demonstrate the probe PT3 provided higher signals with a wild type target (PT1) than does probe PT4, but that probe PT4 provided a much higher signal with mutant template (PT2) than did PT3.

```
PT1                                         SEQ ID NO:20
5' TCCCAATAAAAGTGACTCTCAGCGAGCCTCAATGCTCCCAGTGC
TATTCA 3'

PT2                                         SEQ ID NO:21
5' TCCCAATAAAAGTGACTCTCAGCAAGCCTCAATGCTCCCAGTGC
TATTCA 3'

PT3                                         SEQ ID NO:22
5' GGAGCATTGAGGCTCG 3'

PT4                                         SEQ ID NO:23
5' GGAGCATTGAGGCTTG 3'
```

EXAMPLE 7

Determination of SNPs in DNA Isolated from Plant Materials

A process of the invention is used here to determine the genotype of rice DNAs at a known SNP site.

A particular target produced by amplification of a segment of the rice genome is interrogated in this Example. It was found that this target produces high background signal values if nothing is done to eliminate one strand of the amplified DNA target and did not exhibit discrimination between two primers that were designed to detect a SNP present in some rice strains. This Example illustrates how one can purposefully destroy one of the amplified DNA strands and interrogate the other strand. For this case in particular, such manipulations result in greatly reduced background light signals from the target, permitting clear determination of the interrogation signals.

Probes RS1 (SEQ ID NO:24) and RS2 (SEQ ID NO:25) were dissolved at a concentration of 50 pmole/µL in water. Probe RS1 contained phosphothioate linkages at the first four 5'-terminal linkages that are not cleaved by the enzyme used in the reaction. DNA was isolated from rice and was at a concentration of 10 µg/mL.

Five coded DNA samples and two DNA samples of known genotype (the "G" allele and the "T" allele) were obtained and subjected to amplification with probes RS1 (SEQ ID NO:24) and RS2 (SEQ ID NO:25). The DNA was then treated with T7 Exonuclease 6 for 15 minutes at 37° C. and purified. The resulting purified DNA was subjected to pyrophosphorylation reactions using probes RS3 (SEQ ID NO:26), RS4 (SEQ ID NO:27), or no probe and the reaction products added to L/L reagent (Promega, F202A) and light production measured.

The following results were obtained:

| | Relative Light Units Measured | | |
|---|---|---|---|
| DNA Analyzed | WT Probe (RS3 G Allele) | Variant Probe (RS4 T Allele) | No Probe |
| #1 | 784.5 | 307.5 | 229.9 |
| #2 | 286.3 | 882.7 | 227.9 |
| #3 | 291.5 | 862.4 | 202.9 |
| #4 | 560.4 | 195.5 | 158.2 |
| #5 | 706.8 | 235.5 | 187.7 |
| G Allele | 810.7 | 250.0 | 189.2 |
| T Allele | 416.6 | 1121 | 243.4 |

| Net Light Units, Ratio and Called Genotype | | | | |
|---|---|---|---|---|
| | Net Light Units* | | | |
| DNA Analyzed | WT Probe | Variant Probe | Ratio** | Called Genotype |
| #1 | 554.6 | 77.6 | 7.1 | G Allele |
| #2 | 58.4 | 654.8 | 0.09 | T Allele |
| #3 | 88.6 | 659.5 | 0.13 | T Allele |
| #4 | 402.2 | 37.3 | 10.8 | G Allele |
| #5 | 519.1 | 47.8 | 10.9 | G Allele |
| G Allele Std. Deviation | 621.5 | 60.8 | 10.2 | G Allele |
| T Allele Std. Deviation | 173.2 | 877.6 | 0.20 | T Allele |

*Net light units = total light units − no primer values.
**Ratio = Net light units WT primer/net light units variant primer After these results were obtained, the identity of the DNA samples was uncoded and all the called genotypes agreed with the previously determined genotype of these samples. These results demonstrate the assay described in this Example can be used to determine SNPs in plant DNA and that removal of one DNA strand of a sample can help eliminate high background signals from a template, permitting SNPs to be determined.

```
RS1 5'C*C*C*A*ACACCTTACAGAAATTAGC 3'    SEQ ID NO:24

(* signifies the presence of a
phosphorothioate
phosphorothioate linkage
between the indicated bases.)

RS2 5'TCTCAAGACACAAATAACTGCAG 3'        SEQ ID NO:25

RS3 5'AGAACATCTGCAAGG 3'                SEQ ID NO:26

RS4 5'AGAACATCTGCAAGT 3'                SEQ ID NO:27
```

EXAMPLE 8

Discrimination of Repeated DNA Sequences Using Pyrophosphorylation-Based Assay Methods This Example illustrates an assay for determining the number of repeats of a four base pair sequence in a DNA. Discrimination of such repeat sequences has been found to be very useful for identification of forensic samples. The probes in this set, TR1 (SEQ ID NO:31), TR2 (SEQ ID NO:32) and TR3 (SEQ ID NO:33) were designed to exactly match known alleles of the THO 1 locus with 6, 7, and 8 repeats respectively, of a CATT sequence.

Probes TR1–TR3 were suspended in water to a concentration of 1 mg/mL. Targets that were homozygous for THO 1 alleles with 6, 7 and 8 repeats were amplified using the protocol in the Gene Print™ System instructions (Promega). These targets were named allele 6 (SEQ ID NO:28), allele 7 (SEQ ID NO:29) and allele 8 (SEQ ID NO:30), respectively. Gel-purified targets were PCR amplified and then further purified using the Wizard™ PCR Clean-up system (Promega, A7170) and the concentration of the DNA measured by DNAQuant (Promega). These targets were adjusted to a concentration of 1 µg/mL and to 3.3 µg/mL by the addition of deionized water. The following solutions containing probes were assembled in a final volume of 20 µL by the addition of water.

| Solution | Probe | Target (ng) |
|---|---|---|
| #1 | — | allele 6, 1 |
| #2 | TR1 | allele 6, 1 |
| #3 | TR2 | allele 6, 1 |
| #4 | TR3 | allele 6, 1 |
| #5 | — | allele 7, 1 |
| #6 | TR1 | allele 7, 1 |
| #7 | TR2 | allele 7, 1 |
| #8 | TR3 | allele 7, 1 |
| #9 | — | allele 8, 1 |
| #10 | TR1 | allele 8, 1 |
| #11 | TR2 | allele 8, 1 |
| #12 | TR3 | allele 8, 1 |
| #13 | — | allele 6, 3.3 |
| #14 | TR1 | allele 6, 3.3 |
| #15 | TR2 | allele 6, 3.3 |
| #16 | TR3 | allele 6, 3.3 |
| #17 | — | allele 7, 3.3 |
| #18 | TR1 | allele 7, 3.3 |
| #19 | TR2 | allele 7, 3*3 |
| #20 | TR3 | allele 7, 3.3 |
| #21 | — | allele 8, 3.3 |
| #22 | TR1 | allele 8, 3.3 |
| #23 | TR2 | allele 8, 3.3 |
| #24 | TR3 | allele 8, 3.3 |

These solutions were heated at 95° C. for 3 minutes, then permitted to cool by incubation at room temperature for 10 minutes.

The following master mix was made.

| Component | Amount (µL)/reaction |
|---|---|
| 10X DNA Polymerase Buffer | 4 |
| 40 mM Sodium Pyrophosphate | 0.5 |
| 10 µM ADP | 0.4 |
| Klenow exo-, 10 U/µL | 0.5 |
| NDPK, 1 U/µL | 0.2 |
| Nanopure water | 14.4 |

This solution was mixed and 20 µL of this solution were added to solutions 1–24 above, and the resulting solutions incubated for 15 minutes at 37° C. After this incubation, 4 µL of the resulting solution were added to 100 µL of L/L reagent(Promega, F202A) and the light produced was immediately measured using a Turner® TD20/20 luminometer. The following data were obtained.

| Solution | Relative Light Units |
|---|---|
| #1 | 3.97 |
| #2 | 50.79 |
| #3 | 5.94 |
| #4 | 6.03 |
| #4 | 3.79 |
| #5 | 67.23 |
| #7 | 28.94 |
| #8 | 6.73 |
| #9 | 3.19 |
| #10 | 49.52 |
| #11 | 30.99 |
| #12 | 30.63 |
| #13 | 8.62 |
| #14 | 256.90 |
| #15 | 16.74 |
| #16 | 13.83 |
| #17 | 6.73 |
| #18 | 206.5 |
| #19 | 110.2 |
| #20 | 15.35 |
| #21 | 6.49 |
| #22 | 271.9 |
| #23 | 150.5 |
| #24 | 154.8 |

The values from the no probe reactions above were subtracted from the values for the various probe/target matches and the resulting values are shown in the table below.

| Allele Assayed | TR1 Probe | TR2 Probe | TR3 Probe |
|---|---|---|---|
| Relative Light Units With 1 ng of Target | | | |
| Allele 6 | 44.46 | −0.01 | −0.44 |
| Allele 7 | 61.07 | 23.17 | 0.44 |
| Allele 8 | 43.97 | 25.83 | 24.95 |
| Relative Light Units With 3.3 ng of Target | | | |
| Allele 6 | 245.08 | 4.88 | 1.73 |
| Allele 7 | 196.58 | 100.24 | 5.14 |
| Allele 8 | 262.22 | 140.78 | 144.83 |

If, in the repeat region, the probe contains the same number of repeats as the target or fewer, no mismatching bases should be present at the 3' end of the probe and a relatively strong signal is obtained. The TR1 probe shows such a signal with targets containing 6, 7 or 8 repeats. However, if the probe contains more repeats in this region than are present in the target, mismatched bases are expected at the 3' end of the probe that should greatly reduce the signal developed. As expected, the TR3 probe gave a strong signal against the allele 8 target, but gave a much weaker signal against the allele 7 and 6 targets. Because the signal generated using the various probes can be used to determine the number of repeated units in the repeat region, this method can be used to determine the alleles present in samples.

Using the above method, probes containing the same number or fewer repeated sequences as the target produced similar light output. When more repeats were present in the probe than the target, low analytical outputs were observed. The number of repeats in the target could thus accurately be determined by an indicative change in the analytical output, here, luminescence, between the separately assayed samples.

EXAMPLE 9

Discrimination of Repeated DNA Sequences Using Pyrophosphorylation Based Assay Methods Using Another Class of Probes A surprising result is presented in this Example that demonstrates that a class of probes that should only produce signals with targets of a certain class, essentially give equivalent signals with additional targets. Although these results do not match the predicted results, they can still be used to determine the allelic composition of samples.

The probes in the Example above were designed to hybridize to alleles of THO 1 that are used for genotyping humans. They were designed to hybridize as illustratively shown below for probe TR2 with targets of three alleles.

Hybridization of probe TR2 (top strand) with an Allele 6 target (bottom strand):
CCCATTGGCCTCTTCCTCCCTTATTTCCCTCATT
$(CATT)_4$ CATTCATTCACC
GGGTAACCGGAGAAGGAGGGAATAAAGGGAGTAA
$(GTAA)_4$ GTAAGTGG Hybridization of probe TR2 (top strand) with an Allele 7 target (bottom strand):
CCCATTGGCCTCTTCCTCCCTTATTTCCCTCATT
$(CATT)_4$ CATTCATTCACC
GGGTAACCGGAGAAGGAGGGAATAAAGGGAGTAA
$(GTAA)_4$ GTAAGTAAGTGG Hybridization of probe TR2 (top strand) with an Allele 8 target (bottom strand):
CCCATTGGCCTCTTCCTCCCTTATTTCCCTCATT
$(CATT)_4$ CATTCATTCACC
GGGTAACCGGAGAAGGAGGGAATAAAGGGAGTAA
$(GTAA)_4$ GTAAGTAAGTAAG TGGATGG 5'

As described in Example 8, when the target contains fewer repeats than the probe, mismatched bases can occur at the 3' end of the probe, creating a double strand DNA region that is a very poor substrate for the pyrophosphorylation reaction. These predictions were verified with the results obtained.

```
Allele 6
5'GGTGAATGAATGAATGAATGAATGAATGAGGGAAATAAGGGAGGAAGAGGC    SEQ ID NO:28

CAATGGG 3'

Allele 7
5'GGTGAATGAATGAATGAATGAATGAATGAATGAGGGAAATAAGGGAGGAAG    SEQ ID NO:29

AGGCCAATGGG 3'

Allele 8
5'GGTAGGTGAATGAATGAATGAATGAATGAATGAATGAATGAGGGAAATAAG    SEQ ID NO:30

GGAGGAAGAGGCCAATGGG 3'

TR1
5' CCCATTGGCCTGTTCCTCCCTTATTTCCCTCATTCATTCATTCATTCATT    SEQ ID NO:31

CATTCACC 3'

TR2
5' CCCATTGGCCTGTTCCTCCCTTATTTCCCTCATTCATTCATTCATTCATT    SEQ ID NO:32

CATTCATTCACC 3'

TR3
5' CCCATTGGCCTGTTCCTCCCTTATTTCCCTCATTCA                 SEQ ID NO:33

TTCATTCATTCATTCATTCATTCACC 3'
```

In this Example, a new form of probe is used in the reactions. These probes are designed to extend beyond the repeat region and hybridize to the target following this DNA segment when they are hybridized to the allele with the correct number of repeat segments. The predicted hybridization segments for the allele 7 probe (TR6) with the allele 6, 7, and 8 targets are shown below.

Hybridization of probe TR6 (top strand) with an Allele 6 target (bottom strand):
CCCATTGGCCTCTTCCTCCCTTATTTCCCTCATT
(CATT)$_4$CATTCATTCACC
GGGTAACCGGAGAAGGAGGGAATAAAGGGAGTAA
(GTAA)$_4$GTAAGTGGATGG Hybridization of probe TR6 (top strand) with an Allele 7 target (bottom strand):
CCCATTGGCCTCTTCCTCCCTTATTTCCCTCATT
(CATT)$_4$CATTCATTCACC
GGGTAACCGGAGAAGGAGGGAATAAAGGGAGTAA
(GTAA)$_4$GTAAGTAAGTGGA TGG 5'

Hybridization of probe TR6 (top strand) with an Allele 8 target (bottom strand):
CCCATTGGCCTCTTCCTCCCTTATTTCCCTCATT
(CATT)$_4$CATTCATTCACC
GGGTAACCGGAGAAGGAGGGAATAAAGGGAGTAA
(GTAA)$_4$GTAAGTAAGTAAT GGAGTGG 5'

As shown above, probe TR6 was designed to form a product without 3' end mismatches with only allele 7. Thus, this probe was expected to only give a strong signal with the allele 7 target.

In order to test the actual signals that such probes would give with various targets, probes TR4 (SEQ ID NO:34), TR5 (SEQ ID NO:35), TR6 (SEQ ID NO:36), TR7 (SEQ ID NO:37) and TR8 (SEQ ID NO:38) were dissolved in water to a concentration of 1 mg/mL. These probes were used with the targets Allele 6 (SEQ ID NO:28), Allele 7 (SEQ ID NO:29) and Allele 8 (SEQ ID NO:30) to generate the following solutions. The final volume of these solutions was adjusted to 20 µL by the addition of water. The probes were used at a concentration of 1 µg/reaction.

| Soln. | Probe | Target (ng) |
|---|---|---|
| #1 | — | Allele 6, 1 |
| #2 | TR4 | Allele 6, 1 |
| #3 | TR5 | Allele 6, 1 |
| #4 | TR6 | Allele 6, 1 |
| #5 | TR7 | Allele 6, 1 |
| #6 | TR8 | Allele 6, 1 |
| #7 | — | Allele 7, 1 |
| #8 | TR4 | Allele 7, 1 |
| #9 | TR5 | Allele 7, 1 |
| #10 | TR6 | Allele 7, 1 |
| #11 | TR7 | Allele 7, 1 |
| #12 | TR8 | Allele 7, 1 |
| #13 | — | Allele 8, 1 |
| #14 | TR4 | Allele 8, 1 |
| #15 | TR5 | Allele 8, 1 |
| #16 | TR6 | Allele 8, 1 |
| #17 | TR7 | Allele 8, 1 |
| #18 | TR8 | Allele 8, 1 |
| #19 | — | Allele 6, 3.3 |
| #20 | TR4 | Allele 6, 3.3 |
| #21 | TR5 | Allele 6, 3.3 |
| #22 | TR6 | Allele 6, 3.3 |
| #23 | TR7 | Allele 6, 3.3 |
| #24 | TR8 | Allele 6, 3.3 |

-continued

| Soln. | Probe | Target (ng) |
|---|---|---|
| #25 | — | Allele 7, 3.3 |
| #26 | TR4 | Allele 7, 3.3 |
| #27 | TR5 | Allele 7, 3.3 |
| #28 | TR6 | Allele 7, 3.3 |
| #29 | TR7 | Allele 7, 3.3 |
| #30 | TR8 | Allele 7, 3.3 |
| #31 | — | Allele 8, 3.3 |
| #32 | TR4 | Allele 8, 3.3 |
| #33 | TR5 | Allele 8, 3.3 |
| #34 | TR6 | Allele 8, 3.3 |
| #35 | TR7 | Allele 8, 3.3 |
| #36 | TR8 | Allele 8, 3.3 |

These solutions were heated at 95° C. for 3 minutes, then cooled at room temperature for 10 minutes. A master mix was assembled and added to these solutions as in the previous Example. The resulting solutions were then heated at 37° C. for 15 minutes and were sampled as in the previous Example. The samples were added to L/L reagent (Promega, F202A) and the light output was immediately measured as in the previous Example. The following results were obtained.

| Target | — | TR4 | TR5 | TR6 | TR7 | TR8 |
|---|---|---|---|---|---|---|
| | Relative Light Units From Reactions Containing Probes With 1 ng of Target | | | | | |
| Allele 6 | 2.14 | 47.40 | 33.87 | 11.45 | 7.57 | 7.98 |
| Allele 7 | 2.06 | 53.00 | 30.97 | 30.43 | 12.38 | 10.41 |
| Allele 8 | 2.51 | 21.30 | 27.54 | 30.99 | 39.04 | 14.84 |
| (none) | (nd) | 2.28 | 2.30 | 2.59 | 3.12 | 3.43 |
| Expected Allele Detected | — | A 5 | A 6 | A 7 | A 8 | A 9 |
| | Relative Light Units From Reactions Containing Probes With 3.3 ng of Target | | | | | |
| Allele 6 | 8.52 | 282.6 | 291.5 | 90.62 | 61.34 | 46.49 |
| Allele 7 | 12.23 | 276.2 | 237.8 | 286.4 | 103.4 | 74.92 |
| Allele 8 | 10.33 | 170.6 | 242.5 | 264.4 | 264.9 | 111.9 |
| (none) | (nd) | 3.56 | 3.11 | 3.25 | 3.63 | 3.60 |
| Expected Allele Detected | — | A 5 | A 6 | A 7 | A 8 | A 9 |

Surprisingly, these probes did not provide the expected detection pattern. For example, probe TR6 was expected to only give a strong signal with a target with allele 7 (A 7). Although the probe did show a lower signal with allele 6 (A 6) than with allele 7 (90.6 vs. 286.4 units, respectively), very little difference was seen between the signals with alleles 7 and 8 (A 8) (286.4 vs. 264.4 units respectively). In general, all the probes exhibited substantially equal reactivity with any target that had the same number of repeated units or greater than the number of repeated units in the probe. These same probes showed lower signals with targets having fewer repeat units than those present in the probe, with the signal strength seen decreasing as the difference in the number of repeat units increased. Thus, although these probes clearly did not provide the expected signal patterns, they can be used to determine THO 1 alleles.

```
Allele 6
5'GGTGAATGAATGAATGAATGAATGAATGAGGGAAATAAGGGAGGAAGAGGC    SEQ ID NO:28

CAATGGG 3'

Allele 7
5'GGTGAATGAATGAATGAATGAATGAATGAATGAGGGAAATAAGGGAGGAAG    SEQ ID NO:29

AGGCCAATGGG 3'

Allele 8
5'GGTAGGTGAATGAATGAATGAATGAATGAATGAATGAATGAGGGAAATAAG    SEQ ID NO:30

GGAGGAAGAGGCCAATGGG 3'

TR4
5' CCCATTGGCCTGTTCCTCCCTTATTTCCCTCATTCATTCATT            SEQ ID NO:34

CATTCATTCACC 3'

TR5
5' CCCATTGGCCTGTTCCTCCCTTATTTCCCTCATTCATTCATTCATT        SEQ ID NO:35

CATTCATTCACC 3'

TR6
5' CCCATTGGCCTGTTCCTCCCTTATTTCCCTCATTCATTCATTCATT        SEQ ID NO:36

CATTCATTCATTCACC 3'

TR7
5' CCCATTGGCCTGTTCCTCCCTTATTTCCCTCATTCATTCATT            SEQ ID NO:37

CATTCATTCATTCATTCATTCACC 3'

TR8
5' CCCATTGGCCTGTTCCTCCCTTATTTCCCTCATTCATTCATT            SEQ ID NO:38

CATTCATTCATTCATTCATTCATTCACC 3'
```

EXAMPLE 10

Additional Probes for Detection of THO 1 Alleles

Additional probes are used in this Example to demonstrate that the creation of additional mismatches between THO 1 allele targets and probes can result in the formation of probe/target combinations that provide strong signals with essentially one THO 1 allele.

Probes TR 9 (SEQ ID NO:39), TR10 (SEQ ID NO:40) and TR11 (SEQ ID NO:41) were dissolved at 1 mg/mL and assembled into reactions with target at 3 ng/reaction with allele 6 (SEQ ID NO:28), allele 7 (SEQ ID NO:29), and allele 8 (SEQ ID NO:30) of THO 1 and without any target as described in the Example above. These solutions were heated and cooled as in the previous Example. The resulting solutions were treated with master mix, incubated, added to L/L reagent (Promega, F202A) and the light produced measured as in the previous Example. The following results were obtained.

| | Relative Light Units | | | |
|---|---|---|---|---|
| Target | Probe TR9 | Probe TR10 | Probe TR11 | none |
| Allele 6 | 59.74 | 35.86 | 75.78 | 8.96 |
| Allele 7 | 51.73 | 2.32 | 15.85 | 10.54 |
| Allele 8 | 58.58 | 25.37 | 33.67 | 9.85 |
| (none) | 47.27 | 34.24 | 3.676 | (nd) |

The values for the probe alone and target alone reactions were subtracted from the values for the combined reactions and are shown in the table below.

| | Relative Light Units | | |
|---|---|---|---|
| Target | Probe TR9 | Probe TR10 | Probe TR11 |
| Allele 6 | 3.51 | −7.34 | 63.14 |
| Allele 7 | −6.08 | −22.46 | 1.63 |
| Allele 8 | 1.46 | −18.72 | 20.14 |

Increasing the number of mismatched bases between the probe and target lowers the signal value measured, and in many cases decreases the values seen below those attributable from background reactions. In particular, probes TR9, which has a mismatch of 2 base pairs, and TR10, which has an A to C mutation 3 bases from the end of the probe, do not exhibit the ability to detect THO 1 alleles. However, probe TR11, which has a A to G change 3 bases from the end of the probe, produced a measurable signal with the allele 6 target that is greater than the signals seen with the other targets.

Probes TR12 (SEQ ID NO:42) and TR13 (SEQ ID NO:43) were then used as above. The following data were obtained.

| | Relative Light Units | |
|---|---|---|
| Target | Probe TR12 | Probe TR13 |
| Allele 6 | 9.7 | 9.8 |
| Allele 7 | 5.0 | 7.1 |
| Allele 8 | 10.4 | 12.6 |
| (none) | 3.0 | 2.9 |

These probes, having additional mismatches four base pairs from the 3' end of the probe, only provided very low light signals and apparently did not discriminate between the alleles of THO 1. Thus, these data suggest that probes that can provide allele-specific signals can be identified by designing probes with base pair mismatches placed in the probe sequence near the 3' end of the probe.

were discriminated with probes specific for the number of repeats using a pyrophosphorylation based assay. The targets were prepared by standard PCR amplification of each of the (Promega, DC5111) TPOX bands that were previously gel-purified. The PCR cycling parameters were 94° C., 1 minute (94° C., 15 seconds; 60° C., 30 seconds; 72° C., 60 seconds)×35, 68° C., 10 minutes. The correct size of the PCR products was confirmed on a 4% polyacrylamide gel electrophoresis. The PCR products were purified using Wizard® PCR Purification System (Promega, A7170) and resuspended in water to a concentration of 10 ng/µL. The interrogation sequence probes were P6 (SEQ ID NO:44), P7 (SEQ ID NO:45), P8 (SEQ ID NO:46), P9 (SEQ ID NO:47), P10 (SEQ ID NO:48), P11 (SEQ ID NO:49), P12 (SEQ ID NO:50) and P13 (SEQ ID NO:51).

Targets containing between 6 and 13 TGAA repeats were each interrogated with each of the interrogation probes listed above. The target alleles used were A6 (SEQ ID NO:52), A7 (SEQ ID NO:53), A8 (SEQ ID NO:54), A9 (SEQ ID NO:55), A10 (SEQ ID NO:56), A11 (SEQ ID NO:57), A12 (SEQ ID NO:58) and A13 (SEQ ID NO:59), respectively. The probes were at a final concentration of 2.5 µM in the solution, 10 ng of target were used per reaction and the

```
Allele 6
5'GGTGAATGAATGAATGAATGAATGAATGAGGGAAATAAGGGAGGAAGAGGC   SEQ ID NO:28

CAATGGG 3'

Allele 7
5'GGTGAATGAATGAATGAATGAATGAATGAATGAGGGAAATAAGGGAGGAAG   SEQ ID NO:29

AGGCCAATGGG 3'

Allele 8
5'GGTAGGTGAATGAATGAATGAATGAATGAATGAATGAATGAGGGAAATAAG   SEQ ID NO:30

GGAGGAAGAGGCCAATGGG 3'

TR9
5' CCCATTGGCCTGTTCCTCCCTTATTTCCCTCATTCATTCATT             SEQ ID NO:39

CATTCATTCATTCAGC 3'

TR10
5' CCCATTGGCCTGTTCCTCCCTTATTTCCCTCATTCATTCATT             SEQ ID NO:40

CATTCATTCATTCCCC 3'

TR11
5' CCCATTGGCCTGTTCCTCCCTTATTTCCCTCATTCATTCATT             SEQ ID NO:41

CATTCATTCATTCGCC 3'

TR12
5' CCCATTGGCCTGTTCCTCCCTTATTTCCCTCATTCATTCATT             SEQ ID NO:42

CATTCATTCATTGACC 3'

TR13
5' CCCATTGGCCTGTTCCTCCCTTATTTCCCTCATTCATTCATT             SEQ ID NO:43

CATTCATTCATTAACC 3'
```

EXAMPLE 11

Discrimination of Repeated DNA Sequences Using Pyrophosphorylation-based Assay Methods-III In this Example, PCR targets spanning between 6 to 13 copies of the TPOX four nucleotide short tandem repeat volume was increased to 20 µL with water. The solutions were heated at 95° C. for 2 minutes, then cooled at room temperature over 10 minutes.

Twenty microliters of master mix were added to each solution (14.7 µL water, 4 µL 10X DNA polymerization buffer, 5 µL 40 mM NaPPi, 0.4 µL 10 µM ADP, 0.2 µL NDPK (1 U/μL), 0.2 μL Klenow exo- (10 U/μL)) and they were further incubated at 37° C. for 15 minutes. Then, 4 μL of the solution were added to 100 μL of L/L reagent and the light output read with a Turner® TD20/20 luminometer. The relative light units (rlu) obtained are reported below:

| Target | Raw rlu numbers Probe | | | | | | | | |
|---|---|---|---|---|---|---|---|---|---|
| | P6 | P7 | P8 | P9 | P10 | P11 | P12 | P13 | None |
| A6 | 57.62 | 16.80 | 15.65 | 28.51 | 23.37 | 25.31 | 26.70 | 47.48 | 14.08 |
| A7 | 23.29 | 73.44 | 22.39 | 37.28 | 20.31 | 25.01 | 26.29 | 44.24 | 25.06 |
| A8 | 25.04 | 20.82 | 54.63 | 35.78 | 20.69 | 21.02 | 22.99 | 37.51 | 18.37 |
| A9 | 28.83 | 21.60 | 25.03 | 85.98 | 30.71 | 28.55 | 29.54 | 50.86 | 21.48 |
| A10 | 27.69 | 25.53 | 30.30 | 42.38 | 61.04 | 30.21 | 27.71 | 46.30 | 32.80 |
| A11 | 30.29 | 35.07 | 30.67 | 51.20 | 40.37 | 69.92 | 39.12 | 58.52 | 30.00 |
| A12 | 35.36 | 25.43 | 29.71 | 45.14 | 28.44 | 38.76 | 63.31 | 57.05 | 40.24 |
| A13 | 39.35 | 27.67 | 29.92 | 42.56 | 33.59 | 32.80 | 36.04 | 84.37 | 32.70 |
| None | 8.67 | 6.29 | 9.15 | 27.98 | 14.18 | 16.51 | 16.22 | 32.98 | 4.66 |

The above values were adjusted for background and the negative numbers converted to zero to provide the data in the table below.

| Target | Probe | | | | | | | |
|---|---|---|---|---|---|---|---|---|
| | P6 | P7 | P8 | P9 | P10 | P11 | P12 | P13 |
| A6 | 40 | 1 | 0 | 0 | 0 | 0 | 1 | 5 |
| A7 | 0 | 47 | 0 | 0 | 0 | 0 | 0 | 0 |
| A8 | 3 | 1 | 32 | 0 | 0 | 0 | 0 | 0 |
| A9 | 3 | 0 | 0 | 41 | 0 | 0 | 0 | 1 |
| A10 | 0 | 0 | 0 | 0 | 19 | 0 | 0 | 0 |
| A11 | 0 | 0 | 0 | 1 | 1 | 28 | 0 | 0 |
| A12 | 0 | 0 | 0 | 0 | 0 | 0 | 12 | 0 |
| A13 | 3 | 0 | 0 | 0 | 0 | 0 | 0 | 23 |

The data indicate that the interrogation probes can recognize the presence of the related homozygote alleles of the TPOX locus. Similarly, heterozygote targets were assayed with the same set of interrogation probes. Ten nanograms of each purified PCR target were included in each interrogation reaction. The reaction conditions were identical to those for the homozygote targets described above. The rlu values obtained are reported below.

| Target | Raw rlu numbers Probe | | | | | | | | |
|---|---|---|---|---|---|---|---|---|---|
| | P6 | P7 | P8 | P9 | P10 | P11 | P12 | P13 | None |
| A6, A13 | 91.09 | 36.85 | 40.90 | 50.88 | 41.93 | 41.33 | 83.69 | 83.69 | 31.78 |
| A11, A12 | 55.94 | 48.13 | 54.35 | 62.64 | 50.92 | 84.19 | 80.33 | 66.41 | 54.62 |
| A9, A10 | 61.75 | 43.49 | 47.71 | 93.76 | 77.91 | 37.18 | 39.11 | 59.74 | 33.37 |
| A7, A8 | 35.66 | 76.04 | 62.03 | 36.03 | 27.92 | 30.07 | 31.92 | 51.40 | 50.52 |
| None | 6.29 | 4.87 | 6.22 | 20.83 | 10.89 | 11.86 | 12.41 | 28.64 | 4.32 |

The values were adjusted for background and the negative numbers converted to zero to provide the data in the table below.

|        | Probe |      |      |      |      |       |       |       |
|--------|-------|------|------|------|------|-------|-------|-------|
| Target | P6    | P7   | P8   | P9   | P10  | P11   | P12   | P13   |
| A6, A13 | 57.35 | 4.53 | 7.23 | 2.59 | 3.58 | 2.01 | 6.45 | 27.59 |
| A11, A12 | 0 | 0 | 0 | 0 | 0 | 22.03 | 17.62 | 0 |
| A9, A10 | 26.42 | 9.58 | 12.45 | 43.88 | 37.97 | 0 | 0 | 2.05 |
| A7, A8 | 0 | 24.98 | 9.62 | 0 | 0 | 0 | 0 | 0 |

As can be seen from the results in the table above, this method accurately identified each of the heterozygote targets, although probe P6 also identified one false positive for an unknown reason.

Interrogation Probe Sequences:

SEQ ID NO:44
P6 5' GGCACTTAGGGAACCCTCAC TGAA TGAA TGAA TGAA

TGAA TGAA TATT 3'

SEQ ID NO:45
P7 5' GGCACTTAGGGAACCCTCAC TGAA TGAA TGAA TGAA

TGAA TGAA TGAA TATT 3'

SEQ ID NO:46
P8 5' GGCACTTAGGGAACCCTCAC TGAA TGAA TGAA TGAA

TGAA TGAA TGAA TGAA TATT 3'

SEQ ID NO:47
P9 5' GGCACTTAGGGAACCCTCAC TGAA TGAA TGAA TGAA

TGAA TGAA TGAA TGAA TGAA TATT 3'

-continued

SEQ ID NO:48
P10 5' GCACTTAGGGAACCCTCAC TGAA TGAA TGAA TGAA

GAA TGAA TGAA TGAA TGAA TGAA TATT

SEQ ID NO:49
P11 5' GGCACTTAGGGAACCCTCAC TGAA TGAA TGAA TGAA

TGAA TGAA TGAA TGAA TGAA TGAA TGAA TATT 3'

SEQ ID NO:50
P12 5' GGCACTTAGGGAACCCTCAC TGAA TGAA TGAA TGAA

TGAA TGAA TGAA TGAA TGAA TGAA TGAA TGAA TATT 3'

SEQ ID NO:51
P13 5' GGCACTTAGGGAACCCTCAC TGAA TGAA TGAA TGAA

TGAA TGAA TGAA TGAA TGAA TGAA TGAA TGAA

TGAA TATT 3'

Target Alleles:

A6:

5' GGCACTTAGGGAACCCTCACTGAATGAATGAATGAATGA    SEQ ID NO:52

ATGAATGTTTGGGCAAATAAACGCTGACAAGGACAGAAGGG

CCTAGCGGGAAGGGAACAGGAGTAAGACCAGCGCACAGCCCGACTTGTG

TTCAGAAGACCTGGGATTGGACCTGAGGATTCAATTTTGGATGAATCTC

TTAATTAACCTGTGTGGTTCCCAGTTCCTCCCCTGAGCGCCCAGGACAG

TAGAGTCAACCTCA 3'

A7:

5' GGCACTTAGGGAACCCTCACTGAATGAATGAATGAATGA    SEQ ID NO:53

ATGAATGAATGTTTGGGCAAATAAACGCTGACAAGGACAGAAGGG

CCTAGCGGGAAGGGAACAGGAGTAAGACCAGCGCACAGCCCGACTTGTG

TTCAGAAGACCTGGGATTGGACCTGAGGATTCAATTTTGGATGAATCTC

TTAATTAACCTGTGTGGTTCCCAGTTCCTCCCCTGAGCGCCCAGGACAG

TAGAGTCAACCTCA 3'

A8:

5' GGCACTTAGGGAACCCTCACTGAATGAATGAATGAATGA    SEQ ID NO:54

ATGAATGAATGAATGTTTGGGCAAATAAACGCTGACAAGGACAGAAGGG

-continued

CCTAGCGGGAAGGGAACAGGAGTAAGACCAGCGCACAGCCCGACTTGTG

TTCAGAAGACCTGGGATTGGACCTGAGGATTCAATTTTGGATGAATCTC

TTAATTAACCTGTGTGGTTCCCAGTTCCTCCCCTGAGCGCCCAGGACAG

TAGAGTCAACCTCA 3'

A9:

5' GGCACTTAGGGAACCCTCACTGAATGAATGAATGAATGA          SEQ ID NO:55

ATGAATGAATGAATGAATGTTTGGGCAAATAAACGCTGACAAGGACAGAAGGG

CCTAGCGGGAAGGGAACAGGAGTAAGACCAGCGCACAGCCCGACTTGTG

TTCAGAAGACCTGGGATTGGACCTGAGGATTCAATTTTGGATGAATCTC

TTAATTAACCTGTGTGGTTCCCAGTTCCTCCCCTGAGCGCCCAGGACAG

TAGAGTCAACCTCA 3'

A10:

5' GGCACTTAGGGAACCCTCACTGAATGAATGAATGAATGA          SEQ ID NO:56

ATGAATGAATGAATGAATGAATGTTTGGGCAAATAAACGCTGACAAGGACAGA

AGGGCCTAGCGGGAAGGGAACAGGAGTAAGACCAGCGCACAGCCCGACTTGTG

TTCAGAAGACCTGGGATTGGACCTGAGGATTCAATTTTGGATGAATCTC

TTAATTAACCTGTGTGGTTCCCAGTTCCTCCCCTGAGCGCCCAGGACAG

TAGAGTCAACCTCA 3'

A11:

5' GGCACTTAGGGAACCCTCACTGAATGAATGAATGAATGA          SEQ ID NO:57

ATGAATGAATGAATGAATGAATGAATGTTTGGGCAAATAAACGCTGACAAGGA

CAGAAGGGCCTAGCGGGAAGGGAACAGGAGTAAGACCAGCGCACAGCCCGACT

TGTGTTCAGAAGACCTGGGATTGGACCTGAGGATTCAATTTTGGATGAATCTC

TTAATTAACCTGTGTGGTTCCCAGTTCCTCCCCTGAGCGCCCAGGACAG

TAGAGTCAACCTCA 3'

A12:

5' GGCACTTAGGGAACCCTCACTGAATGAATGAATGAATGA          SEQ ID NO:58

ATGAATGAATGAATGAATGAATGAATGAATGTTTGGGCAAATAAACGCTGACA

AGGACAGAAGGGCCTAGCGGGAAGGGAACAGGAGTAAGACCAGCGCACAGCCC

GACTTGTGTTCAGAAGACCTGGGATTGGACCTGAGGATTCAATTTTGGATGAA

TCTCTTAATTAACCTGTGTGGTTCCCAGTTCCTCCCCTGAGCGCCCAGGACAG

TAGAGTCAACCTCA 3'

A13:

5' GGCACTTAGGGAACCCTCACTGAATGAATGAATGAATGA          SEQ ID NO:59

ATGAATGAATGAATGAATGAATGAATGAATGAATGTTTGGGCAAATAAACGCT

GACAAGGACAGAAGGGCCTAGCGGGAAGGGAACAGGAGTAAGACCAGCGCACA

-continued

GCCCGACTTGTGTTCAGAAGACCTGGGATTGGACCTGAGGATTCAATTTTGGA

TAGAGTCAACCTCA 3'

EXAMPLE 12

Interrogation for Loss of Heterozygosity

In certain types of disease states such as some cancers, there is a change in the heterozygosity of the locus of certain alleles. For example, a non-cancerous cell may be heterozygous at a particular locus. In a cancer cell, however, one of the two alleles may be lost or deleted at the particular locus. This is referred to as loss of heterozygosity.

This type of loss of heterozygosity (LOH) reaction was created by PCR-amplifying 25 ng (1 µL) and 50 ng (2 µL) of two E. coli targets (W3110, DH5α) with probes 10730 (SEQ ID NO:60) and 10731 (SEQ ID NO:61) as described below. These probes span the ΔM15 93 bp deletion present in DH5α DNA, but not present in W3110 DNA. The number of PCR cycles was optimized so amplification of the "heterozygote" target (1 µL W3110 and 1 µL DH5α) produced one-half the amount of DNA in each band as did amplification of the "homozygote" target (2 µL W3110 or 2 µL DH5α) under the same amplification conditions.

PCR targets spanning the locus of interest were created in duplicate as follows: 2 µL E. coli genomic DNA, W3110 or DH5α for homozygote sample (50 ng); 1 µL each W3110 and DH5α for the heterozygote sample; 1 µL of W3110 or DH5α for the LOH sample.

| 5 µl | 10X Taq buffer with 15 mM MgCl₂ (Promega, M188A) |
| 0.5 µL | Probe 10730 (50 pmol) |
| 0.5 µL | Probe 10731 (50 pmol) |
| 1 µL | 10 mM dNTPs |
| 1 µL | Taq DNA Polymerase (Promega, M186A) |
| 40 µL | water |

PCR cycling parameters were 96° C., 1 minute; (94° C., 15 seconds; 60° C., 30 seconds; 72° C., 45 seconds)×20; 72° C., 45 seconds. The PCR reaction was purified with 500 µL Wizard™ PCR Purification Resin (Promega, A7181) according to manufacturer instructions and eluted with 25 µL water.

The duplicate DNA targets (1 µL) were then interrogated in duplicate, with 1 µg (200 pmol) probe 10732 (SEQ ID NO:62), a sequence common to both W3110 and DH5α; 1 µg (200 pmol) probe 10733 (SEQ ID NO:63), a sequence completely matching only W3110 DNA; and 1 µg (200 pmol) probe 10734 (SEQ ID NO:64), a sequence completely matching only DH5α DNA. Four microliters of the interrogation reaction were combined with 100µl L/L reagent (Promega, F202A) and the light output measured.

|  | homozygotes | | | | heterozygotes | | LOH | | | | oligo |
|---|---|---|---|---|---|---|---|---|---|---|---|
|  | W1 | W2 | D1 | D2 | W | D | W1 | W2 | D1 | D2 | alone |
| No oligo | 93 | 131 | 59 | 115 | 129 | 83 | 101 | 59 | 63 | 71 | — |
| 10732 | 91 | 372 | 542 | 480 | 447 | 403 | 307 | 53 | 362 | 352 | 4 |
| 10732 | 95 | 465 | 536 | 494 | 479 | 419 | 295 | 257 | 364 | 349 | 4 |
| 10733 | 95 | 373 | 112 | 95 | 251 | 191 | 218 | 173 | 67 | 76 | 6 |
| 10733 | 86 | 353 | 108 | 88 | 245 | 187 | 204 | 158 | 77 | 68 | 6 |
| 10734 | 185 | 212 | 427 | 384 | 337 | 264 | 181 | 161 | 182 | 263 | 111 |
| 10734 | 179 | 199 | 409 | 378 | 318 | 258 | 159 | 127 | 182 | 282 | 111 |

The deletion-specific interrogation oligonucleotide (10734) gave high background. In general these data show the utility of the technology for determination of LOH. However, two samples, the first W/W homozygote and first D LOH, give aberrant data for an unknown reason.

| 10730 | 5' CACTTTATGCTTCCGGCTCGTATG 3' | SEQ ID NO:60 |
| | (lacZ) | |
| 10731 | 5' GGGATAGGTTACGTTGGTGTAGATGG 3' | SEQ ID NO:61 |
| | (lacZ) | |
| 10732 | 5' GTTGGGAAGGGCGATCGGTG 3' | SEQ ID NO:62 |
| | (common lac probe) | |
| 10733 | 5' GGGATGTGCTGCAAGGCGATT 3' | SEQ ID NO:63 |
| | (wt lac probe) | |
| 10734 | 5' GGATTCACTGGCCGTCGTGG 3' | SEQ ID NO:64 |
| | (deletion lac probe) | |

EXAMPLE 13

Interrogation For Loss of Heterozygosity—CMV

The use of an interrogation assay to determine loss of heterozygosity with a synthetic cytomegalovirus (CMV) target is demonstrated in this Example.

The CMV target was chosen because the interrogating probe oligonucleotides (9211 (SEQ ID NO:71) and 9212 (SEQ ID NO:72) had been previously used and well characterized. Oligonucleotides 10800 (SEQ ID NO:65) and 10801 (SEQ ID NO:66) were annealed to produce a synthetic target, "A", representing a fragment of the CMV genome. Likewise, oligonucleotides 10803 (SEQ ID NO:67) and 10805 (SEQ ID NO:68) were annealed to produce a synthetic target, "G" representing a fragment of the CMV genome. Targets A and G are identical except at one nucleotide position where they have the nucleotide resulting in their name. Both targets have SacI overhangs.

The targets were cloned into the SacI restriction site of pZERO-2 plasmid (Invitrogen) and transformed into TOP10 E. coli cells (Invitrogen). The presence of the correct nucleotide sequence in the A and G clones was confirmed by sequencing. However, the G clone was found to contain an unintended mutation at the nucleotide position three bases in from the 5' end of the region that anneals to the interrogation probes. Because this mismatch is near the 5' end of the interrogation probe annealing sequence, it should not affect the interrogation results.

The following five target solutions were created with the A and G clones:

1. Hetero: 125 pg A and 125 pg G/microliter
2. LOH A: 125 pg A and no G/microliter
3. LOH G: no A and 125 pg G/microliter
4. Mix Ag: 125 pg A and 62 pg G/microliter
5. Mix Ga: 62 pg A and 125 pg G/microliter These target solutions were PCR amplified with the JH67 (SEQ ID NO:69) and 11077 (SEQ ID NO: 70) probes in the following reaction:

2 µL Target solution
1 µL Probes JH67 and 11077 (50 pmol each)
1 µL 10 mM dNTPs
5 µL 10X Taq buffer
1 µL Taq DNA polymerase
40 µL water The PCR cycling parameters were: 96° C., 1 minute; (94° C., 15 seconds; 60° C., 30 seconds; 72° C., 45 seconds)×15; 72° C., 45 seconds. The entire PCR reaction was then purified with 500 µL Wizard™ PCR purification resin (Promega, A7170) according to manufacturer's instructions. The DNA was eluted with 30 µL TE buffer. A standard interrogation reaction with 6 µL target and 1 µg interrogation probe, was performed with the exception that 2 units of Klenow exo- were used per reaction. Four microliters of the final reaction were combined with 100 µL of L/L reagent and the relative light units measured.

|  | Heterzygote | | LOH A | | LOH G | | Mix Ag | | Mix Ga | | Oligo Alone |
|---|---|---|---|---|---|---|---|---|---|---|---|
| No oligo | 30 | 40 | 65 | 29 | 34 | 51 | 19 | 59 | 26 | 41 | — |
| A oligo | 279 | 340 | 74 | 329 | 27 | 27 | 258 | 309 | 50 | 164 | 5.2 |
|  | 308 | 372 | 76 | 339 | 20 | 26 | 351 | 330 | 83 | 167 | 5.2 |
| G oligo | 302 | 324 | 37 | 91 | 285 | 272 | 127 | 106 | 245 | 302 | 6.3 |
|  | 278 | 325 | 30 | 87 | 256 | 187 | 113 | 124 | 215 | 357 | 6.3 |
| A:G ratio | 1.01 | 1.10 | 2.26 | | 3.76 | 0.09 | 0.11 | 2.54 | 2.78 | 0.29 | 0.50 |
| G:A ratio | 0.99 | 0.91 | 0.44 | | 0.27 | 11.59 | 8.71 | 0.39 | 0.36 | 3.46 | 1.99 |

These data illustrate that LOH can be determined using this method with appropriate interrogation probes.

```
10800   5' CGTGTATGCCACTTTGATATTACACCCATGAACGTG   SEQ ID NO:65
           CTCATCGACGTGAACCCGCACAACGAGCT 3'

10801   5' CGTTGTGCGGGTTCACGTCGATGAGCACGTTCATGG   SEQ ID NO:66
           GTGTAATATCAAAGTGGCATACACGAGCT 3'

10803   5' CGTGTATGCCACTTTGATATTACACCCGTGAACGTG   SEQ ID NO:67
           CTCATCGACGTGAACCCGCCAAACGAGCT 3'

10805   5' CGTTGTGCGGGTTCACGTCGATGAGCACGTTCACGG   SEQ ID NO:68
           GTGTAATATCAAAGTGGCATACACGAGCT 3'

JH67    5' TCACACAGGAAACAGCTATGACCATG 3'         SEQ ID NO:69

11077   5' GCAAGGCGATTAAGTTGGGTAACG 3'           SEQ ID NO:70
           (M13 forward probe)

9211    5' CACTTTGATATTACACCCATG 3'              SEQ ID NO:71

9212    5' CACTTTGATATTACACCCGTG 3'              SEQ ID NO:72
```

EXAMPLE 14

Multiplex Analysis of Congenital Adrenal Hyperplasia (CAH) Gene

Congenital adrenal hyperplasia (CAH) is a group of autosomal recessive diseases resulting from a wide range of mutations in the steroid 21-hydroxylase (CYP21) gene that contains 10 exons. There is a high level of nucleic acid homology (98% in exons, 96% in introns) between CYP21, the functional gene, and CYP21P, the nonfunctional pseudogene. The many types of mutations in this gene that can lead to disease include complete gene deletions, large gene conversions, single point mutations, and a small 8 bp deletion [See, White, et al., Hum. Mutat., 3:373–378, (1994)].

The majority of the CAH disease-causing mutations are sequences present in the nonexpressed CYP21P pseudogene, and arise in the CYP21 gene through recombination between CYP21P and CYP21. Thus, one mutation detection strategy specifically detects the CYP21 gene, and not the CYP21P pseudogene. The frequency of disease-carrying alleles in the population is about 1 in 50.

The CAH target was interrogated for a variety of mutations using Klenow exo- and yeast NDPK, and the results were compared to a similar analysis using Tne triple mutant thermostable DNA polymerase and a thermostable Pfu NDPK. Both wild type CAH PCR products, mutant synthetic targets, and a pseudogene PCR product amplified from the cloned CYP21P pseudogene were utilized as targets in this assay. They are listed below.

Primer pairs used in PCR amplification and the resulting products are as follows.

| Primers | Size PCR Segment | Segment Amplified |
| --- | --- | --- |
| 10912 + 10909 | 1400 bp | 5' end CYP21 |
| 11461 + 11480 | 918 bp | 5' end CYP21 |
| 10910 + 11286 | 1492 bp | 3' end CYP21 |
| 11535 + 11286 | 1496 bp | 3' end CYP21 |
| 10912 + 10911 | 2680 bp | pseudogene (CYP21P) |

Synthetic targets and interrogation oligos utilized are listed below.

PCR reactions were assembled to amplify regions of the CAH gene with 4 different probe sets, using undigested human genomic DNA (Promega, G3041) as target (25 ng per reaction). For amplification of the pseudogene, human genomic DNA was predigested with the restriction enzyme Bcl I, which specifically cleaves the CYP21 gene upstream of the forward PCR probe, thus permitting only amplification of CYP21P [Krone, Clinical Chem. 44(10):2075–2082 (1998)].

The 2680 bp PCR product was amplified from 50 ng of digested DNA and subsequently cloned into the plasmid vector pGEM-T Easy (Promega, A1380) following the manufacturer's protocol. A clone was selected and sequenced (USB Sequenase kit, US70770) to confirm it was indeed the pseudogene. The cloned CYP21P gene in the pGEM-T Easy vector was used in subsequent amplifications to obtain pure pseudogene PCR product for mutation interrogation analysis (100 pg of plasmid per PCR reaction).

The use of thermostable enzymes to interrogate the CAH gene has also permitted the interrogation of up to 6 multiple sites within one reaction. The method used in this Example is illustrative of routine studies carried out in screening laboratories where usual results show the presence of an expected gene (or the absence of a mutant gene) in almost all of the samples, and only rarely shows the presence of a mutant gene. In the case illustrated here, a qualitative result is provided from which the exact mutation present can be determined in a subsequent assay.

Thus, equal volumes of the CAH wild type (WT) 918 bp and 1496 bp PCR product) were combined (to thus span the entire CAH gene) and interrogated either separately at each mutation site, or as a multiplexed group. The discrimination ratio was good both in the separate reactions for the combined PCR products, as well as the multiplexed reaction. In addition, the multiplexed reaction using the CAH wild type PCR products and either 6 wild type interrogation oligo probes or 6 mutant interrogation oligo probes was combined with an equimolar amount of synthetic target (mutant synthetic target for each mutation site; 0.2 pmoles either PCR product or synthetic target), to simulate a heterozygote sample.

| Target DNA | Tne/Pfu NDPK, No Oligo | Tne/Pfu NDPK, WT Oligo | Tne/Pfu NDPK Mutant Oligo | Probe for Mutation Site | Mutant Synthetic Target Added |
| --- | --- | --- | --- | --- | --- |
| CAH WT | | | | | |
| 918 bp + 1496 bp | 172.7 | 553.0 | 180.2 | 1 | |
| Same | 172.7 | 535.7 | 184.0 | 2 | |
| Same | 172.7 | 494.8 | 182.0 | 3 | |
| Same | 172.7 | 486.7 | 148.7 | 4 | |
| Same | 172.7 | 471.7 | 187.9 | 5 | |
| Same | 172.7 | 317.5 | 179.7 | 6 | |
| Same | 172.7 | 297.5 | 246.4 | 7 | |
| Same | 523.7 | 1929.0 | 499.5 | 1, 2, 3, 4, 5 and 6 | |
| Same | 506.0 | 1882.0 | 2234.0 | 1 | 1 |
| Same | 525.4 | 1848.0 | 1505.0 | 2 | 2 |
| Same | 535.9 | 1735.0 | 2877.0 | 3 | 3 |
| Same | 547.5 | 1880.0 | 4879.0 | 4 | 4 |
| Same | 552.4 | 2000.0 | 3864.0 | 5 | 5 |
| Same | 482.9 | 1938.0 | 2189.0 | 6 | 6 |
| Same | 514.5 | 1791.0 | 4192.0 | 2 + 4 | 2 + 4 |
| Same | 537.6 | 1752.0 | 3427.0 | 5 + 6 | 5 + 6 |

Because of the large size of the CAH gene and the large number of different mutations that may be present, the use of the thermostable enzymes, and thus the increased stringency of the detection procedure, was found to be highly advantageous with this complex target. Mutation sites that interrogated poorly using Klenow exo- and yeast NDPK at 37° C., were more successfully interrogated when using the Tne triple mutant polymerase and Pfu NDPK at elevated temperatures. In addition, use of the thermostable enzymes permitted the multiplexing of numerous wild type or mutant interrogation oligos in the same interrogation assay, to obtain the rapid screening for mutations that may be present.

11143 5' CGGAGCCTCCACCTCCCG     SEQ ID NO:73
CAH interrogator oligo 6 (wild type) for mutation site 1

-continued 11085 5' CACCCTCCAGCCCCCAGC 3'  SEQ ID NO:74
CAH interrogator 01190 2 (pseudogene mutant) for
mutation site 2

11084 5' CGGAGCCTCCACCTCCTG 3'  SEQ ID NO:75
CAH interrogator oligo 1 (pseudogene mutant) for
mutation site 1

11086 5' CCTCACCTGCAGCATCAAC 3'  SEQ ID NO:76
CAH interrogator oligo 3 (pseudogene mutant) for
mutation site 3

11144 5' CACCCTCCAGCCCCCAAC 3'  SEQ ID NO:77
CAH interrogator oligo 7 (wild type) for mutation
site 2

11145 5' CCTCACCTGCAGCATCATC 3'  SEQ ID NO:78
CAH interrogator oligo 8 (wild type) for mutation
site 3

11087 5' CCTGGAAGGGCACTT 3'  SEQ ID NO:79
CAH interrogator oligo 4 (pseudogene mutant) for
mutation site 4

11146 5' CCTGGAAGGGCACGT 3'  SEQ ID NO:80
CAH interrogator oligo 9 (wild type) for mutation
site 4

11088 5' GATTCAGCAGCGACTGTA 3'  SEQ ID NO:81
CAH interrogator oligo 5 (pseudogene mutant) for
mutation site 5

11147 5' GATTCAGCAGCGACTGCA 3'  SEQ ID NO:82
CAH interrogator oligo 10 (wild type) for mutation
site 5

11287 5' CGAGGTGCTGCGCCTGCG 3'  SEQ ID NO:83
CAH interrogation olgio 11 (wild type) for mutation
site 6

11288 5'CGAGGTGCTGCGCCTGTG 3'  SEQ ID NO:84
CAH interrogation oligo 12 (pseudogene mutant) for
mutation site 6

11641 5'GGGATCACATCGTGGAGATG 3'  SEQ ID NO:85
CAH interrogation oligo 23 (wild type) for mutation
site 7

11642 5'GGGATCACAACGAGGAGAAG 3'  SEQ ID NO:86
CAH interrogation oligo 24 (pseudogene mutant) for
mutation site 7

EXAMPLE 15

Detection of Chromosomal DNA Without Amplification: I

In theory, direct detection of a single copy gene in chromosomal DNA should be possible if enough DNA can be assayed. The amount of human genomic DNA needed can be calculated as follows:

$$\frac{(1 \times 10^{-9} \text{ g DNA})(5 \times 10^{9} \text{ bases/genome})}{(1 \times 10^{3} \text{ bases specific target})} =$$

approximately 5 mg of DNA

However, as the amount of DNA interrogated increases, nonspecific DNA signal from this DNA also increases. Therefore, chromosomal DNA in amounts approaching even 1 µg of DNA would produce very high background.

Increasing the copies of target DNA per chromosome is one way to overcome this limitation. Many such sequences are known. The absolute sequence of the repeated DNA in different species can vary as does the number of copies of the sequence in the genome. For example, there are estimated to be 500–1000 copies of a sequence known as the rep sequence in the *E. coli* chromosome. The Alu sequence is present in the haploid human chromosome in approximately 300,000 copies. The estimated amount of human chromosomal DNA needed to detect the Alu sequence is:

$$\frac{5 \times 10^{-3} \text{ grams DNA (single copy gene requirement)}}{3 \times 10^{5} \text{ copies per genome}} =$$

$1.7 \times 10^{-8}$ grams (or about 17 ng of DNA)

In this example, probes to two regions of the Alu sequence (Alu 1 oligonucleotide 11597 (SEQ ID NO:87) and Alu 2 oligonucleotide 11598 (SEQ ID NO:88)) were used to demonstrate that direct detection of chromosomal DNA is achievable.

The genomic DNA (4.2 µg) was digested to completion (5 hours, 37° C.) with 40 units of Sph I restriction enzyme, which leaves a 3' overhang on the digested fragments. Either 40 ng or 80 ng of the digested genomic DNA was annealed to 1.0 µg of the interrogation probes 11597 and 11598 in separate reactions, and 11597 and 11598 in the same reaction with water added to a final volume of 20 µL. A negative control, without an interrogation probe, was also assembled. The solutions were heated at 92° C. for 3 minutes and cooled at room temperature for 15 minutes.

Twenty microliters of master mix, described below, were added to each annealing reaction and the tubes were further incubated at 37° C. for 20 minutes, then stored on ice. Four microliters of the reaction were added to 100 µL of L/L reagent (Promega F120B) in quadruplicate samples, and relative light units (rlu) measured on a Turner® TD20/20 luminometer. The rlu results are reported below.

Master Mix:

| | |
|---|---|
| 200 µL | 10X DNA Polymerase Buffer |
| 25 µL | 40 mM NaPPi |
| 25 µL | Klenow exo- |
| 10 µL | NDPK 1 U/µL |
| 20 µL | ADP 10 µM |
| 720 µL | water |

| Rxn* 1 | Rxn 2 | Rxn 3 | Rxn 4 | average | Net | Std Dev* |
|---|---|---|---|---|---|---|

-continued

| | | | | | | | |
|---|---|---|---|---|---|---|---|
| No DNA | 3.372 | 3.342 | 3.306 | 3.249 | 3.317 | 0 | 0.052898 |
| alu1 only | 3.92 | 3.625 | 3.756 | 3.799 | 3.775 | 0.458 | 0.12174 |
| alu2 only | 23.18 | 25.47 | 24.58 | 25.19 | 24.61 | 21.29 | 1.020082 |
| 40 ng DNA | 20.63 | 21.98 | 23.91 | 22.3 | 22.21 | 18.39 | 1.347504 |
| alu1 + 40 ng DNA | 53.12 | 57.05 | 52.52 | 36.5 | 49.80 | 46.03 | 9.089798 |
| alu2 + 40 ng DNA | 99.23 | 91.26 | 55.9 | 85.59 | 83.00 | 58.39 | 18.90995 |
| 80 ng DNA | 38.57 | 44.34 | 42.96 | 46.33 | 43.05 | 39.73 | 3.291454 |
| alu1 + 80 ng DNA | 89.25 | 68.01 | 91.43 | 96.14 | 86.21 | 82.44 | 12.46776 |
| alu2 + 80 ng DNA | 156.2 | 156.6 | 149.9 | 143.7 | 151.6 | 127.0 | 6.095353 |
| alu1 + alu2 | 30.65 | 23.82 | 32.57 | 27.60 | 28.66 | 25.34 | 3.820881 |
| alu1 + alu2 + 40 ng DNA | 66.49 | 101.1 | 104.9 | 104.3 | 94.1975 | 65.81 | 18.54682 |

*Std Dev = 1 standard deviation, Rxn = reaction
11597   5' AGACCCCATCTCTAA 3'   (Alu 1)
SEQ ID NO:87
11598   5' GCCTGGGTGACAGAGCA 3'   (Alu 2)
SEQ ID NO:88

EXAMPLE 16

Detection of Chromosomal DNA Without Amplification: II

Another method to detect the presence of the Alu sequence is to perform single probe extension reactions is described herein.

This Example illustrates use of a different type of oligonucleotide probe that is used to form a hairpin structure in the interrogation technology of this invention. This study demonstrates a method for eliminating the need for adding a probe specific to the interrogation site to the interrogation reaction.

Here, the oligonucleotide probe anneals to the target strand downstream of (3' to) the interrogation position in the target strand. The oligonucleotide has at its 5' end an unannealed region of nucleotides followed by about 5 to about 20 nucleotides that are identical to the interrogation region on the target strand. The annealed 3' end of the oligonucleotide is then extended through the interrogation position of the target strand creating what is referred to as extended probe. The hybrid is denatured and a hairpin structure formed between the extended probe strand and the 5' end of the oligonucleotide probe. This region is then assayed in a standard interrogation reaction to determine if a mismatch is present or not.

Four probes were designed to represent different types of hairpin formations that an extended probe strands may assume. These probes are 10207 (SEQ ID NO:177), 10208 (SEQ ID NO:178), 10209 (SEQ ID NO:179), and 10212 (SEQ ID NO:180).

These probes are predicted to form the following self-hybridized secondary structures when allowed to self-anneal:

SEQ ID NO:89

10207   5' A-T-G-A-A-C-G-T-A-C-G-T-C-G-G

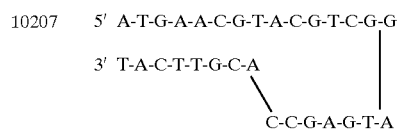

SEQ ID NO:90

10208 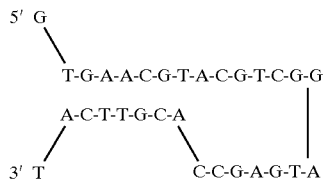

SEQ ID NO:91

10209 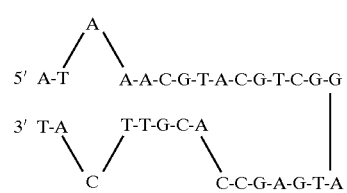

SEQ ID NO:92

10212 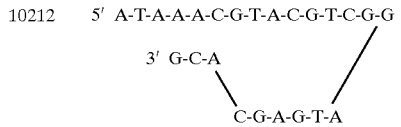

Probes are designed to bind to a target Alu sequence and be extended. Following extension, the probe can form a "hairpin" structure—forming a stretch of double strand DNA. This DNA is then detected in a "probeless" pyrophosphorylation assay. If the extended probe sequence extends beyond the segment of the probe designed to form one segment of the hairpin, the product is not expected to be detected because the product has a 3' overhang. In order to prevent such a situation, the probes that have been designed can be used in reactions missing one of the four DNA bases. By performing the reactions in this way, the probe is not extended beyond the region of hybridization. Scheme 1 illustrates how two such probes hybridize to an Alu sequence.

Scheme 1

Genbank#AF085897

5' CTCCAGCCTCGGTGACAGAGCAAGACCCTGTCTCAAAAAAAA

Oligo A          3' TGTCTCGTTCTGGGAC

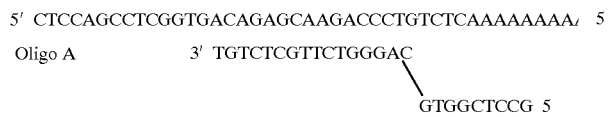

GTGGCTCCG 5

Genbank#AL022238

5' CTCCAGCCTGAGCAACACAGCAAGACCCTGTCTCAAAACAAAAC

Oligo B          3' TTGTGTCGTTCTGGGAC

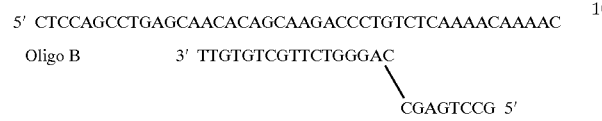

CGAGTCCG 5'

The predicted extended products of these probes and the secondary structure of the hairpins that the extended products can form are shown in Scheme 2, below.

Scheme 2

Genbank#AF085897
Extension of oligo A:

5' CTCCAGCCTCGGTGACAGAGCAAGACCCTGTCTCAAAAAAAA
                                                                   3'
              CGGAGCCACTGTCTCGTTCTGGGAC

GTGGCTCCG 5'

Hairpin
Secondary structure:

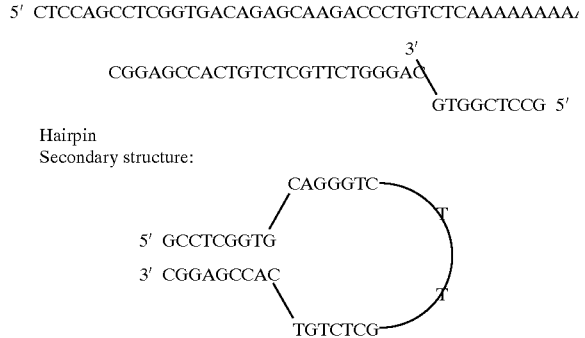

Genbank#AL022238
Extension of oligo B:

5' CTCCAGCCTGAGCAACACAGCAAGACCCTGTCTCAAAACAAAAC
        3' CGGACTCGTTGTGTCGTTCTGGGAC

CGAGTCCG 5'

Hairpin
Secondary structure:

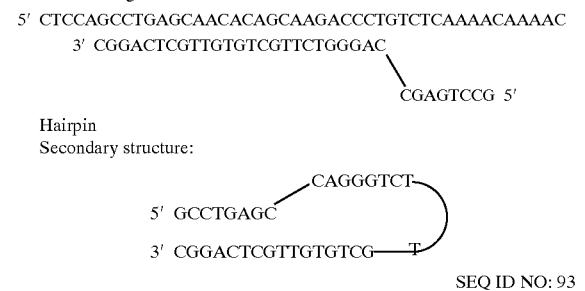

SEQ ID NO: 93
Oligo A
5' CTCCAGCCTCGGTGACAGAGCAAGACCCTGTCTCAAAAAAAAGCCTCGGT GCAGGGTCTTGCTCTGT 3'

SEQ ID NO: 94
Oligo B
5'
CTCCAGCCTGAGCAACACAGCAAGACCCTGTCTCAAAACAAAACGCCTGA GCAGGGTCTTGCTGTGTT 3'

EXAMPLE 17

Speciation—Detection of Mitochondrial DNA Specific to Various Animals

In this example, a segment of mitochondrial DNA comprising a segment of the cytochrome B gene was amplified from a variety of animal species using PCR primers 11590 (SEQ ID NO:95) and 11589 (SEQ ID NO:96) (PNAS 86:6196–6200). These PCR primers were diluted in 10 mM Tris, pH 7.5, to a final concentration of 0.22 µg/µL. The genomic DNAs used were bovine (Clontech, 6850-1), chicken (Clontech, 6852-1), dog (Clontech, 6950-1) and human (Promega, G1521).

The PCR reactions were assembled to include 5 µL 10X buffer with 15 mM $MgCl_2$ (Promega, M188J), 1 µL dNTPs 10 mM (Promega, C144G), 2 µL primer 11590, 2 µL primer 11589, 0.5 µL Taq polymerase 5 U/µL (Promega, M186E), and 38.5 µL water. To each tube was then added 1 µL (100 ng) of genomic DNA. The PCR cycling parameters were (15 seconds, 94° C.; 15 seconds, 55° C.; 30 seconds, 72° C.)×30. The size of PCR products was confirmed by running an aliquot on an agarose gel and visualizing with ethidium bromide (EtBr) staining. The PCR products were then separated from free nucleotides (Promega, A7170) and an aliquot run on an agarose gel. All samples produced a PCR product of the same size.

Each PCR DNA was then used in an assay to determine if it could be specifically identified with a species-specific probe. One microliter of interrogation probe (1 µg/µL) and 17 µL water were combined with 2 µL of the appropriate PCR product and heated at 91° C. for 3 minutes, then cooled at room temperature for 15 minutes. Twenty microliters of master mix (described below) were added to each tube and each was further incubated at 37° C. for 15 minutes. Four microliters of the solutions were then added to 100 µL/L reagent (Promega F120B), and the relative light output (rlu) measured on a Turner® TD20/20 luminometer. The rlu average values from two reactions, minus the DNA background values, along with the standard deviation values are listed below.

| Master mix: | |
|---|---|
| 312 µL | 10X DNA pol buffer (Promega M195A) |
| 39 µL | NaPPi 40 mM (Promega E350B) |
| 39 µL | Klenow exo minus (Promega M128B) |
| 15.6 µL | NDPK 1 U/µL |
| 31.2 µL | ADP 10 µM (Sigma) |
| 1123 µL | water (Promega AA399) |

Averages from 2 reactions. Net light units are calculated by subtracting

-continued

| Probe | the DNA background | | | | Standard Deviations | | | | |
|---|---|---|---|---|---|---|---|---|---|
| | No DNA | Human DNA | Chicken DNA | Cow DNA | Dog DNA | No DNA | Human DNA | Chicken DNA | Cow DNA | Dog DNA |
| comzoo | −0.096 | 44.15 | 14.25 | 119.7 | 124.6 | 0.654 | 7.000 | 23.33 | 3.465 | 8.63 |
| huzoo1 | 1.771 | 38 | −40 | −51.85 | −63.55 | 0.137 | 38.96 | 31.74 | 6.505 | 12.52 |
| huzoo2 | −0.889 | 101.6 | −23.35 | −0.05 | −48.75 | 0.761 | 3.959 | 0.141 | 8.768 | 2.19 |
| chzoo1 | 43.07 | −30.4 | 34.05 | −2.75 | −31.15 | 7.078 | 1.909 | 6.364 | 2.687 | 8.70 |
| chzoo2 | −0.361 | 57.6 | 50.7 | 33.05 | −3.25 | 0.075 | 43.77 | 29.34 | 12.59 | 21.43 |
| cozoo2 | 1.925 | 90.95 | 125.1 | 202.6 | 132.5 | 0.208 | 20.08 | 13.22 | 8.627 | 19.30 |
| dozoo2 | 0.966 | | | 71.8 | 158.7 | 0.180 | | | 9.546 | 1.98 |

The data demonstrate that the primers detect the mitochondrial PCR product. Both of the human-specific probes (11576 (SEQ ID NO:97) and 11583 (SEQ ID NO:98)) were shown to be specific for human mitochondrial DNA. The common probe, 11582 (SEQ ID NO:99), detected all of the species, but was less efficient with chicken DNA. The chicken-specific probe, 11577 (SEQ ID NO:100), was specific for chicken mitochondrial DNA, but the other chicken-specific probe, 11584 (SEQ ID NO:101), detected all the species except dog. The cow-specific probe, 11588 (SEQ ID NO:102), gave the best detection signal for cow DNA, but also detected the other species. The dog-specific probe, 11586 (SEQ ID NO:103), was assayed only with dog and cow DNA, but detected the dog DNA better than cow DNA. A cleaner PCR product provides DNA with less background.

```
11590   zooamp2   5' AAACTGCAGCCCCTCAGAATGATATTTGTCCTCA 3'   SEQ ID NO:95

11589   zooamp1   5' AAAAAGCTTCCATCCAACATCTCAGCATGATGAAA 3'  SEQ ID NO:96

11576   huzoo1    5' CCAGACGCCTCA 3'                         SEQ ID NO:97

11583   huzoo2    5' ACCTTCACGCCA 3'                         SEQ ID NO:98

11582   comzoo    5' TGCCGAGACGT 3'                          SEQ ID NO:99

11577   chzoo1    5' GCAGACACATCC 3'                         SEQ ID NO:100

11584   chzoo2    5' GGAATCTCCACG 3'                         SEQ ID NO:101

11588   cozoo2    5' ACATACACGCAA 3'                         SEQ ID NO:102

11586   dozoo2    5' ATATGCACGCAA 3'                         SEQ ID NO:103
```

EXAMPLE 18

Trisomy Detection

Detection of a simulated trisomy sample is demonstrated in this Example. The nucleic acid probes and targets were previously described in Example 13. These include the CMV probes 9211 (SEQ ID NO:71) and 9212 (SEQ ID NO:72), the p-ZERO-2 clone of the double-stranded synthetic CMV wild type target CMV-A (10800 (SEQ ID NO:65) and 10801 (SEQ ID NO:66)), and the p-ZERO-2 clone of the double-stranded synthetic CMV mutant target CMV-G (10803 (SEQ ID NO:67) and 10805 (SEQ ID NO:68)).

Each p-ZERO-2 plasmid (1 μg) was digested to completion with Pst I restriction enzyme at 37° C. for 1 hour. Ten microliters of the digest were then further diluted with 20 μL of water.

The following Master Mix was assembled.

| 60 μl | 10X DNA polymerase buffer (Promega M195A) |
|---|---|
| 7.5 μl | 40 mM NaPPi (Promega C113) |
| 1.5 μl | 10 U/μL Klenow exo- (Promega M128A) |
| 3 μL | NDPK |
| 6 μL | 10 μM ADP (Promega A5285) |
| 225 μL | water (Promega AA399) |

The following solutions were assembled using the digested and diluted templates.

| Solution | Template | Probe (μL) | Water | Simulated phenotype | rlu |
|---|---|---|---|---|---|
| 1 | 1 μL CMV-A | 1 μL 9211 | 18 | homoz* A | 53.27 |
| 2 | 1 μL CMV-A | 1 μL 9212 | 18 | homoz A | 7.19 |
| 3 | 1 μL CMV-G | 1 μL 9211 | 18 | homoz G | 5.78 |
| 4 | 1 μL CMV-G | 1 μL 9212 | 18 | homoz G | 63.84 |
| 5 | 1 μL CMV-A 1 μL CMV-G | 1 μL 9211 | 17 | heteroZ* 1:1 | 54.08 |
| 6 | 1 μL CMV-A 1 μL CMV-G | 1 μL 9212 | 17 | heteroZ 1:1 | 61.54 |
| 7 | 2 μL CMV-A 1 μL CMV-G | 1 μL 9211 | 16 | trisomy 2:1 (A:G) | 90.87 |
| 8 | 2 μL CMV-A 1 μL CMV-G | 1 μL 9212 | 16 | trisomy 2:1 (A:G) | 64.74 |
| 9 | 1 μL CMV-A 2 μL CMV-G | 1 μL 9211 | 16 | trisomy 1:2 (A:G) | 50.86 |

-continued

| Solution | Template | Probe (μL) | Water | Simulated phenotype | rlu |
|----------|----------|------------|-------|---------------------|-----|
| 10 | 1 μL CMV-A<br>2 μL CMV-G | 1 μL 9212 | 16 | trisomy<br>1:2 (A:G) | 111.0 |

*homoZ = homozygous; heteroZ = heterozygous.

The solutions were heated at 95° C. for 3 minutes then cooled for 10 minutes at room temperature. Then, 20 μl master mix were added, and the solutions further heated at 37° C. for 15 minutes. Four microliters of the solutions were then added to 100 μL of L/L reagent (Promega F202A) and the relative light output measured immediately on a Turner® TD20/20 luminometer. The rlu values are listed above.

The rlu values demonstrate that the 1:2 (A:G) template mix exhibits a 1:2 rlu ratio, whereas the heterozygous 1:1 A:G rlu ratio is close to 1:1. A contemplated method is thus shown to be useful in detecting trisomy.

```
CMV Interrogation oligos
Wild Type CMV-A Probe:  5' CACTTTGATATTACACCCATG 3'  SEQ ID NO:71
    (9211)

Mutant CMV-G probe:     5' CACTTTGATATTACACCCGTG 3'  SEQ ID NO:72
    (9212)

10800   5' CGTGTATGCCACTTTG ATATTACACCCATGAACGTG    SEQ ID
                                                    NO:65
        CTCATCGACGTGAACCCGCA CAACGAGCT 3'

10801   5' CGTTGTGCGGGTTCAC GTCGATGAGCACGTTCATGG    SEQ ID
                                                    NO:66
        GTGTAATATCAAAGTGGCAT ACACGAGCT 3'

10803   5' CGTGTATGCCACTTTG ATATTACACCCGTGAACGTG    SEQ ID
                                                    NO:67
        CTCATCGACGTGAACCCGCA CAACGAGCT 3'

10805   5' CGTTGTGCGGGTTCAC GTCGATGAGCACGTTCACGG    SEQ ID
                                                    NO:68
        GTGTAATATCAAAGTGGCAT ACACGAGCT 3'
```

EXAMPLE 19

Analysis of SNP Heterozygosity Level in DNA Isolated from Plant Materials

Eight different rice DNA samples, with varying amounts of two alleles differing at an SNP site, were analyzed to determine the ability of pyrophosphorylation to detect the degree of heterozygosity in a plant sample. The DNA genotypes (G and T) are described in Example 7.

Eight coded heterozygous rice DNA samples and two homozygous rice DNA samples were obtained (Texas A&M, Crop Biotechnology Center) and PCR amplified with primers RS1 (SEQ ID NO:24) and RS2 (SEQ ID NO:25) as described in Example 7. The resulting PCR products were then treated with T7 Exonuclease 6 and purified as described in Example 7. The resulting DNA was interrogated by combining 4 μL of the PCR product with 150 pmoles of interrogation oligonucleotide and water to a final volume of 20 μL. This solution was incubated at 95° C. for 2 minutes, then at 37° C. for 10 minutes. Interrogation oligonucleotides used were RS3 (SEQ ID NO:26), RS4 (SEQ ID NO:27), and none. Twenty microliters of master mix were then added and the solution further incubated at 37° C. for 15 minutes. These solutions were then combined with 100 μL of L/L reagent (Promega, F202A) and light output measured in a Berthold Eg&G microlumat plus luminometer. The relative light units (rlu) were corrected for no oligonucleotide background and are listed below:

| Sample | G (RS3) Allele | T (RS4) Allele | % G | % T |
|--------|----------------|----------------|------|------|
| 1 | 100,366 | 119,046 | 45.7 | 54.3 |
| 2 | 83,428 | 163,241 | 33.8 | 66.2 |
| 3 | 90,309 | 90,628 | 49.9 | 50.1 |
| 4 | 168,074 | 35,835 | 82.4 | 17.6 |
| 5 | 173,422 | 31,403 | 84.7 | 15.3 |
| 6 | 166,516 | 13,692 | 92.4 | 7.6 |
| 7 | 171,933 | 17,384 | 90.8 | 9.2 |
| 8 | 103,047 | 1,724 | 98.4 | 1.6 |

These G:T ratios were further confirmed by the following study. The eight heterozygote samples and the two homozygote samples were re-amplified as previously described, but the PCR reaction also included 1 μL of $^{32}$PdATP and $^{32}$PdCTP. Ten microliters of the resulting PCR product were then digested with 1 μL restriction endonuclease AccI in 2.5 mM MgCl$_2$ in the PCR buffer for one hour at 37° C. AccI cuts the G allele PCR product into a 120 bp doublet, but will not cut the 240 bp fragment from the T allele PCR product. The digest was run on a 10% acrylamide TBE gel, dried for one hour at 65° C. and resulting bands quantified for one hour on a Molecular Dynamics Fluoroimager screen. The following values were obtained.

| Sample | % G | % T |
|--------|------|------|
| 1 | 47.6 | 52.4 |
| 2 | 35.8 | 64.2 |
| 3 | 57.2 | 42.8 |
| 4 | 77.6 | 22.3 |
| 5 | 81.1 | 18.9 |
| 6 | 89.2 | 10.8 |
| 7 | 85.4 | 14.6 |
| 8 | nd | nd |

No values were generated for sample 8 because the PCR reaction was not successful. The correlation coefficient between the two data sets was 0.992036.

RS1  5' CCCAACACCTTACAGAAATTAGC 3'  SEQ ID NO:24

RS2  5' TCTCAAGACACAAATAACTGCAG 3'  SEQ ID NO:25

RS3  5' AGAACATCTGCAAGG 3'  SEQ ID NO:26

RS4  5' AGAACATCTGCAAGT 3'  SEQ ID NO:27

EXAMPLE 20

Interrogation using Fluorescent Labels

This example demonstrates that nucleotides released from the 3'-terminus of a probe hybridized to a target nucleic acid of interest by a process of the invention can be detected by mass spectrometry or by fluorimetric HPLC and thereby provide evidence of the presence or absence of the target nucleic acid in a nucleic acid sample or of a specific base at an interrogation position of the target.

The interrogation probe is designed to have a fluorescent label attached to the 5'-terminal nucleotide. Fluorescent tags, such as fluorescein or rhodamine, can be incorporated into the probe during synthesis with a fluorescent molecule attached to the phosphoramadite nucleotide present at the 5'-end of the oligonucleotide that will be used as a probe (Glen Research).

Probes PT5 (SEQ ID NO:104) and PT6 (SEQ ID NO:105) are used to PCR-amplify a region of human genomic DNA spanning about 500 base pairs encoding the prothrombin gene. Probe PT5 has phosphorothioate linkages between the first five bases at the 5' end.

The PCR cycling parameters were as follows: 94° C., 2 minutes; (94° C., 30 seconds; 60° C., 1 minutes; 70° C., 1 minutes)×40; 70° C., 5 minutes. Fifty units of T7 gene 6 Exonuclease (USB Amersham) were added to 25 µL of the PCR reaction and the solution was incubated for 30 minutes at 37° C. Magnetic silica (Promega, A1330) was used to remove free nucleotides from the solution and the remaining DNA was eluted with 100 µL of water. The PCR product is treated with T7 gene 6 Exonuclease (USB Amersham) and purified from free nucleotides as described above.

The prothrombin interrogation probes are 11265 (SEQ ID NO:106), that is totally complementary to a segment of the mutant prothrombin sequence, and 11266 (SEQ ID NO:107), that is totally complementary to a segment of the wild-type prothrombin sequence. Each of these probes has a destabilizing mutation eight bases from the 3' end. And each of these probes has a label at its 5'-end, incorporated during synthesis of the probe as described above.

The purified PCR product is interrogated in separate reactions with each of the two interrogation probes (wild-type and mutant). Interrogation reactions, with the target molecule in molar excess over the probe molecule, for each of the interrogation probes are assembled as follows:

40 µL  PCR product
15 pmol  Interrogation oligo water is added to a final volume of 50 µL.

The reactions are incubated at 95° C. for 3 minutes and then at 37° C. for 15 minutes.

Fifty microliters of master mix are then added. The composition of the master mix containing Klenow exo- is described in Example 1 with the exception that there is no ADP and no NDPK. The reaction then proceeds at 37° C. for 15 minutes. The hybrid is then denatured by incubating the reaction at 95° C. for 3 minutes, adding 100 µL water to dilute the separated strands and placing the resulting denatured solution tube on ice.

The solutions are then split in half and analyzed using two different methods. In one method, the size of the labeled probe in the solutions is analyzed by silicon desorption ionization mass spectroscopy (Wei, J. et al. *Nature.* 399:243–246, 1999). This method is sensitive to femtomole and attomole levels of analyte. The samples are prepared for spectrometry as described in that paper. Essentially, analytes are dissolved in a deionized water/methanol mixture (1:1) at concentrations typically ranging from 0.001 to 10.0 µM. Aliquots (at least 0.5 to 1.0 µL, corresponding to at least 0.5 femtomol to 100 picomol analyte) of solution are deposited onto the porous surfaces and allowed to dry before mass spectrometry analysis.

These studies are performed on a Voyager DE-STR, time-of-flight mass spectrometer (PerSeptive Biosystems) using a pulsed nitrogen laser (Laser Science) operated at 337 nm. Once formed, ions are accelerated into the time-of-flight mass analyzer with a voltage of 20 kV. Other liquid chromatography-mass spectrometry (LC-MS) instrumentation may also be used for analysis (Niessen W. *J. Chromatog. A* 794:407–435 (1998)

In a second method, the size of the denatured labeled probe strand in the solution is analyzed by HPLC using a fluorescence detector as described in Jain, et al. *Biochem. Biophys. Res. Commun.* 200:1239–1244 (1994) or Levitt, B. et al. *Anal. Biochem.* 137:93–100 (1984). The size of the denatured labeled probe strand is confirmed on an ABI 377.

The size of the labeled probe strand present in the denatured solution indicates whether or not a nucleotide was released from the 3'-terminus of the probe, and therefore whether a match or mismatch base pair existed at the 3' terminus of the probe/template hybrid. For the denatured solution containing wild-type probe, the observance of a labeled probe that is shorter than the length of the original probe indicates that there is a matched base at the 3'-terminus of at least one allele in the original sample and therefore, that at least one allele in the original sample is wild-type. For the denatured solution containing mutant probe, the observance of a labeled probe that is shorter than the length of the original probe indicates that there is a matched base at the 3'-terminus of at least one allele in the original sample and therefore, that at least one allele in the original sample is wild-type. In both cases, the analytical output can be quantified to determine whether the genotype is homozygous or heterozygous at that locus.

PT5    5' ATAGCACTGGGAGCATTGAGGC 3'  SEQ ID NO:104

PT6    5' GCACAGACGGCTGTTCTCTT 3'    SEQ ID NO:105

11265  5' GTGATTCTCAGCA 3'           SEQ ID NO:106

11266  5' GTGATTCTCAGCG 3'           SEQ ID NO:107

EXAMPLE 21

Determination of the Minimum Cell Population That Can be Detected in a Complex Cell Mixture This example was designed to illustrate that a small cell population can be detected in a background of other cells using a contemplated process. Thus, RNA was isolated from a cell mixture that contained increasing numbers of K562 cells (ATCC CCL 243) in a constant background of $1 \times 10^6$ NIH-3T3 cells (ATCC CRL 1658). The RNA was then used for RT-PCR of the bcr/abl translocation transcript, which is specific to the K562 cells due to chromosomal translocation. A translocation takes place in the region of the bcr gene along with involvement of a segment of the abl gene. The NIH-3T3 cells possess no translocation and are thus wild type for the bcr and abl transcripts.

NIH-3T3 cells were washed with phosphate-buffered saline and centrifuged at 2000× g for 5 minutes to pellet the cells. The supernatant was removed and the cell pellet was resuspended in SV RNA lysis buffer (Promega Corp., #Z3100) to a final concentration of $1 \times 10^6$ cells/175 μL of lysis buffer. Similarly, K562 cells were washed in phosphate-buffered saline and centrifuged at 2000× g for 5 minutes to pellet the cells. The supernatant was removed and the cell pellet was resuspended in SV RNA lysis buffer to a final concentration of $1 \times 10^6$ cells in 175 μL of lysis buffer. The cell lysates were passed through an 18-gauge needle to shear the genomic DNA.

The cell lysates were combined as listed below, and SV lysis buffer was added to a final volume of 350 μL. Sample 2 used a 1:1000 dilution of the K562 lysate, samples 3, 4, and 5 used a 1:100 dilution of the K562 lysate, and samples 6 through 10 used undiluted lysate.

| Sample | Number NIH-3T3 | Volume (μL) NIH-3T3 | Number K562 | Volume (μL) K562 |
|---|---|---|---|---|
| 1 | $1 \times 10^6$ | 175 | 0 | 0 |
| 2 | $1 \times 10^6$ | 175 | 10 | 1.75 |
| 3 | $1 \times 10^6$ | 175 | 100 | 1.75 |
| 4 | $1 \times 10^6$ | 175 | 500 | 8.75 |
| 5 | $1 \times 10^6$ | 175 | 1000 | 17.5 |
| 6 | $1 \times 10^6$ | 175 | $1 \times 10^4$ | 1.75 |
| 7 | $1 \times 10^6$ | 175 | $5 \times 10^4$ | 8.75 |
| 8 | $1 \times 10^6$ | 175 | $1 \times 10^5$ | 17.5 |
| 9 | $1 \times 10^6$ | 175 | $5 \times 10^5$ | 87.5 |
| 10 | $1 \times 10^6$ | 175 | $1 \times 10^6$ | 175 |

Total RNA was then isolated from the combined lysates listed above using the SV Total RNA Isolation System according to manufacturer's instructions (Promega, Z3100). The RNAs were each eluted into 100 μL water and stored at −20° C. until used.

The resulting RNA concentration of each sample was determined by UV spectroscopy of 10 μL of the appropriate sample mixed with 300 μL water. In set A, the samples were a combination of NIH-3T3 cells and K562 cells as listed above. In set B, the samples were only K562 cells in the number and volume as listed above. The spectroscopy results are listed below. Absorbance at OD260 measures the amount of DNA, the absorbance at OD280 measures the amount of protein, and 260/280 ratio determines the purity of the RNA with a high purity sample having a 260/280 ratio of about 2.0.

| Sample | OD260 | OD280 | 260/280 | concentration (ng/mL) |
|---|---|---|---|---|
| 1A | 0.104 | 0.051 | 2.04 | 124 |
| 2A | 0.103 | 0.047 | 2.19 | 124 |
| 3A | 0.113 | 0.055 | 2.05 | 135 |
| 4A | 0.088 | 0.042 | 2.09 | 106 |
| 5A | 0.110 | 0.056 | 1.96 | 132 |
| 6A | 0.112 | 0.054 | 2.07 | 134 |
| 7A | 0.091 | 0.043 | 2.12 | 109 |
| 8A | 0.103 | 0.050 | 2.06 | 124 |
| 9A | 0.124 | 0.057 | 2.17 | 149 |
| 10A | 0.162 | 0.078 | 2.07 | 194 |
| 1B | 0.008 | 0.006 | 1.33 | na* |
| 2B | 0.005 | 0.004 | 1.25 | na |
| 3B | 0.002 | 0.004 | 0.50 | na |
| 4B | 0.001 | 0.003 | 0.33 | na |
| 5B | 0.001 | 0.001 | 1.00 | na |
| 6B | 0.002 | 0.002 | 1.00 | na |
| 7B | 0.002 | 0.003 | 0.67 | na |
| 8B | 0.001 | 0.000 | na | na |
| 9B | 0.037 | 0.018 | 2.05 | 44 |
| 10B | 0.067 | 0.303 | 2.23 | 80 |

*na = too low to be accurately measured.

The very low values for 1B through 8B indicate the lack of sensitivity for spectroscopy at very low nucleic acid concentrations as well known in the art.

RT-PCR reactions for bcr-abl product, which is K562 specific due to the chromosomal translocation, were set up using the RT-PCR system (Promega, A1250) according to manufacturer's instructions with 5 μL total RNA and the amplification primers 9261 and 10860 (below) to provide a 200 base pair RT-PCR product. The 10860 oligonucleotide has three phosphorothioate linkages at the 5' terminus. The RT-PCR cycling parameters were 48° C. 45 minutes, 95° C. 2 minutes, 40×(94° C. 30 seconds, 65° C. 1 minute, 68° C. 1 minute), 68° C. 7 minutes, 4° C. soak.

```
9261   5' GGAGCTGCAGATGCTGACCAAC 3' amplification
       primer SEQ ID NO:108

10860  5' GCTACTGGCCGCTGAAGGGC 3' amplification
       primer SEQ ID NO:109

11065  5' GCTGACCATCAATAAGGAAG 3' interrogation
       primer SEQ ID NO:110
```

Five microliters of the resulting amplification products were run on a 1.5% agarose gel. The 200 bp bcr/abl band was detectable in samples 3B through 10B and 3A through 10A. Therefore, the bcr/abl translocation using the method described above, was easily detected in 100 K562 cells in a background of $1 \times 10^6$ NIH-3T3 cells.

In a separate set of reactions, the products of the RT-PCR reaction (25 μL) were treated with 0.5 units of T7 gene 6 exonuclease for 30 minutes at 37° C. Samples were then purified using MagneSil™ magnetic silica particles.

Thus, twenty-five microliters of PCR product was combined with 1.5 mg of particles in 150 μL of binding buffer (0.4 M guanidine thiocyanate+0.08 M potassium acetate). The compositions were incubated for 2 minutes at room temperature. The particles were captured by placing the tube on a magnetic stand and the supernatant was removed. The particles were washed four times with 150 μL of 70% ethanol. The particles were resuspended in 50 μL of water and incubated for 2 minutes at room temperature. Then, 150 μL of binding buffer (no particles) was added and the tube incubated for 2 minutes at room temperature. The particles were captured and washed three times with 150 μL of 70% ethanol. The final wash was removed and the particles were permitted to air dry for 10 minutes at room temperature. The particles were then resuspended in 100 μL of water and incubated for 2 minutes at room temperature. The particles were captured and the supernatant containing the purified PCR product was transferred to a clean tube. When 5 µL of each purified RT-PCR product were used for an interrogation assay, a graph of the statistical data indicated that 10 K562 cells could be detected because the −4 sigma value of the 10-cell interrogation assay does not intersect with the +4 sigma value for the 0 cell control interrogation reaction. Thus, using this technique, 0.001% of a mixed cell population could be detected.

The following master mix was assembled:

| | |
|---|---|
| 10X buffer (Promega, M190) | 20 µL |
| 25 mM MgCl$_2$ | 20 µL |
| water | 51 µL |
| 40 mM NaPPi | 5 µL |
| 10 uM ADP | 2 µL |
| 5 U/µL Tne triple mutant polymerase (1 U/reaction) | 1 µL |
| 0.5 U/µL Pfu NDPK (0.1 U/reaction) | 1 µL |

The sample (5 µL) and the 11065 interrogation oligo (1 µg) were combined in water to a final volume of 20 µL. They were heated to 95° C. for 3 minutes, then incubated for 10 minutes at 60° C. Then 20 µL master mix was added and the reaction incubated for 15 minutes at 60° C. Then 100 µL of L/L were added, and the light output (average rlu) was measured on a Turner® TD 20/20 luminometer. The background RLU was subtracted and averaged results from 3 readings are listed below.

| K562 cell number | NIH-3T3 cell number | bcr/abl Detection | |
|---|---|---|---|
| | | Average rlu | Sigma |
| 0 | 1 × 10$^6$ | 82.26 | 0.47 |
| 10 | 1 × 10$^6$ | 162.43 | 9.39 |
| 100 | 1 × 10$^6$ | 793.23 | 34.43 |
| 500 | 1 × 10$^6$ | 1512.72 | 86.33 |
| 1000 | 1 × 10$^6$ | 2042.83 | 116.02 |
| 10000 | 1 × 10$^6$ | 2792.50 | 68.42 |

EXAMPLE 22

Automation of PCR Clean-up and ATP Measurement Steps of an Interrogation Reaction The ability to automate the PCR clean-up and the ATP measurement steps of an interrogation reaction are demonstrated in this example. The robot is also capable of automating the addition of the interrogation master mix and permitting for the incubation time prior to the luciferase reaction; however, that is not demonstrated in this particular example.

The PCR procedure detailed in Example 7, using the same PCR amplification primers, the same SNP interrogation primers and the same amplification profile, is used here to determine the genotype of 189 rice genomic DNAs at a known SNP site. After the PCR reactions were completed, 25 µL of each of the 50 µL PCR reactions was transferred to a well of a Dynex™ V-bottom 96-well plate and placed on a Biomek™ 2000 robot (Beckman). T7 Exonuclease 6 (1 µL) was added to each well and the plate incubated at 37° C. for 30 minutes. The robot was programmed and completed the following steps as listed below:

(1) The robot mixed magnetic silica particles (Promega) in a guanidine thiocyanate solution by pipetting up and down in a trough.

(2) 180 µL of the particles were drawn into a set of 8 micropipette tips and transferred to column one of the plate. This same set of 8 tips transferred 180 µL of the particles to each column of the plate.

(3) Separate tips were used to mix the contents of the wells by pipetting up and down four times. In this step, a tip unique for every well was used.

(4) The robot moved the plate to a station containing a magnetic pin array where the particles were captured on the side of the well and the supernatant removed as waste and placed in a trough.

(5) The robot performed three 70% ethanol washes, using a new set of tips—a unique tip for every well.

(6) After removal of the last wash solution, the robot gripper arm then moved the plate off the magnet to a separate station where it added 50 µL water to each well.

(7) The water was mixed with the particles by pipetting up and down and then 150 µL 0.4 M guanidine thiocyanate, 0.08 M potassium acetate were added to each well. One row of 8 tips was used to dispense the solution, whereas a unique tip for each well was used to mix the contents of the well.

(8) The robot moved the plate back to the magnetic pin array.

(9) The contents of the wells were mixed by pipetting up and down, the particles were captured on the wall of the well and the supernatant was removed to the waste trough.

(10) Three rounds of 100 µl 70% ethanol washes were performed.

(11) After the final wash was removed, the particles were permitted to air dry for 10 minutes.

(12) The gripper arm of the robot then removed the plate from the magnet to a separate stand.

(13) 100 µL water were added to each well and the contents of the well mixed with a tip unique to each well, by pipetting up and down.

(14) The plate was put on the magnet and the water containing the DNA, separated from the particles, was transferred to a clean plate.

At this point a multichannel pipetter was used to manually transfer 10 µL of the contents of each well to a luminometer 96 well plate and the interrogation oligo (150 pmoles in 10 µL) was added to each well. Then, 10 µL of 0.6 N NaOH were added to each well and the plate incubated for 5 minutes at room temperature to denature the double stranded DNA. Then 10 µL of 0.1 M Tris pH 7.3 were added to neutralize the solution and permit the interrogation oligonucleotide to anneal to the template DNA, if it were capable of annealing The plate was transferred to a Berthold™ luminometer and warmed to 37° C. for 5 minutes. The luminometer then automatically added 100 µL of L/L reagent. The data were transferred to the Excel® spreadsheet for analysis. The data are documented below. Of a total of 192 samples, 189 samples were able to be distinguished as homozygote wild type or mutant, or heterozygotes by the use of this method.

| | |
|---|---|
| Total Samples Called: | 189 |
| WT Homozygotes | 108 |
| Mutant Homozygotes | 74 |

| | |
|---|---|
| Heterozygotes | 7 |
| No Calls | 3 |
| % Samples Called | 97.4 |
| Average WT RLUs | 289791.96 |
| Average mutant RLUs | 294958.30 |
| Control Values: | |
| Control WT Interrogation | 1100 rlu |
| Control Mutant Interrogation | 1300 rlu |

| | | |
|---|---|---|
| RS1 5'C*C*C*AACACCTTACAGAAATTAGC 3' | | SEQ ID NO:24 |
| (* signifies the presence of a phosphorothioate linkage between the indicated bases.) | | |
| RS2 5'TCTCAAGACACAAATAACTGCAG 3' | | SEQ ID NO:25 |
| RS3 5'AGAACATCTGCAAGG 3' | | SEQ ID NO:26 |
| RS4 5'AGAACATCTGCAAGT 3' | | SEQ ID NO:27 |

| I.D. | WT Monoplex | Mutant Monoplex | No Interr. | Adj. WT Average | Adj. Mutant Average | Ratio | Call |
|---|---|---|---|---|---|---|---|
| A1 | 199749 | 507274 | 185645 | 14104.00 | 321629.00 | 0.0420 | Mutant Homozygote |
| A2 | 458265 | 95890 | 92591 | 365674.00 | 3299.00 | 0.9911 | WT Homozygote |
| A3 | 759556 | 161615 | 160051 | 599505.00 | 1564.00 | 0.9974 | WT Homozygote |
| A4 | 498118 | 351711 | 138786 | 359332.00 | 212925.00 | 0.6279 | Heterozygote |
| A5 | 195485 | 53873 | 86935 | 108550.00 | −33062.00 | 1.4380 | WT Homozygote |
| A6 | 49647 | 244903 | 46486 | 3161.00 | 198417.00 | 0.0157 | Mutant Homozygote |
| A7 | 71513 | 307323 | 59663 | 11850.00 | 247660.00 | 0.0457 | Mutant Homozygote |
| A8 | 322849 | 80613 | 63968 | 258881.00 | 16645.00 | 0.9396 | WT Homozygote |
| A9 | 277232 | 52362 | 52128 | 225104.o0 | 234.00 | 0.9990 | WT Homozygote |
| A10 | 54809 | 293085 | 44761 | 10048.00 | 248324.00 | 0.0389 | Mutant Homozygote |
| A11 | 302564 | 43711 | 43365 | 259199.00 | 346.00 | 0.9987 | WT Homozygote |
| A12 | 271769 | 57301 | 45478 | 226291.00 | 11823.00 | 0.9503 | WT Homozygote |
| B1 | 294153 | 949381 | 289250 | 4903.00 | 660131.00 | 0.0074 | Mutant Homozygote |
| B2 | 141633 | 575781 | 137968 | 3665.00 | 437813.00 | 0.0083 | Mutant Homozygote |
| B3 | 713771 | 571635 | 128947 | 584824.00 | 442688.00 | 0.5692 | Heterozygote |
| B4 | 184624 | 98392 | 98706 | 85918.00 | −314.00 | 1.0037 | WT Homozygote |
| B5 | 293297 | 53877 | 49345 | 243952.00 | 4532.00 | 0.9818 | WT Homozygote |
| B6 | 232345 | 34581 | 29098 | 203247.00 | 5483.00 | 0.9737 | WT Homozygote |
| B7 | 325601 | 142317 | 138329 | 187272.00 | 3988.00 | 0.9791 | WT Hotmozygote |
| B8 | 62215 | 281539 | 48648 | 13567.00 | 232891.00 | 0.0550 | Mutant Homozygote |
| B9 | 328210 | 67103 | 65440 | 262770.00 | 1663.00 | 0.9937 | WT Homozygote |
| B10 | 270590 | 74764 | 72931 | 197659.00 | 1833.00 | 0.9908 | WT Homozygote |
| B11 | 317326 | 54672 | 54072 | 263254.00 | 600.00 | 0.9977 | WT Homozygote |
| B12 | 343235 | 71537 | 64609 | 278626.00 | 6928.00 | 0.9757 | WT Homozygote |
| C1 | 756526 | 164558 | 161686 | 594840.00 | 2872.00 | 0.9952 | WT Homozygote |
| C2 | 567636 | 133446 | 121643 | 445993.00 | 11803.00 | 0.9742 | WT Homozygote |
| C3 | 659442 | 283021 | 149965 | 509477.00 | 133056.00 | 0.7929 | WT Homozygote |
| C4 | 165142 | 652352 | 139950 | 25192.00 | 512402.00 | 0.0469 | Mutant Homozygote |
| C5 | 260593 | 48904 | 46766 | 213827.00 | 2138.00 | 0.9901 | WT Homozygote |
| C6 | 70456 | 332594 | 66055 | 4401.00 | 266539.00 | 0.0162 | Mutant Homozygote |
| C7 | 268615 | 55585 | 53627 | 214988.00 | 1958.00 | 0.9910 | WT Homozygote |
| C8 | 265788 | 52417 | 50841 | 214947.00 | 1576.00 | 0.9927 | WT Homozygote |
| C9 | 218246 | 65177 | 60855 | 157391.00 | 4322.00 | 0.9733 | WT Homozygote |
| C10 | 31062 | 30995 | 28923 | 2139.00 | 2072.00 | 0.5080 | signal/Bkg Low |
| C11 | 407704 | 65466 | 62189 | 345515.00 | 3277.00 | 0.9906 | WT Homozygote |
| C12 | 82010 | 351069 | 56481 | 25529.00 | 294588.00 | 0.0797 | Mutant Homozygote |
| D1 | 653788 | 366405 | 360959 | 292829.00 | 5446.00 | 0.9817 | WT Homozygote |
| D2 | 184581 | 661894 | 176450 | 8131.00 | 505444.00 | 0.0158 | Mutant Homozygote |
| D3 | 764581 | 327686 | 217446 | 547135.00 | 110240.00 | 0.8323 | WT Homozygote |
| D4 | 706754 | 216238 | 179087 | 527667.00 | 37151.00 | 0.9342 | WT Homozygote |
| D5 | 69660 | 327874 | 67779 | 1881.00 | 260095.00 | 0.0072 | Mutant Homozygote |
| D6 | 56895 | 303900 | 50699 | 6196.00 | 253201.00 | 0.0239 | Mutant Homozygote |
| D7 | 373792 | 82464 | 79207 | 294585.00 | 3257.00 | 0.9891 | WT Homozygote |
| D8 | 344957 | 64456 | 57610 | 287347.00 | 6846.00 | 0.9767 | WT Homozygote |
| D9 | 302895 | 75707 | 74534 | 228361.00 | 1173.00 | 0.9949 | WT Homozygote |
| D10 | 382257 | 76015 | 69250 | 313007.00 | 6765.00 | 0.9788 | WT Homozygote |
| D11 | 62715 | 326270 | 54740 | 7975.00 | 271530.00 | 0.0285 | Mutant Homozygote |
| D12 | 72334 | 429302 | 63801 | 8533.00 | 365501.00 | 0.0228 | Mutant Homozygote |
| E1 | 291395 | 974002 | 284355 | 7040.00 | 689647.00 | 0.0101 | Mutant Homozygote |
| E2 | 846719 | 380934 | 208940 | 637779.00 | 171994.00 | 0.7876 | WT Homozygote |
| E3 | 268317 | 436356 | 238130 | 30187.00 | 198226.00 | 0.1322 | Mutant Homozygote |
| E4 | 1025425 | 215357 | 225516 | 799909.00 | −10159.00 | 1.0129 | WT Homozygote |
| E5 | 385114 | 84055 | 76639 | 308475.00 | 7416.00 | 0.9765 | WT Homozygote |
| E6 | 349652 | 72824 | 65685 | 283967.00 | 7139.00 | 0.9755 | WT Homozygote |
| E7 | 57669 | 257988 | 53889 | 3780.00 | 204099.00 | 0.0182 | Mutant Homozygote |
| E8 | 350706 | 81980 | 73186 | 277520.00 | 8794.00 | 0.9693 | WT Homozygote |
| E9 | 187804 | 59978 | 57690 | 130114.00 | 2288.00 | 0.9827 | WT Homozygote |

-continued

| I.D. | WT Monoplex | Mutant Monoplex | No Interr. | Adj. WT Average | Adj. Mutant Average | Ratio | Call |
|---|---|---|---|---|---|---|---|
| E10 | 419892 | 74603 | 64973 | 354919.00 | 9630.00 | 0.9736 | WT Homozygote |
| E11 | 114204 | 44254 | 45919 | 68285.00 | −1665.00 | 1.0250 | WT Homozygote |
| E12 | 72764 | 431146 | 59266 | 13498.00 | 371880.00 | 0.0350 | Mutant Homozygote |
| F1 | 182251 | 133298 | 140425 | 41826.D0 | −7127.00 | 1.2054 | signal Bkg Low |
| F2 | 1085040 | 263816 | 262330 | 822710.00 | 1486.00 | 0.9982 | WT Homozygote |
| F3 | 1149638 | 288799 | 277169 | 872469.00 | 11630.00 | 0.9868 | WT Homozygote |
| F4 | 1298679 | 369636 | 343923 | 954756.00 | 25713.00 | 0.9738 | WT Homozygote |
| F5 | 421495 | 90313 | 85890 | 335605.00 | 4423.00 | 0.9870 | WT Homozygote |
| F6 | 248386 | 43837 | 50870 | 197516.00 | −7033.00 | 1.0369 | WT Homozygote |
| F7 | 395810 | 79728 | 73931 | 321879.00 | 5797.00 | 0.9823 | WT Homozygote |
| F8 | 437260 | 84282 | 76015 | 361245.00 | 8267.00 | 0.9776 | WT Homozygote |
| F9 | 92817 | 419474 | 70407 | 22410.00 | 349067.00 | 0.0603 | Mutant Homozygote |
| F10 | 69232 | 176622 | 65238 | 3994.00 | 111384.D0 | 0.0346 | Mutant Homozygote |
| F11 | 405233 | 79452 | 73190 | 332043.00 | 6262.00 | 0.9815 | WT Homozygote |
| F12 | 347235 | 60861 | 49639 | 297596.00 | 11222.00 | 0.9637 | WT Homozygote |
| G1 | 661728 | 199046 | 197228 | 464500.00 | 1818.00 | 0.9961 | WT Hooozygote |
| G2 | 1316486 | 379375 | 354161 | 962325.00 | 25214.00 | 0.9745 | WT Homozygote |
| G3 | 372004 | 1299117 | 359896 | 12108.00 | 939221.00 | 0.0127 | Mutant Homozygote |
| G4 | 295045 | 1059830 | 288259 | 6786.00 | 771571.00 | 0.0087 | Mutant Homozygote |
| G5 | 102109 | 404399 | 94908 | 7201.00 | 309491.00 | 0.0227 | Mutant Homozygote |
| G6 | 374825 | 93518 | 83355 | 291470.00 | 10163.00 | 0.9663 | WT Homozygote |
| G7 | 91658 | 439103 | 85492 | 6166.00 | 353611.00 | 0.0171 | Mutant Homozygote |
| G8 | 389514 | 1o111s | 90483 | 299031.00 | 10632.00 | 0.9657 | WT Homozygote |
| G9 | 352032 | 65176 | 59725 | 292307.00 | 5451.00 | 0.9817 | WT Homozygote |
| G10 | 61225 | 229948 | 40071 | 21154.00 | 189877.00 | 0.1002 | Mutant Homozygote |
| G11 | 97339 | 513948 | 82923 | 14416.00 | 431025.00 | 0.0324 | Mutant Homozygote |
| G12 | 94130 | 526318 | 83889 | 10241.00 | 442429.00 | 0.0226 | Mutant Homozygote |
| H1 | 529590 | 1465949 | 532127 | −2537.00 | 933822.00 | −0.0027 | Mutant Homozygote |
| H2 | 443487 | 1315342 | 414585 | 28902.00 | 900757.00 | 0.0311 | Mutant Homozygote |
| H3 | 1372124 | 437675 | 473109 | 899015.00 | −35434.00 | 1.0410 | WT Homozygote |
| H4 | 385710 | 1401153 | 334935 | 50775.00 | 1066218.00 | 0.0455 | Mutant Homozygote |
| H5 | 417722 | 93776 | 87874 | 329848.00 | 5902.00 | 0.9824 | WT Homozygote |
| H6 | 98909 | 433581 | 87379 | 11530.00 | 346202.00 | 0.0322 | Mutant Homozygote |
| H7 | 96824 | 333184 | 80419 | 16405.00 | 252765.00 | 0.0609 | Mutant Homozygote |
| H8 | 518543 | 115426 | 101354 | 417189.00 | 14072.00 | 0.9674 | WT Homozygote |
| H9 | 423527 | 96796 | 84702 | 338825.00 | 12094.00 | 0.9655 | WT Homozygote |
| H10 | 434588 | 102160 | 97889 | 336699.00 | 4271.00 | 0.9875 | WT Homozygote |
| H11 | 428308 | 83111 | 76995 | 351313.00 | 6116.00 | 0.9829 | WT Homozygote |
| H12 | 387833 | 82556 | 72483 | 315350.00 | 10073.00 | 0.9690 | WT Homozygote |
| | | | | 0.00 | Not Determined | 0.0000 | |
| A1 | 58027 | 222183 | 57684 | 343.00 | 164499.00 | 0.0021 | Mutant Homozygote |
| B1 | 185071 | 51454 | 55494 | 129577.00 | −4040.00 | 1.0322 | WT Homozygote |
| C1 | 295696 | 122251 | 125871 | 169825.00 | −3620.00 | 1.0218 | WT Homozygote |
| D1 | 57147 | 151617 | 58288 | −1141.00 | 93329.00 | −0.0124 | Mutant Homozygote |
| E1 | 160272 | 365059 | 152760 | 7512.00 | 212299.00 | 0.0342 | Mutant Homozygote |
| F1 | 140035 | 323425 | 127593 | 12442.00 | 195832.00 | 0.0597 | Mutant Homozygote |
| G1 | 340699 | 125807 | 126213 | 214486.00 | −406.00 | 1.0019 | WT Homozygote |
| H1 | 42236 | 164029 | 38652 | 3584.00 | 125377.00 | 0.0278 | Mutant Homozygote |
| A2 | 44991 | 208056 | 38228 | 6763.00 | 169828.00 | 0.0383 | Mutant Homozygote |
| B2 | 70844 | 252510 | 58554 | 12290.00 | 193956.00 | 0.0596 | Mutant Homozygote |
| C2 | 121370 | 327497 | 105696 | 15674.00 | 221801.00 | 0.0660 | Mutant Homozygote |
| D2 | 276654 | 97372 | 94479 | 182175.00 | 2893.00 | 0.9844 | WT Homozygote |
| E2 | 320433 | 129999 | 123842 | 196591.00 | 6157.00 | 0.9696 | WT Homozygote |
| F2 | 78482 | 204964 | 73273 | 5209.00 | 131691.00 | 0.0380 | Mutant Homozygote |
| G2 | 125103 | 335824 | 104245 | 20858.00 | 231579.00 | 0.0826 | Mutant Homozygote |
| H2 | 240462 | 45557 | 42355 | 198107.00 | 3202.00 | 0.9841 | WT Homozygote |
| A3 | 243958 | 55075 | 52528 | 191430.00 | 2547.00 | 0.9869 | WT Homozygote |
| B3 | 91970 | 264544 | 85181 | 6789.00 | 179363.00 | 0.0365 | Mutant Homozygote |
| C3 | 336897 | 119084 | 117108 | 219789.00 | 1976.00 | 0.9911 | WT Homozygote |
| D3 | 271665 | 58558 | 59833 | 211832.00 | −1275.00 | 1.0061 | WT Homozygote |
| E3 | 337079 | 125908 | 122511 | 214568.00 | 3397.00 | 0.9844 | WT Homozygote |
| F3 | 143218 | 353952 | 128180 | 15038.00 | 225772.00 | 0.0624 | Mutant Homozygote |
| G3 | 347214 | 132332 | 133270 | 213944.00 | −938.00 | 1.0044 | WT Homozygote |
| H3 | 154490 | 40370 | 43119 | 111371.00 | −2749.00 | 1.0253 | WT Homozygote |
| A4 | 33118 | 153268 | 24474 | 8644.00 | 128794.00 | 0.0629 | Mutant Homozygote |
| B4 | 332295 | 135622 | 128922 | 203373.00 | 6700.00 | 0.9681 | WT Homozygote |
| C4 | 285837 | 91412 | 87076 | 198761.00 | 4336.00 | 0.9787 | WT Homozygote |
| D4 | 318153 | 70585 | 65242 | 252911.00 | 5343.00 | 0.9793 | WT Homozygote |
| E4 | 239939 | 297176 | 111888 | 128051.00 | 185288.00 | 0.4087 | Heterozygote |
| F4 | 276763 | 99403 | 89728 | 187035.00 | 9675.00 | 0.9508 | WT Homozygote |
| G4 | 138492 | 74565 | 721D5 | 66387.00 | 2460.00 | 0.9643 | WT Homozygote |
| H4 | 346257 | 108363 | 96379 | 249878.00 | 11984.00 | 0.9542 | WT Homozygote |
| A5 | 265294 | 76739 | 76917 | 188377.00 | −178.00 | 1.0009 | WT Homozygote |
| B5 | 275221 | 88736 | 92304 | 182917.00 | −3568.00 | 1.0199 | WT Homozygote |
| C5 | 98000 | 299991 | 97809 | 191.00 | 202182.00 | 0.0009 | Mutant Homozygote |
| D5 | 71935 | 307011 | 67942 | 3993.00 | 239069.00 | 0.0164 | Mutant Homozygote |

-continued

| I.D. | WT Monoplex | Mutant Monoplex | No Interr. | Adj. WT Average | Adj. Mutant Average | Ratio | Call |
|---|---|---|---|---|---|---|---|
| E5 | 125117 | 344353 | 127235 | −2118.00 | 217118.00 | −0.0099 | Mutant Homozygote |
| F5 | 337438 | 139681 | 141316 | 196122.00 | 1635.00 | 1.0084 | WT Homozygote |
| G5 | 320827 | 109590 | 110836 | 209991.00 | −1246.00 | 1.0060 | WT Homozygote |
| H5 | 284119 | 254549 | 83420 | 200699.00 | 171129.00 | 0.5398 | Heterozygote |
| A6 | 196486 | 40731 | 34709 | 161777.00 | 6022.00 | 0.9641 | WT Homozygote |
| B6 | 91086 | 284419 | 73381 | 17705.00 | 211038.00 | 0.0774 | Mutant Homozygote |
| C6 | 287819 | 109940 | 109470 | 178349.00 | 470.00 | 0.9974 | WT Homozygote |
| D6 | 324772 | 96989 | 90618 | 234154.00 | 6371.00 | 0.9735 | WT Homozygote |
| E6 | 104800 | 22690 | 16390 | 88410.00 | 6300.00 | 0.9335 | WT Homozygote |
| F6 | 326617 | 108807 | 100688 | 225929.00 | 8119.00 | 0.9653 | WT Homozygote |
| G6 | 325606 | 108051 | 105410 | 220196.00 | 2641.00 | 0.9881 | WT Homozygote |
| H6 | 272423 | 30D350 | 88598 | 183825.00 | 211752.00 | 0.4647 | Heterozygote |
| A7 | 205580 | 132345 | 52452 | 153128.00 | 79893.00 | 0.6571 | Heterozygote |
| B7 | 128452 | 310516 | 113483 | 14969.00 | 197033.00 | 0.0706 | Mutant Homozygote |
| C7 | 104698 | 305524 | 93208 | 11490.00 | 212316.00 | 0.0513 | Mutant Homozygote |
| D7 | 307564 | 86991 | 85063 | 222501.00 | 1928.00 | 0.9914 | WT Homozygote |
| E7 | 275408 | 101068 | 97206 | 178202.00 | 3862.00 | 0.9788 | WT Homozygote |
| F7 | 120699 | 303920 | 76423 | 44276.00 | 227497.00 | 0.1629 | Mutant Homozygote |
| G7 | 323578 | 103479 | 104487 | 219091.00 | −1008.00 | 1.0046 | WT Homozygote |
| H7 | 251697 | 203978 | 60296 | 191401.00 | 143682.00 | 0.5712 | Heterozygote |
| A8 | 80230 | 276995 | 74846 | 5384.00 | 202149.00 | 0.0259 | Mutant Homozygote |
| B8 | 137609 | 300532 | 104219 | 33390.00 | 196313.00 | 0.1454 | Mutant Homozygote |
| C8 | 48060 | 108280 | 46704 | 1356.00 | 61576.00 | 0.0215 | Mutant Homozygote |
| D8 | 100470 | 264735 | 91454 | 9016.00 | 173281.00 | 0.0495 | Mutant Homozygote |
| E8 | 292829 | 122176 | 116160 | 176669.00 | 6016.00 | 0.9671 | WT Homozygote |
| F8 | 105447 | 326479 | 96111 | 9336.00 | 230368.00 | 0.0389 | Mutant Homozygote |
| G8 | 147067 | 362978 | 136719 | 10348.00 | 226259.00 | 0.0437 | Mutant Homozygote |
| H8 | 332952 | 153555 | 91114 | 241838.00 | 62441.00 | 0.7948 | WT Homozygote |
| A9 | 244720 | 7Q456 | 75204 | 169516.00 | −4748.00 | 1.0288 | WT Homozygote |
| B9 | 112223 | 322330 | 106362 | 5861.00 | 215968.00 | 0.0264 | Mutant Homozygote |
| C9 | 118996 | 327770 | 95704 | 23292.00 | 232066.00 | 0.0912 | Mutant Homozygote |
| D9 | 94361 | 270031 | 81552 | 12809.00 | 188479.00 | 0.0636 | Mutant Homozygote |
| E9 | 142083 | 342389 | 134979 | 7104.00 | 207410.00 | 0.0331 | Mutant Homozygote |
| F9 | 343667 | 131080 | 132731 | 210936.00 | −1651.00 | 1.0079 | WT Homozygote |
| G9 | 138858 | 369893 | 129933 | 8925.00 | 239960.00 | 0.0359 | Mutant Homozygote |
| H9 | 143881 | 66587 | 63328 | 80553.00 | 3259.00 | 0.9611 | WT Homozygote |
| A10 | 252930 | 67971 | 63808 | 189122.00 | 4163.00 | 0.9785 | WT Homozygote |
| B10 | 111801 | 306491 | 101836 | 9965.00 | 204655.00 | 0.0464 | Mutant Homozygote |
| C10 | 332112 | 116649 | 113212 | 218900.00 | 3437.00 | 0.9845 | WT Homozygote |
| D10 | 113247 | 339818 | 98752 | 14495.00 | 241066.00 | 0.0567 | Mutant Homozygote |
| E10 | 158838 | 328193 | 116442 | 42396.00 | 211751.00 | 0.1668 | Mutant Homozygote |
| F10 | 339981 | 125573 | 117205 | 222776.00 | 8368.00 | 0.9638 | WT Homozygote |
| G10 | 111672 | 311430 | 104189 | 7483.00 | 207241.00 | 0.0348 | Mutant Homozygote |
| H10 | 362138 | 145457 | 106673 | 255465.00 | 38784.00 | 0.8682 | WT Homozygote |
| A11 | 253647 | 157356 | 95627 | 158020.00 | 61729.00 | 0.7191 | No Call |
| B11 | 164237 | 359643 | 145067 | 19170.00 | 214576.00 | 0.0820 | Mutant Homozygote |
| C11 | 339294 | 124660 | 120341 | 218953.00 | 4319.00 | 0.9807 | WT Homozygote |
| D11 | 347411 | 112399 | 111482 | 235929.00 | 917.00 | 0.9961 | WT Homozygote |
| E11 | 353768 | 137003 | 142014 | 211754.00 | 5011.00 | 1.0242 | WT Homozygote |
| F11 | 347503 | 131462 | 129637 | 217866.00 | 1825.00 | 0.9917 | WT Homozygote |
| G11 | 136856 | 327747 | 115035 | 21821.00 | 212712.00 | 0.0930 | Mutant Homozygote |
| H11 | 358593 | 150488 | 113576 | 245017.00 | 36912.00 | 0.8691 | WT Homozygote |
| A12 | 73492 | 208038 | 67210 | 6282.00 | 140828.00 | 0.0427 | Mutant Homozygote |
| B12 | 299590 | 106653 | 97203 | 202387.00 | 9450.00 | 0.9554 | WT Homozygote |
| C12 | 23190 | 73050 | 19140 | 4050.00 | 53910.00 | 0.0699 | Mutant Homozygote |
| D12 | 106633 | 318290 | 92331 | 14302.00 | 225959.00 | 0.0595 | Mutant Homozygote |
| E12 | 367938 | 170961 | 159625 | 208313.00 | 11336.00 | 0.9484 | WT Homozygote |
| F12 | 136109 | 348590 | 126033 | 10076.00 | 222557.00 | 0.0433 | Mutant Homozygote |
| G12 | 315191 | 119810 | 58932 | 256259.00 | 60878.00 | 0.8080 | WT Homozygote |
| H12 | 264473 | 60564 | 55720 | 208753.00 | 4844.00 | 0.9773 | WT Homozygote |

EXAMPLE 23

Self-annealing Interrogation Probe

This Example illustrates use of a different type of oligonucleotide probe that is used to form a hairpin structure in the interrogation technology of this invention. This study demonstrates a method for eliminating the need for adding a probe specific to the interrogation site to the interrogation reaction.

Here, the oligonucleotide probe anneals to the target strand downstream of (3' to) the interrogation position in the target strand. The oligonucleotide has at its 5' end an unannealed region of nucleotides followed by about 5 to about 20 nucleotides that are identical to the interrogation region on the target strand. The annealed 3' end of the oligonucleotide is then extended through the interrogation position of the target strand creating what is referred to as extended probe. The hybrid is denatured and a hairpin structure formed between the extended probe strand and the 5' end of the oligonucleotide probe. This region is then assayed in a standard interrogation reaction to determine if a mismatch is present or not.

Four probes were designed to represent different types of hairpin formations that an extended probe strands may assume. These probes are 10207 (SEQ ID NO:89), 10208 (SEQ ID NO:90), 10209 (SEQ ID NO:91), and 10212 (SEQ ID NO:92).

These probes are predicted to form the following self-hybridized secondary structures when allowed to self-anneal:

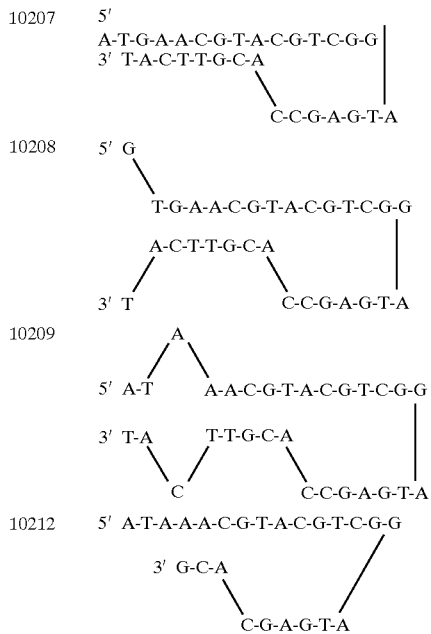

A 5 µL (5 µg) aliquot of each of the four probes was diluted to 100 µL with nanopure water. They were then sequentially diluted 1:10 to a final dilution factor of 1:100,000. Twenty microliters of the diluted probes were heated, in separate tubes, at 95° C. for 3 minutes and cooled to room temperature for 10 minutes to permit self-annealing. Twenty microliters of Master Mix, as described in Example 1, were then added to each tube and the tubes were incubated at 37° C. for 15 minutes. Ten microliters of the solutions were added to 100 µL of L/L reagent (Promega, F202A) and relative light units measured immediately with a Turner® TD20/20 luminometer. The no-probe control resulted in 57.24 relative light units and the remaining probe results are reported below in relative light units (rlu).

| Log dilution | probe | | | |
|---|---|---|---|---|
| | 10207 | 10208 | 10209 | 10212 |
| −5 | 44.89 | 56.22 | 57.57 | 57.80 |
| −4 | 85.21 | 64.56 | 58.26 | 63.15 |
| −3 | 297.7 | 70.53 | 79.12 | 82.65 |
| −2 | 970.5 | 108.4 | 80.06 | 106.7 |

Probe 10207 worked as an efficient target for interrogation as expected, with probe 10208 providing the anticipated negative results. Probe 10212 has only a three base match so it may be unextended, thus resulting in the low values. Probe 10209 likely has the 3' terminal nucleotide unannealed when the hairpin forms due to the mismatch at the third nucleotide in from the 3' end. Such an unannealed 3' terminal nucleotide would account for the low rlu values.

```
10207   5' ATGAACGTACGTCGGATGAGCACGTTCAT 3'
        SEQ ID NO:89

10208   5' GTGAACGTACGTCGGATGAGCACGTTCAT 3'
        SEQ ID NO:90

10209   5' ATAAACGTACGTCGGATGAGCACGTTCAT 3'
        SEQ ID NO:91

10212   5' ATAAACGTACGTCGGATGAGCACG 3'
        SEQ ID NO:92
```

EXAMPLE 24

Interrogation with a Self-Annealing Primer II

This example and FIG. 1 illustrate use of a different type of oligonucleotide probe, a "REAPER™" probe in a process of this invention. This example demonstrates a method for eliminating the need for adding a probe specific to the interrogation site to the interrogation reaction.

Here, the oligonucleotide first probe (SEQ ID NO:112), at its 3'-end, anneals to the target strand (SEQ ID NO:111) at a position downstream of (3' to) the interrogation position in the target strand (FIG. 1A). The probe has at its 5'-end an unannealed region of nucleotides including about 5 to about 20 nucleotides that are identical to a region on the target strand including the interrogation position. This region of identity is present in the same orientation on both the target and the probe strands.

The annealed 3'-end of the probe is then extended through the interrogation position of the target strand forming what is referred to as a first extended probe and an extended first hybrid as is illustrated in FIG. 1B (SEQ ID NO:113). The extended first hybrid is denatured and a second probe (SEQ ID NO:114) is annealed to the first extended probe to form a second hybrid. This second probe is complementary to the first extended probe strand at a region downstream of the interrogation position on the first extended probe strand (FIG. 1C).

The second probe is then extended and a second extended hybrid is formed as illustrated in FIG. 1D. The second extended hybrid is comprised of the first extended probe and second extended probe (SEQ ID NO:115).

The strands of the second extended hybrid are denatured and permitted to renature to form a hairpin structure. Upon hairpin formation, the first extended probe forms a hairpin structure that has a 3'-overhang, whereas the second extended probe forms a hairpin structure that contains a 5'-overhang that provides a substrate for depolymerization. The second extended probe strand is then depolymerized and the analytical output obtained as described elsewhere herein. The analytical output determines the presence or absence of the original target strand or of a particular base in the original target strand as is also discussed elsewhere herein.

SEQ ID NO:111 oligonucleotide is diluted to 1 mg/mL in water. This solution is labeled 111. SEQ ID NO:112 oligonucleotide is diluted to 1 mg/mL in water and this solution is labeled 112. One microliter of each solution 111 and 112 is combined with 18 µL water. The solution is heated to 95° C. for 5 minutes then is cooled at room temperature for 10 minutes to permit oligonucleotides of SEQ ID NOs:111 and 112 to anneal.

To this solution are added dNTP mixture to a final concentration of 0.25 mM for each dNTP, 10×Klenow buffer to a final concentration of 1×, and 5 U of Klenow enzyme. The tube with these components is incubated at 37° C. for 30 minutes. The extended first hybrid DNA so formed (containing SEQ ID NO: 113) is purified (Qiagen, Mermaid system) and eluted into 50 µl of water.

enzyme) indicates that a matched base was present at the 3'-terminus of the hairpin structure and this further indicates the presence of the target strand, and for this particular example, it also indicates the presence of a G base at the interrogation position of the target.

```
5' CCCGGAGAGACCTCCTTAAGGGGCCATATTATTTCGTCGATTCCAGTGTTGGCCAAACGGAT 3' SEQ ID NO: 111

5' GGGGCCATATTATTTCGCCGTTTGGCCAACACTGGAATCGA 3' SEQ ID NO: 112

5' GGGGCCATATTATTTCGCCGTTTGGCCAACACTGGAATCGACGAAATAAT
ATGGCCCCTTAAGGAGGTCTCTCCGGG 3' SEQ. ID NO: 113

5' CCCGGAGAGACCTCCT 3' SEQ ID NO: 114

5' CCCGGAGAGACCTCCTTAAGGGGCCATATTATTTCGTCGATTCCAGTGTT
GGCCAAACGGCGAAATAATATGGCCCC 3' SEQ ID NO: 115
```

To this solution of the purified extended first hybrid is added 1 µL SEQ ID NO:114 oligonucleotide (1 mg/mL) as second probe. The solution is then heated to 95° C. for 5 minutes and is cooled at room temperature to permit 114 and 113 to anneal as illustrated in FIG. 1C to form the second hybrid. To this solution are added a dNTP mixture to a final concentration of 0.25 mM for each dNTP, 10×Klenow buffer to a final concentration of 1×, and 5 U of Klenow enzyme. The tube with these components is incubated at 37° C. for 30 minutes to form a second extended hybrid that contains a second extended probe (oligonucleotide SEQ ID NO: 115).

The SEQ ID NO:115/113 second extended hybrid DNA (FIG. 1D) formed is purified (Qiagen, Mermaid system) to separate the extended hybrid from the unreacted dNTPs and eluted into 50 µL water. (Alternatively, the original 112 oligo is biotinylated at it's 5'-end and this biotin is then also present in strand of SEQ ID NO:113. This biotinylated strand 113 is then denatured from strand 115 and removed from the solution with streptavidin coated paramagnetic particles according to the manufacturer's instructions (Promega, Z5481) and the 115 hairpin structure is allowed to form as below).

This hybrid solution is then heated to 95° C. for 5 minutes diluted to 100 µL with water and is cooled on ice for 10 minutes to permit hairpin structure formation.

The following master mix is assembled and mixed.

| Component | Amount |
|---|---|
| 10X DNA Pol Buffer (Promega, M195A) | 200 µL |
| Klenow exo- (1 U/µL) (Promega M218B) | 12.5 µL |
| 40 mM Sodium Pyrophosphate (Promega C350B) | 25 µL |
| NDPK (1 U/µL) | 10 µL |
| 10 µM ADP (Sigma A5285) | 20 µL |
| Water | 732.5 µL |

Twenty microliters of this master mix are added to 20 µL of the above hairpin-containing solutions after cooling, and the resulting mixtures are heated at 37° C. for 15 minutes. After this incubation, duplicate 4 µL samples of the solution are removed, added to 100 µL of L/L Reagent (Promega, F202A) and the light produced by the reaction is measured immediately using a Turner® TD20/20 luminometer. A positive analytical output at levels over background (no

EXAMPLE 25

Interrogation With a Self-Annealing Primer: III

In this example, the method described in Example 23 is used to detect the presence of E. coli DNA in a sample. A Reaper™ probe (12028) was designed to hybridize to 20 nucleotides of the lac Z gene of E. coli DNA. This region of the lac Z gene is designated SEQ ID NO:117. It is important that the unextended primer does not self-anneal and extend upon itself to form primer dimers or a high level of background noise would result. The primer was designed to minimize this possibility.

12028 5' TTACCCAACTTAATCAGGGGGATGTGCT-GCAAGGC 3' SEQ ID NO:116 lacZ segment SEQ ID NO:117 5' . . . CGTTACCCAACT-TAATCGCCTTGCAGCACATCCCCCTT . . . 3'

The following reaction was set up to hybridize oligonucleotide 12028 to a complementary region of the E. coli lac Z gene. The 12028 oligonucleotide is present in great molar excess in the reaction, so multiple extension rounds are performed to ensure that all of the 12028 oligonucleotide is extended to make SEQ ID NO:116. The extension is performed in the absence of dCTP to halt the extension by the polymerase after addition of 15 bases. Oligonucleotide 12028 was diluted with nanopure water to a final concentration of 100 µg/mL.

| | 1 and 2 | 3 and 4 | 5 and 6 |
|---|---|---|---|
| 10X Thermophilic buffer | 2 µL | 2 µL | 2 µL |
| 25 mM MgCl₂ | 2 µL | 2 µL | 2 µL |
| 1 mg/mL E. coli B DNA (Sigma D4889) | 2 µL | — | 2 µL |
| 100 µg/mL 12028 | — | 1 µL | 1 µL |
| 10 µM dGTP, dATP, TTP | 10 µL | 10 µL | 10 µL |
| water | 4 µL | 5 µL | 3 µL |

The solutions were incubated for 3 minutes at 95° C. to denature the DNA. Then 1 µL of Taq DNA Polymerase (Promega, M1861) at 5 U/µL was added and the incubation at 95° C. proceeded for an additional 2 minutes followed by (95° C. 30 seconds, 55° C. 30 seconds, 72° C. 1 min)×35 cycles, and a 4° C. soak. The tube was then removed and twenty microliters of the solutions were transferred to a fresh tube. One microliter of 1 U/µL Shrimp Alkaline Phosphatase (SAP) was added to each tube and they were then incubated at 37° C. for 30 minutes, followed by an incubation at 65° C. for 15 minutes to remove the terminal phosphate from the residual nucleotides and the 5' end of the oligonucleotides in the solution. The tubes were spun briefly in a microcentrifuge to collect the solution at the bottom of then tube and they were then heated at 95° C. for 3 minutes to denature the DNA. The tubes were then permitted to cool at room temperature for 10 minutes, and permit the stem loop structure to form.

To remove the free nucleotide from the solution, the contents of each tube were separately applied to a Sephadex® G-25 column, prespun according to manufacturer's instructions (Pharmacia), and then centrifuged at 3000 rpm for 2 minutes. Twenty microliters of the eluted solution were added to 5 µL master mix (50 µL 10×DNA Polymerase buffer, 6.25 µL 40 mM NaPPi, 10 µL 10 U/µL Klenow exo minus, 2 µL 1 U/µL NDPK, 5 µL 10 µM ADP and 27 µL water), mixed and incubated for 20 minutes at 37° C. Then 20 µL were removed and added to 100 µL of L/L Reagent (Promega Corp.) The light output was measured immediately in a Turner® TD20/20 luminometer. The results in relative light units (rlu) are listed below.

| Solution | rlu |
|----------|-----|
| 1. | 129 |
| 2. | 105 |
| 3. | 5 |
| 4. | 10 |
| 5. | 150 |
| 6. | 164 |

The background rlu values in solutions 3 and 4 (primer alone) are very low, indicating good removal of the free nucleotides. The higher background in solutions 1 and 2 must therefore result from the *E. coli* DNA. It appears that the efficiency of extension of the 12028 oligonucleotide is in the range of 20–25%. This might be increased through the use of higher nucleotide and/or primer concentrations.
12028/lacZ (SEQ ID NO:116/117) hybrid:

```
lacZ     3'...TTCCCCCTACACGACGTTCCGCTAATTCAACCCATTGC..5'

12028        AGGGGGATGTGCTGCAAGGC 3'

C

T

A

ATTCAACCCATT 5'
```

Extended 12028/lacZ (SEQ ID NO:118/117) hybrid with the nucleotides added by extension underlined:

```
lacZ     3'...TTCCCCCTACACGACGTTCCGCTAATTCAACCCATTGC...5'

12028        AGGGGGATGTGCTGCAAGGCGATTAAGTTGGGTAA3'

C

T

A

ATTCAACCCATT 5'
```

Extended 12028 (SEQ ID NO:118) secondary structure with the nucleotides added by extension underlined:

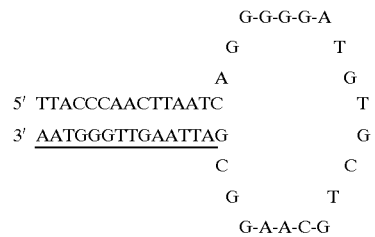

EXAMPLE 26

Detection of DNA Sequences in the Genome of *Campylobacter jejuni*

Oligonucleotides 11453 (SEQ ID NO:119) and 11454 (SEQ ID NO:120) are exactly complementary and can be annealed, thereby forming a synthetic target representing a 70 bp segment of *Campylobacter jejuni*. These two oligonucleotides were diluted in nanopure water to a final concentration of 10 µg/mL. Four microliters of each were then mixed with 232 µL 10 mM Tris pH7.3 to yield a target solution of 0.3 µg/mL of DNA. Oligonucleotides 11451 (SEQ ID NO:121) and 11450 (SEQ ID NO:122) are *Campylobacter jejuni* interrogation probes that bind to opposite strands of the bacterial genome represented in the synthetic target. Oligonucleotide 11451 anneals to oligonucleotide 11454. Oligonucleotide 11450 anneals to oligonucleotide 11453.

The following solutions were assembled in triplicate and nanopure water added to a final volume of 20 µL.

| Solution | 0.3 ng Target | 1 µg Probe | rlu |
|---|---|---|---|
| 1. | + | 11451 | 391 |
| 2. | + | 11450 | 241 |
| 3. | + | none | 28 |
| 4. | − | 11451 | 248 |
| 5. | − | 11450 | 30 |
| 6. | − | none | 24 |

The assembled solutions were incubated at 92° C. for 5 minutes, then cooled at room temperature for 10 minutes. Master mix was prepared as in Example 1 using 10 units Klenow exo-polymerase and 4 units NDPK. Twenty microliters of master mix were added to each tube and incubated at 37° C. for 15 minutes. Five microliters of each solution were then combined with 100 µL of L/L reagent (Promega F202A) and light output measured immediately on a Turner® TD20/20 luminometer. The average relative light units (rlu) are recorded in the table above Using each of the interrogation probes with the target appears to give strong net signal. The top probe (11451) however, gives very strong signal alone, possibly due to hairpin formation, and is less suitable for interrogation. The bottom interrogation probe (11450) is the better for interrogation.

```
11453
5'CTTGAAGCATAGTTCTTGTTTTTAAACTTTGTCCATCTTGAGCCGCTTGA   SEQ ID NO:119
GTTGCCTTAGTTTTAATAGT 3'

11454
5'ACTATTAAAACTAAGGCAACTCAAGCGGCTCAAGATGGACAAAGTTTA    SEQ ID NO:120
AAAACAAGAACTATGCTTCAAG 3'

11451
5'AGTTCTTGTTTTTAAACTTTGTCCATCTTG 3'  SEQ ID NO:121

11450
5'CAAGATGGACAAAGTTTAAAAACAAGAACT 3'  SEQ ID NO:122
```

EXAMPLE 27

Detection of *E. coli* Repetitive Sequence Without Nucleic Acid Amplification In this Example repetitive sequence in *E. coli* is detected without the need for amplification of the target sequence prior to pyrophosphorylation. This target sequence is denoted as 'colirep'.

Oligonucleotide 11707 (SEQ ID NO:123) is totally complementary to a segment of colirep DNA sequence. Twelve microliters of oligonucleotide 11707 solution (1 mg/mL) were combined with 204 µL of water to make solution A. Another solution was prepared by combining 4 µL of 11707 (1 mg/mL) with 204 µL water and 8 µL 10 mM Tris, pH 8.0 to make solution B. The *E. coli* is Sigma cat#D4889, *E. coli* Strain B ultra pure.

Four nanograms (2 µL) *E. coli* DNA were combined with 18 µL solution A and with 18 µL solution B in separate tubes. Similarly, 40 ng *E. coli* DNA was combined with 18 µL solution A and with 18 µL solution B in separate tubes. These solutions were then incubated at 92° C. for 3 minutes and cooled at room temperature for 15 minutes. The following master mix was assembled:

| | |
|---|---|
| 10X DNA Polymerase buffer | 240 µL |
| 40 mM NaPPi | 30 µL |
| Klenow exo- (10 U/µL) | 30 µL |
| NDPK (1 U/µL) | 12 µL |
| 10 µM ADP (Sigma) | 24 µL |
| water | 864 µL |

Twenty microliters of master mix were added to each reaction and they were then incubated at 37° C. for 15 minutes. One hundred microliters of L/L Reagent were then added and the relative light output (rlu) immediately measured with a Turner® TD 20/20 luminometer. The rlu were:

| Solution | rlu-1 | rlu-2 | rlu-3 | Average |
|---|---|---|---|---|
| Tris | 2.85 | 3.562 | 3.059 | 3.157 |
| 11707 (A) | 13.69 | 12.13 | 13.67 | 13.16 |
| 11707 (B) | 7.473 | 7.234 | 6.981 | 7.259 |
| 40 ng DNA + Tris | 75.62 | 75.52 | 73.24 | 74.79 |
| 40 ng DNA + 11707 (A) | 97.71 | 134.2 | 105.1 | 112.3 |
| 40 ng DNA + 11707 (B) | 81.46 | 87.56 | 76.28 | 81.77 |
| 4 ng DNA + Tris | 6.719 | 8.084 | 5.882 | 6.895 |
| 4 ng DNA + 11707 (A) | 24.50 | 25.97 | 25.17 | 25.21 |

-continued

| Solution | rlu-1 | rlu-2 | rlu-3 | Average |
|---|---|---|---|---|
| 4 ng DNA + 11707 (B) | 15.69 | 17.22 | 16.99 | 16.63 |

The data reflect that oligonucleotide probe 11707 can detect *E. coli* DNA without amplification by a process of the invention.

Interrogation oligonucleotide:

11707 5' AGTGACTGGGG 3' SEQ ID NO:123

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

What is claimed is:

1. A method for determining the presence or absence of a predetermined endogenous nucleic acid target sequence in a nucleic acid sample that comprises the steps of:

(A) providing a treated sample that may contain said predetermined nucleic acid target sequence hybridized with a nucleic acid probe that includes an identifier nucleotide in the 3'-terminal region;

(B) admixing the treated sample with a depolymerizing amount of an enzyme whose activity is to release one or more nucleotides from the 3'-terminus of a hybridized nucleic acid probe to form a treated reaction mixture;

(C) maintaining the treated reaction mixture for a time period sufficient to permit the enzyme to depolymerize hybridized nucleic acid and release identifier nucleotides therefrom; and (D) analyzing for the presence of released identifier nucleotides to obtain an analytical output, the analytical output indicating the presence or absence of said endogenous nucleic acid target sequence.

2. The method according to claim 1 wherein said identifier nucleotide is a nucleoside triphosphate.

3. The method according to claim 1 wherein said analytical output is obtained by luminescence spectroscopy.

4. The method according to claim 1 wherein said analytical output is obtained by fluorescence spectroscopy.

5. The method according to claim 4 wherein said released identifier nucleotide includes a fluorescent label.

6. The method according to claim 5 wherein said identifier nucleotide is fluorescently labeled after release from said hybrid.

7. The method according to claim 1 wherein said analytical output is obtained by mass spectrometry.

8. The method according to claim 7 wherein said released identifier nucleotide includes a fluorescent label.

9. The method according to claim 7 wherein said identifier nucleotide is fluorescently labeled after release from said hybrid.

10. The method according to claim 1 wherein said analytical output is obtained by absorbance spectroscopy.

11. The method according to claim 1 including the further steps of forming said treated sample by
   (a) admixing a sample to be assayed with one or more nucleic acid probes to form a hybridization composition, wherein the 3'-terminal region of said nucleic acid probes (i) hybridize with partial or total complementarity to said endogenous nucleic acid target sequence when that sequence is present in the sample and (ii) include an identifier nucleotide;
   (b) maintaining said hybridization composition for a time period sufficient to form a treated sample that may contain said one predetermined nucleic acid target sequence hybridized with a nucleic acid probe.

12. The method according to claim 1 wherein said nucleic acid sample is obtained from a biological sample.

13. A method for determining the presence or absence of at least one predetermined endogenous nucleic acid target sequence in a nucleic acid sample that comprises the steps of:
   (A) admixing a sample to be assayed with one or more nucleic acid probes to form a hybridization composition, wherein the 3'-terminal region of said nucleic acid probes (i) hybridizes with partial or total complementarity to at least one said predetermined endogenous nucleic acid target sequence when that sequence is present in the sample and (ii) includes an identifier nucleotide;
   (B) maintaining said hybridization composition for a time period sufficient to form a treated sample that may contain said predetermined endogenous nucleic acid target sequence hybridized with a nucleic acid probe;
   (C) admixing the treated sample with a depolymerizing amount of an enzyme whose activity is to release one or more nucleotides from the 3'-terminus of a hybridized nucleic acid probe to form a treated reaction mixture;
   (D) maintaining the treated reaction mixture for a time period sufficient to permit the enzyme to depolymerize hybridized nucleic acid and release identifier nucleotides therefrom; and
   (E) analyzing for the presence of released identifier nucleotides to obtain an analytical output, the analytical output indicating the presence or absence of at least one said endogenous nucleic acid target sequence.

14. The method according to claim 13 wherein said identifier nucleotide is a nucleoside triphosphate.

15. The method according to claim 13 wherein said analytical output is obtained by luminescence spectroscopy.

16. The method according to claim 13 wherein said analytical output is obtained by fluorescence spectroscopy.

17. The method according to claim 16 wherein said released identifier nucleotide includes a fluorescent label.

18. The method according to claim 17 wherein said identifier nucleotide is fluorescently labeled after release from said hybrid.

19. The method according to claim 13 wherein said analytical output is obtained by mass spectrometry.

20. The method according to claim 19 wherein said released identifier nucleotide includes a fluorescent label.

21. The method according to claim 20 wherein said identifier nucleotide is fluorescently labeled after release from said hybrid.

22. The method according to claim 13 wherein said analytical output is obtained by absorbance spectroscopy.

23. The method according to claim 13 wherein said sample contains a plurality of predetermined endogenous nucleic acid target sequences and is admixed with a plurality of said nucleic acid probes.

24. The method according to claim 23 wherein the analytical output obtained when one of said nucleic acid probes hybridizes with partial complementarity to one endogenous target nucleic acid sequence is greater than the analytical output when all of the nucleic acid probes hybridize with total complementarity to their respective nucleic acid target sequences.

25. The method according to claim 23 wherein the analytical output obtained when one of said nucleic acid probes hybridizes with partial complementarity to one endogenous target nucleic acid sequence is less than the analytical output when all of the nucleic acid probes hybridize with total complementarity to their respective nucleic acid target sequences.

26. The method according to claim 23 wherein the analytical output obtained when one of said nucleic acid probes hybridizes with, total complementarity to one endogenous nucleic acid target sequence is greater than the analytical output when all of the nucleic acid probes hybridize with partial complementarity to their respective nucleic acid target sequences.

27. The method according to claim 23 wherein the analytical output obtained when one of said nucleic acid probes hybridize with total complementarity to one endogenous target nucleic acid sequence is less than the analytical output when all of the nucleic acid probes hybridize with partial complementarity to their respective nucleic acid target sequences.

28. The method according to claim 13 wherein said enzyme whose activity is to release nucleotides is a template-dependent polymerase that, in the presence of pyrophosphate ions, depolymerizes hybridized nucleic acids whose bases in the 3'-terminal region are matched with total complementarity.

29. The method according to claim 13 wherein said enzyme whose activity is to release nucleotides exhibits a 3'→5'-exonuclease activity, depolymerizing hybridized nucleic acids having one or more mismatched bases in the 3'-terminal region of the hybridized probe.

30. A method for determining the presence or absence of a first endogenous nucleic acid target in a nucleic acid sample containing that target or a substantially identical second target that comprises the steps of:
   (A) admixing said sample to be assayed with one or more nucleic acid probes to form a hybridization composition, wherein said first and second endogenous nucleic acid targets comprise a region of sequence identity except for at least a single nucleotide at a predetermined position that differs between the endogenous targets, and wherein said nucleic acid probe (i) is substantially complementary to said nucleic acid target region of sequence identity and comprises at least one nucleotide at an interrogation position, said interrogation position of the probe being aligned with said predetermined position of a target when a target and probe are hybridized and (ii) includes an identifier nucleotide in the 3'-terminal region;

(B) maintaining said hybridization composition for a time period sufficient to form a treated sample wherein the nucleotide at said interrogation position of said probe is aligned with the nucleotide at said predetermined position of said target in said region of identity;

(C) admixing the treated sample with a depolymerizing amount an enzyme whose activity is to release one or more nucleotides from the 3'-terminus of a hybridized nucleic acid probe to form a treated reaction mixture;

(D) maintaining the treated reaction mixture for a time period sufficient to release identifier nucleotide and depolymerize said hybridized nucleic acid probe; and (E) analyzing for the presence of released identifier nucleotide to obtain an analytical output, said analytical output indicating the presence or absence of said nucleotide at said predetermined region and thereby the presence or absence of a first or second nucleic acid target.

31. The method according to claim 30 wherein said analytical output is obtained by fluorescence spectroscopy.

32. The method according to claim 31 wherein said identifier nucleotide is fluorescently labeled after release from said hybrid.

33. The method according to claim 30 wherein said analytical output is obtained by mass spectrometry.

34. The method according to claim 30 wherein said released identifier nucleotide includes a fluorescent label.

35. The method according to claim 30 wherein said identifier nucleotide is a nucleoside triphosphate.

36. The method according to claim 35 wherein said analytical output is obtained by luminescence spectroscopy.

37. The method according to claim 36 wherein said analytical output is obtained by absorbance spectroscopy.

38. The method according to claim 30 wherein said nucleic acid target sequence is selected from the group consisting of deoxyribonucleic acid and ribonucleic acid.

39. The method according to claim 30 further comprising a first probe and a second probe.

40. The method according to claim 39 wherein said sample to be assayed comprises a plurality first nucleic acid targets and second substantially identical nucleic acid targets.

41. The method according to claim 40 wherein said first probe comprises a nucleotide at said interrogation position that is complementary to a first target nucleic acid at said predetermined position, and said second probe comprises a nucleotide at the interrogation position that is complementary to a second target nucleic acid at said predetermined position.

42. The method according to claim 40 wherein the analytical output obtained when one of said nucleic acid probes hybridizes with partial complementarity to one target nucleic acid sequence is greater than the analytical output when all of the nucleic acid probes hybridize with total complementarity to their respective nucleic acid target sequences.

43. The method according to claim 40 wherein the analytical output obtained when one of said nucleic acid probes hybridizes with partial complementarity to one target nucleic acid sequence is less than the analytical output when all of the nucleic acid probes hybridize with total complementarity to their respective nucleic acid target sequences.

44. The method according to claim 40 wherein the analytical output obtained when one of said nucleic acid probes hybridizes with total complementarity to one nucleic acid target sequence is greater than the analytical output when all of the nucleic acid probes hybridize with partial complementarity to their respective nucleic acid target sequences.

45. The method according to claim 40 wherein the analytical output obtained when one of said nucleic acid probes hybridizes with total complementarity to one target nucleic acid sequence is less than the analytical output when all of the nucleic acid probes hybridize with partial complementarity to their respective nucleic acid target sequences.

46. The method according to claim 30 wherein said enzyme whose activity is to release nucleotides is a template-dependent polymerase that, in the presence of pyrophosphate ions, depolymerizes hybridized nucleic acids whose bases in the 3'-terminal region are matched with total complementarity.

47. The method according to claim 30 wherein said enzyme whose activity is to release nucleotides exhibits a 3'→5'-exonuclease activity, depolymerizing hybridized nucleic acids having one or more mismatched bases in the 3'-terminal region of the hybridized probe.

48. A one-pot method for determining the presence or absence of at least one predetermined endogenous nucleic acid target sequence in a nucleic acid sample that comprises the steps of:

(A) admixing a treated sample that may contain said predetermined endogenous nucleic acid target sequence hybridized to a nucleic acid probe whose 3'-terminal region is completely complementary to said predetermined nucleic acid target sequence and includes an identifier nucleotide with (i) a depolymerizing amount of an enzyme whose activity in the presence of pyrophosphate is to release identifier nucleotide as a nucleoside triphosphate from the hybridized nucleic acid probe, (ii) adenosine 5' diphosphate, (iii) pyrophosphate and (iv) NDPK to form a treated reaction mixture;

(b) maintaining the treated reaction mixture at a temperature of about 25 to about 80 degrees C. for a time period sufficient to permit the enzyme to depolymerize hybridized nucleic acid probe, release an identifier nucleotide in the 3'-terminal region as a nucleoside triphosphate and to convert said nucleoside triphosphate and said adenosine 5' diphosphate to adenosine 5' triphosphate; and (d) analyzing for the presence of adenosine 5' triphosphate to obtain an analytical output, the analytical output indicating the presence or absence of at least one said nucleic acid target sequence.

49. The method according to claim 48 wherein said analytical output is obtained by luminescence spectroscopy.

50. The method according to claim 48 including the further steps of forming said treated sample by (a) admixing a sample to be assayed with one or more nucleic acid probes to form a hybridization composition, wherein the 3'-terminal region of said nucleic acid probe (i) hybridizes with partial or total complementarity to a nucleic acid target sequence when that sequence is present in the sample and (ii) includes an identifier nucleotide;

(b) maintaining said hybridization composition for a time period sufficient to form a treated sample that may contain said one predetermined nucleic acid target sequence hybridized with a nucleic acid probe.

51. The method according to claim 48 wherein said depolymerizing enzyme maintains activity at 60–90° C.

52. The method according to claim 48 wherein said depolymerizing enzyme is selected from the group consisting of the Tne triple mutant DNA polymerase, Bst DNA polymerase, Ath DNA polymerase, Taq DNA polymerase and Tvu DNA polymerase.

53. The method according to claim 48 wherein said NDPK is that encoded by *Pyrococcus furiosis*.

54. A method for determining the presence or absence of a specific base in an endogenous nucleic acid target sequence in a sample to be assayed that comprises the steps of:

(A) admixing a sample to be assayed with one or more nucleic acid probes to form an endogenous hybridization composition, wherein the 3'-terminal region of at least one of said nucleic acid probes (i) is substantially complementary to said endogenous nucleic acid target sequence and comprises at least one predetermined nucleotide at an interrogation position, and (ii) includes an identifier nucleotide, and wherein said nucleic acid target sequence comprises at least one specific base whose presence or absence is to be determined (B) maintaining said hybridization composition for a time period sufficient to form a treated sample, wherein said interrogation position of the probe is a nucleotide that is aligned with said specific base to be identified in said endogenous target sequence, when present, so that base pairing can occur;

(C) admixing the treated sample with an enzyme whose activity is to release one or more nucleotides from the 3'-terminus of a hybridized nucleic acid probe to depolymerize the hybrid and form a treated reaction mixture;

(D) maintaining the treated reaction mixture for a time period sufficient to release an identifier nucleotide therefrom; and (E) analyzing for the presence or absence of released identifier nucleotide to obtain an analytical output that indicates the presence or absence of said specific base to be identified.

55. The method according to claim 54 wherein the identifier nucleotide is at the interrogation position.

56. The method according to claim 54 wherein said analytical output is obtained by fluorescence spectroscopy.

57. The method according to claim 56 wherein said identifier nucleotide is fluorescently labeled after release from said hybrid.

58. The method according to claim 54 wherein said analytical output is obtained by mass spectrometry.

59. The method according to claim 56 wherein said released identifier nucleotide includes a fluorescent label.

60. The method according to claim 58 wherein said released identifier nucleotide includes a fluorescent label.

61. The method according to claim 54, wherein said nucleic acid target sequence is selected from the group consisting of deoxyribonucleic acid and ribonucleic acid.

62. The method according to claim 61, further comprising a first probe, a second probe, a third probe and a fourth probe.

63. The method according to claim 62, wherein said interrogation position of said first probe comprises a nucleic acid residue that is a deoxyadenosine or adenosine residue, said interrogation position of said second probe comprises a nucleic acid residue that is a deoxythymidine or uridine residue, said interrogation position of said third probe comprises a nucleic acid residue that is a deoxyguanosine or guanosine residue, and said fourth nucleic acid probe comprises a nucleic acid residue that is a deoxycytosine or cytosine residue.

64. The method according to claim 54 wherein said sample to be assayed comprises a plurality of endogenous nucleic acid target sequences in which the presence or absence of a plurality of specific bases is interrogated.

65. The method according to claim 64 wherein the analytical output obtained when one of said exogenous nucleic acid probes hybridizes with partial complementarity to one target nucleic acid sequence is greater than the analytical output when all of the nucleic acid probes hybridize with total complementarity to their respective nucleic acid target sequences.

66. The method according to claim 64 wherein the analytical output obtained when one of said nucleic acid probes hybridizes with partial complementarity to one target endogenous nucleic acid sequence is less than the analytical output when all of the nucleic acid probes hybridize with total complementarity to their respective nucleic acid target sequences.

67. The method according to claim 64 wherein the analytical output obtained when one of said nucleic acid probes hybridizes with total complementarity to one endogenous nucleic acid target sequence is greater than the analytical output when all of the nucleic acid probes hybridize with partial complementarity to their respective nucleic acid target sequences.

68. The method according to claim 64 wherein the analytical output obtained when one of said nucleic acid probes hybridize with total complementarity to one target nucleic acid sequence is less than the analytical output when all of the nucleic acid probes hybridize with partial complementarity to their respective nucleic acid target sequences.

69. The method according to claim 54 wherein said enzyme whose activity is to release nucleotides is a template-dependent polymerase that, in the presence of pyrophosphate ions, depolymerizes hybridized nucleic acids whose bases in the 3'terminal region of the probe are matched with total complementarity.

70. The method according to claim 54 wherein said enzyme whose activity is to release nucleotides exhibits a 3'→5'-exonuclease activity, depolymerizing hybridized nucleic acids having one or more mismatched bases at the 3'-terminus of the hybridized probe.

71. A method for determining the number of known sequence repeats present in a nucleic acid target sequence in a nucleic acid sample that comprises the steps of:

(A) providing a plurality of separate treated samples, each treated sample containing a nucleic acid target sequence hybridized with a nucleic acid probe wherein (a) the nucleic acid target sequence contains (i) a plurality of known sequence repeats and (ii) a non-repeated region downstream of the repeats, and (b) the nucleic acid probe is one of a plurality of different probes wherein said probes differ in the number of complementary sequence repeats contained therein, each nucleic acid probe containing (i) a plurality of sequence repeats complementary to the known sequence repeat of alleles of the target nucleic acid, (ii) an identifier nucleotide in the 3'-terminal region of the probe and (iii) a 5'-terminal locker sequence that is complementary to the non-repeated region of the target and comprises 1 to about 20 nucleotides, (B) admixing each treated sample with a depolymerizing amount of an enzyme whose activity is to release one or more nucleotides from the 3'-terminus of a hybridized nucleic acid probe to form a treated depolymerization reaction mixture;

(C) maintaining the treated depolymerization reaction mixtures for a time period sufficient to permit the enzyme to depolymerize hybridized nucleic acid probe and release identifier nucleotide therefrom; and (D) analyzing the samples for the presence of released identifier nucleotide to obtain an analytical output indicative of the number of sequence repeats present in said nucleic acid target sequence.

72. The method according to claim 71 wherein said nucleic acid sample comprises two nucleic acid target sequences representing alleles and is homozygous with respect to the number of sequence repeats in the two alleles.

73. The method according to claim 71 wherein said nucleic acid sample comprises two nucleic acid target sequences representing alleles and is heterozygous with respect to the number of sequence repeats in the two alleles.

74. The method according to claim 71 wherein said identifier nucleotide is a nucleotide that is part of the repeated sequence.

75. The method according to claim 71 wherein said identifier nucleotide of the probe sequence is complementary to a non-repeating sequence located 3' to the repeated sequences of the target nucleic acid.

76. The method according to claim 75 wherein said identifier nucleotide is present in a sequence containing 1 to about 20 nucleic acids that is complementary to a non-repeating sequence located 3' to the repeated sequences of the target nucleic acid.

77. The method according to claim 71 wherein a repeated known sequence present in a nucleic acid target sequence has a length of 2 to about 24 bases per repeat.

78. A method for determining whether the nucleic acid target sequence in a nucleic acid sample is an allele from a homozygous or heterozygous locus that comprises the steps of:

(A) providing a plurality of separate treated samples, each sample containing (a) a nucleic acid target sequence hybridized with (b) a nucleic acid probe, said nucleic acid target sequence being that of a first allele, a second allele or a mixture of said first and second alleles from a locus of interest of said nucleic acid target, said alleles differing in sequence at an interrogation position, said nucleic acid probe containing an identifier nucleotide in the 3'-terminal region that is aligned at an interrogation nucleotide position of the target sequence when said probe and target are hybridized;

(B) admixing each treated sample with a depolymerizing amount of an enzyme whose activity is to release one or more nucleotides from the 3'-terminus of a hybridized nucleic acid probe to form a treated reaction mixture;

(C) maintaining the treated reaction mixtures for a time period sufficient to permit the enzyme to depolymerize hybridized nucleic acid probe and an release identifier nucleotide; and (D) analyzing the samples for the presence of released identifier nucleotide to obtain an analytical output, the analytical output indicating whether the nucleic acid target sequence in a nucleic acid sample is an allele from a homozygous or a heterozygous locus.

79. The method of claim 78 wherein said analyzing comprises analyzing the samples for the quantity of released identifier nucleotide to obtain an analytical output, the analytical output indicating whether the nucleic acid target sequence in the nucleic acid sample is homozygous or heterozygous when compared to the analytical output of an appropriate control.

80. The method according to claim 78 wherein said analytical output indicates which allele is present when the nucleic acid target sequence in a nucleic acid sample is homozygous at the locus of interest.

81. The method according to claim 78 wherein said enzyme whose activity is to release nucleotides is a template-dependent polymerase that, in the presence of pyrophosphate ions, depolymerizes hybridized nucleic acids whose bases in the 3'-terminal region are completely complementary to bases of said nucleic acid target.

82. The method according to claim 79 wherein said analytical output is obtained by luminescence spectroscopy.

83. A method for determining the loss of heterozygosity of a locus of an allele that comprises the steps of:

(A) providing a plurality of separate treated samples, each sample containing (a) a nucleic acid target sequence hybridized with (b) a nucleic acid probe, said nucleic acid target sequence being that of a first allele or a mixture of said first allele and a second allele of said nucleic acid target, said alleles differing in sequence at an interrogation position, said nucleic acid probe containing a 3'-terminal region that hybridizes to a region of said nucleic acid target sequence containing said interrogation nucleotide position when said probe and target are hybridized and an identifier nucleotide;

(B) admixing each treated sample with a depolymerizing amount of an enzyme whose activity is to release one or more nucleotides from the 3'-terminus of a hybridized nucleic acid probe to form a treated reaction mixture;

(C) maintaining the treated reaction mixtures for a time period sufficient to depolymerize hybridized nucleic acid probe and an release identifier nucleotide; and (D) analyzing the samples for the quantity of released identifier nucleotide to obtain an analytical output, the analytical output indicating whether the nucleic acid target sequence in a nucleic acid sample has lost heterozygosity at the locus of the allele.

84. The method of claim 83 wherein the quantity of said released identifier nucleotide for said first allele is substantially less that the quantity of said released identifier nucleotide for said first allele of a known heterozygous control, and the quantity of said released identifier nucleotide for said second allele is substantially similar to the quantity of said released identifier nucleotide for said second allele of a known heterozygous control, indicating a loss of heterozygosity at the locus of said first allele.

85. The method of claim 83 wherein the quantity of said released identifier nucleotide for said second allele is substantially less that the quantity of said released identifier nucleotide for said second allele of a known heterozygous control, and the quantity of said released identifier nucleotide for said first allele is substantially similar to the quantity of said released identifier nucleotide for said first allele of a known heterozygous control, indicating a loss of heterozygosity at the locus of said second allele.

86. The method according to claim 83 wherein said analytical output is obtained by luminescence spectroscopy.

87. The method according to claim 83 wherein said analytical output is obtained by absorbance spectrometry.

88. The method according to claim 83 wherein said analytical output is obtained by fluorescence spectroscopy.

89. The method according to claim 88 wherein said released identifier nucleotide includes a fluorescent label.

90. The method according to claim 89 wherein said identifier nucleotide is fluorescently labeled after release from said hybrid.

91. The method according to claim 83 wherein said analytical output is obtained by mass spectrometry.

92. The method according to claim 91 wherein said released identifier nucleotide includes a fluorescent label.

93. The method according to claim 92 wherein said identifier nucleotide is fluorescently labeled after release from said hybrid.

94. The method according to claim 83 wherein said enzyme whose activity is to release nucleotides is a template-dependent polymerase that, in the presence of pyrophosphate ions, depolymerizes hybridized nucleic acids whose bases in the 3'-terminal region are completely complementary to bases of said nucleic acid target.

95. The method according to claim 94 wherein the quantity of said released identifier nucleotide for said first allele is substantially less than the quantity of said released identifier nucleotide for said first and second alleles, indicating a loss of heterozygosity at the locus of said first allele.

96. The method according to claim 94 wherein the quantity of said released identifier nucleotide for said second allele is substantially less than the quantity of said released identifier nucleotide for said first and second alleles, indicating a loss of heterozygosity at the locus of said second allele.

97. A method for determining the presence of trisomy of an allele that comprises the steps of:
(A) providing a plurality of separate treated samples, each sample containing (a) a nucleic acid target sequence hybridized with (b) a nucleic acid probe, said nucleic acid target sequence being that of a first allele, a second allele or a mixture of said first and second alleles of said nucleic acid target, said alleles differing in sequence at an interrogation position, said nucleic acid probe containing a 3'-terminal region that hybridizes to a region of said nucleic acid target sequence containing said interrogation nucleotide position when said probe and target are hybridized and an identifier nucleotide;
(B) admixing each treated sample with a depolymerizing amount of an enzyme whose activity is to release one or more nucleotides from the 3'-terminus of a hybridized nucleic acid probe to form a treated reaction mixture;
(C) maintaining the treated reaction mixtures for a time period sufficient to depolymerize hybridized nucleic acid probe and an release identifier nucleotide; and
(D) analyzing the samples for released identifier nucleotide to obtain an analytical output, the quantity of said analytical output relative to an analytical output of a control sample indicating whether a trisomy is present in the nucleic acid target sequence.

98. The method of claim 97 wherein the ratio of the quantity of said released identifier nucleotide for said first and second allele is about 3 to zero, compared to the ratio of the quantity of said released identifier nucleotide for said first and second allele of a known heterozygous control of about 1 to 1, indicating a trisomy at the locus of said first allele.

99. The method of claim 97 wherein the ratio of the quantity of said released identifier nucleotide for said first and second allele is about zero to 3, compared to the ratio of the quantity of said released identifier nucleotide for said first and second allele of a known heterozygous control of about 1 to 1, indicating a trisomy at the locus of said second allele.

100. The method of claim 97 wherein the ratio of the quantity of said released identifier nucleotide for said first and second allele is about 2 to 1, compared to the ratio of the quantity of said released identifier nucleotide for said first and second allele of a known heterozygous control of about 1 to 1, indicating a trisomy having two copies of the locus of said first allele and one copy of the locus of said second allele.

101. The method of claim 97 wherein the ratio of the quantity of said released identifier nucleotide for said first and second allele is about 1 to 2, compared to the ratio of the quantity of said released identifier nucleotide for said first and second allele of a known heterozygous control of about 1 to 1, indicating a trisomy having one copy of the locus of said first allele and two copies of the locus of said second allele.

102. The method according to claim 97 wherein said analytical output is obtained by luminescence spectroscopy.

103. The method according to claim 97 wherein said analytical output is obtained by absorbance spectrometry.

104. The method according to claim 97 wherein said analytical output is obtained by fluorescence spectroscopy.

105. The method according to claim 104 wherein said released identifier nucleotide includes a fluorescent label.

106. The method according to claim 105 wherein said identifier nucleotide is fluorescently labeled after release from said hybrid.

107. The method according to claim 97 wherein said analytical output is obtained by mass spectrometry.

108. The method according to claim 107 wherein said released identifier nucleotide includes a fluorescent label.

109. The method according to claim 108 wherein said identifier nucleotide is fluorescently labeled after release from said hybrid.

110. The method according to claim 97 wherein said enzyme whose activity is to release nucleotides is a template-dependent polymerase that, in the presence of pyrophosphate ions, depolymerizes hybridized nucleic acids whose bases in the 3'-terminal region are completely complementary to bases of said nucleic acid target.

111. The method according to claim 97 wherein the quantity of said released identifier nucleotide for said first allele is substantially greater than the quantity of said released identifier nucleotide of a homozygous control, indicating that said nucleic acid target sequence has a trisomy.

112. The method according to claim 97 wherein the quantity of said released identifier nucleotide for said second allele is substantially greater than the quantity of said released identifier nucleotide of a homozygous control, indicating that said nucleic acid target sequence has a trisomy.

113. A method for determining the presence or absence of a nucleic acid target sequence containing an interrogation position in a nucleic acid sample that comprises the steps of:
(A) providing a treated sample that contains a nucleic acid sample that may include said nucleic acid target sequence hybridized with a nucleic acid probe that is comprised of three sections, (i) a first section that contains the probe 3'-terminal about 10 to about 30 nucleotides that are complementary to the nucleic acid target sequence at positions beginning about 1 to about 30 nucleic acids downstream of said interrogation position of the target sequence, (ii) a 5'-terminal region of about 10 to about 200 nucleic acids in length and having the identical sequence of said nucleic acid target sequence, and (iii) an optional third section that contains zero to about 50 nucleic acids that are not complementary to said nucleic acid sample, and;

(B) extending said nucleic acid probe in a 3' direction to form a second probe hybridized to the nucleic acid sample as a second hybrid;

(D) denaturing said second hybrid to separate said second probe from said nucleic acid target sequence;

(E) renaturing said aqueous composition to form hairpin structures from said second probe;

(F) admixing the hairpin structure-containing composition with a depolymerizing amount of an enzyme whose activity is to release one or more nucleotides from the 3'-terminus of a nucleic acid hybrid to form a treated reaction mixture;

(G) maintaining the treated reaction mixture for a time period sufficient to permit the enzyme to depolymerize hybridized nucleic acid and release one or more nucleotides from the 3'-terminus therefrom; and (H) analyzing for the presence of released identifier nucleotide to obtain an analytical output, the analytical output indicating the presence or absence of said nucleic acid target sequence.

114. A method for determining the presence or absence of a nucleic acid target sequence, or a specific base within the target sequence, in a nucleic acid sample, that comprises the steps of:

(A) providing a treated sample that contains a nucleic acid sample that may include a nucleic acid target sequence hybridized with a first nucleic acid probe as a first hybrid, said first probe being comprised of at least two sections, a first section containing the probe 3'-terminal about 10 to about 30 nucleotides that are complementary to the target nucleic acid sequence at a position beginning about 5 to about 30 nucleotides downstream of the target interrogation position, a second section of the first probe containing about 5 to about 30 nucleotides that are a repeat of the target sequence from the interrogation position to about 10 to about 30 nucleotides downstream of the interrogation position that does not hybridize to said first section of the probe, and an optional third section of the probe located between the first and second sections of the probe that is zero to about 50 nucleotides in length and comprises a sequence that does not hybridize to either the first or second section of the probe;

(B) extending the first hybrid in the treated sample at the 3'-end of the first probe, thereby extending the first probe past the interrogation position and forming an extended first hybrid that includes an interrogation position;

(C) denaturing an aqueous composition of the extended first hybrid to separate the two nucleic acid strands and form an aqueous composition containing a separated target nucleic acid and a separated extended first probe;

(D) annealing the extended first probe to a second probe that is about 10 to about 30 nucleotides in length and is complementary to the extended first probe at a position beginning about 5 to about 2000 nucleotides downstream of the interrogation position in the extended first probe, thereby forming a second hybrid;

(E) extending the second hybrid at the 3'-end of the second probe until that extension reaches the 5'-end of the extended first probe, thereby forming a second extended hybrid containing a second extended probe whose 3'-region includes an identifier nucleotide;

(F) denaturing an aqueous composition of the extended second hybrid to separate the two nucleic acid strands and form an aqueous composition containing separated extended first and second probes;

(G) cooling the aqueous composition to form a hairpin structure from the separated extended second probe to form a hairpin structure-containing composition;

(H) admixing the hairpin structure-containing composition with a depolymerizing amount of an enzyme whose activity is to release one or more nucleotides from the 3'-terminus of a nucleic acid hybrid to form a treated reaction mixture;

(I) maintaining the reaction mixture for a time period sufficient to release 3'-terminal region identifier nucleotides; and (J) analyzing for the presence of released identifier nucleotide to obtain an analytical output, the analytical output indicating the presence or absence of said predetermined nucleic acid target sequence or a specific base within the target sequence.

115. The method according to claim 114 wherein said analytical output is obtained by luminescence spectroscopy.

116. The method according to claim 114 wherein said analytical output is obtained by fluorescence spectroscopy.

117. The method according to claim 116 wherein said released identifier nucleotide includes a fluorescent label.

118. The method according to claim 117 wherein said identifier nucleotide is fluorescently labeled after release from said hybrid.

119. The method according to claim 114 wherein said analytical output is obtained by mass spectrometry.

120. The method according to claim 119 wherein said released identifier nucleotide includes a fluorescent label.

121. The method according to claim 119 wherein said identifier nucleotide is fluorescently labeled after release from said hybrid.

122. The method according to claim 114 wherein said analytical output is obtained by absorbance spectroscopy.

* * * * *